(12) United States Patent
Rosa et al.

(10) Patent No.: US 9,498,517 B2
(45) Date of Patent: *Nov. 22, 2016

(54) STANNIOCALCIN-1 (STC-1) THERAPY FOR TREATMENT OF RETINAL DISEASES

(71) Applicants: Scott & White Healthcare, Temple, TX (US); The Texas A&M University System, College Station, TX (US)

(72) Inventors: Robert Rosa, Holland, TX (US); Gavin W. Roddy, Temple, TX (US); Darwin J. Prockop, Philadelphia, PA (US)

(73) Assignees: Scott & White Healthcare, Temple, TX (US); The Texas A&M University System, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/789,389

(22) Filed: Jul. 1, 2015

(65) Prior Publication Data

US 2015/0374791 A1    Dec. 31, 2015

Related U.S. Application Data

(63) Continuation of application No. 14/284,911, filed on May 22, 2014, now Pat. No. 9,090,704, which is a continuation of application No. 13/549,770, filed on Jul. 16, 2012, now Pat. No. 8,759,298, which is a continuation-in-part of application No. PCT/US2011/000771, filed on May 3, 2011.

(60) Provisional application No. 61/508,587, filed on Jul. 15, 2011, provisional application No. 61/464,172, filed on Feb. 28, 2011, provisional application No. 61/330,735, filed on May 3, 2010.

(51) Int. Cl.
*A61K 38/17* (2006.01)
*A61K 38/16* (2006.01)
*A61K 38/22* (2006.01)
*A61K 35/28* (2015.01)
*C07K 14/575* (2006.01)
*A61K 9/00* (2006.01)

(52) U.S. Cl.
CPC ............ *A61K 38/22* (2013.01); *A61K 9/0048* (2013.01); *A61K 35/28* (2013.01); *A61K 38/1709* (2013.01); *C07K 14/575* (2013.01)

(58) Field of Classification Search
None
See application file for complete search history.

(56) References Cited

U.S. PATENT DOCUMENTS

| | | | | |
|---|---|---|---|---|
| 6,171,822 B1 * | 1/2001 | Kuestner | ............ | C07K 14/575 435/252.3 |
| 2004/0198658 A1 * | 10/2004 | Olsen | ................... | C07K 14/575 514/8.3 |

OTHER PUBLICATIONS

Wagner et al. J. Exp. Zool. 305A: 769-780, 2006.*

* cited by examiner

*Primary Examiner* — Christine J Saoud
(74) *Attorney, Agent, or Firm* — Hodgson Russ LLP

(57) ABSTRACT

The present invention encompasses methods, compositions, and devices for treating an ocular disease, disorder or condition in a mammal. The invention includes polypeptides that possess anti-inflammatory, anti-apoptotic, immune modulatory and anti-tumorigenic properties, and their application in the treatment of eye disease, particularly diseases of the retina. In particular aspects, the invention includes administration of a therapeutic polypeptide such as a stanniocalcin family member protein for the treatment of an eye disease. Also included are fusion proteins and cells stimulated or modified to express the therapeutic polypeptides as set forth herein.

2 Claims, 61 Drawing Sheets
(8 of 61 Drawing Sheet(s) Filed in Color)

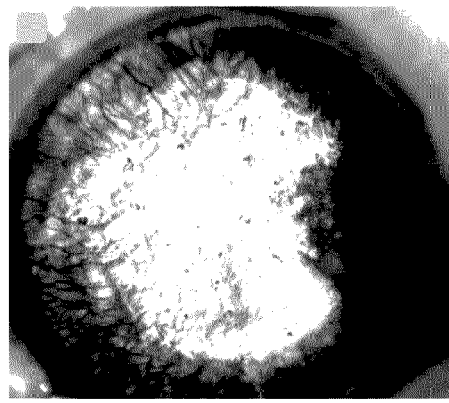
Fig. 1A
Fig. 1B
Fig. 1C
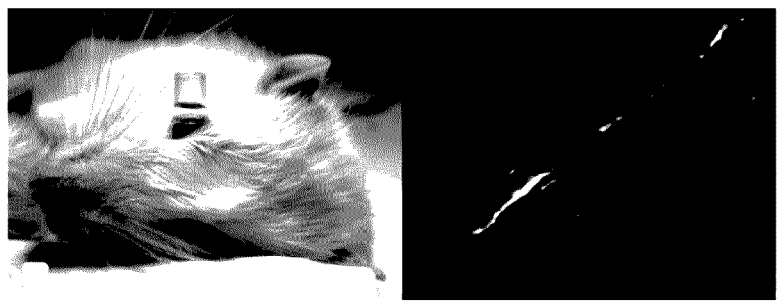
Fig. 2A          Fig. 2B

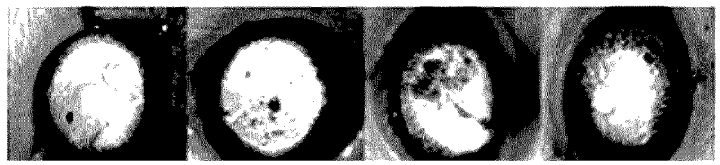
Fig. 3A  Fig. 3B  Fig. 3C  Fig. 3D
Fig. 3E  Fig. 3F  Fig. 3G  Fig. 3H
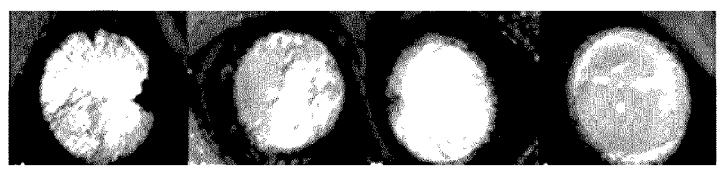
Fig. 3I  Fig. 3J  Fig. 3K  Fig. 3L
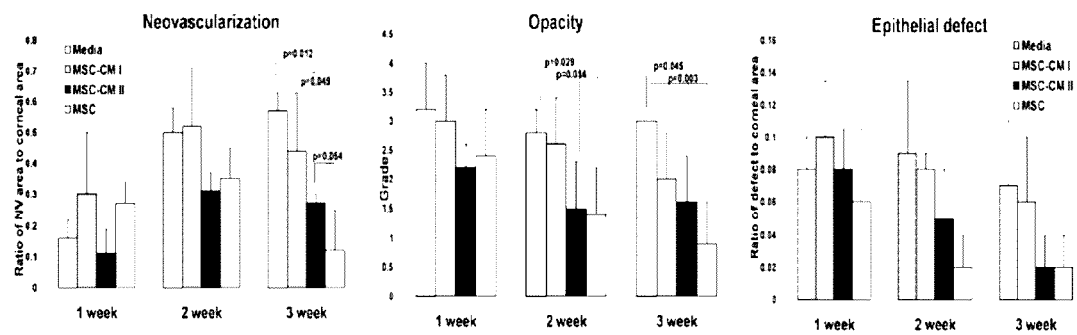

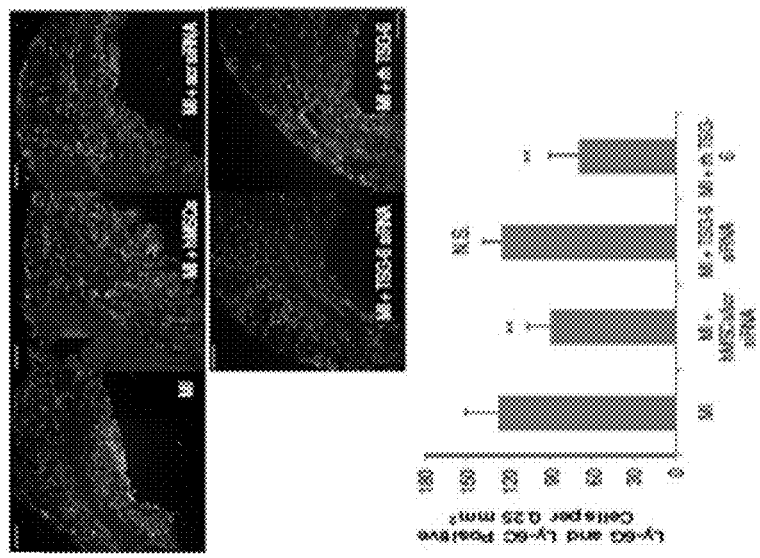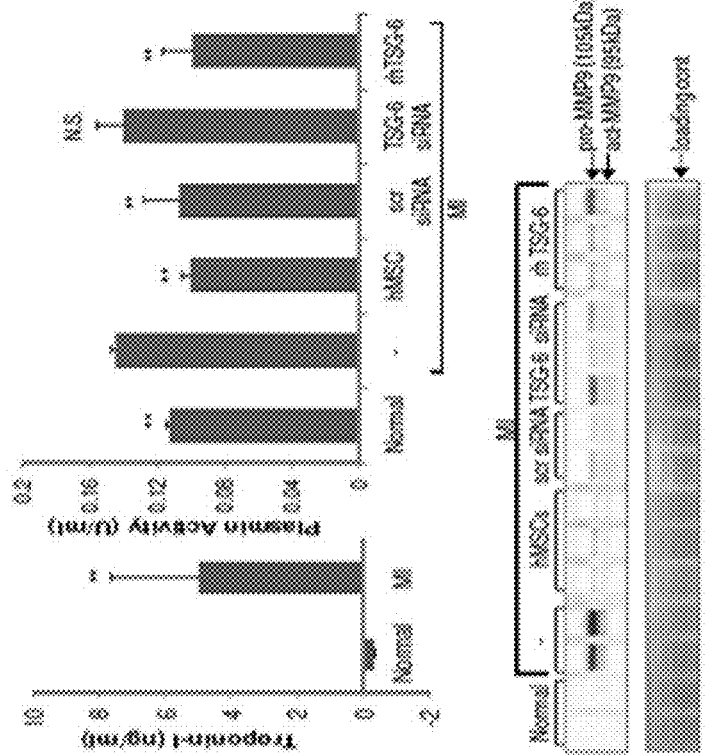

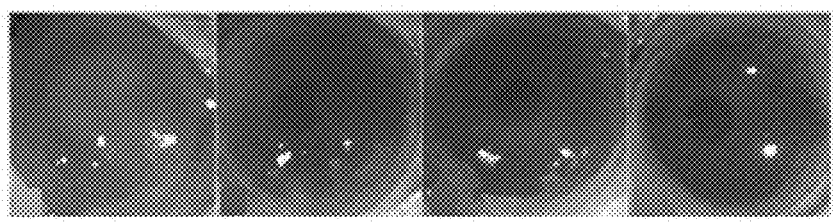
Fig. 19A    Fig. 19B    Fig. 19C    Fig. 19D
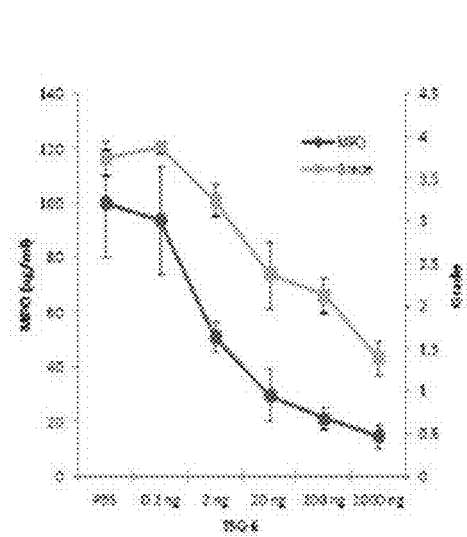 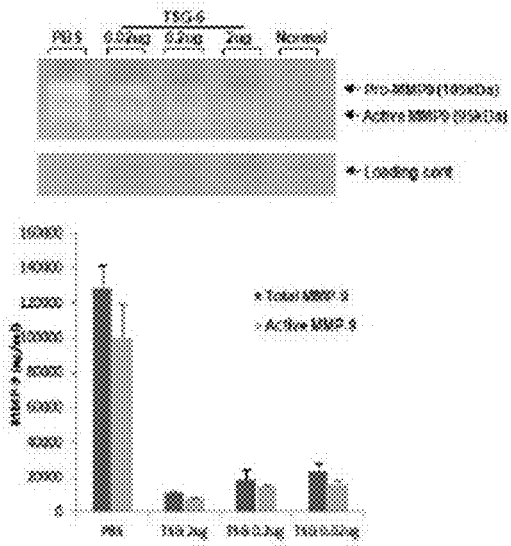
Fig. 19E    Fig. 19F

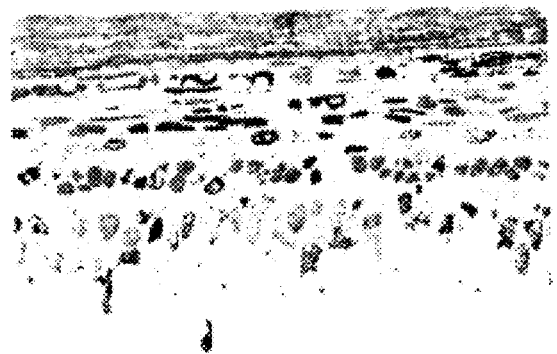
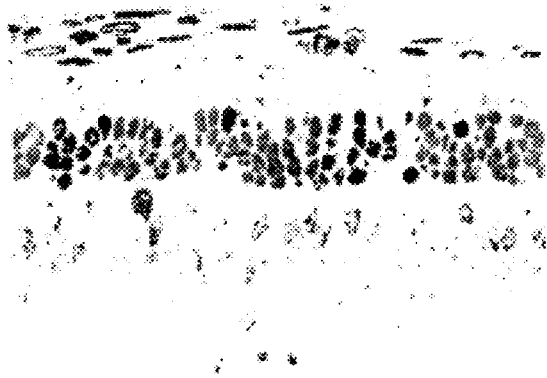
FIG. 23

Fig. 23, continued
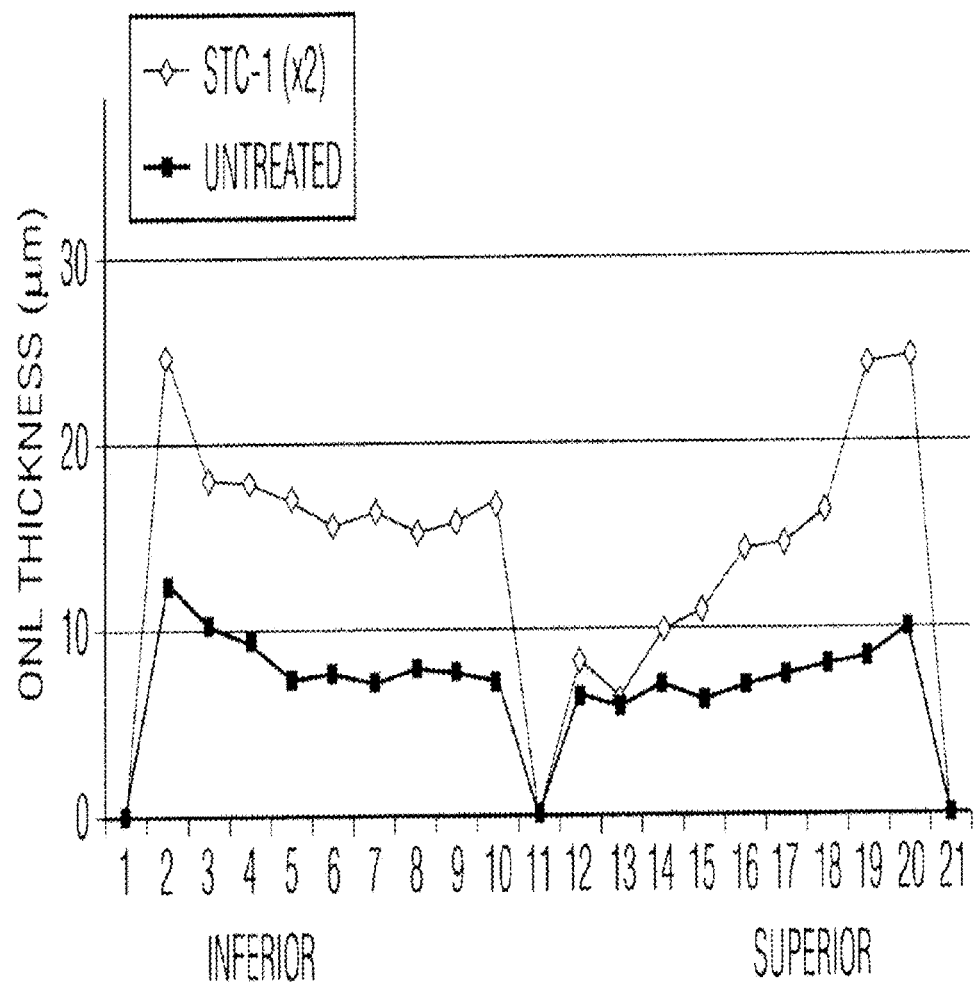

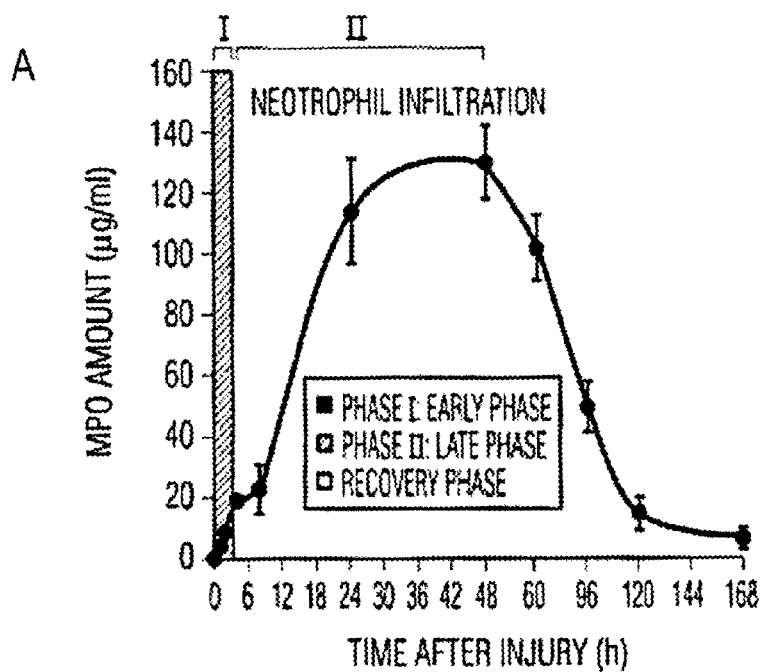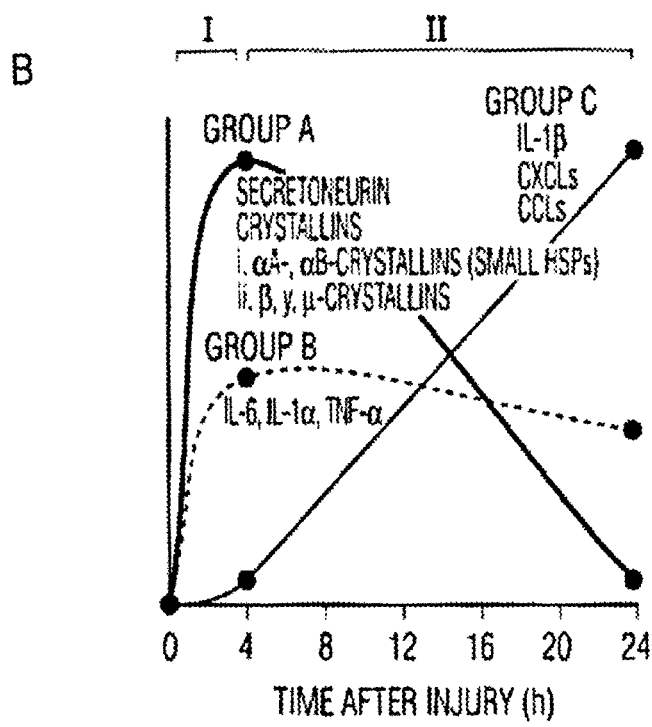
Fig. 31

A
B
Fig. 32

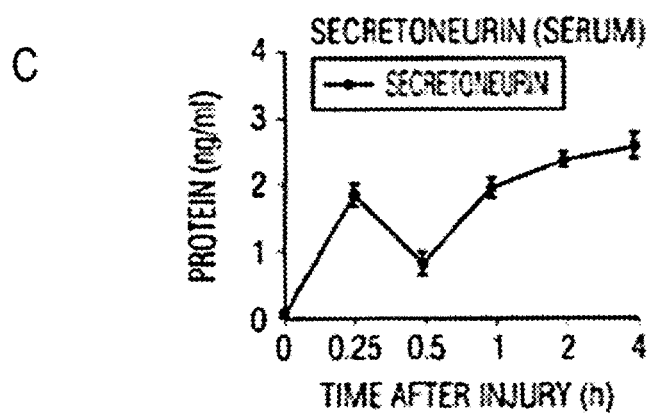
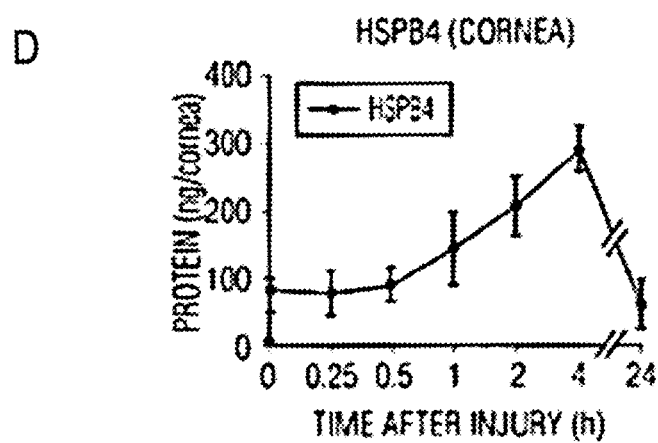
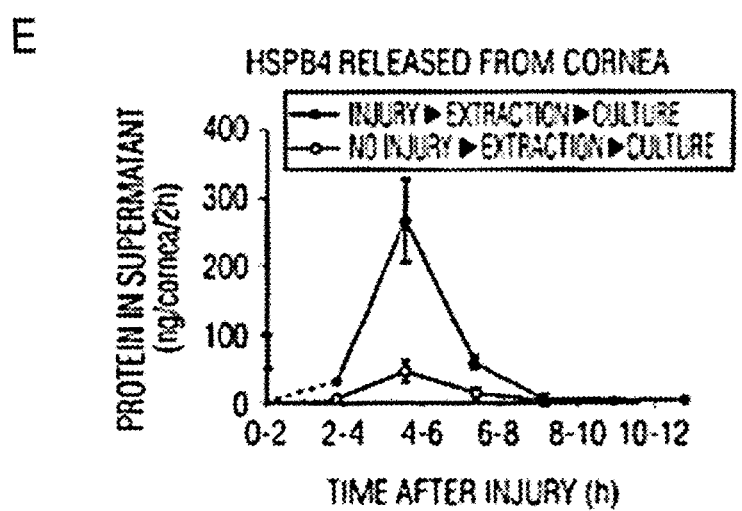
Fig. 32 (continued)

F  SECRETONEURIN (CORNEA)
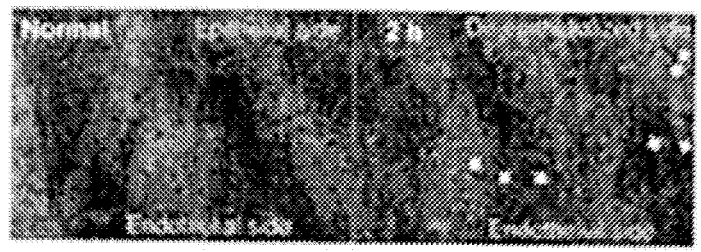
G  HSPB4 (CORNEA)
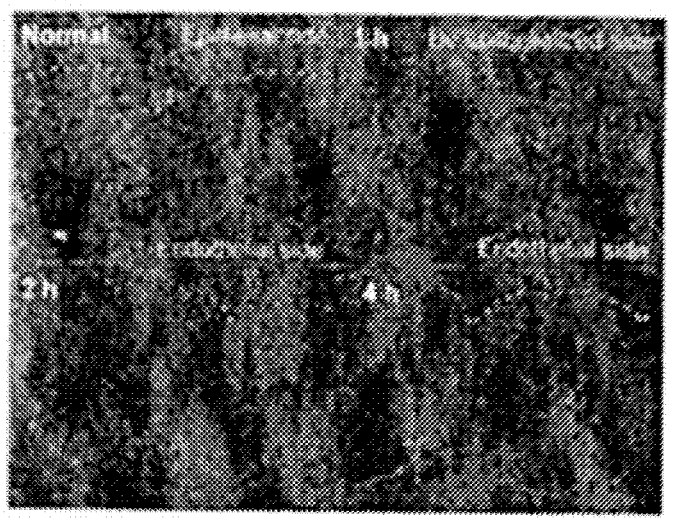
Fig. 32 (continued)

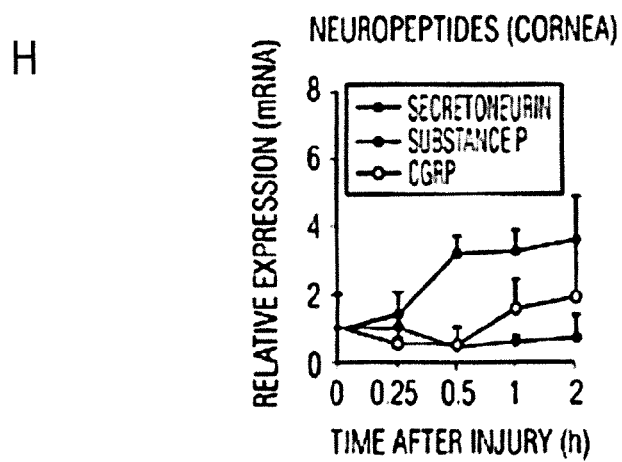
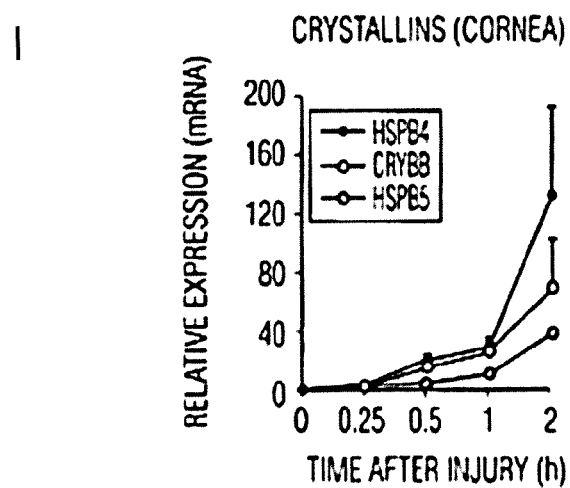
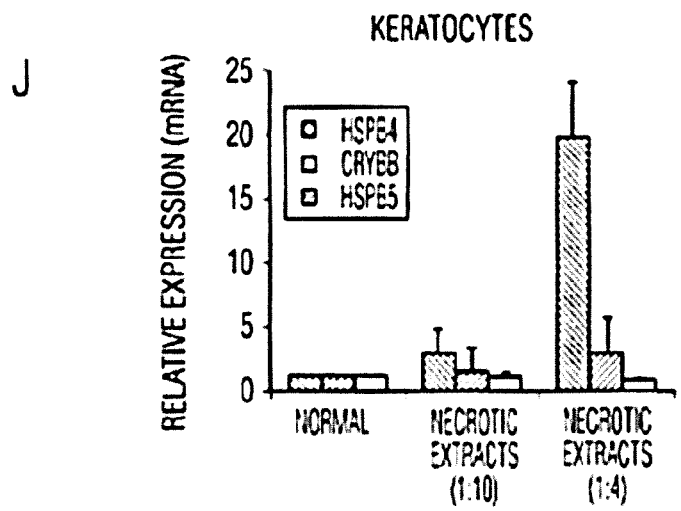
Fig. 32 (continued)

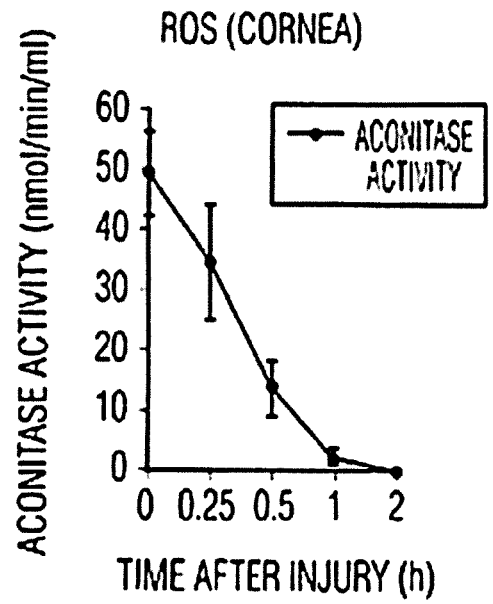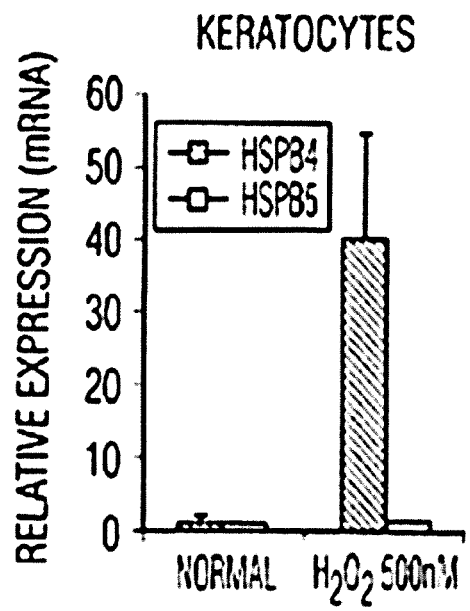
Fig. 32 (continued)

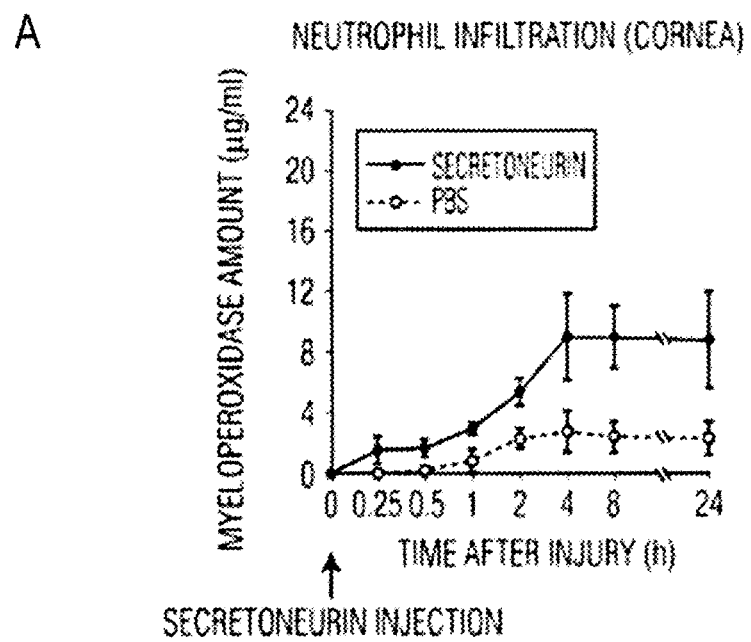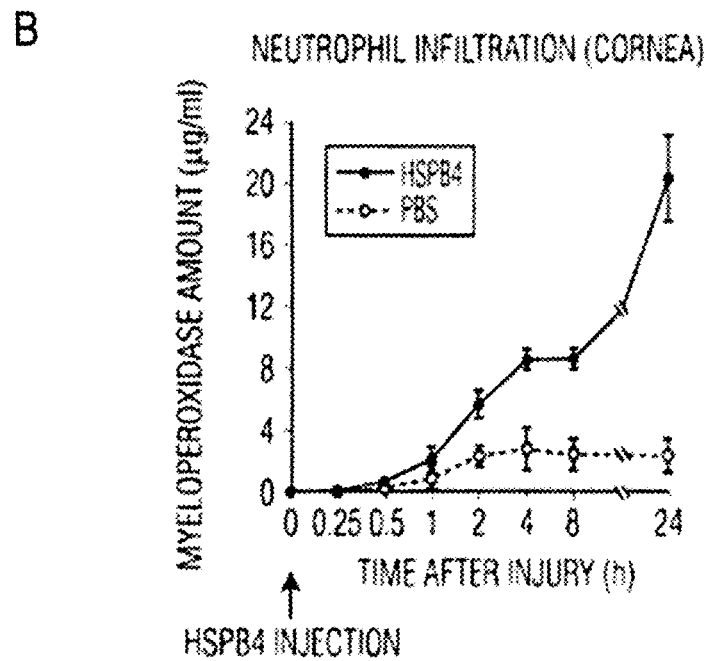
Fig. 33

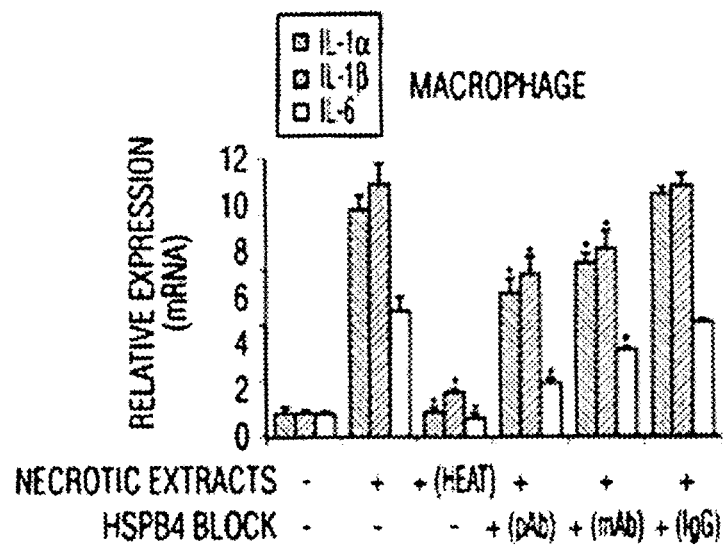
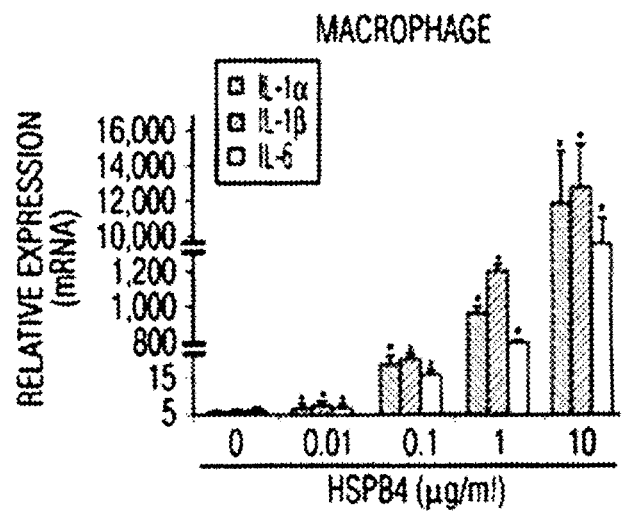
Fig. 34 (continued)

D
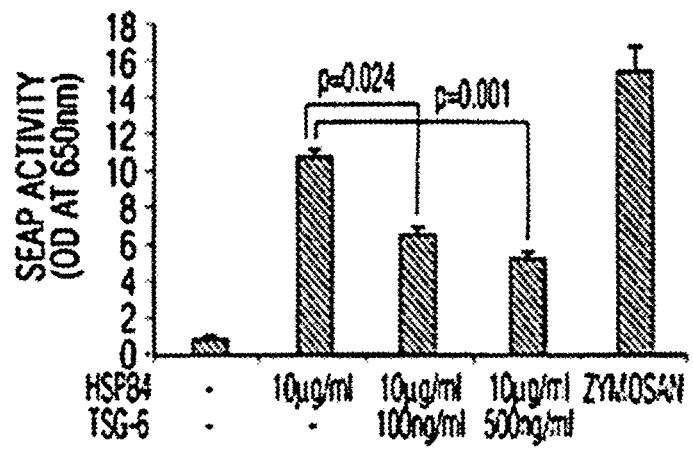
E
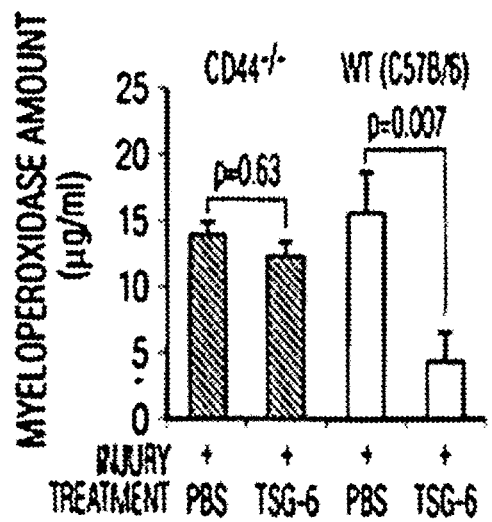
Fig. 35 (continued)

STANNIOCALCIN-1 (STC-1) THERAPY FOR TREATMENT OF RETINAL DISEASES

CROSS-REFERENCE TO RELATED APPLICATIONS

This patent application is a continuation of U.S. patent application Ser. No. 14/284,911, filed May 22, 2014, which is a continuation of U.S. patent application Ser. No. 13/549,770, filed Jul. 16, 2012, now U.S. Pat. No. 8,759,298, which claims priority to U.S. Provisional Patent Application Ser. No. 61/508,587, filed Jul. 15, 2011, and is a continuation-in-part application of PCT/US2011/000771, filed May 3, 2011, which in turn claims priority to provisional application Ser. No. 61/464,172, filed Feb. 28, 2011, and to provisional application Ser. No. 61/330,735, filed May 3, 2010, the contents of each of which of the foregoing applications are incorporated herein by reference.

STATEMENT REGARDING FEDERALLY SPONSORED RESEARCH

This invention was made with government support under Grant No. R21EY020962 awarded by the National Institutes of Health. The government has certain rights in the invention.

BACKGROUND OF THE INVENTION

Eye disease is a significant cause of morbidity in the U.S. and throughout the world. While therapies have improved over time for many eye diseases, there remain many others for which therapy is of limited or no benefit.

Diseases of the retina, including age-related macular degeneration (AMD), retinitis pigmentosa (RP), and diabetic retinopathy (DR), are major causes of legal blindness in the United States. AMD and RP share clinical and pathologic features including end-stage blindness due to photoreceptor and/or retinal pigment epithelium (RPE) cell death. DR is one of the most common complications of diabetes and the leading cause of blindness in people of working age in the United States and other industrialized countries. The estimated prevalence of diabetic retinopathy is nearly 30% and vision-threatening DR is nearly 5% in the adult population with diabetes (Zhang et al., 2010, JAMA 304; 649-656). The Eye Diseases Prevalence Research Group estimated in 2004 that approximately 4.1 million adults 40 years and older have diabetic retinopathy and that 1 of every 12 persons with diabetes in this age group has advanced, vision-threatening retinopathy. (The Eye Diseases Prevalence Research Group, 2004, Arch Ophthalmol 122: 552-563).

Despite adequate glycemic and blood pressure control and lipid-lowering therapy, the number of DR patients continues to grow and therapeutic approaches remain limited. There is a great need for the development of new strategies to prevent and treat DR. Studies have shown that DR has prominent features of chronic, subclinical inflammation. Retinal vessel occlusion and degeneration is a typical feature of DR and is also a cause of neovascularization. Mechanisms leading to capillary degeneration may involve inflammatory cytokine-induced endothelial cell death since inflammatory cytokines such as TNF-α and IL-1β are also known to increase caspase 3 activity and potently induce endothelial cell apoptosis (Aveleira et al., 2010, Diabetes 59:2872-2882; Del Maschio et al., 1996, J Cell Biol 135:497-510). The apoptotic effect of inflammatory cytokines may even be exaggerated in the presence of hyperglycemia (Del Maschio, 1996).

Apoptosis of photoreceptors is a prominent feature in many retinal degenerations, including AMD and RP. Reactive oxygen species (ROS) have been implicated in the initiation and/or exacerbation of cell death in AMD (Fletcher, et al., Ophthalmic Res., Vol. 44, No. 3, pgs. 191-198 (2010); Beatty et al., Surv. Ophthalmol., Vol. 45, No. 2, pgs. 115-134 (2000); Winkler, Mol. Vis., Vol. 5, pg. 32 (1999); Johnson, Curr. Opin. Cln. Nutr. Metab. Care, Vol. 13, pgs. 28-33 (2010); Totan et al., Curr. Eye Res., Vol. 34, No. 12, pgs. 1089-1093 (2009)) and antioxidant vitamin therapy is currently one of the mainstays of treatment in non-exudative AMD and RP (Johnson, 2010; Hartong et al., Lancet, Vol. 368, pgs. 1795-1809 (2006)). Oxidative stress happens when ROS are overproduced or when endogenous antioxidant systems are impaired. Mitochondria have long been recognized as a key source of ROS formation during diabetes (Aiello et al., 1998, Diabetes Care 21:143-156). Mitochondria can generate ROS by leak of electrons to molecular oxygen at electron transport chain (ETC) complexes I, II and III (Jezek et al., 2005, Int J Biochem Cell Biol 37:2478-2503). In diabetes, the metabolism of glucose-derived pyruvate through the ETC complexes is increased because of high-glucose concentration within cells, resulting in superoxide overproduction by mitochondria (Giacco et al., 2010, Circ Res 107:1058-1070). Although not curative, reduction of risk of disease and stabilization of vision have been observed following antioxidant vitamin therapy (Flectcher, 2010; Beatty, 2000; Johnson, 2010; Hartong, 2006). Moreover, two of the top modifiable risk factors in AMD—smoking and light exposure—are thought to injure photoreceptors or RPE through ROS-mediated damage (Flectcher, 2010; Johnson, 2010).

Glaucoma is a group of diseases characterized by progressive optic nerve degeneration that results in visual field loss and irreversible blindness. A critical element in the pathophysiology of all forms of glaucoma is the death of retinal ganglion cells (RGCs). Strategies that delay or halt RGC loss have been recognized as potentially beneficial to preserve vision in glaucoma. In recent years, there has been an exponential increase in data regarding the molecular basis of RGC death resulting from experimental models of acute and chronic optic nerve injury as well as experimental glaucoma. A variety of molecular signals and/or mechanisms which might act alone or in concert can promote RGC death. Possible molecular mechanisms include: neurotrophic factor deprivation, toxic pro-neurotrophins, activation of intrinsic and extrinsic apoptotic signals, mitochondrial dysfunction, excitotoxic damage, and oxidative stress (Almasieh et al., 2012, Prog Retin Eye Res 31:152-81).

Dry, atrophic (nonexudative) age-related macular degeneration, defined as progressive age-related degeneration of the macula associated with retinal pigment epithelial changes including atrophy and drusen, is a common cause of vision loss in adults for which therapy is extremely limited. Patients often develop a slow progressive loss of vision over time. Vitamin therapies and other types of therapy are of limited benefit. More therapeutic options are available for patients with exudative age-related macular degeneration, which is associated with choroidal or subretinal neovascularization. Nevertheless, despite therapy such as laser or pharmacotherapy, many patients develop progressive vision loss. There is the need for therapies to reduce the risk of progressive vision loss in patients with both forms of age-related macular degeneration.

In summary, there is the need for more effective treatment of many common diseases of the eye, such as diseases of the retina, cornea, and glaucoma.

SUMMARY OF THE INVENTION

The present invention is based in part upon the finding that certain polypeptides possessing anti-inflammatory or anti-apoptotic properties are beneficial in the treatment of eye disease.

Certain embodiments of the present invention concern a method of treating or preventing an eye disease in a subject that involves administering to a subject with an eye disease or at risk of developing an eye disease a pharmaceutically effective amount of a composition that includes an isolated polypeptide comprising a domain comprising a stanniocalcin family member polypeptide, wherein the eye disease is treated or prevented. The subject can be, for example, a mammal, such as a rat, a mouse, a rabbit, a dog, a cat, a horse, a sheep, a goat, a primate, or a human subject (such as a patient with an eye disease). In particular embodiments, the subject is a patient (human subject) with the eye disease or at risk of developing the eye disease.

The stanniocalcin family member polypeptide may be, for example, a stanniocalcin-1 (STC-1) polypeptide that has at least 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In some embodiments, the STC-1 polypeptide has between 95% and 99% sequence identity with one of the aforementioned polypeptide sequences. In a particular embodiment, the stanniocalcin family member polypeptide has at least 95% sequence identity to SEQ ID NO:1; and in a specific embodiment, the stanniocalcin family member polypeptide consists of SEQ ID NO:1.

The disease may be any eye disease, but in particular aspects is a disease of the retina, a disease of the cornea, or glaucoma. The disease of the retina may be, for example, a retinal degeneration such as macular degeneration or retinitis pigmentosa. The macular degeneration may be age-related macular degeneration. The age-related macular degeneration may be atrophic nonexudative age-related macular degeneration. The disease of the retina may also be diabetic retinopathy. The diabetic retinopathy may be proliferative diabetic retinopathy (retinopathy associated with neovascularization of the retina) or nonproliferative diabetic retinopathy (diabetic retinopathy without neovascularization but with other findings associated with diabetic retinopathy such as dot and blot hemorrhages and microaneurysms). The diabetic retinopathy may also include diabetic macular edema. The disease may be any disease associated with elevated intraocular pressure. Nonlimiting examples include chronic open angle glaucoma, angle closure glaucoma, and pigmentary glaucoma.

The composition may be administered using any method known to those of ordinary skill in the art. Nonlimiting examples include topical, subconjunctival, sub-Tenon's, intravitreal, subretinal, or injection into the anterior chamber of the eye of a subject. Other modes of administration include systemic administration, including intravenous administration as well as oral administration. In a specific embodiment, the composition is administered intravitreally.

In some aspects the stanniocalcin family member polypeptide is a stanniocalcin-2 (STC-2) polypeptide that has at least 95% sequence identity to SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20. The stanniocalcin family member polypeptide may have between 95% and 99% sequence identity to any of the aforementioned stanniocalcin-2 family members. In more particular aspects, the stanniocalcin family member comprises SEQ ID NO:12, SEQ ID NO:13, SEQ ID NO:14, SEQ ID NO:15, SEQ ID NO:16, SEQ ID NO:17, SEQ ID NO:18, SEQ ID NO:19, or SEQ ID NO:20.

Certain other embodiments involve administering to a subject a pharmaceutically effective amount of a composition that includes cells to treat an eye disease, wherein the cells have been stimulated or genetically modified to overexpress a stanniocalcin family member polypeptide compared to a cell of the same type that has not been stimulated or genetically modified. While any cell type is contemplated, in particular embodiments the cell is a mesenchymal stem cell (MSC), a retinal pigment epithelial cell, a corneal or conjunctival epithelial cell, or a limbal stem cell. In particular aspects, the stanniocalcin family member polypeptide has at least 95% sequence identity to SEQ ID NO:1 or SEQ ID NO:12. The polypeptide may have between 95% and 99% sequence identity to SEQ ID NO:1 or SEQ ID NO:12. The mesenchymal stem cells may be autologous or allogeneic. Autologous cells may be harvested from the subject using any method known to those of ordinary skill in the art, such as by venipuncture or bone marrow aspiration. The cells may be genetically modified in situ to express a stanniocalcin family member polypeptide as set forth herein, and then administered to the subject using any method known to those of ordinary skill in the art. In particular embodiments for the treatment of retinal disease such as retinal degeneration or age-related macular degeneration, the cells are administered by intravtireal or subretinal injection or via an ocular drug delivery device designed for insertion into the vitreous cavity.

Other aspects of the invention pertain to a method of treating or preventing an eye disease in a subject, that involves administering to a subject with an eye disease or at risk of developing an eye disease a pharmaceutically effective amount of a composition that comprises an isolated polypeptide comprising a domain comprising a Tumor Necrosis Factor-Inducible Gene 6 (TSG-6) polypeptide, wherein the eye disease is treated or prevented. Non-limiting examples of such polypeptides include those having at least 95% sequence identity to SEQ ID NO:21, SEQ ID NO:22, SEQ ID NO:23, SEQ ID NO:24, or SEQ ID NO:25. The polypeptide may have between 95% and 99% sequence identity to SEQ ID NO:21, SEQ ID NO:22, SEQ ID NO:23, SEQ ID NO:24, or SEQ ID NO:25. In particular aspects, the eye disease is a disease of the cornea. In certain aspects, the subject has had an injury or condition resulting in a defect of the corneal epithelium, or has had corneal transplantation or other corneal surgery.

Other aspects of the invention involve administering to the subject a pharmaceutically effective amount of a composition that includes cells, wherein the cells have been stimulated or genetically modified to overexpress a TSG-6 family member polypeptide. The cells can be any of the foregoing cell types for delivery of a stanniocalcin family member polypeptide.

The present invention also includes methods of treating a subject with retinal degeneration comprising administering to a subject with retinal degeneration a pharmaceutically effective amount of a composition comprising mesenchymal stem cells, wherein the injection is intravitreal or subretinal. In particular embodiments, the retinal degeneration is retinitis pigmentosa or age-related macular degeneration. In some embodiments, the stem cells have been genetically modified to overexpress a stanniocalcin family member polypeptide as set forth herein. In a particular embodiment, the stanniocalcin family member polypeptide is an STC-1 polypeptide. Overexpression of the stanniocalcin family member polypeptide is overexpression compared to the expression of the same stanniocalcin family member polypeptide by mesenchymal stem cells that have not been genetically modified.

Also included as part of the invention are kits that include (a) a pharmaceutically effective amount a stanniocalcin family member polypeptide or a TSG-6 family member polypeptide in one or more sealed vials. The stanniocalcin family member polypeptide and TSG-6 polypeptide may include any of the sequences previously set forth. The polypeptide may have between 95% and 99% sequence identity to any of the foregoing sequences. In a particular aspect, the kit includes a pharmaceutically effective amount of a STC-1 polypeptide that has at least 95% sequence identity to SEQ ID NO:1. In further aspects, the kit includes a syringe. For example, the syringe may be a tuberculin syringe. The kit may include a 25-gauge needle or a 30-gauge needle. The kit may optionally include instructions for use of the polypeptide either written on a paper or in a computer-readable format. The kit may optionally further include a 1 cc syringe or a 2 cc syringe. In a particular aspects, the stanniocalcin family member polypeptide comprises SEQ ID NO:1. In a particular aspect, the polypeptide is in a lyophilized form, and the kit further includes instructions for reconstituting the lyophilized polypeptide into a carrier for administration to a subject. For example, the carrier may be sterile water, normal saline, or phosphate buffered saline. The carrier may be comprised in one or more separate vials. In some aspects, the kit includes a polypeptide as set forth herein comprised in an ophthalmic drug delivery device, including a biodegradable drug-eluting device.

Other embodiments of the present invention concern methods of treating an eye disease comprising administering to a subject a pharmaceutically effective amount of a polynucleotide expressing a STC-1, STC-2, or TSG-6 polypeptide. The STC-1, STC-2, or TSG-6 polypeptide may be selected from any of the aforementioned polypeptide sequences. In some aspects, the polynucleotide is comprised in an expression cassette wherein the polynucleotide is operatively coupled to a promoter that facilitates expression of the polypeptide in a target cell. In some aspects, the expression cassette is comprised in a vector, such as a cell (such as a MSC), viral vector, a liposome, or a nanoparticle.

Fusion proteins and polynucleotides encoding them (RNA, and DNA, such as DNA polynucleotides in expression vectors) are also contemplated as part of the invention. A fusion protein is a single polypeptide sequence created through the joining of two or more genes which originally coded for separate polypeptides, with functional properties derived from the original polypeptides. The fusion proteins include a first domain that includes a stanniocalcin family member polypeptide or a TSG-6 family member polypeptide and a second domain comprising a second therapeutic polypeptide or a carrier polypeptide to facilitate transfer of the fusion protein into a cell. In a particular aspect, the second therapeutic polypeptide is a CD59 polypeptide or an antiangiogenic polypeptide. The sequence of human CD59 is provided in SEQ ID NO:26 and is associated with GenBank accession number CAG46523. Nonlimiting examples of angiostatic polypeptides include ranibizumab, endostatin, bevacizumab, or aflibercept. Additional non-limiting examples of agents which may be present in the fusion protein or in other covalent or non-covalently associated complexes with a stanniocalcin family member polypeptide or a TSG-6 family member polypeptide are Lucentis, Macugen, Pegaptanib, Ranibizumab, Eylea, Verteporfin, Visudyne, an angiostatic cortisene formulation, such as anecortave acetate suspension (RETAANE). Nonlimiting examples of carrier polypeptides include poly-Arg, a Tat-derived amino acid sequence and *Drosophila* Antennapedia homeodomains. Numerous examples of carrier polypeptides are set for in U.S. Pat. No. 7,939,493, which is herein specifically incorporated by reference in its entirety. In this patent they are designated as "carrier peptides." A "peptide" for purposes of the present patent application is an example of a "polypeptide" and the terms are used interchangeably herein. Other embodiments include a polynucleotide encoding a fusion protein of the present invention.

Ophthalmic drug delivery devices for intravitreal or subconjunctival delivery of the stanniocalcin family member polypeptide, a TSG-6 polypeptide, a fusion protein, or a stimulated or genetically modified cell as set forth herein are also contemplated as part of the present invention. The ophthalmic drug delivery device may comprise an effective amount of any of the foregoing polypeptides, fusion proteins, and cells set forth herein. In some embodiments, the polypeptide has between 95% and 99% sequence identity to any of the foregoing sequences. The polypeptide may be enclosed in a reservoir or in contact with a surface of the drug delivery device. In some aspects, the drug delivery device is a scleral-fixated nonbiodegradable implant. In other embodiments, the drug delivery device is a biodegradable implant designed to be free-floating in the vitreous cavity. In some embodiments, the drug delivery device further comprises cells that express the STC-1 polypeptide in the reservoir or in contact with a surface of the drug delivery device. In particular aspects, the ophthalmic drug delivery device is OZURDEX™, VITRASERT™, I-VATION™, RETISERT™, or ILUVIEN™. Other non-limiting examples of drug delivery devices include Ocusert®, collagen shields, or a delivery device comprising polyacrylic acid, polyvinyl alcohol, silicone elastomer, hydroxy propyl cellulose, ethyl cellulose, cellulose acetate phthalate and polymethacrylic acid, or hyaluronic acid.

Also included are pharmaceutical compositions for ophthalmic delivery comprising a therapeutically effective amount of at least one therapeutic polypeptide selected from any of Tables 1, 2, or 3, or a polypeptide that has at least 95% sequence identity to a protein set forth in any of Tables 1, 2, or 3 or a polypeptide that has between 95% and 99% sequence identity to any of the polypeptides set forth in Tables 1, 2, or 3. The pharmaceutical composition may optionally comprise one or more additional therapeutic agents suitable for ophthalmic delivery. Non-limiting examples of additional therapeutic agents include antibiotics, anti-inflammatory agents, anti-proliferative agents, anti-neovascular agents (such as agents which antagonize the function of neovascular growth factors (i.e., vascular endothelial growth factor (VEGF), endothelial cell surface receptors, and/or extracellular matrix (ECM) proteins, which are important mediators of neovascularization), antiviral agents (i.e., idoxuridine, vidarabine, trifluorothymidine), beta-andrenergic blockers (timolol maleate, levobunolol), corticosteroids, retinoic acid formulations, vitamins, topical anesthetics (i.e., proparacaine hydrochloride, tetracaine hydrochloride), and the like. Other examples include bevacizumab (Avastin), pegaptanib (Macugen), Lucentis (ranibizumab), verteporfin (Visudyne), and CD59.

Additional non-limiting, particular examples of therapeutic agents that can be included in the pharmaceutical compositions of the invention include Avastin (bevacizumab), Lucentis (ranibizumab), cyclosporine, erythromycin, tobramycin, gentamcyin, fluoroquinolones, medroxyprogesterone acetate, hypromellose, carboxymethylcellulose sodium, and olopatadine. The compositions may be comprised in a vial, such as in a kit. The therapeutic agent may be fused or linked to the therapeutic polypeptides described herein.

BRIEF DESCRIPTION OF THE FIGURES

The patent or application file contains at least one drawing executed in color. Copies of this patent or patent application publication with color drawing(s) will be provided by the Office upon request and payment of the necessary fee.

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown.

FIG. 1, comprising FIGS. 1A through 1C, is a series of images depicting induction of corneal inflammation and neovascularization, one week post-injury. FIG. 1A is an image demonstrating that on slit lamp examination, corneal inflammation with active new vessels was observed. FIG. 1B is an image of immunofluorescent staining for VEGF showing the marked increase in VEGF expression in cornea. VEGF as green and the nuclei counterstained as blue. FIG. 1C is an image depicting Hematoxylin-eosin staining revealing that the cornea was densely infiltrated with inflammatory cells.

FIG. 2, comprising FIGS. 2A and 2B, is a series of images depicting application of cells to cornea. FIG. 2A is an image of a 6-mm-diameter hollow plastic tube placed to keep the eye open and the cells or media applied to the cornea into a customized applicator. FIG. 2B is an image depicting engraftment of MSCs in the cornea confirming by identification of PKH26-labeled cells in corneas by fluorescein microscopy.

FIG. 3, comprising FIGS. 3A through 3L, is a series of images depicting photography of cornea one (FIGS. 3A-3D), two (FIGS. 3E-3H), and three weeks (FIGS. 3I-3L) post-injury. With time, neovascularization and opacity markedly decreased in the corneas with MSCs (FIGS. 3D, 3H, 3L) or MSC-CM media three times (FIGS. 3C, 3G, 3K), while increased in the control (FIGS. 3A, 3E, 3I). Corneas treated with MSC-CM once (FIGS. 3B, 3F, 3J) showed the intermediate outcome.

FIG. 4, comprising

FIG. 5, comprising

FIG. 6, comprising

FIG. 9, comprising FIG. 9A is an image depicting clearance of human Alu sequences from blood after IV infusion of about $2\times10^6$ hMSCs into mice. Values are mean+/−SD; n–6. FIG. 9B is an image depicting standard curves for real time PCR assays of human Alu sequences in 7 organs. Values indicate ΔΔCt for primers for mouse/human GAPDH genes and Alu sequences on same samples. FIG. 9C is an image depicting tissue distribution of human Alu sequences 15 mm after IV infusion of about $2\times10^6$ hMSCs into mice. Values are mean+/−SD; n–6. FIG. 9D is an image depicting standard curves for real time RT-PCR assays of human mRNA for GAPDH. Values indicate AACt for primers for mouse/human GAPDH genes and cDNA for human-specific GAPDH on same samples. FIG. 9E is an image depicting kinetics of hMSCs in lung and 6 other tissues after IV infusion of about $2\times10^6$ hMSCs, Values are mean+/−SD; n–6. FIG. 9F is an image depicting appearance of hMSCs in heart after IV infusion of about $1\times10^6$ hMSCs one day after permanent ligation of the left anterior descending coronary artery.

FIG. 10, comprising FIG. 10A is an image depicting realtime RT-PCR for human-specific mRNA in lung 10 hr after IV infusion of $2\times10^6$ hMSCs. Values are fold increase over values for cultured hMSCs, normalized by ΔΔCt for hGAPDH. Symbols: hMSCs con, sample of hMSCs added to lung from control mouse before extraction of RNA; hMSCs IV 1 and 2, samples from lungs of 2 mice 10 hr after IV infusion of hMSCs. FIG. 10B is an image depicting real-time RT-PCR for human TSG-6 in mouse lung. About $2\times10^6$ hMSCs were infused IV into naïve mice (IV-nor) or mice at 1 hr after MI (IV-MI) and lungs were recovered 0.25 hr to 24 hr later. Values are +/−SD; n–2 or 3 for normal mice; n=6 for MI mice. FIG. 10C is an image depicting real-time RT-PCR for TSG-6 in hMSCs and human fibroblasts from the same donor incubated in serum-free medium with 10 ng/ml TNF-α for 24 or 48 hr. Results with two passages of the same cells are shown. Values are +/−SD; n–3. FIG. 10D is an image depicting ELISAs for TSG-6 in medium from hMSCs and human fibroblasts incubated in serum-free medium with 10 ng/ml TNF-α for 48 hr. Values are ±/−SD; n=3. FIG. 10E is an image depicting real-time RT-PCR assays for TSG-6 of control hMSCs (Con), hMSCs treated with transfection reagents only (no siRNA), hMSCs transfected with a scrambled siRNA (scr siRNA) or hMSCs transduced with TSG-6 siRNA (TSG-6 siRNA). Cells were incubated with or without 10 ng/ml TNF-α for 6 hr. Values are +/−SD; n=3. FIG. 10F is an image depicting ELISAs for TSG-6 in medium after incubation of cells with or without TNF-α for 48 hr. Symbols: as in FIG. 10E. Values are +/−SD; n=3.

FIG. 11, comprising FIGS. 11A through 11E, is a series of images depicting assays of serum and heart. FIG. 11A is an image depicting an assay for cardiac troponin I in serum 48 hr after MI. Values are +/−SD; p<0.01 with n=3 (Normal) or 6 mice (MI) per group. FIG. 11B, is an image depicting plasmin activity in serum 48 hr after MI. Symbols: Normal, naïve mice; −, MI only; hMSCs, 2×10$^6$ hMSCs infused IV 1 hr after MI; scr siRNA, 2×10$^6$ hMSCs transduced with scrambled siRNA infused IV 1 hr after MI; TSG-6 siRNA, 2×10$^6$ hMSCs transduced with TSG-6 siRNA infused IV 1 hr after MI; rhTSG-6, 30 μg rhTSG-6 protein infused IV 1 hr and again 24 hr after MI. Values are +/−SD; p<0.01 with n=3 mice per group. N.S.=not significant. FIG. 11C, is an image depicting hearts assayed for pro- and active-matrix MMP9 on a gelatin zymogen gel 48 hr after MI. Image is reversed. Symbols: as in FIG. 11B. FIGS. 11D and 11E are images depicting granulocyte and monocyte infiltration in the heart 48 hr after MI. Sections stained with anti-Ly-6G and Ly-6C. Symbols: as in FIG. 11B except 100 μg rhTSG-6 protein was infused IV 1 hr and again 24 hr after MI. Magnification×4. Scale bars, 250 μm. Values are +/−SD; n=3 or 4 for each group. p<0.001; N.S.=not significant.

FIG. 12, comprising FIG. 12A is an image depicting MI. Heart with no treatment. FIG. 12B is an image depicting MI+hMSCs. 2×10$^6$ hMSCs infused IV 1 hr after MI. FIG. 12C is an image depicting MI+scr siRNA, 2×10$^6$ hMSCs transduced with scrambled siRNA infused IV 1 hr after MI. FIG. 12D is an image depicting MI+TSG-6 siRNA. 2×10$^6$ hMSCs transduced with TSG-6 siRNA infused IV 1 hr after MI. FIG. 12E is an image depicting MI+hTSG-6 100 μg rhTSG-6 protein infused IV 1 hr and again 24 hr after MI. FIG. 12F is an image depicting Infarct size measurements (%) obtained by midline length measurement from every 10$^{th}$ section of the infarct area for a total of 20 sections per heart (Takagawa et al., 2007). Values are +/−SD; n=3 or 4 mice per group; ***p<0.0001 compared to MI controls; N.S. not significant compared to MI controls; *p<0.05 for MI+MSCs versus MI+rhTSG-6.

FIG. 16, panel A-panel F are photographic images of the cornea. FIGS. 16A-16C are images depicting PBS-treated control. FIG. 16 panel D-16 panel F are images depicting TSG-6-treated cornea. FIG. 16 panel A, 16 panel D depict postoperative day 3. FIG. 16 panel B, 16 panel E depict postoperative day 7. FIG. 16 panel C, 16 panel F depict postoperative day 21. Bottom frames: Clinical evaluations of opacity (left frame) and neovascularization (right frame) of the cornea.

(FIG. 17 panel A-17 panel D) Hematoxylin-eosin staining of cornea. (FIG. 17 panel A, 17 panel B) PBS-treated cornea. (FIG. 17 panel C, 17 panel D) TSG-6-treated cornea. (FIG. 17 panel A, 17 panel C) Postoperative day 3. (FIG. 17 panel B, 17 panel D) Postoperative day 21. (FIG. 17 upper graph) Myeloperoxidase assay. (FIG. 17 lower right graph) Gel zymography for MMP-9. (FIG. 17, lowe left graph) ELISA for total and active MMP-9.

FIG. 19, comprising FIGS. 19A through 19D, is a series of images demonstrating that TSG-6 up to the concentration of 2 ug is effective in reducing corneal opacity, inflammation, and MMP-9 production. (FIGS. 19A-19D) Photography of cornea. (FIG. 19A) PBS-treated cornea. (FIG. 19B) TSG-6 0.02 ug-treated cornea. (FIG. 19C) TSG-6 0.2 ug-treated cornea. (FIG. 19D) TSG-6 2 ug-treated cornea. (FIG. 19E) Myeloperoxidase assay and clinical grading of opacity. (FIG. 19F) Gel zymography and ELISA for MMP-9.

FIG. 23. Two injections of STC-1 rescued retinal degeneration in the rhodopsin mutant transgenic rat. Upper frame: representative posterior segment histology showed thickened ONL in STC-1 treated eyes compared to UI controls. The ONL is the outer nuclear layer of the retina that contains the nuclei of the rods and cones. Lower frame: representative plot of ONL layer thickness taken from a total of 54 measurements (27 superior retina and 27 inferior retina) demonstrated STC-1 significantly improved ONL thickness compared to UI controls.

DETAILED DESCRIPTION

Figures 4A, 4B:
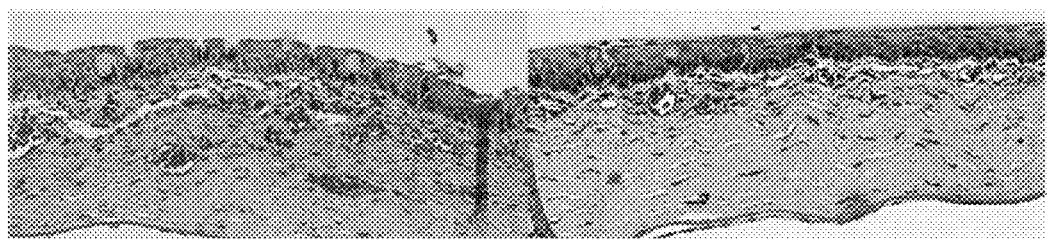
FIGS. 4A through 4D, is a series of images depicting hematoxylin-eosin staining of cornea three weeks post-injury. Control (FIG. 4A) and corneas treated with MSC-conditioned media once (FIG. 4B) were densely infiltrated with inflammatory cells in the stroma and goblet cells in the epithelium. The infiltration was markedly reduced in the corneas with MSC-conditioned media three times (FIG. 4C) or MSCs (FIG. 4D).

The present invention in part relates to the finding that certain anti-apoptotic or anti-inflammatory polypeptides have application as therapies in the treatment of eye disease. For example, the inventors have found that STC-1 is useful in the treatment of eye disease. Accordingly, these polypeptides and analogues thereof are useful as therapeutic agents in ocular diseases, including but not limited to diseases of the cornea and retina.

A. Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used.

As used herein, the term "autologous" is meant to refer to any material derived from the same individual to which it is later to be re-introduced into the individual.

As used herein, the term "biocompatible lattice," is meant to refer to a substrate that can facilitate formation into three-dimensional structures conducive for tissue development. Thus, for example, cells can be cultured or seeded onto such a biocompatible lattice, such as one that includes extracellular matrix material, synthetic polymers, cytokines, growth factors, etc. The lattice can be molded into desired shapes for facilitating the development of tissue types. Also, at least at an early stage during culturing of the cells, the medium and/or substrate is supplemented with factors (e.g., growth factors, cytokines. extracellular matrix material, etc.) that facilitate the development of appropriate tissue types and structures.

As used herein, the term "bone marrow stromal cells," "stromal cells," "mesenchymal stem cells," "mesenchymal stromal cells" or "MSCs" are used interchangeably and refer to a cell derived from bone marrow (reviewed in Prockop, 1997), peripheral blood (Kuznetsov et al., 2001), adipose tissue (Guilak et al., 2004), umbilical cord blood (Rosada et al., 2003), synovial membranes (De Bari et al., 2001), and periodontal ligament (Seo et al., 2005), embryonic yolk sac, placenta, umbilical cord, skin, and blood (U.S. Pat. Nos. 5,486,359 and 7,153,500), fat, and synovial fluid. MSCs are characterized by their ability to adhere to plastic tissue culture surfaces (Friedenstein et al.; reviewed in Owen & Friedenstein, 1988), and by being effective feeder layers for hematopoietic stem cells (Eaves et al., 2001). In addition, MSCs can be differentiated both in culture and in vivo into osteoblasts and chondrocytes, into adipocytes, muscle cells (Wakitani et al., 1995) and cardiomyocytes (Fukuda and Yuasa, 2006), into neural precursors (Woodbury et al, 2000; Deng et al., 2001, Kim et al., 2006; Marcsehi et al., 2006; Krampera et al, 2007). Mesenchymal stem cells (MSCs) may be purified using methods known in the art (Wakitani et al., 1995; Fukuda and Yuasa, 2006; Woodbury et al., 2000; Deng et al., 2001; Kim et al., 2006; Mareschi et al., 2006; Krampera et al., 2007), and serve as progenitors for mesenchymal cell lineages, including bone, cartilage, ligament, tendon, adipose, muscle, cardiac tissue, stroma, dermis, and other connective tissues. (See U.S. Pat. Nos. 6,387,369 and 7,101,704).

As used herein, the term "modulate" is meant to refer to any change in biological state, including increasing, decreasing, and the like.

The terms "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. Unlike pluripotent stem cells, lineage-committed progenitor cells are generally considered to be incapable of giving rise to numerous cell types that phenotypically differ from each other. Instead, progenitor cells give rise to one or possibly two lineage-committed cell types.

"Ocular region" or "ocular site" means any area of the ocular globe (eyeball), including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of areas of the eyeball in an ocular region include, but are not limited to, the anterior chamber, the posterior chamber, the vitreous cavity, the choroid, the suprachoroidal space, the conjunctiva, the subconjunctival space, the episcieral space, the intracorneal space, the subretinal space, sub-Tenon's space, the epicorneal space, the sclera, the pars plana, surgically-induced avascular regions, the macula, and the retina.

"Ocular condition" means a disease, ailment or condition which affects or involves the eye or one of the parts or regions of the eye. Broadly speaking, the eye includes the eyeball, including the cornea, and other tissues and fluids which constitute the eyeball, the periocular muscles (such as the oblique and rectus muscles) and the portion of the optic nerve which is within or adjacent to the eyeball.

"Graft" refers to a cell, tissue, organ, or otherwise any biological compatible lattice for transplantation.

"Glaucoma" means primary, secondary and/or congenital glaucoma. Primary glaucoma can include open angle and closed angle glaucoma. Secondary glaucoma can occur as a complication of a variety of other conditions, such as injury, inflammation, pigment dispersion, vascular disease and diabetes. The increased pressure of glaucoma causes blindness because it damages the optic nerve where it enters the eye. Thus, in one non-limiting embodiment, by lowering reactive oxygen species, STC-1, or MSCs which express increased amounts of STC-1, may be employed in the treatment of glaucoma and prevent or delay the onset of blindness.

"Inflammation-mediated" in relation to an ocular condition means any condition of the eye which can benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic retinopathy, uveitis, proliferative vitreoretinopathy (PVR), sympathetic ophthalmia, Vogt-Koyanagi-Harada (VKH) syndrome, histoplasmosis, and uveal diffusion.

"Injury" or "damage" are interchangeable and refer to the cellular and morphological manifestations and symptoms resulting from an inflammatory-mediated condition, such as, for example, inflammation, as well as tissue injuries caused by means other than inflammation, such as chemical injury, including chemical burns, as well as injuries caused by infections, including but not limited to, bacterial, viral, or fungal infections.

"Intraocular" means within or under an ocular tissue. An intraocular administration of a drug delivery system includes administration of the drug delivery system to a sub-tenon, subconjunctival, suprachoroidal, subretinal, intravitreal, anterior chamber, and the like location. An intraocular administration of a drug delivery system excludes administration of the drug delivery system to a topical, systemic, intramuscular, subcutaneous, intraperitoneal, and the like location.

"Macular degeneration" refers to any of a number of disorders and conditions in which the macula degenerates or loses functional activity. The degeneration or loss of functional activity can arise as a result of, for example, cell death, decreased cell proliferation, loss of normal biological function, or a combination of the foregoing. Macular degeneration can lead to and/or manifest as alterations in the structural integrity of the cells and/or extracellular matrix of the macula, alteration in normal cellular and/or extracellular matrix architecture, and/or the loss of function of macular cells. The cells can be any cell type normally present in or near the macula including RPE cells, photoreceptors, and capillary endothelial cells. Age-related macular degeneration, or ARMD, is the major macular degeneration related condition, but a number of others are known including, but not limited to, Best macular dystrophy, Stargardt macular dystrophy, Sorsby fundus dystrophy, Mallatia Leventinese, Doyne honeycomb retinal dystrophy, and RPE pattern dystrophies. Age-related macular degeneration (AMD) is described as either "dry" or "wet." The wet, exudative, neovascular form of AMD affects about 10-20% of those with AMD and is characterized by abnormal blood vessels growing under or through the retinal pigment epithelium (RPE), resulting in hemorrhage, exudation, scarring, or serous retinal detachment. Eighty to ninety percent of AMD patients have the dry form characterized by atrophy of the retinal pigment epithelium and loss of macular photoreceptors. Drusen may or may not be present in the macula. There may also be geographic atrophy of retinal pigment epithelium in the macula accounting for vision loss. At present there is no cure for any form of AMD, although some success in attenuation of wet AMD has been obtained with photodynamic and especially anti-VEGF therapy.

"Drusen" is debris-like material that accumulates with age below the RPE. Drusen is observed using a funduscopic eye examination. Normal eyes may have maculas free of drusen, yet drusen may be abundant in the retinal periphery. The presence of soft drusen in the macula, in the absence of any loss of macular vision, is considered an early stage of AMD. Drusen contains a variety of lipids, polysaccharides, and glycosaminoglycans along with several proteins, modified proteins or protein adducts. There is no generally accepted therapeutic method that addresses drusen formation and thereby manages the progressive nature of AMD.

"Ocular neovascularization" (ONV) is used herein to refer to choroidal neovascularization or retinal neovascularization, or both.

"Retinal neovascularization" (RNV) refers to the abnormal development, proliferation, and/or growth of retinal blood vessels, e.g., on the retinal surface.

"Subretinal neovascularization" (SRNVM) refers to the abnormal development, proliferation, and/or growth of blood vessels beneath the surface of the retina.

"Cornea" refers to the transparent structure forming the anterior part of the fibrous tunic of the eye. It consists of five layers, specifically: 1) anterior corneal epithelium, continuous with the conjunctiva; 2) anterior limiting layer (Bowman's layer); 3) substantia propria, or stromal layer; 4) posterior limiting layer (Descemet's membrane); and 5) endothelium of the anterior chamber or keratoderma.

"Retina" refers to the innermost layer of the ocular globe surrounding the vitreous body and continuous posteriorly with the optic nerve. The retina is composed of layers including the: 1) internal limiting membrane; 2) nerve fiber layer; 3) layer of ganglion cells; 4) inner plexiform layer; 5) inner nuclear layer; 6) outer plexiform layer; 7) outer nuclear layer; 8) external limiting membrane; and 9) a layer of rods and cones.

"Retinal degeneration" refers to any hereditary or acquired degeneration of the retina and/or retinal pigment epithelium. Non-limiting examples include retinitis pigmentosa, Best's Disease, RPE pattern dystrophies, and age-related macular degeneration.

"Allogeneic" refers to a graft derived from a different animal of the same species. As defined herein, an "allogeneic bone marrow stromal cell (BMSC)" is obtained from a different individual of the same species as the recipient.

"Xenogeneic" refers to a graft derived from an animal of a different species.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. Preferably, the transplant is a human neural stem cell.

"Donor antigen" refers to an antigen expressed by the donor tissue to be transplanted into the recipient.

"Alloantigen" is an antigen that differs from an antigen expressed by the recipient.

As used herein, a "therapeutically effective amount" is the amount of an agent which is sufficient to provide a beneficial effect to the subject to which the agent is administered.

As used herein "endogenous" refers to any material from or produced inside an organism, cell or system.

"Exogenous" refers to any material introduced from or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

An "isolated polypeptide" refers to a polypeptide that has been substantially purified or separated from other components which naturally accompany it.

A "polypeptide" as used herein refers to a consecutive series of 5 or more amino acid residues. As used herein, a "peptide," and a "protein" are examples of polypeptides so long as they include a consecutive series of 5 or more amino acid residues.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and nonviral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

B. Therapeutic Polypeptides

The present invention pertains to use of therapeutic polypeptides in various contexts. For example, some aspects of the present invention pertain to methods for treating an eye disease comprising contacting the eye of a subject with a STC-1 polypeptide, a STC-2 polypeptide, or a TSG-6 polypeptide. In some aspects, the subject is administered a composition comprising cells that overexpress a STC-1 polypeptide, a STC-2 polypeptide, or a TSG-6 polypeptide.

1. Stanniocalcin 1

The stanniocalcin (STC) family of proteins includes stanniocalcin 1 (STC-1), stanniocalcin 2 (STC-2), and is defined herein to further refer to molecules that have at least 30% sequence identity to a naturally occurring STC-1 or STC-2 protein and have at least one common biological function of a naturally occurring STC-1 or STC-2 protein. STC-1 is a mammalian protein that has been implicated to play an autocrine and paracrine role in mammals, leading to various effects. It is expressed in many tissues, but is not normally detected in the circulation. In mice, it has been shown to affect calcium homeostasis, bone and muscle structure, and angiogenesis through effects of a variety of cells including osteoblasts, osteoclasts, myocytes, and endothelial cells. STC-1 has also been implicated to be involved in calcium homeostasis in the heart. STC-1 has also been shown to be secreted by mesenchymal stem cells (MSCs) that have been exposed to injured fibroblasts (Block et al., 2009). Some examples of STC-1 polypeptides are set forth in Table 1 below. In each case where an amino acid or polynucleotide sequence referenced herein is attributed to a database accession number, the amino acid and/or polynucleotide sequence archived in the database for the accession number is incorporated herein by reference as that sequence is presented in the database on the filing date of this specification. Each sequence attributed to an accession number recited herein can be readily accessed via, for example, the National Center for Biotechnology (NCBI) database, which is available online to the public.

TABLE 1

STC-1 Proteins and Precursors

| SEQ ID NO: | Description | Species | Additional Information |
|---|---|---|---|
| 1 | 240 AA, STC-1, | Human, source HEK293 | |
| 2 | 240 AA, STC-1 with C-terminal Flag tag (10 AA) | Human; source— HEK293 | |
| 3 | 247 AA | Human | Accession: AAL79522.1 |
| 4 | 247 AA | Human | Accession: EAW63610.1 |
| 5 | 247 aa, STC-1 precursor | Human | Accession: NP_003146.1 |
| 6 | 247 aa, STC-1 | Synthetic construct | Accession: ABM84894.1 |
| 7 | 247 aa, STC-1 | Synthetic construct | Accession: ABM81739.1 |
| 8 | 247 aa, STC-1 precursor | Mus musculus | Accession: NP_033311.3 |
| 9 | 247 AA, STC-1 precursor | Rattus norvegicus | Accession: NP_112385.1 |
| 10 | 247 AA, STC-1 | Rattus norvegicus | Accession: EDM02180.1 |
| 11 | 246 AA, STC-1 | Mus musculus | Accession: AAP47156.1 |

2. Stanniocalcin 2

Stanniocalcin 2 (STC-2) is related to STC-1. It is expressed in a wide variety of tissues. In the ovary of certain mammals, it has been shown to be a paracrine hormone that regulates granulosa cell formation. STC-2 has also been shown to be upregulated in neuronal cells by oxidative stress and hypoxia. Induced STC-2 expression has been shown to be an essential feature of the survival component of the unfolded protein response (UPR) (Ito et al., Mol. Cell Biol. 24 (21):9456-9469). Some examples of STC-2 polypeptides are set forth in Table 2 below.

TABLE 2

STC-2 Proteins and Precursors

| SEQ ID NO: | Description | Species | Additional Information |
|---|---|---|---|
| 12 | STC-2, 302 aa | Human | Accession: AAV38398.1 |
| 13 | STC-2, 302 aa | Human | Accession: AAH13958.1 |
| 14 | STC-2, 302 aa | Human | Accession: AAH06352.1 |
| 15 | STC-2, 302 aa | Human | Accession: AAH00658.1 |
| 16 | STC-2 precursor, 302 aa | Human | Accession: NP_003705.1 |
| 17 | STC-2, 296 aa | Mus musculus | Accession: EDL23779.1 |
| 18 | STC-2, 296 aa | Mus musculus | Accession: AAH12206.1 |
| 19 | STC-2, 296 aa | Rattus norvegicus | Accession: EDM04038.1 |
| 20 | STC-2 precursor, 296 aa | Rattus norvegicus | Accession: NP_071566.1 |

3. Tumor Necrosis Factor-Inducible Gene 6 Protein

Tumor Necrosis Factor-Inducible Gene 6 Protein, also known as TNF-stimulated gene 6 protein or TSG-6, is a 30 kDa secreted protein that is a member of the hyaluronan-binding protein family. It contains a hyaluronan-binding LINK domain. TSG-6 is involved in extracellular matrix stability and cell migration. Expression of TSG-6 is induced by signaling molecules such as tumor necrosis factor α (TGF-α) and interleukin 2 (IL-2). Expression of TSG-6 is also correlated with proteoglycan synthesis in vascular smooth muscle cells. Some examples of TSG-6 polypeptides are set forth in Table 3 below.

TABLE 3

TSG-6 Proteins and Precursors

| SEQ ID NO: | Description | Species | Additional Information |
|---|---|---|---|
| 21 | TSG-6, 277 aa | Human | Accession: P98066 |
| 22 | TSG-6, 277 aa | Human | Accession CAD13434.1 |
| 23 | TSG-6, 277 aa | Human | Accession: CAD12353.1 |
| 24 | TSG-6 precursor, 277 aa | Human | Accession: NP_009046.2 |
| 25 | TSG-6 precursor, 275 aa | Mus musculus | Accession: NP_033424.1 |

Throughout this application, the term "therapeutic polypeptide" is intended to refer to a polypeptide that has a therapeutic effect on an eye disease in a mammalian subject.

It is well understood by the skilled artisan that, inherent in the definition of a "therapeutic polypeptide" (including therapeutic STC-1 polypeptide, STC-2 polypeptide, and TSG-6 polypeptide) is the concept that there is a limit to the number of changes that may be made within a defined portion of the molecule and still result in a molecule with an acceptable level of equivalent biological activity, e.g., ability of the polypeptide to retain at least 95% of the biological activity of the naturally occurring protein sequence (including any of the full-length protein sequences set forth in Tables 1, 2, or 3). "Therapeutic polypeptide" is thus defined herein as any therapeutic polypeptide in which some, or most, of the amino acids may be substituted so long as the polypeptide retains substantially similar activity in the context of the uses set forth herein.

An amino acid sequence of any length is contemplated within the definition of therapeutic polypeptide so long as the polypeptide retains an acceptable level of equivalent biological activity of the native sequence. For example, a STC-1 polypeptide, a STC-2 polypeptide, or a TSG-6 polypeptide includes homologs, variants, and fragments of the native sequences of STC-1, STC-2, and TSG-6 so long as the polypeptide retains an acceptable level of equivalent biological activity as the native sequence of STC-1, STC-2, or TSG-6, respectively. Biological activities of STC-1, STC-2, and TSG-6 are set forth in this section. Variants of therapeutic polypeptides will preferably have at least 80%, 82%, 84%, 86%, 88%, 90%, 92%, 94%, 96%, 98%, 99% or greater sequence identity to the native sequence of the therapeutic polypeptide. Examples of a native sequence of STC-1 include SEQ ID NOs: 1, 3, or 4. Examples of a native sequence of STC-2 include SEQ ID NOs: 12, 13, 14, and 15. Examples of a native sequence of TSG-6 include SEQ ID NOs: 21, 22, and 23. A "native sequence" polypeptide comprises a polypeptide having the same amino acid sequence as the corresponding polypeptide derived from nature.

"Percent (%) amino acid sequence identity" or "homology" with respect to a polypeptide sequence identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

The present invention may utilize therapeutic polypeptides purified from a natural source or from recombinantly-produced material. Those of ordinary skill in the art would know how to produce these polypeptides from recombinantly-produced material. This material may use the 20 common amino acids in naturally synthesized proteins, or one or more modified or unusual amino acids. Generally, "purified" will refer to a therapeutic polypeptide composition that has been subjected to fractionation to remove various other proteins, polypeptides, or peptides, and which composition substantially retains its activity. "Purified" and "isolated" are used interchangeably herein. Purification may be substantial, in which the therapeutic polypeptide is the predominant species, or to homogeneity, which purification level would permit accurate degradative sequencing. An "isolated polypeptide" includes a polypeptide that has been separated from a cell that produced the polypeptide where the polypeptide is purified from a natural source.

Therapeutic polypeptides may be amino acid sequence mutants of the naturally occurring polypeptide sequence. Amino acid sequence mutants of the polypeptide can be substitutional mutants or insertional mutants. Insertional mutants typically involve the addition of material at a non-terminal point in the peptide. This may include the insertion of a few residues, an immunoreactive epitope, or simply a single residue. The added material may be modified, such as by methylation, acetylation, and the like. Alternatively, additional residues may be added to the N-terminal or C-terminal ends of the peptide. Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

C. Therapeutic Nucleic Acids

Various aspects of the present invention require polynucleotides encoding any of the foregoing therapeutic polypeptides. For example, various embodiments include methods for treating an eye disease that involve contacting the eye with an expression cassette that includes a promoter that is active in a cell of the mammalian eye, operably linked to a polynucleotide encoding either a therapeutic polypeptide as set forth herein.

1. Polynucleotides Generally

In some embodiments, the polynucleotides may be derived from genomic DNA or may be complementary DNA (cDNA). cDNA is DNA prepared using messenger RNA (mRNA) as a template. Thus, a cDNA does not contain any interrupted coding sequences and usually contains almost exclusively the coding region(s) for the corresponding protein. In other embodiments, the polynucleotide may be produced synthetically.

It may be advantageous to combine portions of the genomic DNA with cDNA or synthetic sequences to generate specific constructs. For example, where an intron is desired in the ultimate construct, a genomic clone will need to be used. Introns may be derived from other genes in addition to the gene encoding the therapeutic polypeptide. The cDNA or a synthesized polynucleotide may provide more convenient restriction sites for the remaining portion of the construct and, therefore, would be used for the rest of the sequence.

In certain embodiments, one may wish to employ constructs which include other elements, for example, those which include C-5 propyne pyrimidines. Oligonucleotides which contain C-5 propyne analogues of uridine and cytidine have been shown to bind RNA with high affinity (Wagner et al., 1993).

2. Expression Cassettes

Certain embodiments of the invention pertain to methods utilizing compositions that include an expression cassette. In particular, the methods for treating eye disease may involve administering a therapeutic polynucleotide that is comprised in an expression cassette.

Throughout this application, the term "expression cassette" is meant to include any type of genetic construct containing a nucleic acid coding for a gene product in which part or all of the nucleic acid encoding sequence is capable of being transcribed. The transcript may be translated into a protein or polypeptide, but it need not be. Thus, in certain embodiments, expression includes both transcription of a gene and translation of a mRNA into a polypeptide.

In order for the expression cassette to effect expression of a therapeutic polypeptide, the polynucleotide encoding the polynucleotide will be under the transcriptional control of a promoter. A "promoter" is a control sequence that is a region of a nucleic acid sequence at which initiation and rate of transcription are controlled. It may contain genetic elements at which regulatory proteins and molecules may bind such as RNA polymerase and other transcription factors. The phrase "operatively linked" means that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence. One of skill in the art would understand how to use a promoter or enhancer to promote expression of therapeutic polynucleotide.

In certain embodiments of the invention, the delivery of an expression cassette in a cell may be identified in vitro or in vivo by including a marker in the expression vector. The marker would result in an identifiable change to the transfected cell permitting easy identification of expression. The selectable marker employed is not believed to be important, so long as it is capable of being expressed along with the polynucleotide of the expression cassette. Examples of selectable markers are well known to one of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). One of skill in the art would be familiar with use of IRES in expression cassettes.

Expression cassettes can include a multiple cloning site (MCS), which is a nucleic acid region that contains multiple restriction enzyme sites, any of which can be used in conjunction with standard recombinant technology to digest the vector. See Carbonelli et al. (1999); Levenson et al. (1998); Cocea (1997). "Restriction enzyme digestion" refers to catalytic cleavage of a nucleic acid molecule with an enzyme that functions only at specific locations in a nucleic acid molecule. Techniques involving restriction enzymes and ligation reactions are well known to those of skill in the art of recombinant technology.

In expression, one will typically include a polyadenylation signal to effect proper polyadenylation of the transcript. The nature of the polyadenylation signal is not believed to be crucial to the successful practice of the invention, and/or any such sequence may be employed. One of skill in the art would understand how to use these signals to effect proper polyadenylation of the transcript.

In certain embodiments of the present invention, the expression cassette comprises a virus or engineered construct derived from a viral genome. The ability of certain viruses to enter cells via receptor-mediated endocytosis and, in some cases, integrate into the host cell chromosomes, have made them attractive candidates for gene transfer in to mammalian cells. However, because it has been demonstrated that direct uptake of naked DNA, as well as receptor-mediated uptake of DNA complexes, is possible, expression vectors need not be viral but, instead, may be any plasmid, cosmid or phage construct that is capable of supporting expression of encoded genes in mammalian cells, such as pUC or Bluescript™. plasmid series. One of ordinary skill in the art would be familiar with use of viruses as tools to promote expression of the polypeptide.

In certain embodiments of the invention, a treated cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

3. Viral Vectors

In certain embodiments, the methods and compositions of the invention utilize expression cassettes which includes the therapeutic polypeptide in an expression cassette carried in a vector. One of ordinary skill in the art would understand use of vectors since these experimental methods are well-known in the art. In particular, techniques using "viral vectors" are well-known in the art. A viral vector is meant to include those constructs containing viral sequences sufficient to (a) support packaging of the expression cassette and (b) to ultimately express a recombinant gene construct that has been cloned therein.

One method for delivery of the recombinant DNA involves the use of an adenovirus expression vector. Although adenovirus vectors are known to have a low capacity for integration into genomic DNA, this feature is counterbalanced by the high efficiency of gene transfer afforded by these vectors. Adenoviruses are currently the most commonly used vector for gene transfer in clinical settings. Among the advantages of these viruses is that they are efficient at gene delivery to both nondividing and dividing cells and can be produced in large quantities. The vector comprises a genetically engineered form of adenovirus.

Knowledge of the genetic organization or adenovirus, a 36 kb, linear, double-stranded DNA virus, allows substitution of large pieces of adenoviral DNA with foreign sequences up to 7 kb (Grunhaus et al., 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus is particularly suitable for use as a gene transfer vector because of its mid-sized genome, ease of manipulation, high titer, wide target-cell range and high infectivity. A person of ordinary skill in the art would be familiar with experimental methods using adenoviral vectors.

Other types of viral vectors contemplated for use in the present invention include Adeno-associated virus (AAV), lentivirus, Herpes simplex virus (HSV), and Vaccinia virus.

4. Nonviral Vectors

Several non-viral methods for the transfer of expression vectors into cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and Lipofectamine-DNA complex, cell sonication (Fechheimer et al., 1987), gene bombardment using high velocity microprojectiles (Yang et al., 1990), polycations (Boussif et al., 1995) and receptor-mediated transfection (Wu and Wu, 1987; Wu and Wu, 1988). Some of these techniques may be successfully adapted for in vivo or ex vivo use. A person of ordinary skill in the art would be familiar with the techniques pertaining to use of nonviral vectors, and would understand that other types of nonviral vectors than those disclosed herein are contemplated by the present invention.

In a further embodiment of the invention, the expression cassette may be entrapped in a liposome or lipid formulation. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution.

Nanoparticles, such as chitosan nanoparticles are also contemplated as nonviral vectors for use in the context of the present invention.

D. Targeted Diseases and Conditions

The present invention contemplates methods of treating a subject with an eye disease or condition that includes administering to the subject a composition that includes a therapeutic polypeptide as set forth herein in a pharmaceutical preparation suitable for delivery to the subject. The eye disease may be any disease in which apoptosis or inflammation has been implicated to play a role in the pathophysiology. Non-limiting examples are set forth below.

1. Ocular Injuries a. Foreign Bodies

25% of all ocular injuries involve foreign bodies on the surface of the cornea. No scarring will occur if the injury affects only the corneal epithelium; but if it also affects the Bowman zone, scarring is possible. After removal of the foreign body, the eye is treated with a sulfonamide or antibiotic and, if there is ciliary congestion and photophobia, or if the removal of the foreign body were difficult, it is treated with a cycloplegic such as 5% homatropine. In some instances, the therapeutic compositions of the present invention are designed to accelerate healing of the injury caused by the foreign body and to prevent infection, and to improve the clinical outcome.

b. Chemical Burns

Chemical burns are treated by first diluting the chemical by flushing the eye with fluid, and then preventing infection through the use of topical antibiotics.

Intraocular pressure may be reduced by applying timolol, epinephrine, acetazolamide, or other similar agents. If epithelialization of the cornea is incomplete after one week, there is a danger of stromal necrosis, in addition to the risk of infection. It is therefore critical that the healing be accelerated to reduce these risks.

Severe scarring is another common result of chemical burns. The therapeutic compositions of the present invention are designed to accelerate the healing of the corneal erosion caused by the chemical burns, to prevent stromal necrosis and infection of the eye, and to reduce corneal scarring and thereby restore/preserve corneal transparency.

Unexpectedly the compositions of the present invention are able to prevent or reduce scar formation while simultaneously enhancing ocular healing, wound repair, and maintaining corneal transparency. While not wishing to be bound by any specific mechanism of action, it appears that these beneficial effects can be obtained due to the anti-inflammatory actions of the compositions. In some instances, the beneficial effects can be obtained due to the combination of anti-inflammatory and anti-apoptotic actions of the compositions of the invention.

c. Lacerations

Lacerations of the cornea are followed by prolapse of the iris, which closes the injury. As in all eye injuries, there is a risk of infection. Lacerations also may extend to the sclera, which is a much more severe injury. In such a case, surgery is required to remove prolapsed uveal tissue from the injured area, and the sclera is closed with sutures. The therapeutic compositions of the present invention are designed to accelerate the healing of the laceration and to prevent infection.

2. Optic Neuropathies

Optic neuropathies affect the optic nerve, which may affect vision adversely. Traumatic optic neuropathies may be caused when the head is struck by an object, such as a ball, or if it is pierced by an object such as a bullet. Toxic optic neuropathies are caused by chemicals toxic to the optic nerve; a common example is the ingestion of methanol. Deficiency optic neuropathies can result from vitamin deficiencies such as a B12 deficiency and may cause lesions in the optic nerve. Hereditary optic neuropathies can be caused by mutations in the nuclear or mitochondrial genomes. The therapeutic and prophylactic compounds of this invention could be used to heal the optic nerve through anti-inflammatory and anti-apoptotic mechanisms. They may also create an environment which would reduce or prevent mutations in optic cell genomes.

3. Inflammatory Conditions

Inflammation-mediated conditions of the eye which may be treated by the methods of the invention include but are not limited to uveitis, macular edema, age-related macular degeneration, retinal detachment, ocular tumors, fungal or viral infections, multifocal choroiditis, diabetic uveitis, proliferative vitreoretinopathy (PVR), sympathetic opthalmia, Vogt Koyanagi-Harada (VKH) syndrome, histoplasmosis, and uveal diffusion. In a non-limiting embodiment, the inflammation-mediated condition of the eye is uveitis. In another non-limiting embodiment, the inflammation-mediated condition of the eye is proliferative vitreoretinopathy (PVR).

Suspensions of microspheres may be used as an anti-inflammatory therapy of the eye, especially for treating inflammatory conditions of the ocular adnexa, palpebral or bulbar conjunctiva, cornea and anterior segment of the globe. Common therapeutic applications for anti-inflammatory suspensions of microspheres include viral, allergic conjunctivitis, acne rosacea, iritis and iridocyclitis. Microspheres may also be used to ameliorate inflammation associated with, corneal injury due to chemical or thermal burns, or penetration of foreign bodies. Such conditions may result from surgery, injury, allergy or infection to the eye and can cause severe discomfort.

Notably, microspheres have considerable therapeutic advantages in reducing inflammatory responses, compared to the prevalent topical ocular use of NSAI agents and corticosteroids. Use of topical steroids is associated with a number of complications, including posterior subcapsular cataract formation, elevation of intraocular pressure, secondary ocular infection, retardation of corneal wound healing, uveitis, mydriasis, transient ocular discomfort and ptosis. Numerous systemic complications also may arise from the topical ocular application of corticosteroids. These complications include adrenal insufficiency, Cushing's syndrome, peptic ulceration, osteoporosis, hypertension, muscle weakness or atrophy, inhibition of growth, diabetes, activation of infection, mood changes and delayed wound healing.

4. Ocular Surgical Applications

Compositions of microspheres in accordance with the present invention, may also be used to ameliorate inflammation associated with ocular surgery, and in this context are particularly useful in a prophylactic modality as well as in promoting healing and reducing scarring as has been detailed above.

Of particular suitability is the use of the compositions of the invention for: post trabeculectomy (filtering surgery); post pterygium surgery; post ocular adnexa trauma and surgery; post intraocular surgery and specifically: post lensectomy, post vitrectomy, post retinal detachment surgery, and post epi- and subretinal membrane peeling.

It will be appreciated by the artisan that these are intended to serve as non-limitative examples of prevalent surgical procedures for which the compositions and methods of the invention are useful.

5. Retinal Disease

The invention provides a method of preventing or treating various ocular diseases or conditions of the retina, including the following: maculopathies/retinal degeneration: macular degeneration, including age-related macular degeneration (ARMD), such as non-exudative age-related macular degeneration and exudative age-related macular degeneration; choroidal neovascularization; retinopathy, including diabetic retinopathy, acute and chronic macular neuroretinopathy, central serous chorioretinopathy; and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, Lyme Disease, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coats disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease, Traumatic/surgical diseases: sympathetic ophthalmia, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, ocular histoplasmosis syndrome (OHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic diseases with associated retinal dystrophies, congenital stationary night blindness, cone dystrophies, Stargardt's disease and fundus flavimaculatus, Best's disease, pattern dystrophy of the retinal pigment epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigment epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

5. Other Anterior Ocular Conditions

An anterior ocular condition is a disease, ailment or condition which affects or which involves an anterior (i.e., front of the eye) ocular region or site, such as a periocular muscle, an eyelid or an eyeball tissue or fluid which is located anterior to the posterior wall of the lens capsule or ciliary muscles. Thus, an anterior ocular condition primarily affects or involves the conjunctiva, the cornea, the anterior chamber, the iris, the posterior chamber (behind the iris but in front of the posterior wall of the lens capsule), the lens or the lens capsule and blood vessels and nerve which vascularize or innervate an anterior ocular region or site.

Thus, an anterior ocular condition can include a disease, ailment or condition, such as for example, aphakia; pseudophakia; astigmatism; blepharospasm; cataract; conjunctival diseases; conjunctivitis, including, but not limited to, atopic keratoconjunctivitis; corneal injuries, including, but not limited to, injury to the corneal stromal areas; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

Other diseases or disorders of the eye which may be treated in accordance with the present invention include, but are not limited to, ocular cicatricial pemphigoid (OCP), Stevens Johnson syndrome and cataracts.

6. Other Ocular Conditions

A posterior ocular condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e., the optic disc), and blood vessels and nerves which vascularize or innervate a posterior ocular region or site. Thus, a posterior ocular condition can include a disease, ailment or condition, such as for example, acute macular neuroretinopathy; Behcet's disease; choroidal neovascularization; diabetic retinopathy; uveitis; ocular histoplasmosis; infections, such as fungal or viral-caused infections; macular degeneration, such as acute macular degeneration, non-exudative age-related macular degeneration and exudative age-related macular degeneration; edema, such as macular edema, cystoid macular edema and diabetic macular edema; multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial or venous occlusive disease, retinal detachment, uveitic retinal disease; sympathetic ophthalmia; Vogt-Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, and glaucoma. Glaucoma can be considered a posterior ocular condition because the therapeutic goal is to prevent the loss of or reduce the occurrence of loss of vision due to damage to or loss of retinal ganglion cells or retinal nerve fibers (i.e., neuroprotection).

In some embodiments, the ophthalmic disorder is ocular inflammation resulting from, e.g., iritis, conjunctivitis, seasonal allergic conjunctivitis, acute and chronic endophthalmitis, anterior uveitis, uveitis associated with systemic diseases, posterior segment uveitis, chorioretinitis, pars planitis, masquerade syndromes including ocular lymphoma, pemphigoid, scleritis, keratitis, severe ocular allergy, corneal abrasion and blood-aqueous barrier disruption. In yet another embodiment, the ophthalmic disorder is post-operative ocular inflammation resulting from, for example, photorefractive keratectomy, cataract removal surgery, intraocular lens implantation, vitrectomy, corneal transplantation, forms of lamellar keratectomy (DSEK, etc), and radial keratotomy.

E. Mesenchymal Stem Cells

Certain embodiments of the present invention involve administering to a subject with an eye disease a therapeutically effective amount of a composition that includes a MSC. The MSC in the composition can be modified or unmodified (i.e., the MSC can be biochemicaly and/or genetically manipulated in any number of ways that are further described herein, or can be used without biochemical manipulation (i.e., stimulation) and/or without genetic modification. In one embodiment, the MSC in a therapeutic composition of the invention has been modulated to overexpress a therapeutic protein as set forth herein.

Notwithstanding the foregoing description of targeted diseases and conditions for which the present invention can provide a prophylactic or therapeutic benefit, it is considered that modified or unmodified MSCs, or combinations thereof, are useful for treatment of diseases which include but are not necessarily limited to corneal disease, glaucoma and retinal disease. In particular embodiments, the modified or unmodified mesenchymal stem cells can be used for therapy of any stage or severity of glaucoma, or for corneal epithelial injury, or for corneal trauma, or for age-related macular degeneration, or for retinitis pigmentosa, or for Stevens-Johnson Syndrome, or for ocular cicatricial pemphigoid, or any combination thereof. In connection with age-related macular degeneration, a preferred embodiment includes intravitreal and/or subretinal injection of the mesenchymal stem cells.

1. MSCs Generally

Based upon the disclosure provided herein, MSCs can be obtained from any source. The MSCs may be autologous with respect to the recipient (obtained from the same host) or allogeneic with respect to the recipient. In addition, the MSCs may be xenogeneic to the recipient (obtained from an animal of a different species), for example rat MSCs may be used to suppress inflammation in a human.

In a further non-limiting embodiment, MSCs used in the present invention can be isolated, from the bone marrow of any species of mammal, including but not limited to, human, mouse, rat, ape, gibbon, bovine. In a non-limiting embodiment, the MSCs are isolated from a human, a mouse, or a rat. In another non-limiting embodiment, the MSCs are isolated from a human.

Based upon the present disclosure, MSCs can be isolated and expanded in culture in vitro to obtain sufficient numbers of cells for use in the methods described herein provided that the MSCs are cultured in a manner that promotes aggregation and formation of spheroids. For example, MSCs can be isolated from human bone marrow and cultured in complete medium (DMEM low glucose containing 4 mM L-glutamine, 10% FBS, and 1% penicillin/streptomycin) in hanging drops or on non-adherent dishes. However, the invention should in no way be construed to be limited to any one method of isolating and culturing medium. Rather, any method of isolating and culturing medium should be construed to be included in the present invention provided that the MSCs are cultured in a manner that promotes aggregation and formation of spheroids.

Any medium capable of supporting MSCs in vitro may be used to culture the MSCs. Media formulations that can support the growth of MSCs include, but are not limited to, Dulbecco's Modified Eagle's Medium (DMEM), alpha modified Minimal Essential Medium (αMEM), and Roswell Park Memorial Institute Media 1640 (RPMI Media 1640) and the like. Typically, 0 to 20% fetal bovine serum (FBS) or 1-20% horse serum is added to the above medium in order to support the growth of MSCs. A defined medium, however, also can be used if the growth factors, cytokines, and hormones necessary for culturing MSCs are provided at appropriate concentrations in the medium. Media useful in the methods of the invention may contain one or more compounds of interest, including but not limited to antibiotics, mitogenic or differentiation compounds useful for the culturing of MSCs. The cells may be grown in one non-limiting embodiment, at temperatures between 27° C. to 40° C., in another non-limiting embodiment at 31° C. to 37° C., and in another non-limiting embodiment in a humidified incubator. The carbon dioxide content may be maintained between 2% to 10% and the oxygen content may be maintained between 1% and 22%; however, the invention should in no way be construed to be limited to any one method of isolating and culturing MSCs. Rather, any method of isolating and culturing MSCs should be construed to be included in the present invention.

Antibiotics which can be added into the medium include, but are not limited to, penicillin and streptomycin. The concentration of penicillin in the culture medium is about 10 to about 200 units per ml. The concentration of streptomycin in the culture medium is about 10 to about 200 µg/ml.

2. Mesenchymal Stem Cells Modified to Express a Therapeutic Protein

In a non-limiting embodiment, the mesenchymal stem cells are cultured under conditions which, as noted hereinabove, provide for the aggregation of the mesenchymal stem cells into a spheroidal aggregate, and provide for optimal expression of the therapeutic protein(s).

In one non-limiting embodiment, the mesenchymal stem cells are cultured in a medium, such as complete culture medium (CCM), for example, which includes serum in an amount effective to upregulate one or more of the hereinabove noted therapeutic proteins. For example, the medium may include fetal bovine serum in an amount of up to 20%. In a non-limiting embodiment, the fetal bovine serum is present in an amount of about 17%. The mesenchymal stem cells are cultured under conditions and for a period of time (for example, 7 or 8 days) sufficient to provide a sufficient number of cells for further culturing. The culture medium may include growth factors other than or in addition to serum to upregulate one or more of the hereinabove noted therapeutic proteins.

In one non-limiting embodiment, the spheroids can be prepared by culturing the MSCs on bacterial plates (as distinct from plates treated for culture of animal cells) so that the MSCs aggregate spontaneously into spheroids (Bartosh, 2010).

The cells then are cultured under conditions which promote the formation of spheroidal aggregates of the cells. In one non-limiting embodiment, the cells are cultured as hanging drops. Each drop of cells contains mesenchymal stem cells in an amount which provides for optimal expression of the at least one therapeutic protein. In a non-limiting embodiment, the hanging drops of the cells are cultured in a medium, such as complete culture medium, containing fetal bovine serum in an amount of up to 20%. In a non-limiting embodiment, the fetal bovine serum is present in an amount of about 17%.

In another non-limiting embodiment, each hanging drop of mesenchymal stem cells that is cultured contains from about 10,000 to about 500,000 cells/drop. In another non-limiting embodiment, each hanging drop of mesenchymal stem cells that is cultured contains from about 10,000 to about 250,000 cells/drop. In a further non-limiting embodiment, each hanging drop of cells contains from about 10,000 to about 25,000 cells/drop. In yet another non-limiting embodiment, each hanging drop of cells contains about 25,000/drop.

The hanging drops of mesenchymal stem cells are cultured for a period of time sufficient for forming spheroidal aggregates of the mesenchymal stem cells. In general, the drops of cells are cultured for a period of time of up to 4 days.

Once the spheroidal aggregates of the mesenchymal stem cells are formed, the mesenchymal stem cells may, if desired, be dissociated from the spheroids by incubating the spheroids in the presence of a dissociation agent, such as trypsin and/or EDTA, for example.

The invention comprises the treatment of an MSC in culture to express therapeutic proteins that are effective in treating a disease of the eye. For example, the MSCs can be cultured in the presence of TNF-α. In some instances, the MSCs can be pre-activated by culturing in the presence of IFN-μγ. In other instances, the MSCs can be pre-activated by culturing in the presence of IL-1B. In some instances, MSCs can be pre-activated using any combination of TNF-α, IFN-μ, and IL-1B. Pre-activation of the MSCs induce the cells to secrete therapeutic proteins. Thus, the MSCs themselves, the secreted proteins, or the combination of both provide a source of a therapeutic composition. In one embodiment, a recombinant version of the therapeutic protein secreted from the pre-activated MSCs can be used as a therapeutic composition.

In some instances, the MSCs are contacted with an agent that induces MSCs to secrete therapeutic proteins in a culturing medium. The culturing medium generally comprises a base media. Non-limiting examples of base media useful in the methods of the invention include Minimum Essential Medium Eagle, ADC-1, LPM (Bovine Serum Albumin-free), F10 (HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM—without serum), Yamane, IMEM-20, Glasgow Modification Eagle Medium (GMEM), Leibovitz L-15 Medium, McCoy's 5A Medium, Medium M199 (M199E—with Earle's salt base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713. DM 145, Williams' G, Neuman & Tytell, Higuchi, MCDB 301, MCDB 202, MCDB 501, MCDB 401, MCDB 411, MDBC 153. A preferred medium for use in the present invention is DMEM. These and other useful media are available from GIBCO, Grand Island, N.Y., USA and Biological Industries, Bet HaEmek, Israel, among others. A number of these media are summarized in *Methods in Enzymology*, Volume LVIII, "Cell Culture", pp. 62-72, edited by William B. Jakoby and Ira H. Pastan, published by Academic Press, Inc.

Additional non-limiting examples of media useful in the methods of the invention can contain fetal serum of bovine or other species at a concentration of at least 1% to about 30%, preferably at least about 5% to 15%, mostly preferably about 10%. Embryonic extract of chicken or other species can be present at a concentration of about 1% to 30%, preferably at least about 5% to 15%, most preferably about 10%.

In a non-limiting embodiment, the MSCs are isolated from the mammal into which the treated MSC are to be introduced; however, the MSCs may also be isolated from an organism of the same or different species as the mammal F. Genetic Modification of Therapeutic Cells In some embodiments of the present invention the subject is administered a therapeutically effective amount of cells that have been modified to overexpress a therapeutic protein of the present invention. For example, the cells of the invention may be transformed stably or transiently with a nucleic acid of interest prior to introduction into the eye of the mammal Nucleic acid sequences of interest include, but are not limited to those encoding gene products TSG-6 and biologically active fragments and analogs thereof, and STC-1 and biologically active fragments and analogs thereof. Methods of transformation of cells such as MSCs are known to those skilled in the art, as are methods for introducing cells into a bone at the site of surgery or fracture.

In cases in which a gene construct is transfected into a cell, the heterologous gene is linked operably to regulatory sequences required to achieve expression of the gene in the cell. Such regulatory sequences typically include a promoter and a polyadenylation signal. In particular embodiments, the gene expresses a protein as set forth in any of Tables 1-3 or an amino acid sequence that has at least 95% sequence identity to a protein as set forth in any of Tables 1-3.

In a non-limiting embodiment, the gene construct is provided as an expression vector that includes the coding sequence for a heterologous protein operably linked to essential regulatory sequences such that when the vector is transfected into the cell, the coding sequence will be expressed by the cell. The coding sequence is linked operably to the regulatory elements necessary for expression of that sequence in the cells. The nucleotide sequence that encodes the protein may be cDNA, genomic DNA, synthesized DNA or a hybrid thereof, or an RNA molecule such as mRNA.

The gene construct includes the nucleotide sequence encoding the beneficial protein is linked operably to the regulatory elements and may remain present in the cell as a functioning cytoplasmic molecule, a functioning episomal molecule, or it may integrate into the cell's chromosomal DNA. Exogenous genetic material may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The cells of the present invention can be transfected using well known techniques readily available to those having ordinary skill in the art. Exogenous genes may be introduced into the cells using standard methods where the cell expresses the protein encoded by the gene. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, vectors are used to introduce DNA with desired sequences into the cell. The vector may be any vector as set forth in the foregoing sections.

The MSCs, in a non-limiting embodiment, may have one or more genes modified or may be treated such that the modification has the ability to cause the MSCs to self-destruct or "commit suicide" because of such modification, or upon presentation of a second drug (e.g., a prodrug) or signaling compound to initiate such destruction of the MSCs.

G. Therapy

1. General

Some embodiments of the present invention include methods of using cells expressing a polypeptide as set forth herein as a therapy to inhibit inflammation in the context of an ocular disease.

Cells can be suspended in an appropriate diluent. Suitable excipients for injection solutions are those that are biologically and physiologically compatible with the cells and with the recipient, such as buffered saline solution or other suitable excipients. The composition for administration can be formulated, produced and stored according to standard methods complying with proper sterility and stability.

The dosage of the cells varies within wide limits and may be adjusted to the individual requirements in each particular case. The number of cells used depends on the weight and condition of the recipient, the number and/or frequency of administrations, and other variables known to those of skill in the art, including, but not limited to, the age and sex of the patient, the disease or disorder being treated, and the extent and severity thereof.

In particular embodiments, the therapeutic polypeptide is a human therapeutic polypeptide. In other embodiments, the polypeptide is derived from a non-human source, such as a mouse, rat, rabbit, horse, cow, or primate.

For treatment of eye disease, the therapeutic cells, polypeptides, or polynucleotides may be administered using any method known to those of ordinary skill in the art. For example, administration may be intravenous, intracameral, intravitreous, subconjunctival, sub-Tenon's, subretinal, or topical to the corneal surface. Administration may be intraoperative in some embodiments, such as by injection into the eye. The therapeutic polypeptides of the present invention may be delivered directly to the eye (for example: topical ocular drops or ointments; slow release devices in the cul-de-sac or implanted adjacent to the sclera or within the eye; periocular, conjunctival, sub-tenons, intracameral, intravitreal, or intracanalicular injections) or systemically (for example: orally, intravenous, subcutaneous or intramuscular injections; parenterally, dermal or nasal delivery) using techniques well known by those skilled in the art. It is further contemplated that the agents of the invention may be formulated in intraocular insert or implant devices.

Often, treatment dosages are titrated upward from a low level to optimize safety and efficacy. Generally, daily dosages will fall within a range of about 0.01 to 20 mg protein per kilogram of body weight. Typically, the dosage range will be from about 0.1 to 5 mg protein per kilogram of body weight. In some embodiments for intravitreal injection, a dose includes 0.01 to 5 mg of polypeptide. In more specific embodiments, a dose includes between 0.1 and 2.0 mg. The polypeptide is formulated in a carrier volume ranging from 0.2 ml to 5 ml. In more particular embodiments, the carrier volume is between 0.5 and 2.0 ml. Nonlimiting examples of carriers include sterile water, normal saline, phosphate buffered saline, and optionally including any of the excipients set forth herein.

Various modifications or derivatives of the proteins, such as addition of polyethylene glycol chains (PEGylation), may be made to influence their pharmacokinetic and/or pharmacodynamic properties.

To administer the protein by other than parenteral administration, the protein may be coated or co-administered with a material to prevent its inactivation. For example, the protein may be administered in an incomplete adjuvant, co-administered with enzyme inhibitors or administered in liposomes. Enzyme inhibitors include pancreatic trypsin inhibitor, disopropylfluorophosphate (DEP) and trasylol. Liposomes include water-in-oil-in-water, CGF emulsions, as well as conventional liposomes (Strejan et al. (1984) J. Neuroimmunol. 7:27).

The compositions of the present invention optionally comprise one or more excipients. Excipients commonly used in solution compositions intended for topical application to the eyes, such as solutions, include, but are not limited to, tonicity agents, preservatives, chelating agents, buffering agents, surfactants and antioxidants. Suitable tonicity-adjusting agents include mannitol, sodium chloride, glycerin, sorbitol and the like. Suitable preservatives include p-hydroxybenzoic acid ester, benzalkonium chloride, benzododecinium bromide, polyquaternium-1 and the like. Suitable chelating agents include sodium edetate and the like. Suitable buffering agents include phosphates, borates, citrates, acetates, tromethamine, and the like. Suitable surfactants include ionic and nonionic surfactants, though nonionic surfactants are preferred, such as polysorbates, polyethoxylated castor oil derivatives, polyethoxylated fatty acids, polyethoxylated alcohols, polyoxyethylene-polyoxypropylene block copolymers, and oxyethylated tertiary octylphenol formaldehyde polymer (tyloxapol). Suitable antioxidants include sulfites, thiosulfate, ascorbates, BHA, BHT, tocopherols, and the like. The compositions of the present invention optionally comprise an additional active agent. The compositions of the present invention may contain one or more nonionic, anionic, or cationic polymers as lubricants or as viscosity agents, including but not limited to hydroxypropyl methylcelluloses (HPMCs), methylcelluloses, carboxymethylcelluloses (CMCs), polyethylene glycols (PEGs), poloxamers, polypropylene glycols, xanthan gums, guar gums, carbomers, polyvinyl alcohols (PVAs), polyvinylpyrrolidones (PVPs), alginic acids and salts, gellan gums, carrageenans, and chitosans.

An "effective amount" of a therapeutic polypeptide, polynucleotide, or cells is an amount that will ameliorate one or more of the well known parameters that characterize medical conditions of the eye disease to be treated.

Although the compositions of this invention can be administered in simple solution, they are more typically used in combination with other materials such as carriers, preferably pharmaceutical carriers. Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g., Remington's Pharmaceutical Science, 17th Ed. (Mack Publishing Company, Easton, Pa., 1990). Alternatively, compositions of the invention may be introduced into a patient's body by implantable drug delivery systems [Urquhart et al., *Ann. Rev. Pharmacol. Toxicol.* 24:199 (1984).

Therapeutic formulations may be administered in many conventional dosage formulations. Formulations typically comprise at least one active ingredient, together with one or more pharmaceutically acceptable carriers. In some embodiments, the ophthalmic compositions are formulated to provide for an intraocular concentration of about 0.1-100 nanomolar (nM) or, in a further embodiment, 1-10 nM. Peak plasma concentrations of up to 20 micromolar may be achieved for systemic administration. Topical compositions are delivered to the surface of the eye one to four times per day according to the routine discretion of a skilled clinician. The pH of the formulation should be 4-9, or 4.5 to 7.4. Systemic formulations may contain about 10 mg to 1000 mg, about 10 mg to 500 mg, about 10 mg to 100 mg or to 125 mg, for example, of the therapeutic protein.

The formulations conveniently may be presented in unit dosage form and may be prepared by any methods well known in the art of pharmacy. See, e.g., Gilman et al. (eds.) (1990), The Pharmacological Bases of Therapeutics, 8th Ed., Pergamon Press; and Remington's Pharmaceutical Sciences, supra, Easton, Pa.; Avis, et al. (eds.) (1993) Pharmaceutical Dosage Forms: Parenteral Medications Dekker, N.Y.; Lieberman et al. (eds.) (1990), Pharmaceutical Dosage Forms: Tablets, Dekker, N.Y.; and Lieberman et al. (eds.) (1990), Phamiaceutical Dosage Forms: Disperse Systems, Dekker, N.Y.

In additional non-limiting embodiments, the present invention contemplates administration of the proteins by gene therapy methods, e.g., administration of an isolated nucleic acid encoding a protein of interest. The proteins of the present invention have been well-characterized, both as to the nucleic acid sequences encoding the proteins and the resultant amino acid sequences of the proteins. Engineering of such isolated nucleic acids by recombinant DNA methods is well within the ability of one skilled in the art. Codon optimization, for purposes of maximizing recombinant protein yields in particular cell backgrounds, also is well within the ability of one skilled in the art.

There are two major approaches for introducing a nucleic acid encoding the protein (optionally contained in a vector) into a patient's cells; in vivo and ex vivo. For in vivo delivery, the nucleic acid is injected directly into the patient, usually at the site where the protein is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. Commonly used vectors for ex vivo delivery of the gene are retroviral and lentiviral vectors.

Preferred in vivo nucleic acid transfer techniques include transfection with viral vectors such as adenovirus, Herpes Simplex I virus, adeno-associated virus, lipid-based systems (useful lipids for lipid-mediated transfer of the gene are DOTMA, DOPE and DC-Chol, for example), naked DNA, and transposon-based expression systems. For review of the currently known gene marking and gene therapy protocols see Anderson, et al, *Science* 256:808-8 13 (1992). See also WO 93/25673 and the references cited therein.

Therapeutic compositions and formulations thereof of the invention can be used, for example, for reducing inflammation due to seasonal or bacterial conjunctivitis, for reducing post-surgical pain and inflammation, to prevent or treat inflammatory tissue damage associated with fungal or bacterial infections of the eye, to treat herpes zoster ophthalmicus, to reduce intraocular pressure, or to treat endophthalmitis.

More particularly, in one non-limiting embodiment, the present invention provides a method for treating an ophthalmic disorder in a mammal (e.g., including human and non-human primates), the method comprising administering to the eye of the mammal a therapeutically effect amount of a formulation of the present invention comprising a lipid phase, an aqueous phase and a therapeutic agent as hereinabove described, wherein the therapeutic agent is useful for treating the ophthalmic disorder. In one embodiment, the ophthalmic disorder is post-operative pain.

In employing the liposome formulations of the present invention, in a non-limiting embodiment, administration is ocularly, which term is used to mean delivery of therapeutic agents through the surface of the eye, including the sclera, the cornea, the conjunctiva and the limbus, or into the anterior chamber or vitreous chamber of the eye. Ocular delivery can be accomplished by numerous means, for example, by topical application of a formulation such as an eye drop, by injection, or by means of an electrotransport drug delivery system.

In another non-limiting embodiment, the therapeutic cells or therapeutic proteins employed for treating a disease or disorder of the eye may be contained in a nanoparticle. Such nanoparticles may be formed by methods known to those skilled in the art.

Such nanoparticles may be administered ocularly, i.e., through the surface of the eye, including the sclera, cornea, conjunctiva, and the limbus, or into the anterior chamber of the eye. Such ocular administration may be accomplished by any of a variety of means, including, in a non-limiting embodiment, by topical application of a formulation such as an eye drop, by injection, or by means of an electotransport drug delivery system.

2. Combination Therapy

The compositions and/or cells of the present invention are suitable for use in combination with other therapeutic agents for treatment of eye disease. They can be comprised in the same formulation or in different formulations. Non-limiting examples of other agents for use in the treatment of eye disease contemplated by the present invention include artificial tears, anti-glaucoma agents, such as beta-blockers including timolol, betaxolol, levobetaxolol, carteolol, miotics including pilocarpine, carbonic anhydrase inhibitors, prostaglandins, serotonergics, muscarinics, dopaminergic agonists, adrenergic agonists including apraclonidine and brimonidine; anti-angiogenesis agents; anti-infective agents including quinolones such as ciprofloxacin, and aminoglycosides such as tobramycin and gentamicin; non-steroidal and steroidal anti-inflammatory agents, such as suprofen, diclofenac, ketorolac, rimexolone and tetrahydrocortisol; growth factors, such as EGF; immunosuppressant agents; and anti-allergic agents including olopatadine; prostaglandins such as latanoprost; 15-keto latanoprost; travoprost; and unoprostone isopropyl.

H. Examples

The invention is now described with reference to the following Examples. These Examples are provided for the purpose of illustration only, and the invention is not limited to these Examples, but rather encompasses all variations which are evident as a result of the teachings provided herein. Those of skill in the art should, in light of the present disclosure, appreciate that many changes can be made in the specific embodiments which are disclosed and still obtain a like or similar result without departing from the spirit and scope of the invention.

Example 1

MSCs and MSC-Derived Factors Suppressed Inflammation and Neovascularization, and Promoted Wound Healing in Chemically-Injured Rat Cornea Beneficial effects of MSCs and MSC-derived factors have been observed in suppressing corneal inflammation/neovascularization and promoting wound healing (Oh et al., 2008). Corneal inflammation, neovascularization, and delayed wound healing were induced in rats by applying 100% ethanol for 30 sec and scraping both the epithelium in the limbus and the whole cornea. The reliability and reproducibility of this model was previously confirmed and repetitively used by other researchers (Cho et al., 1998; Avila et al., 2001; Ti et al., 2002; Espana et al., 2003; Homma et al, 2004; Oh et al., 2009b). Massive infiltration of inflammatory cells and growth of new vessels in cornea were induced in this model (FIG. 1).

Immediately after injury, rat MSCs or conditioned media (CM) derived from MSC cultures were put into an applicator and allowed to remain in the damaged cornea for two hours. A 6-mm-diameter hollow tube was used as an applicator (FIG. 2). This method of application has previously been proven effective for applying stem cells to cornea (Homma et al., 2004; Ueno et al., 2007). The following were the four groups that were studied and subjected to different treatments: (1) 200 µL of fresh media (control group, n=10), (2) 200 µL of supernatants collected from the MSCs culture (MSC-CM I group, n=10), (3) 200 µL MSC-CM applied for two hours a day over three consecutive days (MSC-CM II group, n=10), (4) 200 µL of media containing $2 \times 10^6$ MSCs (MSC group, n=10).

Effects of MSCs or MSC-CM on the cornea were determined in three ways: (I) gross examination by slit-lamp biomicroscopy based on the findings of transparency, neovascularization (NV), and epithelial defects, (2) histological analysis for infiltration of inflammatory cells (hematoxylin-eosin staining) or CD4+ T cells (immunofluorescent staining), and (3) ELISA and real time PCR assays for inflammation- and angiogenesis-related cytokines. As a result, it was found that corneal inflammation and NV rapidly decreased in MSC-treated corneas over time after injury, while they gradually increased in the vehicle-treated controls (FIG. 3). The degree of corneal inflammation and NV was the lowest in the MSC group and the highest in the control group. Notably, it was observed that MSC-CM was also effective in reducing corneal inflammation and NV in proportion to the number of MSC-CM applications. More specifically, corneas treated three times with MSC-CM (MSC-CM II group) were more transparent compared to both the controls and the corneas that were treated only once with MSC-CM (MSC-CM I group). Re-epithelialization was faster in the corneas treated with MSCs and MSC-CM.

Figures 4C, 4D:
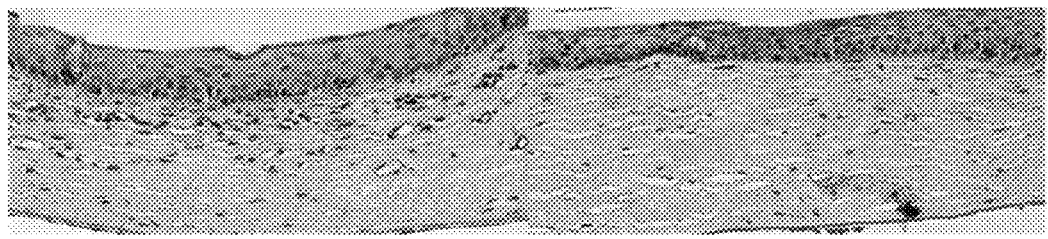
Figure 5A:
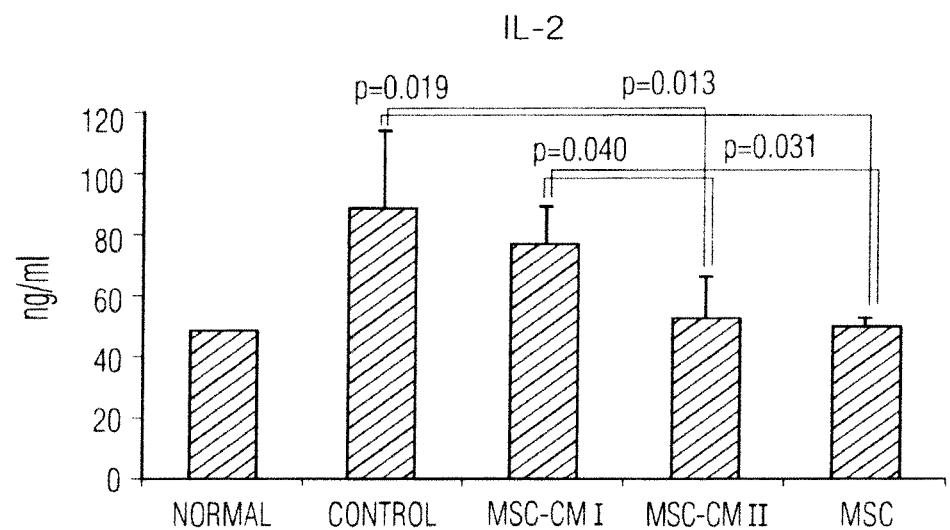
FIGS. 5A through 5D, is a series of images demonstrating inflammation-related cytokine expression evaluated by ELISA. IL-2 and IFN-γ were repressed in the corneas treated with MSCs or MSCs-conditioned media three times (MSC-CM II) compared to the control.
Figure 5B:
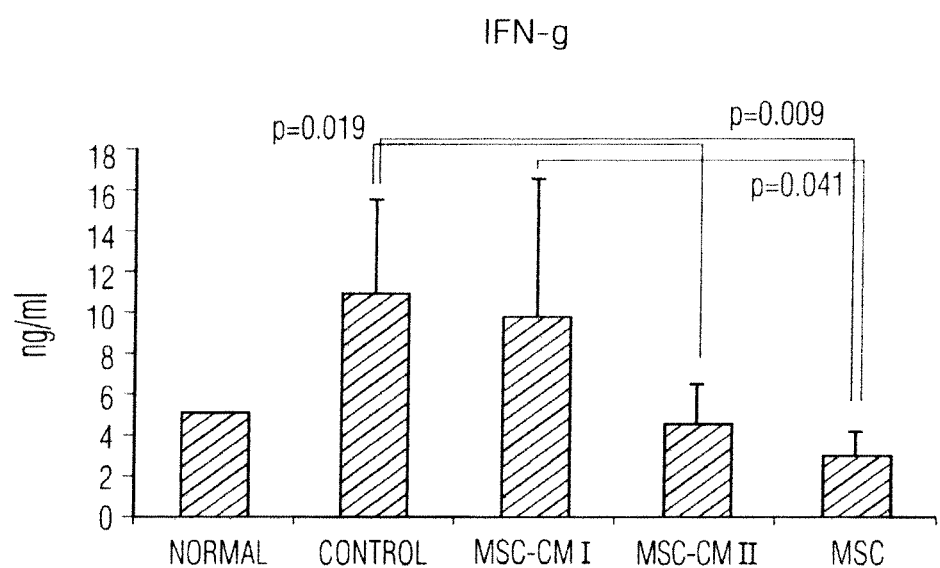
Figure 5C:
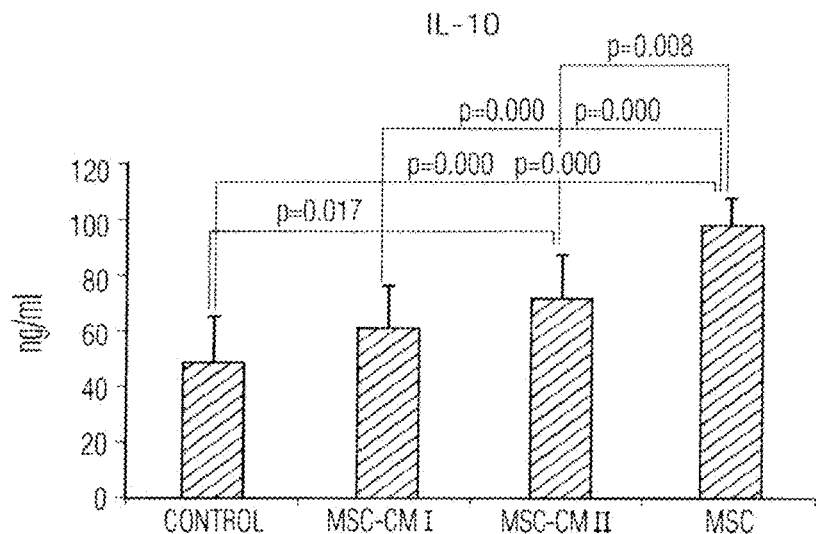
Figure 5D:
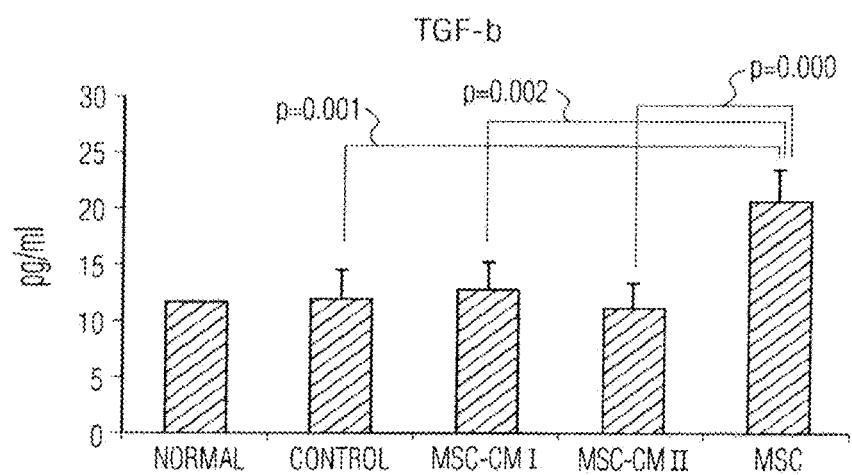
Figure 6A:
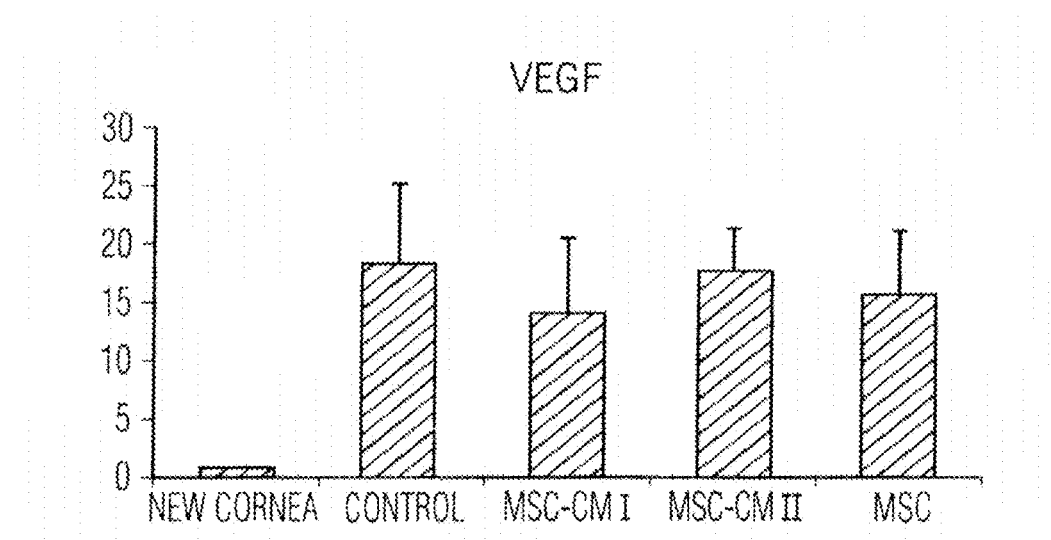
FIGS. 6A through 6D, is a series of images depicting real-time PCR for angiogenesis-related cytokines. Upregulation of TSP-1 was observed in the corneas treated with MSC or MSC-conditioned media three times (MSCCM II), compared to the control. MMP-2 and MMP-9 were downregulated in the MSC group. There were no differences in the expression of VEGF. Values were expressed as folds relative to fresh corneas without an injury.
Figure 6B:
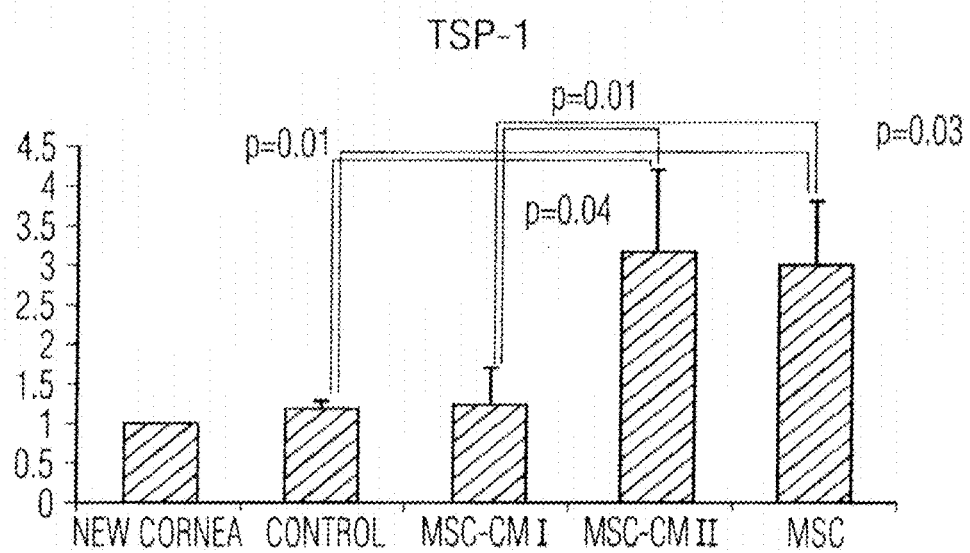
Figure 6C:
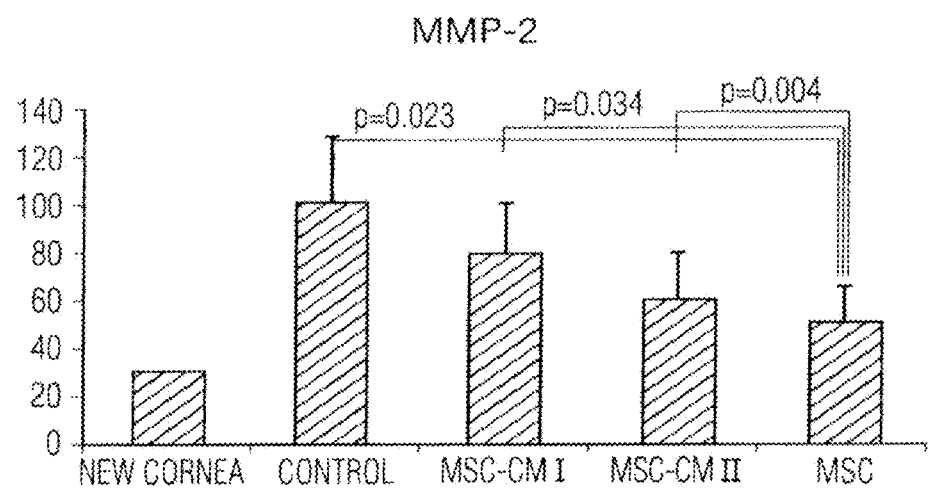
Figure 6D:
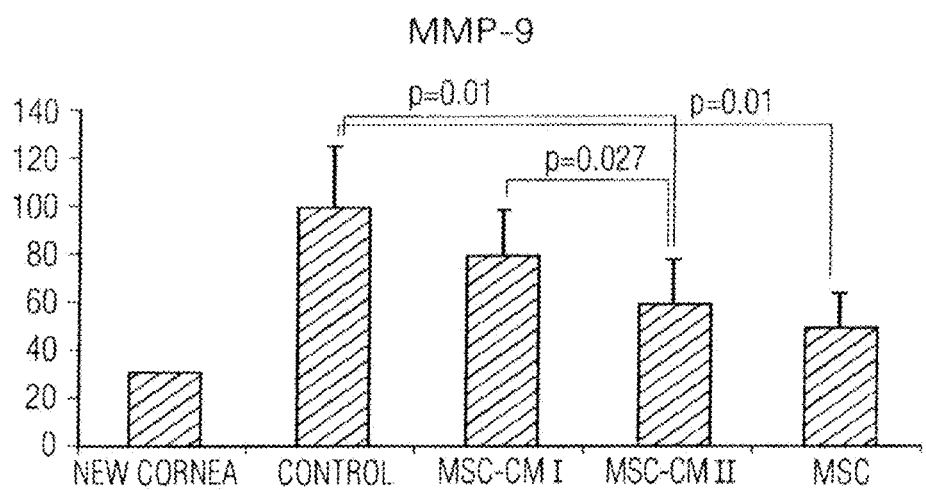

Similar to clinical findings, histological analysis (FIG. 4) revealed that MSCs and MSC-CM II groups had fewer inflammatory cell infiltrates than the control and MSC-CM I groups. Comparisons between MSCs and MSC-CM II groups showed that corneas treated with MSCs had significantly fewer inflammatory cells than those treated with MSC-CM three times.

ELISA showed that production of proinflammatory cytokines IL-2 and IFN-µ was decreased in MSC- and MSC-CM-treated corneas (FIGS. 5 A, B). In contrast, large quantities of anti-inflammatory cytokines IL-10 and TGF-B were detected in MSC-treated corneas (FIGS. 5 C, D)

In order to determine the mechanisms associated with regression of new vessels by MSCs, the expression of angiogenesis-related cytokines, TSP-1, MMP-2, MMP-9, and VEGF was evaluated. Real time RT-PCR revealed that the level of an anti-angiogenic factor, TSP-1, was significantly upregulated in MSC and MSC-CM II groups (FIG. 6). The expression of pro-angiogenic factors, MMP-2 and MMP-9, was significantly repressed in MSC-treated corneas, compared to control corneas.

Example 2

Figure 7:
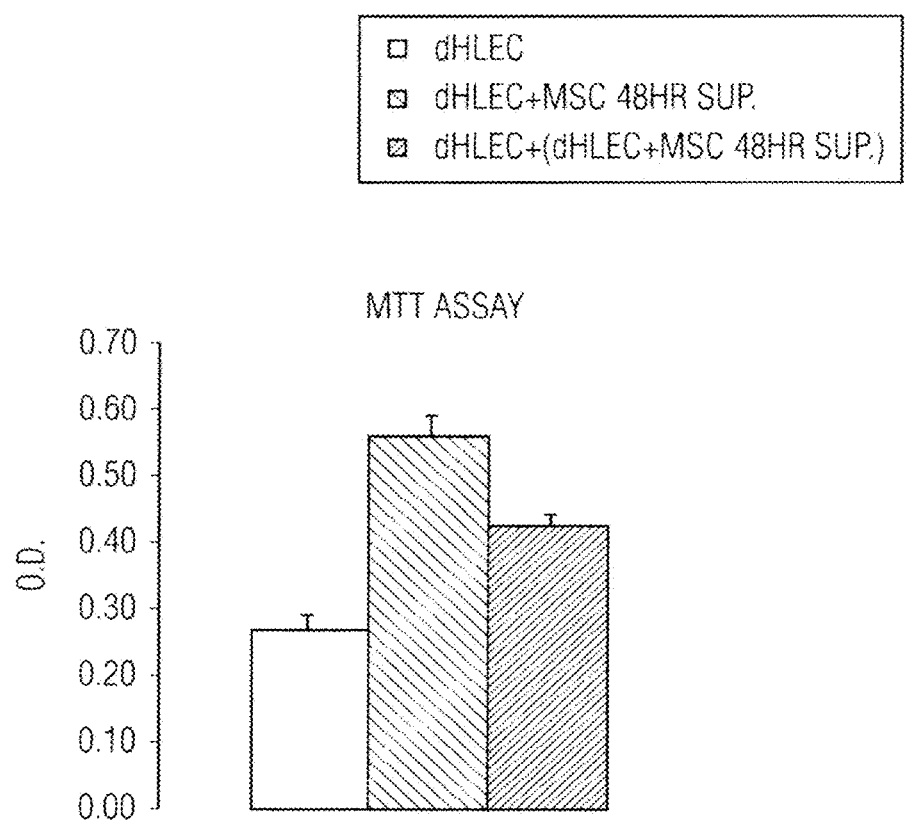
FIG. 7 is an image depicting cytotoxicity test of human corneal epithelial cells (HLECs) after chemical damage. When cultured with hMSCs-derived medium for 48 hours, damaged HLECs were significantly decreased compared to HLECs without hMSCs-conditioned medium.

Human MSC-Conditioned Media Rescued Human Corneal Epithelial Cells from Chemically-Induced Apoptosis Human corneal epithelial cells (hCECs) were chemically damaged by incubation in 15% ethanol for 30 seconds. Damaged hCECs were cultured with one of the following: (1) hMSC-conditioned media, (2) conditioned media from hMSC-damaged hCECs coculture, or (3) fresh media. Then, survival of hCECs was evaluated with MTT assay. The result showed that the proportion of damaged hCECs was significantly decreased when cultured with hMSC-conditioned media (FIG. 7).

Example 3

Figure 8:
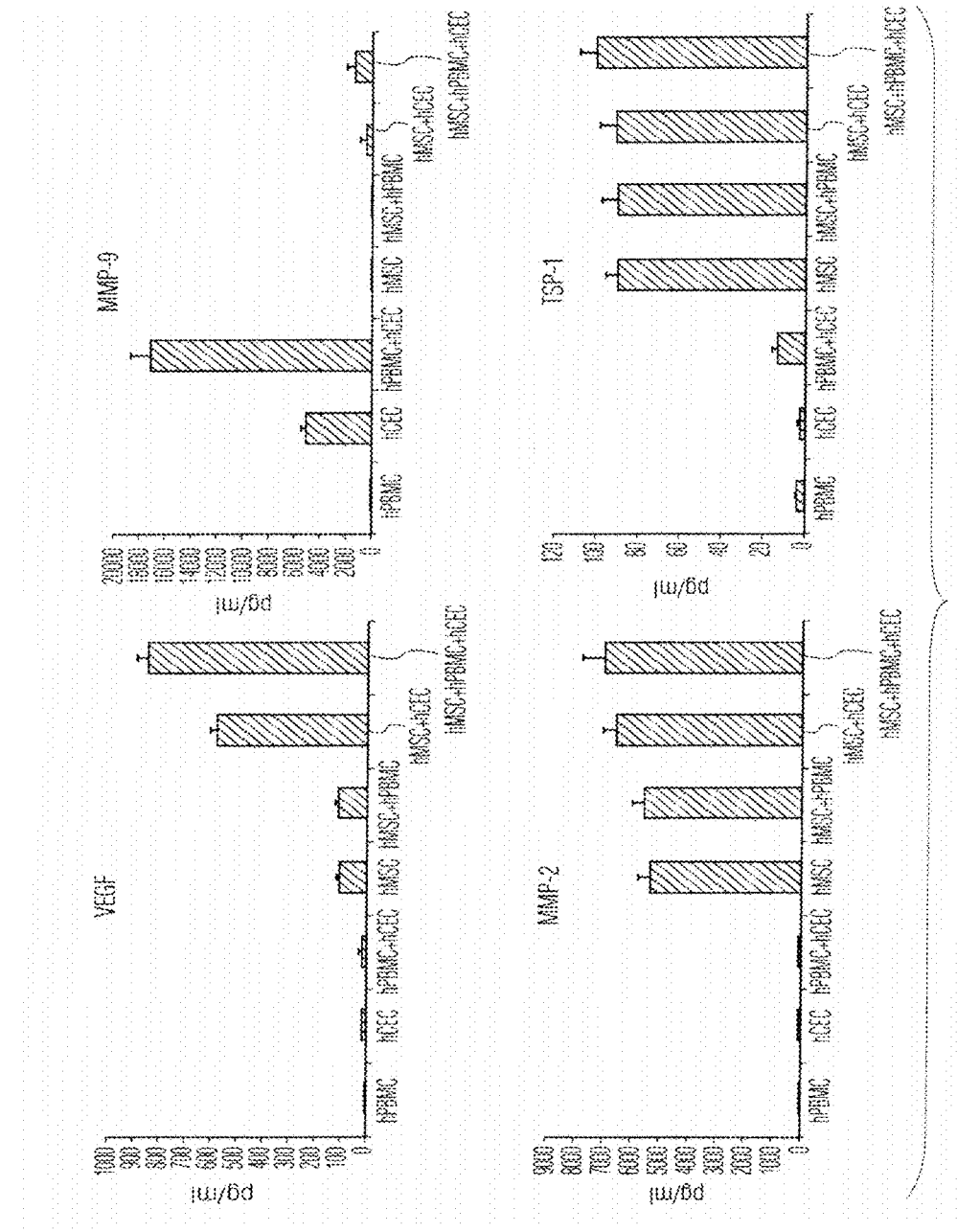
FIG. 8 is an image depicting cytokine secretion evaluated by ELISA. The expression of VEGF, MMP-9, MMP-2, and TSP-I were quantified in various cocultures of hMSCs/hCECs/hPBMCs. The hCECs were prepared after treatment with 15% ethanol for 30 sec. Data represent at least three experiments.

Production of MMP-9 is Significantly Suppressed in Chemically-Damaged Human Corneal Epithelial Cells by hMSCs The following experiments were performed to evaluate how MSCs affected corneal epithelial cells in terms of inflammatory and angiogenic cytokine secretion. The hCECs were chemically damaged, then they were cocultured with hMSCs for 24 hours, and finally the cell-free supernatant was analyzed for cytokine concentration by ELISA. The coculture groups were as follows: (I) hPBMCs (human peripheral blood mononuclear cells), (2) hCECs, (3) hPBMCs/hCECs, (4) hMSCs, (5) hMSCs/hPBMCs, (6) hMSCs/hCECs, and (7) hMSCs/hPBMCs/hCECs. As a result, it was observed that MSCs constitutively secreted VEGF, MMP-2, and TSP-1 (FIG. 8). It is important to note that MMP-9, which is highly secreted by damaged hCECs, was significantly suppressed by hMSCs (FIG. 8, upper right). In fact, as a consequence of hMSC suppression the level of MMP-9 was reduced from 100% to 8%. Based on these results, it was believed that the suppression of MMP-9, a key player in corneal inflammation, angiogenesis, and wound healing would be one of the mechanisms responsible for MSC action during corneal regeneration. MMP-9 is one of the pro-inflammatory proteases that has its activation significantly inhibited by TSG-6 (Milner and Day, 2003; Milner et al., 2006).

The results presented herein demonstrate that application of either MSCs or conditioned medium from the MSCs decreased inflammation and neovascularization in a rat model for noninfectious inflammation of the cornea. Without wishing to be bound by any particular theory, the beneficial effects of the MSCs are at least in part explained by the effects of decreasing the levels of inflammatory cytokines and inflammation-related proteases both in the rat model of corneal damage and in cocultures with conical epithelial cells. Therefore the data are consistent with the hypothesis that the beneficial effects of MSCs are explained by the production by the cells of the anti-inflammatory protein TSG-6 and/or the anti-apoptotic protein STC-1.

Example 4

Use of Pre-Activated MSCs for the Treatment of Cornea

Figure 10A:
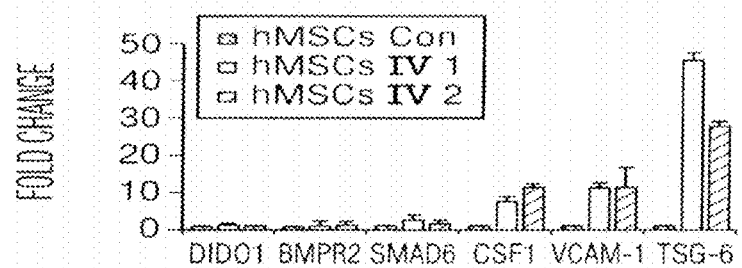
FIGS. 10A through 10F, is a series of images depicting activation of hMSCs to Express TSG-6.
Figure 10B:
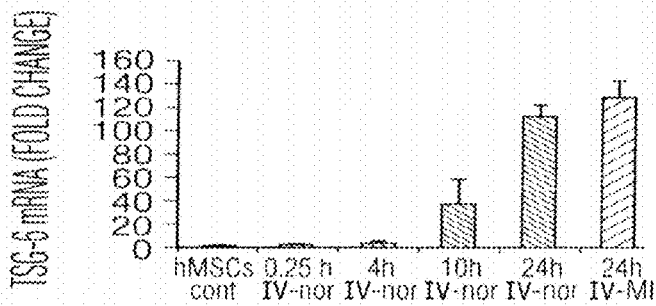
Figure 10C:
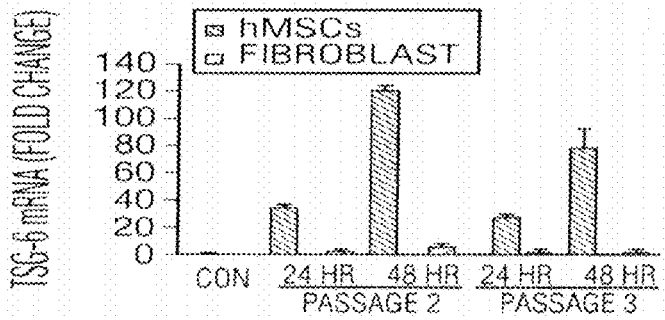
Figure 10D:
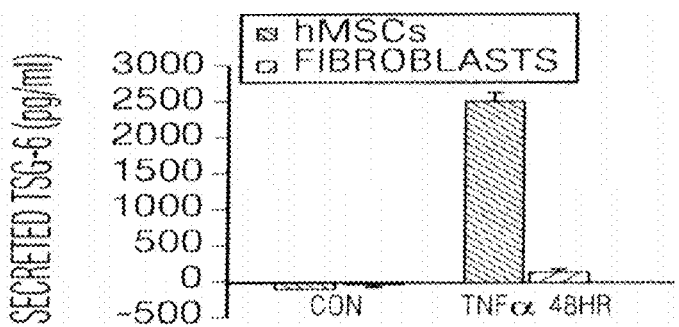
Figure 10E:
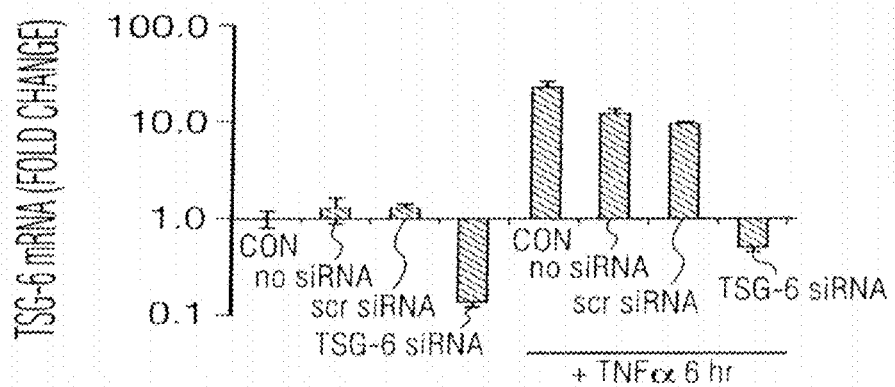
Figure 10F:
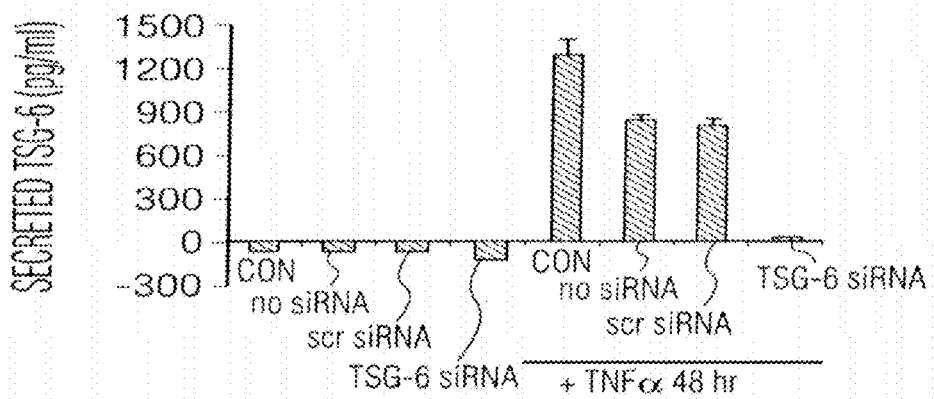
Figure 12A:
FIGS. 12A through 12F, is a series of images depicting assays of Infarct Size 3 wk after MI. Each heart was cut from the apex through the base into over 400 sequential 5 μm sections and stained with Masson Trichrome. Every 20th section is shown from typical specimens.
Figure 12B:
Figure 12C:
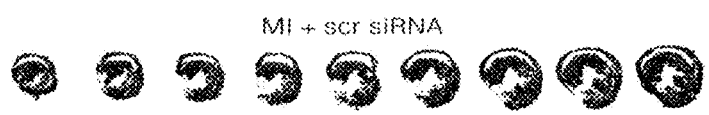
Figure 12D:
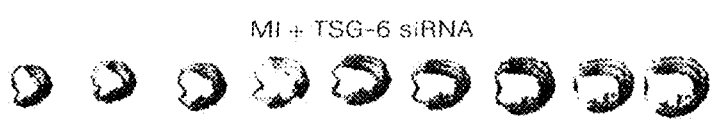
Figure 12E:
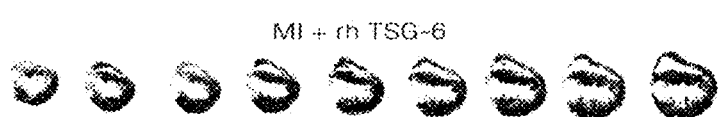
Figure 12F:
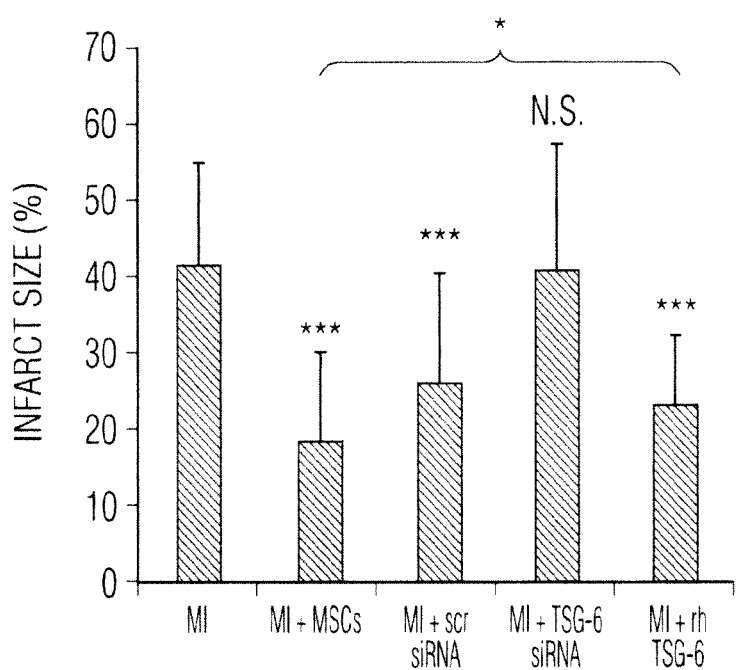

The following experiments were designed to test whether MSCs preactivated in culture to express therapeutic proteins would be more effective in reducing inflammation and neovascularization following chemically-induced injury to the cornea than standard cultures of MSCs. The experiments were set up to compare standard preparations of MSCs with MSCs pre-activated in culture with TNFα (FIGS. 10C and D) in the rat model in terms of the minimum number of cells required to produce (a) significant improvements in neovascularization, opacity, epithelial defects, and infiltration of inflammatory cells as in FIGS. 3 and 4; (b) significant decreases in the inflammatory cytokine IFN-μ (FIG. 5); and (c) significant decreases in the inflammation-related proteases MMP-2 and MMP-9 (FIG. 6). In parallel standard preparations and pre-activated MSCs by intracameral injection (IC; into anterior chamber) in the model are compared using the same measures of effectiveness.

As summarized in Table 4, the initial experiments are carried out with both rat MSCs and human MSCs (hMSCs), since the hMSCs are more relevant to the potential clinical applications of the results, and human and rodent MSCs have proven to be equally effective in other rodent models (Lee et al., 2009; Block et al.; 2009; Ohtaki et al., 2008; Iso et al., 2007; Ortiz et al., 2007; Lee et al., 2006; Munoz et al., 2006).

TABLE 4

|  | MSCs | Delivery | Dose | # Rats |
|---|---|---|---|---|
| 1. Species | hMSCs | Topical | $2 \times 10^4$ | 10 |
|  |  |  | $2 \times 10^5$ | 10 |
|  |  |  | $2 \times 10^6$ | 10 |
|  | rMSCs | Topical | $2 \times 10^4$ | 10 |
|  |  |  | $2 \times 10^5$ | 10 |
|  |  |  | $2 \times 10^6$ | 10 |
| 2. Route | hMSCs | IC | $2 \times 10^3$ | 10 |
|  |  |  | $2 \times 10^4$ | 10 |
|  |  |  | $2 \times 10^5$ | 10 |
|  | rMSCs | IC | $2 \times 10^3$ | 10 |
|  |  |  | $2 \times 10^4$ | 10 |
|  |  |  | $2 \times 10^5$ | 10 |
| 3. acMSCs | Ac h/rMSCs | Topical | $2 \times 10^4$ | 10 |
|  |  |  | $2 \times 10^5$ | 10 |
|  |  |  | $2 \times 10^6$ | 10 |
|  | Ac h/rMSCs | IC | $2 \times 10^3$ | 10 |
|  |  |  | $2 \times 10^4$ | 10 |
|  |  |  | $2 \times 10^5$ | 10 |
|  |  |  | Total | 180 |

The materials and methods employed in the experiments disclosed herein are now described.

Corneal Surface Inflammation Model

Corneal surface inflammation can be created in rats by application of 100% ethanol and mechanical debridement of corneal and limbal epithelium using the protocol described in Oh et al. (2008). This model induces the infiltration of neutrophils, macrophages, neovascularization, and delayed wound healing in cornea (Figure. 1).

MSC's—

Human MSCs (hMSCS) and rat MSCs (rMSCs) can be acquired from standardized preparations currently being distributed by our NIH/NCRR funded center (P40 RR 17447). For hMSCs, the standardized cells can be further screened to select preparations that are over 90% positive for PODXL. PODXL serves as a marker for MSCs that are likely to express other epitopes (c-MET, CXCR4, and CXC3CR1) for early progenitors in vivo. For rMSCs, MSCs can be isolated from the bone marrow of Lewis rats (Javazon et al., 2001).

Route of Treatment Delivery

Topical application (FIG. 2) and IC injection are compared. This comparison allows for the determination of whether IC injection is effective at lower doses than topical application. For topical delivery, a hollow tube can be applied to the cornea, the cells (200 μL) can be put into the tube, and allowed to remain in the cornea for two hours (FIG. 2). The dose of cells can be varied from $2 \times 10^4$ to $2 \times 10^6$, the dose previously found to be effective (FIGS. 3 to 6). Topical application can be repeated on consecutive days for a total of three treatments. For IC injection, the media (5 μL) can be injected once into the anterior chamber of the rat eye. The dose of cells can be varied from $2 \times 10^3$ to $2 \times 10^5$, i.e., to the maximal concentration that can be employed without aggregation of the cells (Lee et al., 2009).

Assays for Corneal Surface Regeneration

The eyes are examined with slit-lamp biomicroscopy and recorded with photography once a week. The clinical outcome is graded by a blinded investigator who is an ophthalmologist under the following criteria: (1) corneal epithelial integrity, (2) transparency, and (3) neovascularization (NV). A 1% fluorescein sodium solution can be used to evaluate the degree of corneal epithelial defects. Subsequently, defects are quantified by the ratio of epithelial defect area to total corneal area, using an image analyzer. The corneal clarity is graded from 0 to 4 using the method in Fantes et al. (1990) and Oh et al. (2008). The corneal NV are quantified by calculating the area of vessel growth with the method used in D'Amato et al. (1994), Oh et al. (2008), and Oh et al. (2009b). After three weeks, corneas are excised, and examined using appropriate assays discussed elsewhere herein.

Assays for Corneal Inflammation

Corneas are either stained with hematoxylin-eosin or subjected to immunostaining with neutrophil- and macrophage-specific markers. The numbers of inflammatory cells are counted on the H&E-stained slides, The numbers of positively-stained cells are counted on the immunostained slides. Also, the infiltration and accumulation of neutrophils in the cornea are quantitated by measuring myeloperoxidase (MPO) activity with the MPO sandwich ELISA assay (Armstrong et al., 1998).

Assays for Modulation of Inflammation-, Angiogenesis-, and Apoptosis-Related Molecules The expression of proteins for inflammation-related factors (IL-1B, IL-2, IFN-μ, IL-6, IL-10, TGF-B1), angiogenesis-related factors (TSP-1, VEGF), apoptosis-related factors (Fas/Fas ligand), and gelatinases (MMP-2, MMP-9) are measured in corneas using ELISA assay.

The results of these experiments are now described. Without wishing to be bound by any particular theory, it is believed that (1) hMSCs are as effective in a rat model of corneal inflammation as rMSCs; (2) the pre-activated MSCs are more effective than the standard preparations of MSCs; (3) one-time IC injection of MSCs are effective at lower doses than topical application.

It is possible that human proteins from hMSCs may not be as effective in the rat model as rMSCs. However, it is believed that hMSCs are as effective as rMSCs, because proteins are highly conserved across species, and it has been previously found that hMSCs worked in various murine models of inflammation (Lee et al., 2009; Block et al.; 2009; Ohtaki et al. 2008; Iso et al., 2007; Ortiz et al., 2007; Lee et al., 2006; Munoz et al., 2006). However, if it is observed that hMSCs are ineffective in rats, rMSCs can be used instead of hMSCs.

MSCs activated with TNF-α may either be ineffective or may produce toxic effects in cornea. It has been observed in preliminary experiments that the activation of hMSCs with TNF-α significantly upregulated some factors to modulate inflammation and other factors to increase cell survival (Lee et al., 2009). However, if TNF-α activation is found ineffective, MSCs can be pre-activated with IFN-μ, IL-1B, or their combinations as reported previously (Ren, et al., 2008). If ineffective, unmodified MSCs can be used for further experiments.

Example 5

Inflammation and Neovascularization of the Cornea can be Reduced by Application of Two of the Therapeutic Proteins Produced by Activated MSCs: The Anti-Inflammatory Protein TSG-6 and the Anti-Apoptotic Protein STC-1

The following experiments were designed to assess the effectiveness of using TSG-6 and STC-1 for treating inflammation and neovascularization of the cornea. Administration of recombinant proteins is an alternative to administering MSCs to the mammal in need thereof. The experiments are carried out as summarized in Table 5.

TABLE 5

| Expt. | Protein | Delivery | Dose | # Rats |
|---|---|---|---|---|
| 1. | TSG-6 | Topical | 1 μg | 10 |
|  |  |  | 10 μg | 10 |
|  |  |  | 100 μg | 10 |
| 2. | STC-1 | Topical | 1 μg | 10 |
|  |  |  | 10 μg | 10 |
|  |  |  | 100 μg | 10 |
| 3. | TSG-6 + STC-1 (1:1) | Topical | 1 μg | 10 |
|  |  |  | 10 μg | 10 |
|  |  |  | 100 μg | 10 |
| 4. | TSG-6 | IC | 0.1 μg | 10 |
|  |  |  | 10 μg | 10 |
|  |  |  | 100 μg | 10 |
| 5. | STC-1 | IC | 0.1 μg | 10 |
|  |  |  | 1 μg | 10 |
| 6. | TSG-6 + STC-1 (1:1) | IC | 0.1 μg | 10 |
|  |  |  | 1 μg | 10 |
|  |  |  | 10 μg | 10 |
|  |  |  | Total | 180 |

Briefly, recombinant TSG-6 (R & D Systems, Minneapolis, Minn.), recombinant STC-1 (BioVendor Laboratory Medicine, Inc.; Czech Republic), and their combinations are applied, respectively, to rat eyes using an appropriate delivery method. If topical application is used, the doses of TSG-6 can be varied from 1 to 100 ng (Lee et al., 2009). Alternatively, if IC injection is used, dosage from 0.1 to 10 ng can be used. The same range of doses are also tested with recombinant STC-1. The maximally effective dose of each protein are determined. Then the proteins are prepared in 1:1 mixtures and the maximally effective dose again are determined.

Without wishing to be bound by any particular theory (1) administration of either TSG-6 or STC-1 is effective in suppressing corneal inflammation and promoting epithelial wound healing in a dosage-dependent manner; (2) alternatively, administration of 1:1 mixtures may be effective at lower doses because of synergistic effects of the proteins; (3) intracameral administration of either or both proteins may be effective in lower doses than topical application.

Example 6

Novel Therapeutic Factors Produced by hMSCs in Response to Corneal Injury

The invention is not limited to only TSG-6 and STC-1. That is, the currently available data do not exclude the hypothesis that MSCs produce their beneficial effects on tissue repair by expression of other therapeutic genes. Therefore, experiments can be designed to test for additional therapeutic genes expressed by MSCs in the rat model for corneal injury. As indicated in the accompanying scheme set forth in FIG. 14, the experiments can be carried out in three complementary phases: Phase I: use hMSCs in the rat model for corneal injury, isolate the total RNA from the treated corneas and assay the total RNA on species-specific microarrays followed by filtering the data from cross-hybridization of the probes. Phase II: repeat the in vivo experiments using rat MSCs that express GFP (available from our NCRR/NIH center for distribution of MSCs), enzymatically digest the samples of cornea, isolate the GFP-expressing rMSCs by FACS sorting, and analyze the RNA with a rat-specific microarray. Phase III: carry out co-culture experiments in transwells with injured corneal epithelial cells (FIGS. 7 and 8) so that the RNA from the MSCs and the target cells can be isolated separately. The microarray data from the three phases of the experiments can be used to identify candidate therapeutic genes using the following criteria: (i) genes upregulated by hMSCs or rMSCs by incubation with injured cornea or corneal epithelial cells, (ii) genes for secretory proteins, and (iii) genes whose functions suggest that they may have anti-inflammatory or immunosuppressive effects. Verifying the roles of the candidate genes can be done using real-time RT-PCR, ELISAs or Western blots, knock down of the specific genes in MSCs with siRNAs or lentiviruses, blocking antibodies, and replacement of the MSCs by the recombinant proteins (FIGS. 10 through 13).

The materials and methods employed in the experiments disclosed herein are now described.

Assays for hMSCs in the Rat Model for Corneal Injury

Figure 9A:
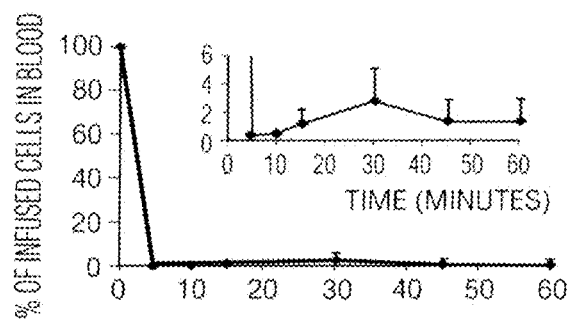
FIGS. 9A through 9F, is a series of images depicting assays for the fate of hMSCs infused into mice.
Figure 9B:
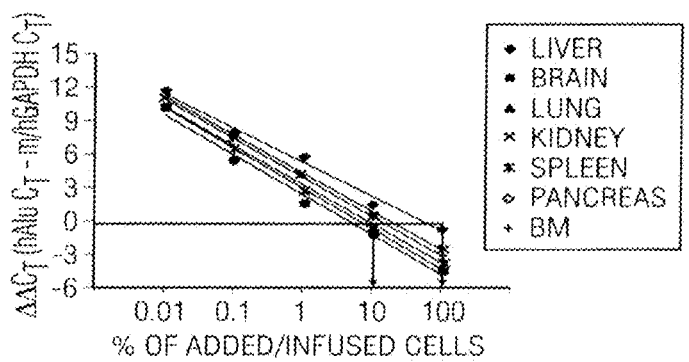
Figure 9C:
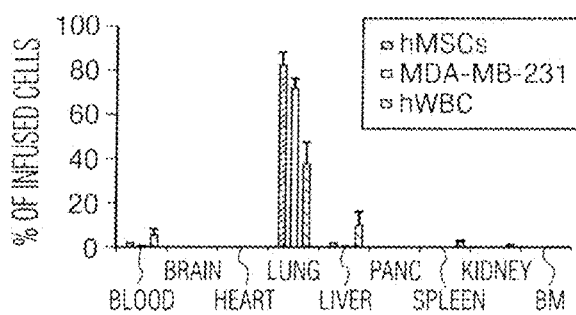
Figure 9D:
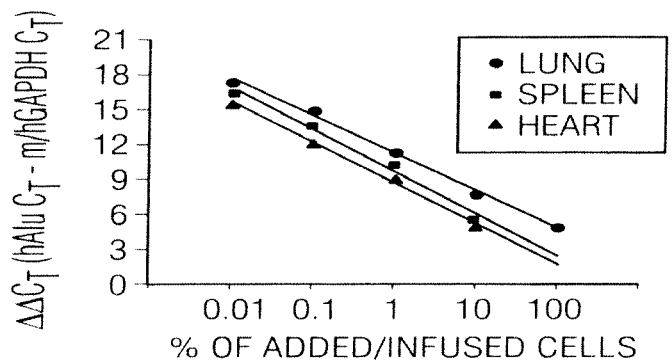
Figure 9E:
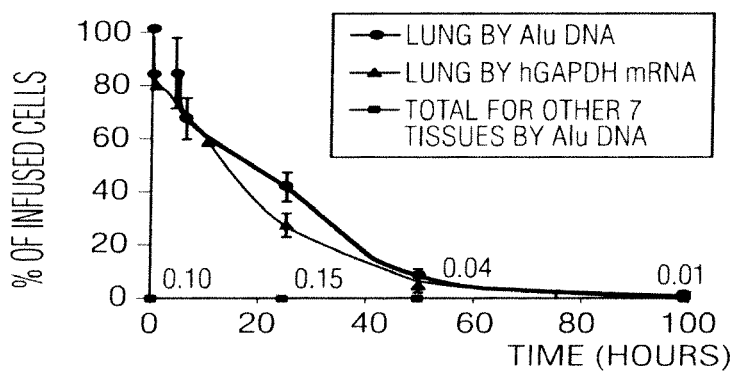
Figure 9F:
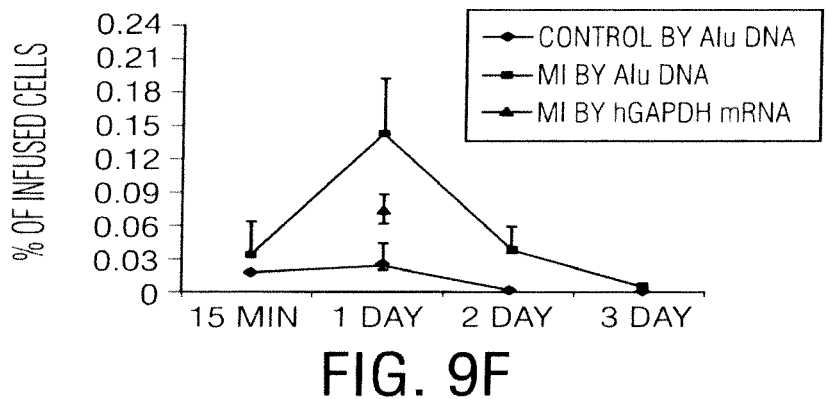

Immediately after injury, the hMSCs ($2 \times 10^6$ cells/200 μl) are placed into an applicator and allowed to remain on the damaged cornea for two hours (FIG. 2A). Eyelids are sutured for rats not to blink in order to prevent the shedding of transplanted cells. One day, one week, two weeks, and three weeks later, the corneas are excised, homogenized (PowerGen; Fisher Scientific), extraction of DNA (Phase Lock Gel; Eppendor/Brinkmann Instruments) and the DNA assayed for the highly repetitive Alu sequences, unique to the human genome, to follow the fate of hMSCs in rat eyes (FIG. 9B). The use of Alu sequences provides a highly sensitive assay since there are about 500,000 copies per cell. However, preliminary experiments indicated that use of conventional procedures greatly overestimated the content of human cells. Therefore, an improved protocol based on the chemical assay for extracted DNA and standard curves for real-time RT-PCR of each tissue is used, The assay for Alu sequences is complemented with a less sensitive assay extracted RNA (Trizol reagent, Invitrogen) human mRNA for GAPDH in order to assay live human cells in the rat tissues (FIG. 9D). The results provide quantitative data on the engraftment of the hMSCs.

Assays of Human and Rat mRNAs in Cornea by Microarrays

To examine the changes occurring in hMSCs applied in injured rat cornea and the changes in rat cornea caused by hMSCs, RNA will be isolated from cornea (Trizol; Invitrogen), and assayed on both rat and human microarrays (Affymetrix, Santa Clara, Calif.). Data will be filtered for cross-hybridization (Ohtaki et al., 2008; Lee et al., 2009), analyzed with the dChip program, and normalized to a variance of 2 SD. For cross-hybridization, three control groups were needed: (i) uninjured rat cornea treated with vehicle, (ii) injured rat cornea treated with vehicle, and (iii) uninjured rat cornea treated with hMSCs. After an analysis of human genes upregulated 2 fold or more in hMSCs, candidate genes to confirm the data by human-specific real-time RT-PCR assays will be selected.

Real-Time RT-PCR and ELISA Analysis

To determine whether the candidate genes are upregulated in cultured hMSCs, real-time RT-PCR is performed in cultured hMSCs. Double stranded cDNA is synthesized (SuperScript III; lnvitrogen) and analyzed by real time RT-PCR (ABI 7900, Sequence Detector; Applied Biosystems). Human-specific primers are obtained from commercial sources or designed from gene sequences. The data is further verified by human-specific ELISA assays either from commercial sources or with kits developed from commercial antibodies. Alternatively, expression of the proteins are verified by Western blots where antibodies are available.

Figure 13:
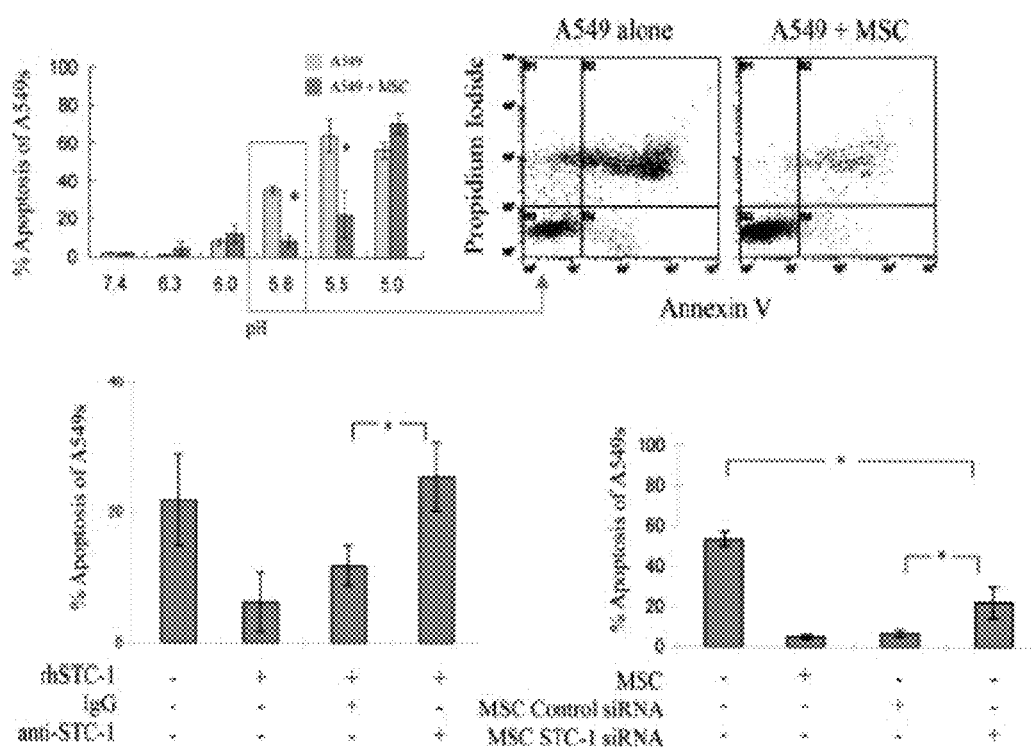
FIG. 13 is an image demonstrating that STC-1 was required and sufficient for reduction of apoptosis of lung epithelial cell line made apoptotic by incubation at low pH in hypoxia. Upper left and right: Cultures of A549 cells became apoptotic when incubated for 24 hours in 1% oxygen at pH 5.8 or 5.5. However, coculture of A549 cells in transwells with MSCs reduced the apoptosis. Lower left: Apoptosis of A549 cells was inhibited by rhSTC-1, and the effects were reversed by anti-STC-1 antibodies. Lower right: MSCs transduced with siRNA for STC-1 were less effective than control MSCs in decreasing apoptosis of A549 cells in the transwell experiment.
Figure 14:
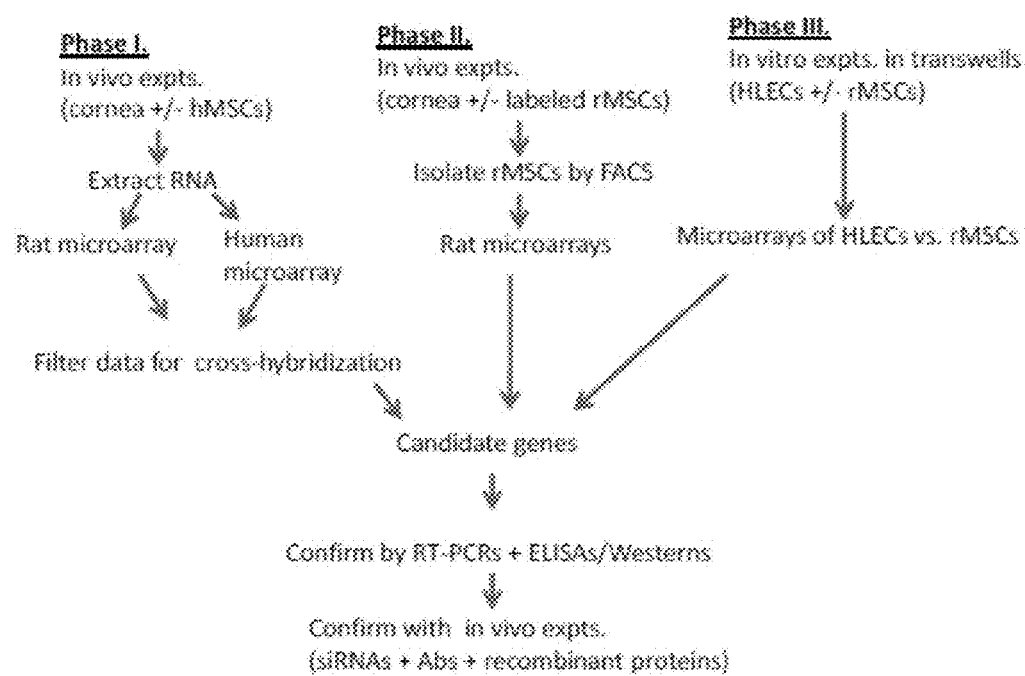
FIG. 14 is a schematic of a strategy to search for additional, novel therapeutic factors produced by hMSCs in response to corneal injury.

Confirmation with Recombinant Protein, siRNA, and Blocking Antibodies

Where recombinant protein is available for the candidate gene selected above, the protein is applied in a rat model to assess whether the protein mimics the effects of MSCs. In addition, MSCs with a knock down of the selected gene either with an siRNA or lentivirus is tested (FIGS. 11 E and F). Also, where blocking antibodies are available, they can be tested in the rat model (FIG. 13).

Assays from Co-Culture in Transwells

The experiments are performed with both hMSCs and rMSCs as described in FIGS. 7 and 8. The separate cell fractions are first assayed with microarrays and the roles of candidate genes confirmed as above.

The results of these experiments are now described. Without wishing to be bound by any particular theory, it is believed that: (1) one or more of the additional cornea-protective genes can be identified from the microarray data; (2) the protein from the candidate gene(s) can be expressed at increased levels in the rat model and the co-cultures with injured lens epithelium; (3) the application of the candidate protein(s) is as effective in suppressing corneal inflammation as hMSCs; (4) both hMSCs not expressing the gene and hMSCs combined with blocking antibody fail to produce beneficial effects on rat model.

Example 7

The Anti-Inflammatory and Anti-Apoptotic Proteins from Adult Stem/Progenitor Cells (MSCs) Protect the Cornea from Injury by Preventing Apoptosis and Suppressing Inflammation The following experiments were designed to determine whether inflammation of the cornea can be reduced by application of two of the therapeutic proteins produced by activated MSCs: the anti-inflammatory protein TSG-6 and/or the anti-apoptotic protein STC-1.

Figure 15:
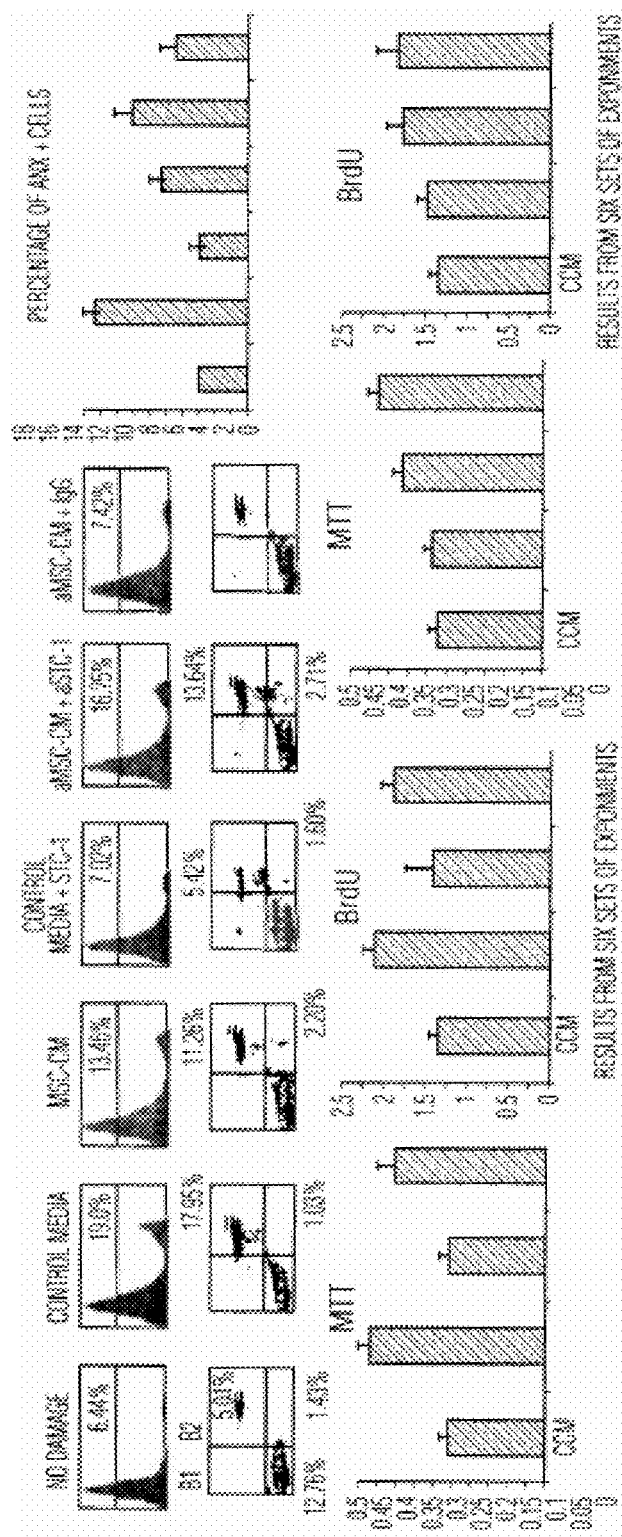
FIG. 15 is a series of images demonstrating that conditioned medium from pre-activated MSCs and rhSTC-1 had the greatest effects in hMSCs improving the viability, increasing the proliferation, and inhibiting the apoptosis of damaged hCEPs.

To test the anti-apoptotic effect of STC-1 in vitro, human corneal epithelial progenitor cells (hCEPs) after exposure to ethanol were cultured for 24 hours with one of the following: (a) conditioned medium from standard cultures of human MSCs (hMSCs), (b) conditioned medium from hMSCs pre-activated to express therapeutic factors by incubation with TNF-α for 24 hr, (c) rhSTC-1, (d) conditioned medium and blocking Ab against rhSTC-1, or (e) IgG. Both fresh medium and the medium conditioned from cultures of human dermal fibroblasts were used as controls. After incubation, the cell viability, proliferation and apoptosis were evaluated using MTT assay, BrdU uptake, and PI/annexin flow cytometry. It was observed that conditioned medium from pre-activated MSCs and rhSTC-1 had the greatest effects in hMSCs improving the viability, increasing the proliferation, and inhibiting the apoptosis of damaged hCEPs (FIG. 15).

Figure 16:
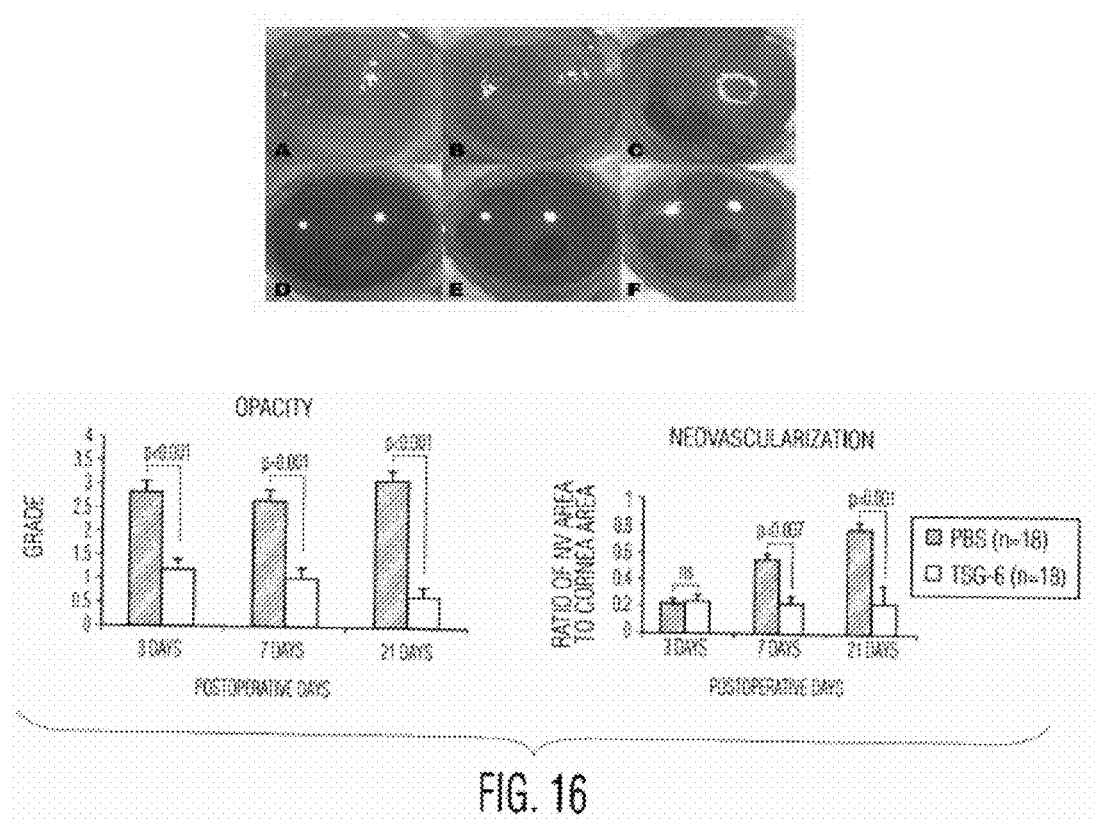
FIG. 16, comprising panels A through panel F, is a series of images demonstrating that intracameral injection of TSG-6 (2 ug) decreased corneal opacity and neovascularization in cornea after injury.
Figure 17:
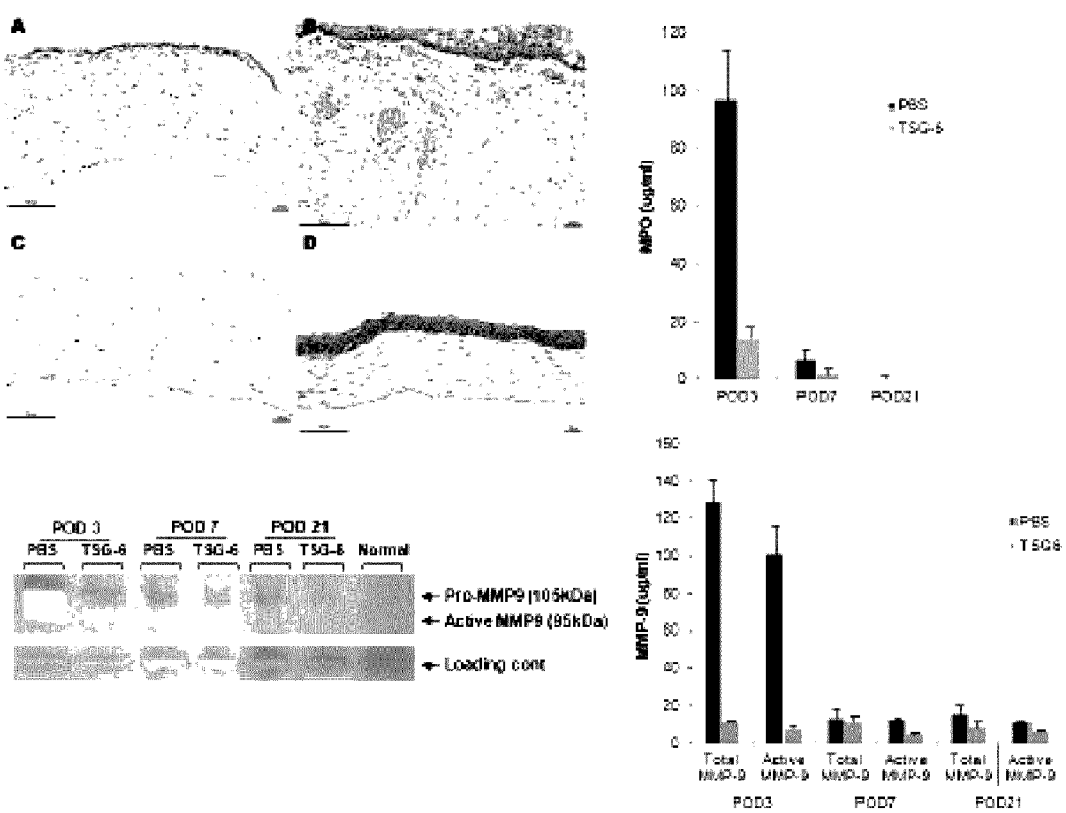
FIG. 17, comprising Figures panel A through panel D, is a series of images demonstrating intracameral injection of TSG-6 (2 ug) decreased the infiltration of neutrophils and production of MMP-9 in cornea after injury.
Figure 18:
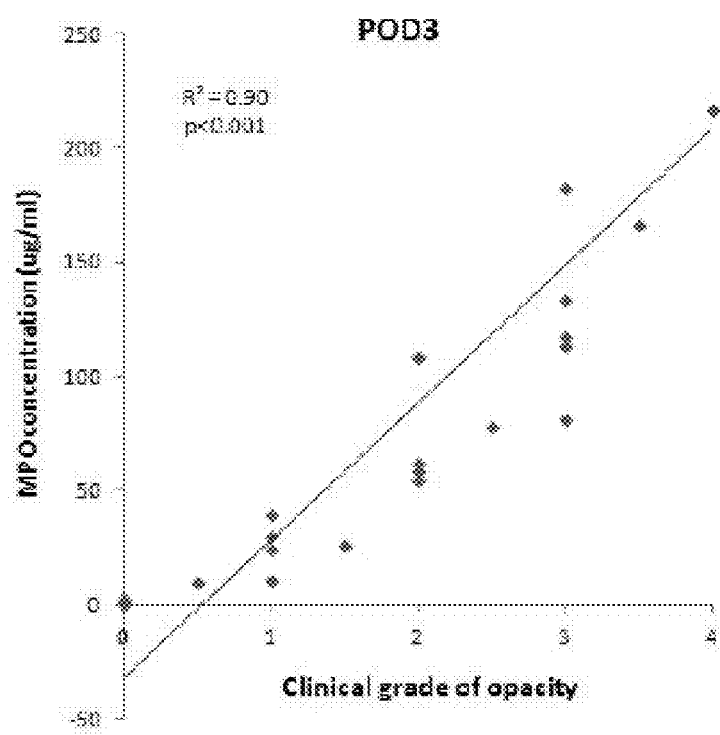
FIG. 18 is a graph depicting correlation between clinical opacity and MPO amount in cornea at post-injury 3 days.
Figure 20:
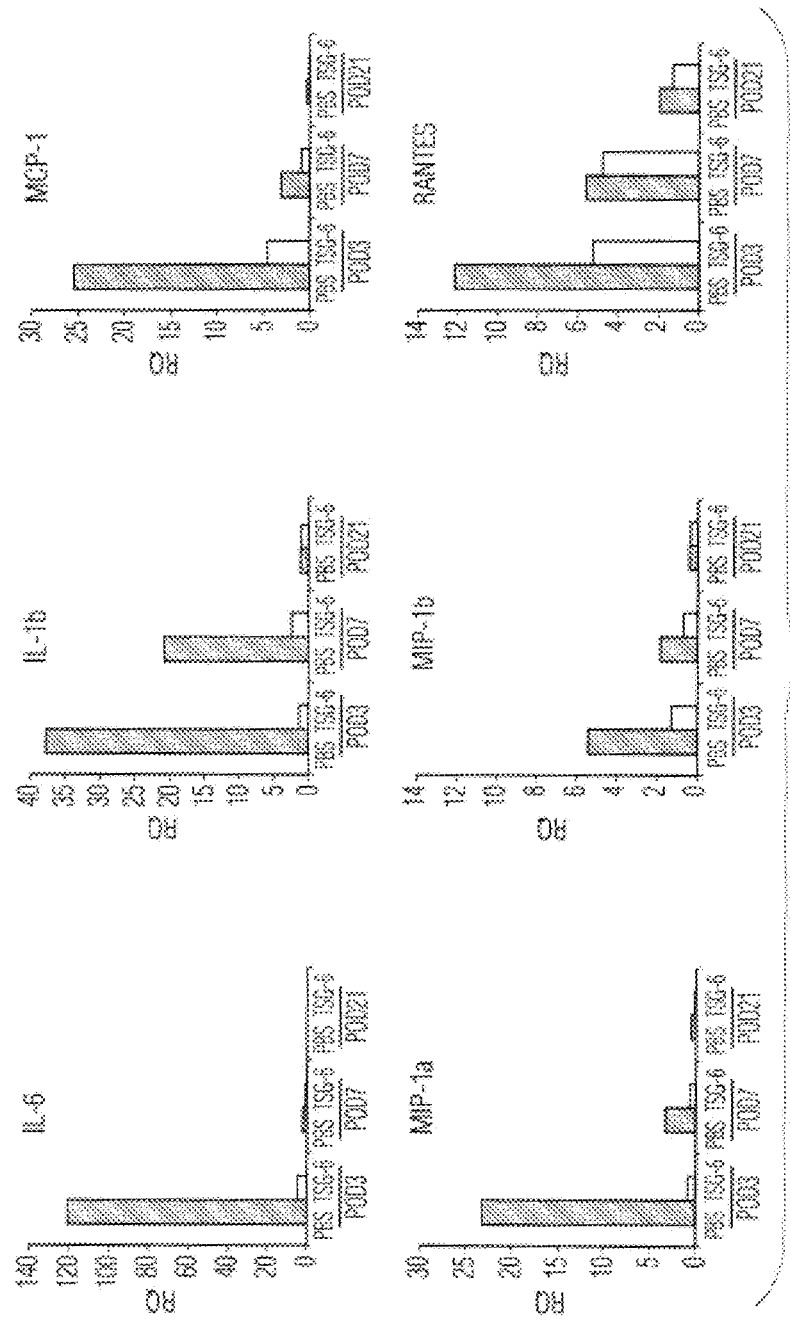
FIG. 20 is an image depicting real time PCR for inflammatory cytokines and chemokines. RQ: relative gene expression. Comparisons are between vehicle treatment (PBS) and TSG-6 treatment (2 micrograms) on post-operative days (POD) 3, 7, and 21.
Figure 21:
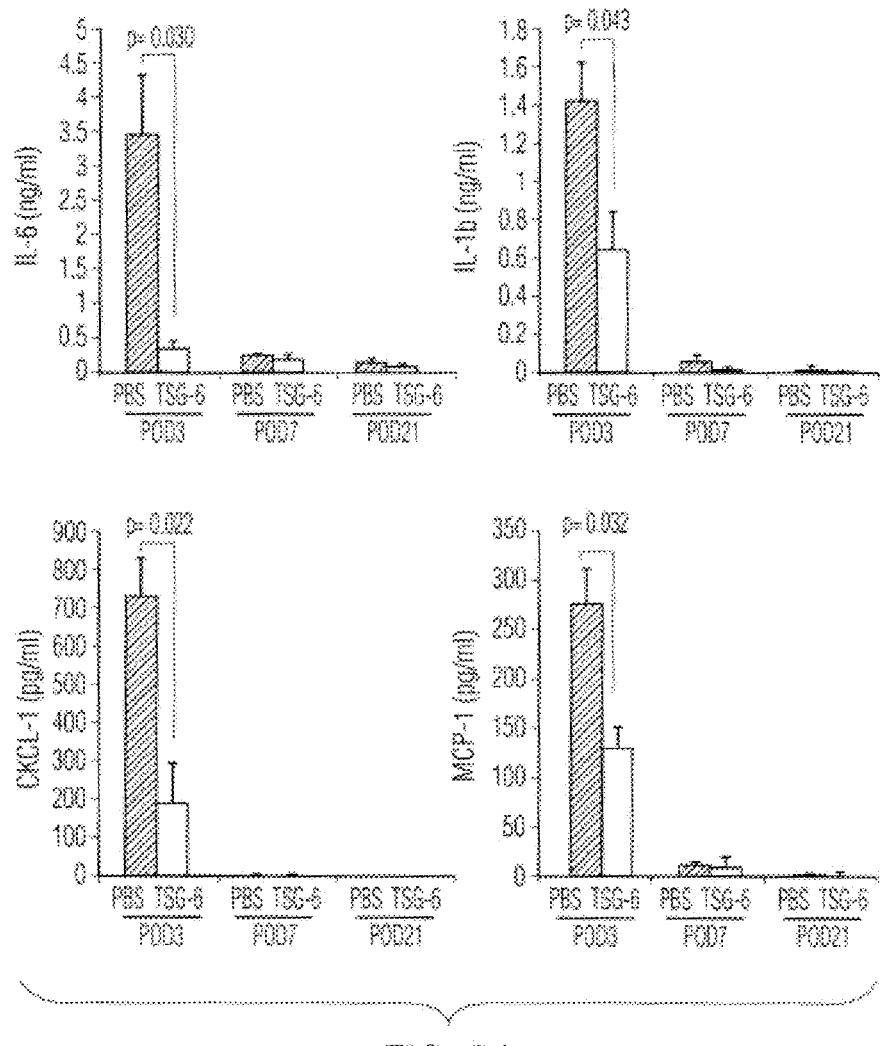
FIG. 21 is an image depicting ELISA for cytokines and chemokines. Conditions as in FIG. 20.
Figure 22:
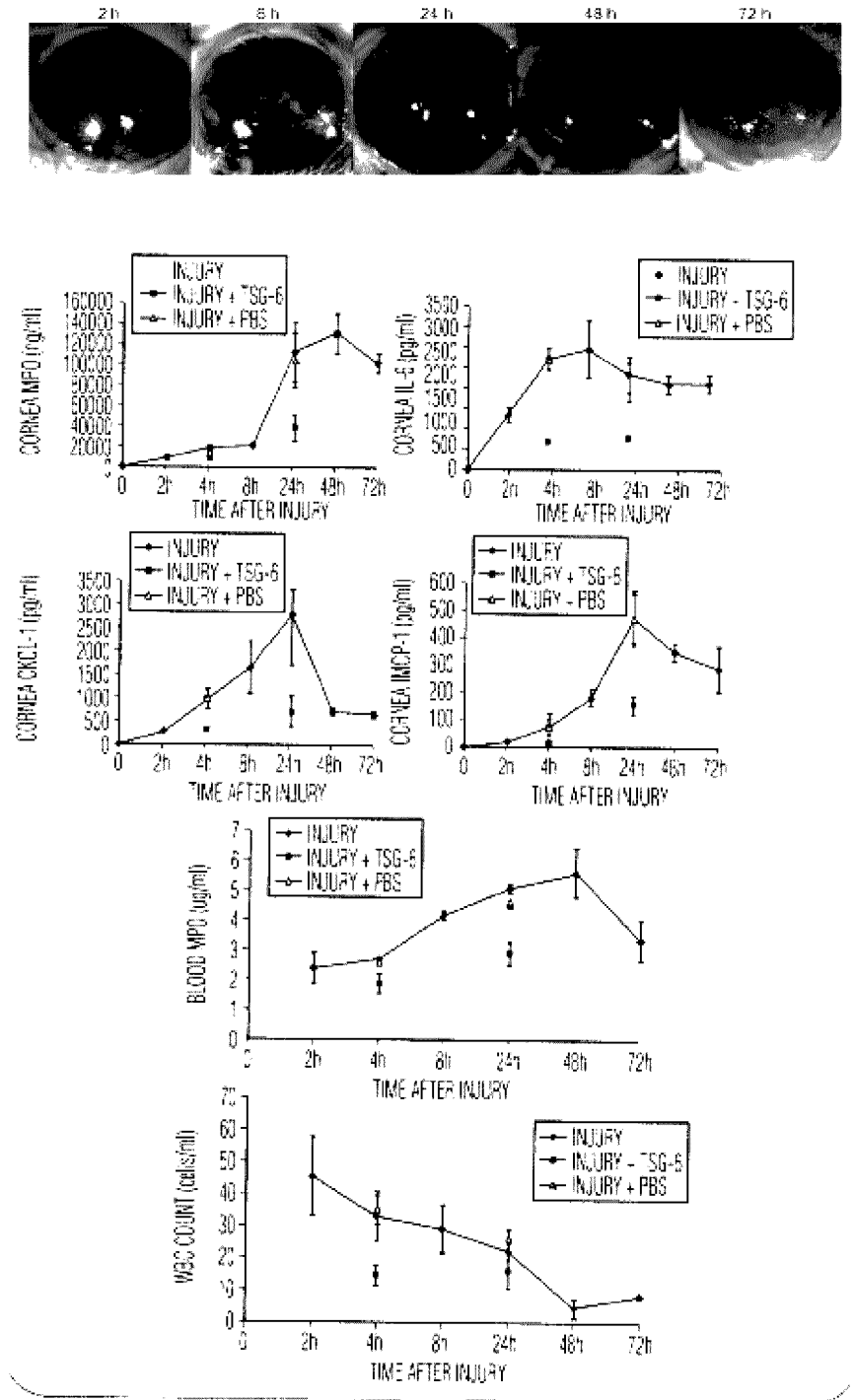
FIG. 22 is an image demonstrating that TSG-6 delayed the time neutrophils started to infiltrate and arrived at its peak as well as decreased the amount of infiltrated neutrophils. The expression pattern of chemokines and cytokines showed similar kinetics. Lower two frames: Blood levels of MPO and leukocytes (WBC).

To test the anti-inflammatory effect of TSG-6 in vivo, corneal surface inflammation was created in Lewis rats by ethanol application and mechanical debridement of corneal and limbal epithelium Immediately after injury, rhTSG-6 (2 ng-2 ug) or the same volume of PBS was injected into the anterior chamber. Effects on the cornea were determined in three ways: (1) gross examination by slit-lamp biomicroscopy based on the findings of transparency and neovascularization (NV), (2) histological analysis for infiltration of inflammatory cell (hematoxylin-eosin staining), (3) myeloperoxidase (MPO) assay for infiltration of neutrophils, (4) ELISA and real time PCR for inflammation-related chemokines and cytokines, (5) Gel zymography and ELISA for total and active MMP-9. Changes in inflammatory markers in systemic circulation were also determined by WBC counting and serum MPO evaluation. It was observed that corneal opacity and neovascularization were significantly decreased in TSG-6-treated corneas compared to PBS-treated controls (FIG. 16). The infiltration of inflammatory cells and expression of MMP-9 were significantly decreased in TSG-6-treated corneas compared to PBS-treated controls (FIG. 17). It was also observed that TSG-6 up to the concentration of 0.002 ug/ml was effective in reducing corneal opacity, inflammation, and MMP-9 production (FIG. 19). Furthermore, it was observed that administration of TSG-6 decreased the expression of inflammatory cytokines and chemokines (FIGS. 20, 21, 22).

The results presented herein demonstrate that therapeutic proteins produced by MSCs in response to an injury signal can protect the corneal surface from damage by increasing the viability and proliferation of corneal epithelial progenitors and by suppressing inflammation in corneal surface.

Example 8

Effect of Intravitreal Administration of STC-1 in Rat Models of Retinal Degeneration 1.1. Rationale.

To determine whether intravitreal administration of STC-1 delays photoreceptor degeneration in vivo, two rodent models of retinal degeneration were used. S334ter-3 rhodopsin transgenic rats were treated at postnatal day 9 (P9) and again at P12 with intravitreal injections of 1 µg STC-1. The rats were sacrificed at P19. Histologic analysis revealed increased outer nuclear (ONL) thickness compared to uninjected (UI) controls. Mean ONL thicknesses of inferior (inf), superior (sup), and total retina were quantified as described previously in Lewin, et al., *Nat Med.* Vol. 4, No. 8, pgs. 967-971 (1998). Total retina ONL thickness was increased significantly in STC-1 treated rats (n=4, p=0.018) (FIG. 23).

Figure 24:
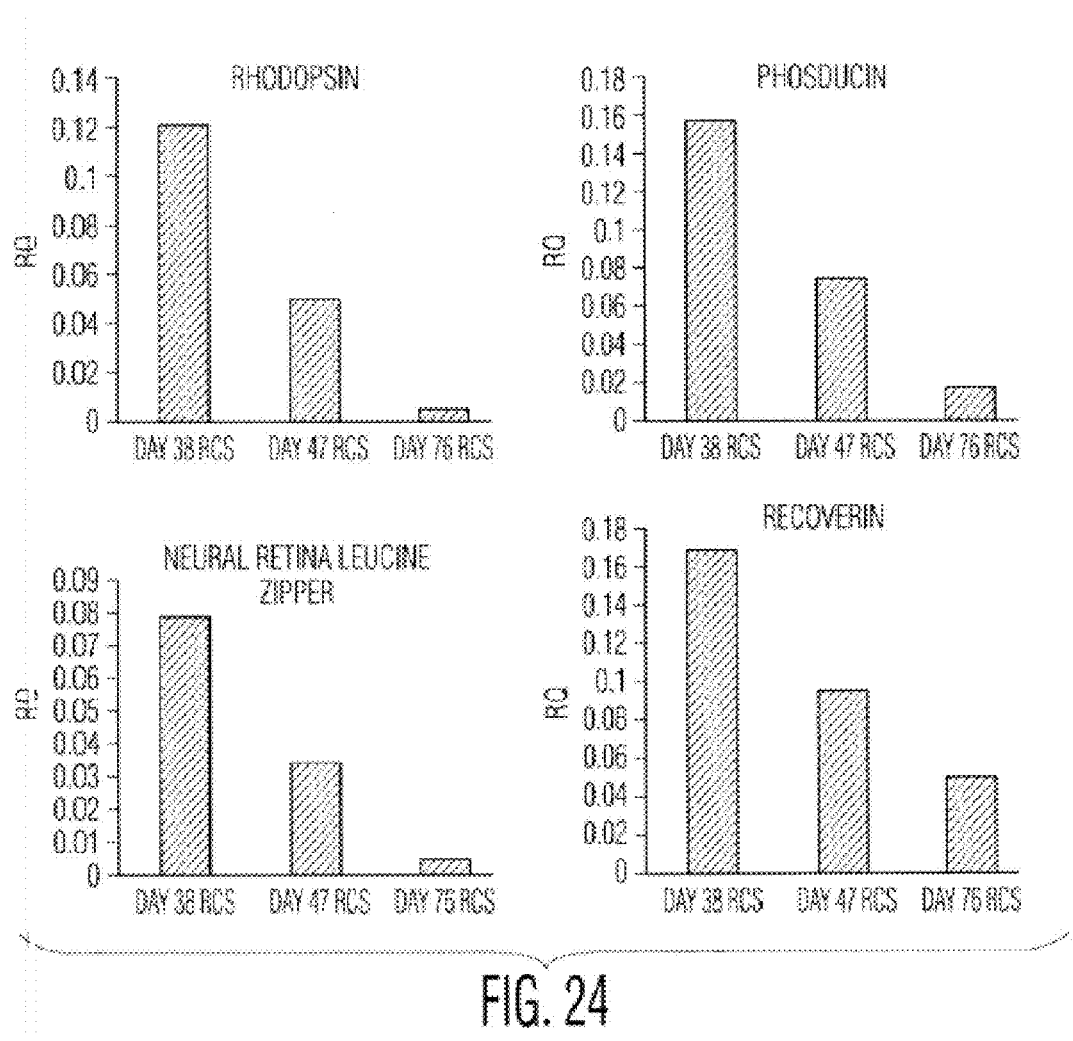
FIG. 24. Age-related loss of mRNAs for photoreceptors in RCS rat. qRT-PCR analysis for the photoreceptor genes: rhodopsin, phosducin, neural retina leucine zipper, and recoverin. Expression of these genes decreases over time in the RCS rat. For qPCR methods see Lee, 2008.

Additionally, the Royal College of Surgeons (RCS) rat model of retinal degeneration was tested. As part of these studies, a gene expression assay was developed that could be used in conjunction with histologic and functional analysis to detect photoreceptor rescue. Expression of photoreceptor specific genes was tested by quantitative real-time PCR (qRT-PCR) in retinas isolated from RCS rats at varying timepoints. Photoreceptor gene expression was shown to decrease over time in the RCS rat in rates comparable with the previously described decline of the ONL in LaVail, et al., *Exp Eye Res.*, Vol. 21, No. 2, pgs. 167-192 (1975) (FIG. 24).

Figure 25:
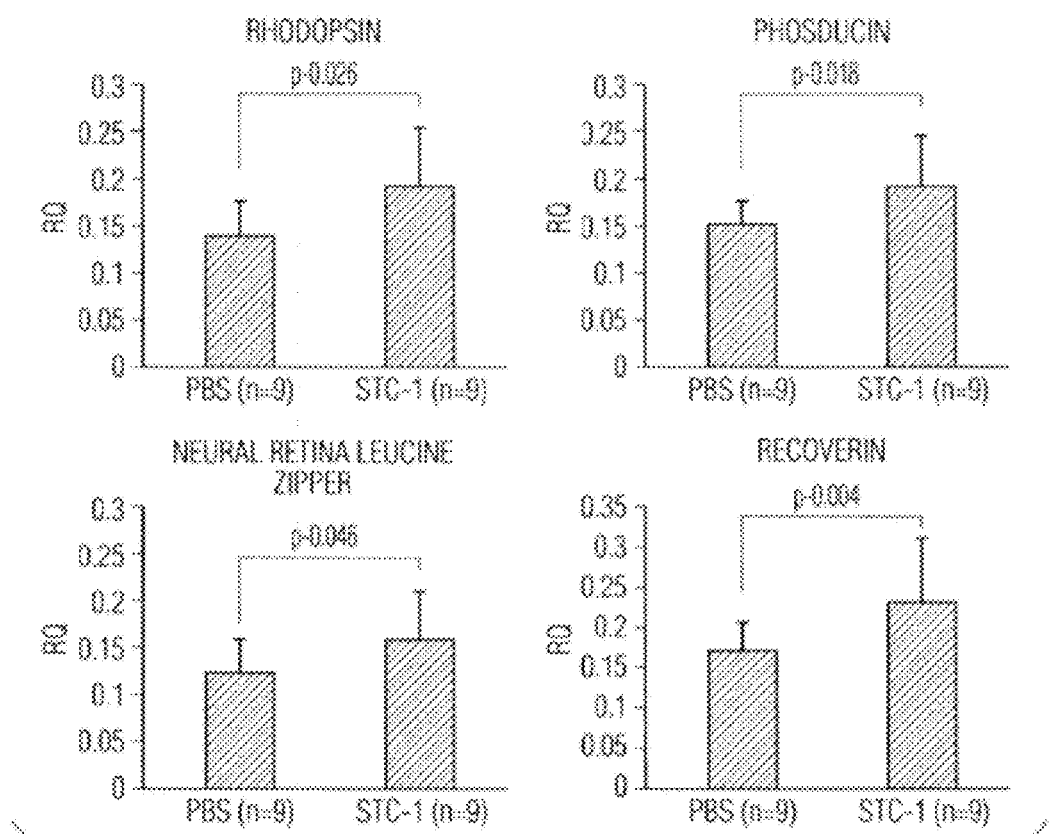
FIG. 25. Rescue of mRNAs for photoreceptors by intravitreal injection of STC-1 in RCS rat. qRT-PCR analysis for photoreceptor genes was conducted as described with respect to FIG. 24.

Utilizing this assay as a basis for quantification of photoreceptor viability, the hypothesis that intravitreal administration of STC-1 would improve photoreceptor viability was tested. Rats received an intravitreal administration of 2.5 μg STC-1. Injections occurred at P21, the approximate time of initiation of ONL decline (LaVail, 1975). The rats were sacrificed, and tissue was collected at P40. Total RNA from the retinas of the rats was extracted using the RNeasy mini kit. (Qiagen). cDNA was generated by reverse transcription (Super Script III; Invitrogen) using 1 μg total RNA. Real time amplification was performed using the Taq Man Universal PCR Master Mix (Applied Biosystems). An 18S rRNA probe (Taq Man) was used for normalization of gene expression. Gene expression analysis showed significant increases in photoreceptor gene expression in STC-1 treated animals compared to PBS injected controls (FIG. 25).

1.2. Design.

Intravitreal administration of STC-1 reduced photoreceptor degeneration in two rodent models of retinal degeneration. As described hereinbelow, the next set of experiments is directed to optimizing the dose, time of administration, and frequency of administration of STC-1 in the RCS rat.

1.2.1. Optimization of Dose of STC-1.

First, the dose of STC-1 which preserves photoreceptor viability most effectively (STC-1$^{OptD}$) is determined. The experiments are carried out as summarized in Table 6. For this experiment, STC-1 is injected at P21 and tissues are harvested at P40. The results are assessed on the basis of photoreceptor gene expression (see FIG. 24).

TABLE 6

Dose of STC-1.

| Therapy | Dose (μg) | Injection | Termination | Evaluations | No. (RCS Rat) |
|---|---|---|---|---|---|
| STC-1 | 2.5 | P21 | P40 | qRT-PCR | 6 |
|  | 1.0 | P21 | P40 | qRT-PCR | 6 |
|  | 0.5 | P21 | P40 | qRT-PCR | 6 |
|  | 0.1 | P21 | P40 | qRT-PCR | 6 |
|  | 0.05 | P21 | P40 | qRT-PCR | 6 |
| PBS | 0 | P21 | P40 | qRT-PCR | fellow eye |

P21, postnatal day 21;
P40, post-natal day 40.
qRT-PCR, for photoreceptor genes as described in FIG. 24.;
fellow eye, indicates the fellow (contralateral) eye is injected as an internal control.
Milestone: Optimal dose of STC-1 = STC-1$^{OptD}$.

In parallel Experiments, as outlined in Table 7 below, the optimal time of administration will be defined and whether two injections are more effective than one will be determined.

TABLE 7

Day of injection and number of treatments.

| Therapy | Dose | 1$^{st}$ inj. | 2$^{nd}$ inj. | Termination | Evaluations | No. (RCS Rat) |
|---|---|---|---|---|---|---|
| STC-1 | STC-1$^{OptD}$ | P14 | none | P40 | qRT-PCR | 6 |
|  | STC-1$^{OptD}$ | P14 | P21 | P40 | qRT-PCR | 6 |
|  | STC-1$^{OptD}$ | P21 | P28 | P40 | qRT-PCR | 6 |
|  | STC-1$^{OptD}$ | P28 | none | P40 | qRT-PCR | 6 |
|  | STC-1$^{OptD}$ | P28 | P35 | P40 | qRT-PCR | 6 |
| PBS | 0 | fellow eye | | P40 | qRT-PCR | fellow eye |

Milestone: Optimal time of administration of STC-1 = STC-1$^{OptT}$.

1.2.2. Histological and Functional Therapeutic Rescue by STC-1$^{OptD}$ and STC-1-$^{OptT}$.

Histologic and functional tests are used to test the ability of STC-1$^{OptD}$ and STC-1$^{OptT}$ to rescue retinal degeneration compared to PBS injected controls. Fixed eyes are sent for quantification of ONL thickness as described in Lewin et al., 1998. Electroretinogram (ERG) analysis is performed as described previously in Ren et al., *Exp Eye Res.*; Vol. 70, No. 4, pgs. 467-473 (2000).

TABLE 8

Histologic and functional tests of photoreceptor rescue.

| Therapy | Dose | Injection(s) | Termination | Evaluations | No. (RCS Rat) |
|---|---|---|---|---|---|
| STC-1 | STC-1$^{OptD}$ | STC-1$^{OptT}$ | P40 | Histology | 6 |
| STC-1 | STC-1$^{OptD}$ | STC-1$^{OptT}$ | P40 | ERG | 6 |
| PBS | 0 |  | P40 |  | fellow eye |

Milestone: Anatomic and functional measurements of the ability of STC-1 to rescue retinal degeneration.

2.1. Rationale.

In order to determine whether cell therapy may provide greater rescue of photoreceptor viability than protein therapy alone, the hypothesis that intravitreally administered human MSCs can survive in the rat vitreous cavity was tested. Vials of frozen passage one human mesenchymal stem cells (hMSCs) were obtained from the Center for the Preparation and Distribution of Adult Stem Cells (website accesible at medicine.tamhsc.edu/irm/msc-distribution.html). Following 24-hour recovery, the hMSCs were plated at a density of 100 cells/cm$^2$ and incubated at 37° C. in complete culture medium (CCM) with 16% fetal bovine serum (FBS) for 8 days until approximately 70% confluence was reached. Passage three cells were used for all experiments.

Figure 26:
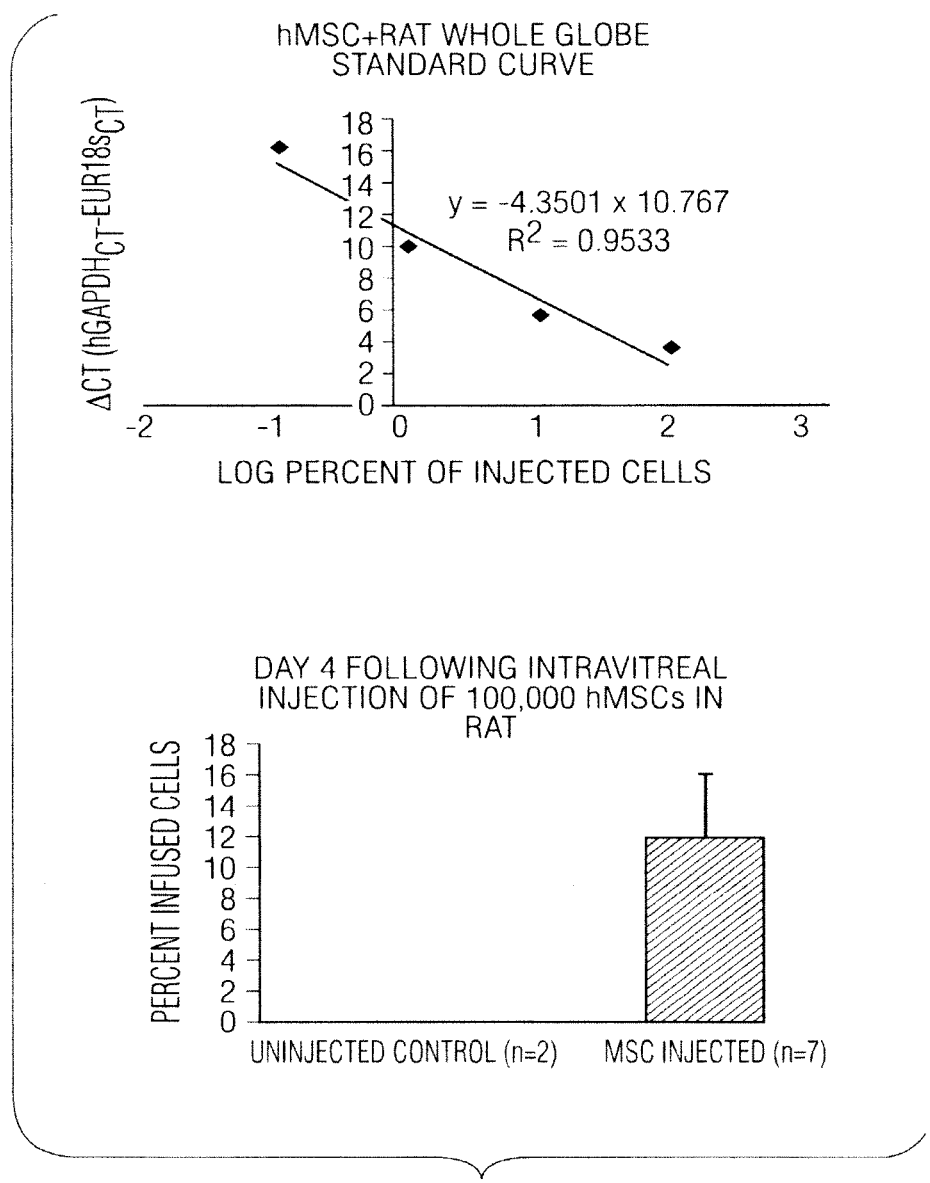
FIG. 26 MSCs survive in the vitreous cavity following injection. Left Panel: standard curve with human specific qRT-PCR for human GAPDH mRNA as a reflection of viable MSCs (see Lee, 2009 for Methods). Varying numbers of human MSCs added to whole globe just before RNA was extracted. Right Panel: Recovery of viable human cells 4 days after intravitreal injection of 100,000 human MSCs.

An intravitreal injection of 1×10$^5$ human MSCs was performed at postnatal day 21. Four days following injection the eye was enucleated and RNA was extracted from the whole globe to evaluate how many human cells remained in the eye cavity. Expression of human GAPDH (hGAPDH) was measured by qRT-PCR as hereinabove described, thereby providing an indication of any surviving human cells in the rat eye. Based on the standard curve generated (FIG. 26, Left Panel), an estimated 10-20% of injected cells remained viable for four days following injection (FIG. 26, Right Panel). Additionally, other secreted factors from MSCs including the anti-inflammatory protein TSG-6 (Lee, 2009), neurotrophic factors (Li, et al., *Graefe's Arch. Clin. Exp. Ophthalmal.*, Vol. 247, No. 4, pgs. 503-514 (2009)) such as CNTF, bDNF, or bFGF, or the retinal-protective protein LIF (Bartosh, et al., *Proc. Nat. Acad. Sci.*, Vol. 107, No. 31, pgs. 13724-13729 (2010); Joly, et al; *J. Neurosci.*, Vol. 28, No. 51, pgs. 13765-13774 (2008)) may act in conjunction with STC-1 to preserve photoreceptor viability.

Figure 27:
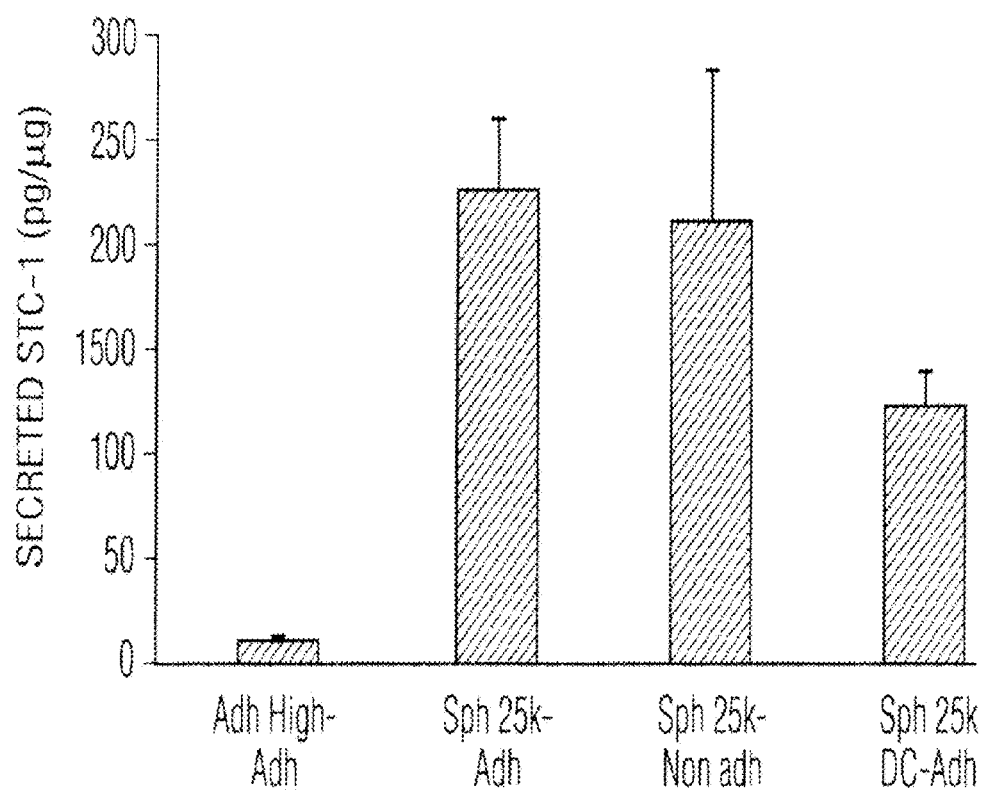
FIG. 27. Activation of expression of STC-1 by culture of human MSCs in hanging drops so that the cells coalesced into spheroids. High density monolayer (Adh High), spheroids (Sph 25k), and spheroid derived MSCs (Sph 25k DC) were transferred to 6 well plates containing 1.5 ml complete culture medium (CCM) and either 200,000 MCSs from high density cultures, eight 25k spheroids, or 200,000 MSCs. After 24 hours, medium was recovered for ELISAs and cells were lysed for protein assays. Figure adapted from (Bartosh, 2010). The results demonstrated an over 20-fold increase in secretion of STC-1 by spheroid MSCs (Sph 25k-Adh, Sph 25k-Non adh, or Sph 25k DC-Adh) compared to standard monolayer cultures of MSCs (Adh High-Adh).

MSCs in standard culture conditions express relatively low levels of therapeutic proteins unless stimulated in culture or activated in vivo by injury signals from the host (Lee, 2009; Bartosh, 2010). A recent report from our laboratory demonstrated that culturing MSCs as 3D spheroids activates the cells to produce large amounts of therapeutic molecules including STC-1 (Bartosh, 2010). Compared to standard culture preparations of MSCs, culture of the cells as 3D spheroids of 25,000 cells (Sph 25K) enhanced secretion of STC-1 about 20-fold. Spheroids can be dissociated into MSC spheroid dissociated cells (Sph 25k DC) which retain the ability to secrete high levels of STC-1 compared to monolayer MSCs (Adh High) (FIG. 27).

2.1.1. Optimization of the Dose of Sph 25k DCs.

First, the dose of Sph 25k DCs which preserves photoreceptor viability (Sph 25k $DC^{OptD}$) most effectively is determined. The experiments are carried out as summarized in Table 9. For this experiment, Sph 25k based on photoreceptor gene expression (see FIG. 24) are injected.

TABLE 9

Dose of Sph 25k DCs.qRT-PCR analysis for photoreceptor genes as described in FIG. 24.

| Therapy | Dose ($\times 10^3$ cells) | Injection | Termination | Evaluations | No. (RCS Rat) |
| --- | --- | --- | --- | --- | --- |
| Sph 25k DCs | 100 | P21 | P40 | qRT-PCR | 6 |
|  | 50 | P21 | P40 | qRT-PCR | 6 |
|  | 10 | P21 | P40 | qRT-PCR | 6 |
| MSCs | 100 | P21 | P40 | qRT-PCR | 6 |
|  | 50 | P21 | P40 | qRT-PCR | 6 |
|  | 10 | P21 | P40 | qRT-PCR | 6 |
| Fbs | 100 | P21 | P40 | qRT-PCR | 6 |
|  | 50 | P21 | P40 | qRT-PCR | 6 |
|  | 10 | P21 | P40 | qRT-PCR | 6 |
| PBS | 0 | P21 | P40 | qRT-PCR | fellow eye |

Milestone: Optimal dose of Sph 25k DCs = Sph 25k $DC^{OptD}$.

2.1.2. Optimization of the Administration Time and Frequency of Sph 25k DCs.

In parallel experiments, carried out as summarized in Table 10 below, the optimal time of administration is defined and whether two injections are more effective than one is determined.

TABLE 10

Time and frequency of administration of Sph 25 k DCs.

| Therapy | Dose | 1st inj. | 2nd inj. | Termination | Evaluations | No. (RCS Rat) |
| --- | --- | --- | --- | --- | --- | --- |
| Sph 25 k DCs | SPH 25 k $DC^{OptD}$ | P14 | none | P40 | qRT-PCR | 6 |
|  | SPH 25 k $DC^{OptD}$ | P14 | P21 | P40 | qRT-PCR | 6 |
|  | SPH 25 k $DC^{OptD}$ | P21 | P28 | P40 | qRT-PCR | 6 |
|  | SPH 25 k $DC^{OptD}$ | P28 | none | P40 | qRT-PCR | 6 |
|  | SPH 25 k $DC^{OptD}$ | P28 | P35 | P40 | qRT-PCR | 6 |

TABLE 10-continued

Time and frequency of administration of Sph 25 k DCs.

| Therapy | Dose | 1st inj. | 2nd inj. | Termination | Evaluations | No. (RCS Rat) |
| --- | --- | --- | --- | --- | --- | --- |
| PBS | 0 | fellow eye |  | P40 | qRT-PCR | fellow eye |

Milestone: Optimal time of administration of Sph 25 k DCs = Sph 25 k $DC^{OptT}$.

2.1.3. Histological and Functional Therapeutic Effects of Sph 25k $DC^{OptD}$ and Sph 25k $DC^{OptT}$.

Histologic and functional tests carried out as described in Table 11 below are used to test the ability of Sph 25k $DC^{OptD}$ and Sph 25k $DC^{OptT}$ to rescue retinal degeneration compared to PBS control.

TABLE 11

Histologic and functional tests of photoreceptor rescue.

| Therapy | Dose | Injection | Termination | Evaluations | No. (RCS Rat) |
| --- | --- | --- | --- | --- | --- |
| Sph 25k DCs | Sph 25k $DC^{OptD}$ | Sph 25k $DC^{OptT}$ | P40 | Histology | 6 |
|  | Sph 25k $DC^{OptD}$ | Sph 25k $DC^{OptT}$ | P40 | ERG | 6 |
| PBS | 0 |  | P40 | Histo/ERG | fellow eye |

Milestone: Anatomic and functional evidence of the rescue effects of Sph 25k DCs.

3.1 Rationale.

It has been proposed that patients with RP undergo cone photoreceptor death due to oxidative damage following rod photoreceptor death (Shen, 2005; Usui, Mol. Ther., Vol. 17, No. 5, pgs. 778-786 (2009)). Increased levels of oxygen have been observed in rodent models of RP including the RCS rat as photoreceptor degeneration occurs (Yu, 2004; Yu, et al., Invest. Ophthalmol. Vis. Sci., Vol. 41, No. 12 pgs. 3999-4006 (2000)). As a result of increased levels of oxygen, oxidative damage to photoreceptors has been observed both in small (Komeima, 2006) and large (Shen, 2005) animal models of RP. Further evidence includes studies that demonstrate antioxidant therapy slows photoreceptor death in animal models of RP (Komeima, 2007). The hypothesis was tested initially in an in vitro model of oxidative RPE injury. Human RPE cells from cell line ARPE-19 (ATCC Catalog No. CRL-2302), were damaged with 450 µM hydrogen peroxide as described previously in Kim, et al., Korean J. Ophthalmol., Vol. 17, No. 1, pgs. 19-28 (2003). As summarized in Table 12 below, one hour after injury, the cells were treated with 250 ng/ml STC-1, or with a vehicle (control).

TABLE 12

In vitro study using STC-1 treatment of hydrogen peroxide-damaged ARPE-19.

| Therapy | Dose | Assays |
| --- | --- | --- |
| STC-1 | 250 ng/ml | TUNEL, mito. potential, lactate production, qRT-PCR |
| Vehicle |  | TUNEL, mito. potential, lactate production, qRT-PCR |

The cells, following treatment, were evaluated for expression of a pro-apoptotic gene (caspase 3/7), cell death (Annexin V & PI staining of cells) and improved cell viability (increased activity of the mitochondrial enzyme MTT). Detection of caspase activity was performed as described in Sharma, et al., *Invest. Ophthalmol. Vis. Sci.*, Vol. 49, No. 11, pgs. 5111-5117 (2008), annexin/PI quantification as described in Bartosh, et al., *Proc. Nat. Acad. Sci.*, Vol. 107, No. 31, pgs. 13724-13729 (2010), and MTT conversion was measured as described previously in Mester, et al., *J. Mol. Neurosci.* (2010).

Figure 28:
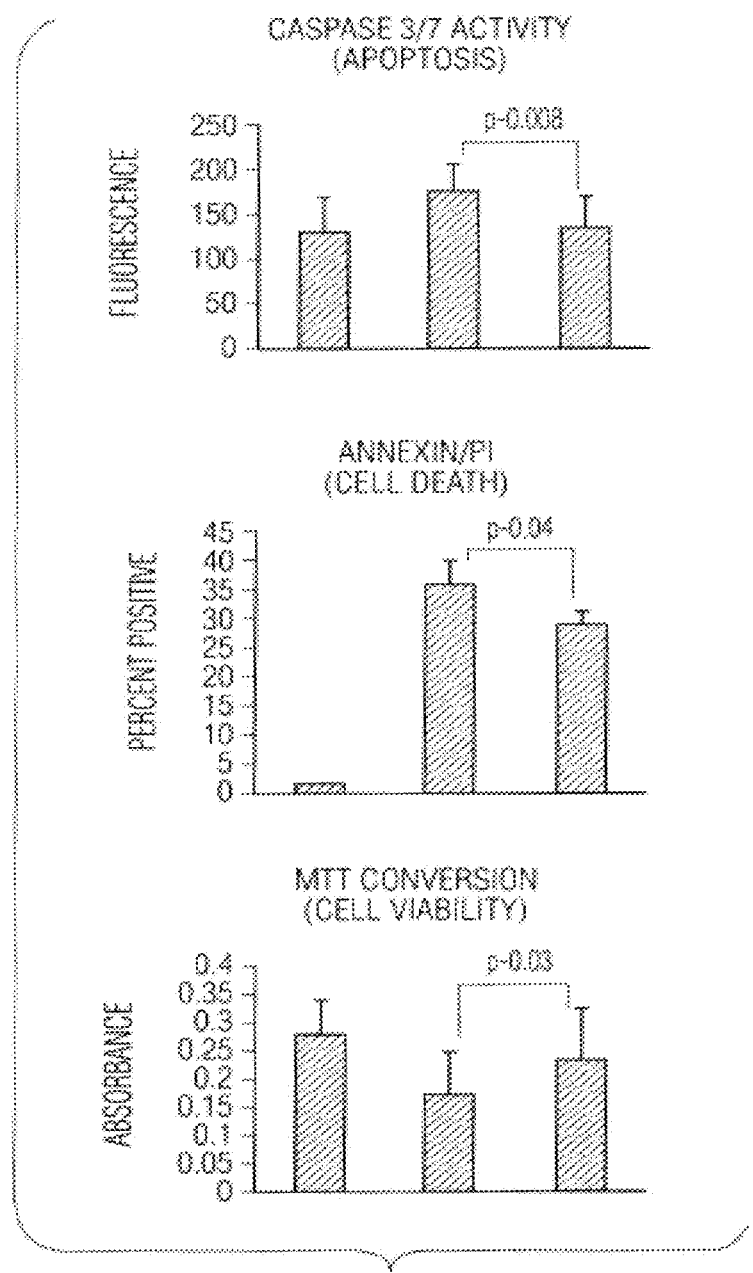
FIG. 28. Anti-apoptotic effects of STC-1 in cultures of RPE cells. Treatment with STC-1 (250 ng/mL) one hour following injury of ARPE-19 with 450 μM $H_2O_2$ reduced expression of a pro-apoptotic gene (caspase 3/7), cell death (Annexin V & PI staining cells) and improved cell viability (increased activity of the mitochondrial enzyme MTT). Detection of caspase activity was performed as described previously in Sharma, et al., *Invest. Ophthalmol. Vis. Sci.*, Vol. 49, No. 11, pgs, 5111-5117 (2008), annexin/PI quantification as described previously in Bartosh, 2010, and MTT conversion was measured as described previously in Mester, et al., *J. Mol. Neurosci.*, (2010).

Following injury, it was observed that treatment with STC-1 reduced apoptosis and improved cell viability compared to vehicle controls (FIG. 28).

Figure 29:
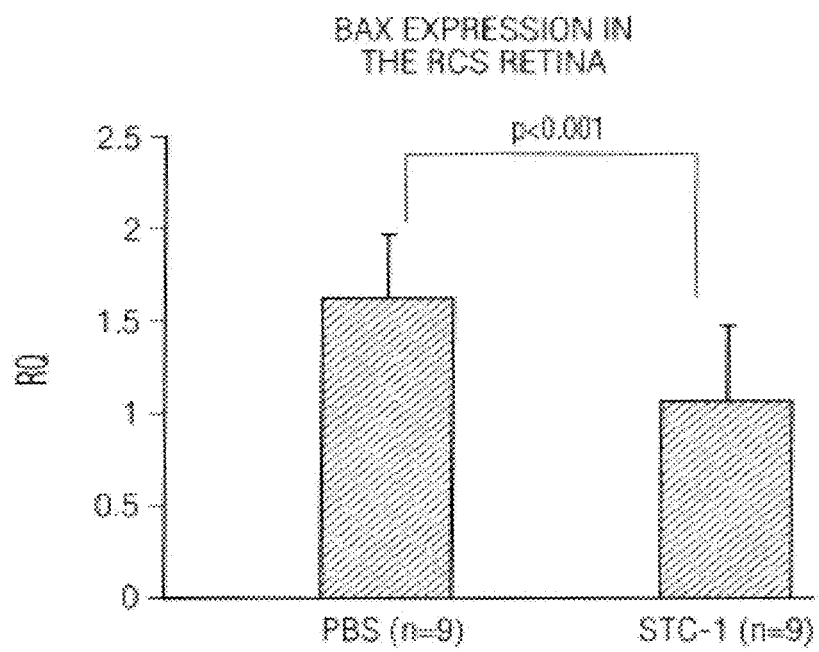
FIG. 29. Anti-apoptotic effect of STC-1 with intravitreal injection in RCS rats. Gene expression of BAX, a transcript that encodes a pro-apoptotic protein, was reduced significantly by STC-1 as quantified by qRT-PCR.

Additionally, following an intravitreal injection of 2.5 µg STC-1 in the RCS rat at P21, gene expression of BAX, a transcript that encodes a pro-apoptotic protein, is reduced significantly in the RCS retina at P40 (FIG. 29) as assessed by qRT-PCR. Therefore, these results are consistent with the idea that STC-1 inhibits apoptosis in the RCS rat retina. The hypothesis that the results are because of the ability of STC-1 to reduce reactive oxygen species by uncoupling oxidative phosphorylation then is tested.

3.2. Design.

In vitro experiments are carried out as summarized in Table 9. In vivo experiments are carried out as summarized in Table 10. First, the in vitro model of hydrogen peroxide induced ARPE-19 injury (Kim, 2003) is used. Apoptosis in vitro is evaluated using TUNEL stain, lactate production (Tanito, *Invest. Ophthalmol. Vis. Sci.*, Vol. 46, No. 3, pgs. 979-987 (2005)), and qRT-PCR. The level of reactive oxygen species, or ROS, is evaluated using measurements of mitochondrial potential. Changes in UCP2 with qRT-PCR also is evaluated.

For in vivo studies, apoptosis in the retina of RCS rats is evaluated using TUNEL stain (Mizukoshi, *Exp. Eye Res.*, Vol. 91, No. 3, pgs. 353-361 (2010)) and qRT-PCR. In addition, levels of ROS are evaluated by measuring tissue aconitase activity as described previously in Tarpey, et al., *Am. J. Physiol. Regul. Integr. Comp. Physiol.*, Vol. 286, No. 3, pgs. 431-444 (2004).

TABLE 10

In vivo study using intravitreal administration of STC-1 in the RCS rat.

| Therapy | Dose | Injection(s) | Termination | Assays | No. (RCS Rats) |
|---------|------|--------------|-------------|--------|----------------|
| STC-1   | STC-1 $^{OptD}$ | STC-1 $^{OptI}$ | P40 | TUNEL, aconitase, qRT-PCR | 6 |
| Vehicle |      |              | P40 | TUNEL, aconitase, qRT-PCR | 6 |

Example 9

Effect of Topical TSG-6 on Corneal Inflammation

Fifteen mice were anesthetized by isoflurane inhalation. In order to create a chemical burn to the cornea, 100% ethanol was applied to the whole cornea including the limbus for 30 seconds, followed by rinsing with 10 ml of balanced salt solution. The whole cornea and limbal epithelium then were scraped mechanically using a surgical blade. (See Oh et al., *Proc. Nat. Acad. of Sci.*, Vol. 107, No. 39, pgs. 16875-16880 (Sep. 28, 2010)). Two mice served as controls Immediately thereafter, 5 µl of PBS were administered intravenously or intraperitoneally to 10 mice, and 2 µg/5 µl of TSG-6 were applied topically to the corneal surfaces of 5 mice. The eyelids of the mice then were closed with one 8-0 silk suture at the lateral third of the lid margin.

Three days later, the mice were killed and the corneas were excised. The corneas then were sectioned into small pieces and lysed in 150 µl of tissue extraction reagent containing protease inhibitors (Invitrogen). The samples then were sonicated on ice and centrifuged twice (15,000×g at 4° C. for 20 minutes). The supernatants were assayed with commercial ELISA kits for myeloperoxidase (MPO) (MPO ELISA kit, Hy Cult Biotech).

Figure 30:
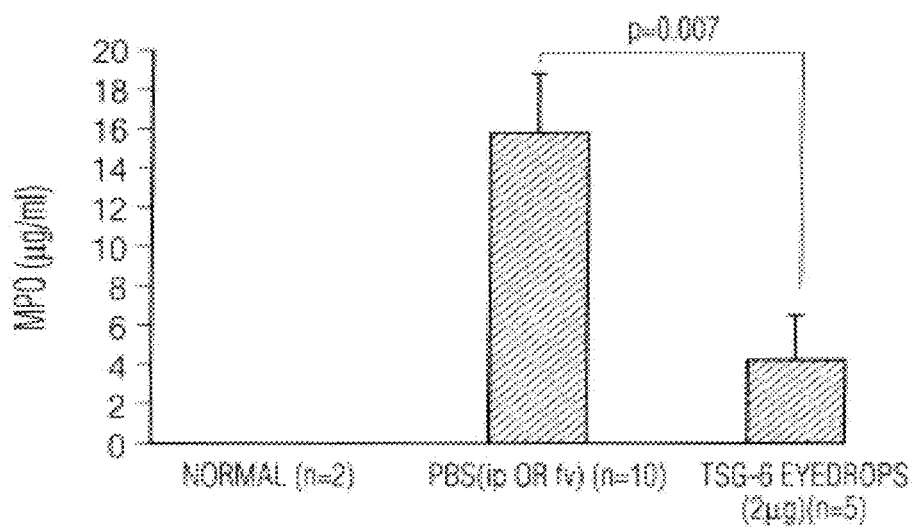
FIG. 30. Immediately after chemical and mechanical injury to mouse corneas, either PBS was administered to the mice intravenously or intraperitoneally, or TSG-6 (2 mg/5 ml) was applied to the surface of the mouse corneas. Lateral tarsorrhaphies then were performed on the eyes of the mice. Three days later, the corneas were extracted and myeloperoxidase (MPO) ELISA assays were performed.

As shown in FIG. 30, topical administration of TSG-6 suppressed corneal inflammation more effectively than the controls.

Example 10

Sterile inflammation now is recognized to play a key role in many diseases that include myocardial infarction, stroke, Alzheimer's disease, and atherosclerosis (Chen et al., *Nat. Rev. Immunol.*, Vol. 10, No. 12, pgs. 826-837 (2010); Rock et al., *Ann. Rev Immunol*, Vol. 28, pgs. 321-342 (2010); Spite et al., *Circ. Res.*, Vol. 107, No. 10, pgs. 1170-1184 (2010)). The molecular and cellular responses of sterile inflammation include over 20 nonmicrobial endogenous stimuli referred to as damage-associated molecular patterns (DAMPs) which signal through pattern recognition receptors (PRRs) on resident macrophages that activate at least three intracellular pathways to upregulate the expression of pro-inflammatory cytokines. In spite of the intense interest in the field, a series of important questions remain unanswered, including whether some DAMPs identified from roles in vitro play important roles in vivo, whether some DAMPS play redundant roles, and whether different tissues used different DAMPs (Matzinger, *Nat. Immunol.*, Vol. 8, No. 1, pgs. 11-13 (2007)).

The cornea is an attractive model system to investigate sterile inflammation because it is accessible readily to experimental manipulations in vivo and in vitro. Moreover, sterile inflammation occurs in diseases of the cornea that include limbal stem cell deficiency, chemical burns, and allergic or autoimmune keratitis (Wagner, *Surv. Ophthalmol.*, Vol. 41, No. 4, pgs. 275-313 (1997); Krachmer, *Cornea*, $2^{nd}$. Ed., Vol. 1, pgs 1179-1308). To examine the temporal sequence and stimuli for sterile inflammation, a model was used in which the cornea was injured by exposure to alcohol followed by scraping to remove the epithelium of the cornea and limbus that contains stem cells. It was observed that the injury provoked two distinct phases of neutrophil infiltration: A small initial Phase I that began in 15 mm and reached a plateau between 4 to 8 hours and a much larger second Phase II that peaked at 24 hours to 48 hours. Analysis of the two phases demonstrated that Phase I was stimulated by the neuropeptide secretoneurin and perhaps other signals. The second, more massive Phase II of neutrophil infiltration was simulated by a small heat shock protein, HSPB4, that was synthesized and released in injured keratocytes of the corneal stroma and that acted as a DAMP to activate resident macrophages.

Methods

Animals. Lewis rats (LEW/Crl) were purchased from Charles River Laboratory (Wilmington, Mass.). HSPB4 knockout mice (Cryaa$^{-/-}$) were generated originally at the National Eye Institute by targeted gene disruption and were maintained in the 129 S6/SvEvTac background (Brady et al. *Proc. Nat. Acad. Sci.*, Vol. 94, No. 3, pgs. 884-889 (1997). 129S6/SvEvTac, C57BL/6 (C57BL/6J) and CD44 knockout mice (CD44h$^{-/-}$; B6.Cg-Cd44tm1Hbg/J) were purchased from the Jackson Laboratory (Bar Harbor, Me.). All animals were used under a protocol approved by the Institutional Animal Care and Use Committee of Texas A&M Health Science Center College of Medicine.

Animal Models of Injury and Treatment

Injury was created by applying 100% ethanol to the whole cornea including the limbus for 30 seconds followed by rinsing with 10 ml of balanced salt solution. Then, the whole corneal and limbal epithelium was scraped mechanically using a surgical blade.

For injection of the recombinant human SN (PolyPeptide Laboratories, HiHerød, Denmark) or HSPB4 (Enzo Life Sciences, Plymouth Meeting, Pa.), 2 µl of the proteins in PBS (0.2 ng SN in 2 µl PBS or 100 ng HSPB4 in 2 µl PBS; the amount of SN or HSPB4 detected in the cornea at 15 min after injury) were injected using a 32 gauge needle into the corneal stroma near the temporal limbus. The proteins were purified by endotoxin binding columns and sterilized prior to use according to the manufacturer's instructions (Endo-Clear, blue; Hycult Biotech Inc. Plymouth Meeting, Pa.), and tested to be free of detectable levels of Gram-negative bacterial endotoxins (<0.01 EU/ml) or proteins (1 ng/ml) using the Limulus amoebocyte lysate kit (Hycult Biotech Inc.) and *E. coli* HCP ELISA kit (Cygnus Technologies, Southport, N.C.).

For macrophage depletion, either 100 µl of clodronate-encapsulated liposome (5 mg clodronate per ml suspension; Encapsula Nano Sciences, Nashville, Tenn.) or the same volume of PBS-encapsulated liposomes were injected subconjunctivally near the limbus on day −2 (2 days before injury) and on day 0 (day of injury). The injection was dispensed over four quadrants (25 µl each) so that a circular bleb around the cornea was formed.

For blocking the release of SN from nerve endings, 20 µl of 2 mM diltiazem solution in isotonic saline (Sigma-Aldrich, St. Louis, Mo.) was applied topically to the cornea 15 min prior to injury (Gonzalez et al., *Invest. Ophthalmol. Vis. Sci.*, Vol. 34, No. 12, pgs. 3329-3335 (1993)). For blocking HSPB4 in the cornea, either mouse monoclonal or rabbit polyclonal antibodies to rat HSPB4 (10 µg or 50 µg in 100 µl PBS; Abcam, Cambridge, Mass.) were injected subconjunctivally near the limbus right before the injury. The same concentration of isotype IgG also was injected as control.

To evaluate the effect of TLR2 inhibition in the injured cornea, rhTSG-6 (2 ng in 5 µL of PBS; R&D Systems, Minneapolis, Minn.) or the same volume of PBS was injected into the anterior chamber of the rat eye immediately after injury.

Cells and Cell Lines

Murine macrophages (RAW 264.7) were obtained from ATCC (Rockville, Md.). Human embryonic kidney (HEK) 293 cells transfected with vectors expressing human TLR2 or TLR4 plus a vector expressing an alkaline phosphatase reporter gene under the control of an inducible NF-kB promoter were purchased from InvivoGen (HEK-Blue™-hTLR2 and HEK-Blue™-hTLR4; San Diego, Calif.). A control cell line not expressing either TLR2 or TLR4 also was obtained and used (HEK-Blue™-Null1). The stable cell line expressing human CD44 (Origene, Rockville, Md.) or PCDNA 3.1 control vector (Invitrogen) was generated. The primary human keratocytes were obtained from ScienCell (Carlsbad, Calif.) and used at passage 5.

Cell Injury Induction

To see the effects of injured cells in vitro, necrotic corneal tissue extracts were prepared. Rat corneas were homogenized in PBS (100 µl per one cornea) using a motor-driven homogenizer followed by five freeze-thaw cycles and 37° C. for 5 hours (Chen, et al., *Nat. Med.*, Vol. 13, No. 7, pgs. 851-856 (2007)). After centrifugation at 12000 rpm for 5 min, the supernatants were prepared as necrotic extracts. Some of necrotic extracts were heat-treated (100° C., 20 min) Necrotic extracts were incubated with the cells in culture at a 1:10 dilution for 2 hours. To evaluate the effect of HSPB4, either antibodies to HSPB4 (10 µg or 50 µg) or isotype 1 gG antibodies also were added to the cultures.

To evaluate the effects of sHSPs and SN, either crystallins (HSPB4, HSPB5, βB crystallin; 0.001 to 10 µg/ml) or SN (0.1 to 10 ng/ml) were added to cultures and the cultures were incubated for 2 hours. To see the effect of TSG-6, 100 ng/ml or 500 ng/ml of rhTSG-6 were added to the cultures. To rule out the possibility of bacterial or LPS contamination of sHSPs, all in vitro experiments were done in the presence of polymyxin B (10 µg/ml) for neutralization of LPS. Moreover, for additional control experiments, sHSPs denatured by heat (100° C., 20 min) were used in parallel sets of experiments. To see whether keratocytes express sHSPs in response to injury, either necrotic extracts or $H_2O_2$ (100 to 500 nM) were added to the cultures of keratocytes.

Measurement of the Myeloperoxidase Amount in the Cornea

For a quantitative measure of neutrophil infiltration, the corneas were assayed for the myeloperoxidase (MPO) concentration (Rat MPO EL1SA kit; HyCult biotech) as reported previously (Oh et al., *Proc. Nat. Acad. Sci.*, Vol 101, No. 39, pgs. 16875-16880 (2010)). For protein extraction, the cornea was cut into small pieces and lysed in 150 µl of tissue extraction reagent (Invitrogen, Carlsbad, Calif.) containing protease inhibitor cocktail (Roche, Indianapolis, Ind.). The samples were sonicated on ice using an ultrasound sonicator. After centrifugation at 12,000 rpm at 4° C. for 20 min, the cleared supernatant was collected and assayed for levels of MPO.

Microarrays

RNA target for microarrays was prepared using the 3' IVT Express Kit (Affymetrix) according to manufacturer's instructions. Briefly, 200 ng of total RNA was used to synthesize first strand cDNA. The cDNA then was converted into double-stranded cDNA and used in in vitro transcription to synthesize biotinylated cRNA. The cRNA was purified with magnetic beads, fragmented, and 12.5 µg were used in the hybridization onto RG-230 2.0 arrays. The arrays were stained, washed, and scanned for fluorescence. Microarray data was normalized and analyzed using the Partek Genomics Suite 6.4 (Partek) and dChip software. For comparative analysis, data were filtered based on fold changes of 2 or more (either up- or down-regulated). For the hierarchical clustering analysis data were filtered using a coefficient of variation higher than 0.6 and a presence call of at least 33%. The expression levels of the filtered genes were standardized and used in hierarchical clustering. A total 6 clusters were selected in each hierarchical clustering on the similar level of hierarchy and studied for enriched Gene Ontology tags based on hypergeometric distribution.

Real-Time RT-PCR

Total RNA from the cornea or the cells was extracted (RNeasy Mini kit; Qiagen, Valencia, Calif.) and used to synthesize double-stranded cDNA by reverse transcription (SuperScript III; Invitrogen). Real-time amplification was performed (Taqman Universal PCR Master Mix Applied Biosystems, Carlsbad, Calif.) and analyzed on an automated instrument (7900HT Fast Real-Time PCR System; Applied Biosystems). PCR probe sets were purchased commercially (Taqman Gene Expression Assay Kits, Applied Biosystems). For assays, reactions were incubated at 50° C. for 2 min, 95° C. for 10 min, and then 40 cycles at 95° C. for 15 sec followed by 60° C. for 1 min. For normalization of gene expression, 18S rRNA probe (Taqman Gene Expression Assays ID, Hs03003631_g1) was used as internal control. The threshold cycle (Ct) was used to detect the increase in the signal associated with an exponential growth of PCR products during the log-linear phase. The expression of molecules was calculated using the algorithm $2^{-\Delta\Delta ct}$.

Western Blot

Clear lysates prepared as described above were measured for protein concentration, and a total of 10 ng protein was fractionated by SDS-PAGE on 10% bis-tris gel (Invitrogen), transferred to nitrocellulose membrane (Invitrogen), and blotted with antibodies against SN (Phoenix Pharmaceuticals, Burlingame, Calif.) or HSPB4 (Abcam).

ELISAs

Protein was extracted from the cornea as described above, and was assayed for levels of pro-inflammatory cytokines and chemokines with commercial ELISA kits for IL-6, IL-1β, and CXCL1/CINC-1 (Quantikine kit; R&D Systems), and for CCL2/MCP-1 (Immunoassay Kit; Invitrogen). For HSPB4 measurement, mouse monoclonal anti-rat antibody to HSPB4 (Abcam) was used as a capture antibody (4 ng/ml) and rabbit polyclonal anti-rat antibody to HSPB4 (Abcam) as a secondary antibody (400 ng/ml).

Release of HSPB4 in Injured Cornea

To measure the amount of HSPB4 released from the cornea after injury, the corneas of rats were harvested immediately after the injury and cultured at 37° C. with 5% $CO_2$ for 12 hours. Every two hours, the culture medium was changed and the concentration of HSPB4 in conditioned medium during each time frame was measured by ELISA.

Histopathology

The cornea was excised after the rat was sacrificed and fixed in 10% paraformaldehyde. The cornea was cut into 4 µm sections and stained with the hematoxylin-eosin (H&E) or subjected to immunohistochemistry. The formalin-fixed corneal section was deparaffinized with ethanol and antigen was retrieved using an epitope retrieval solution (IHC WORLD, Woodstock, Md.). The rabbit polyclonal anti-rat antibody to neutrophil elastase (1:200, Abcam), the mouse monoclonal anti-rat antibody to secretogranin II (1:200, Abcam), or the mouse monoclonal anti-rat antibody to HSPB4 (1:200, Abcam) were used as primary antibodies, and the anti-rabbit IgG (1:5000, Abcam) or the anti-mouse IgG (1:5000, Abcam) as secondary antibodies. The DAPI solution (VECTASHIELD Mounting Medium; Burlingame, Calif.) was used as counterstaining Aconitase Activity Assay To evaluate the oxidative damage in the cornea by injury (Ma et al., Biochem, Biophys. Acta, Vol. 1790, No. 10. pgs. 1021-1029 (2009), loss of aconitase activity in the corneal lysates was measured using an aconitase assay kit according to the manufacturer's protocol (Cayman Chemical Company, Ann Arbor, Mich.)

NF-kB Translocation Assays

About $1 \times 10^5$ mouse macrophages were plated in 8 well chamber slides (Lab-Tek II Chamber Slide; Nalge Nunc, Rochester, N.Y.) and incubated for 1 hour in 0.2 mL of 2% FBS in α-MEM with or without 10 µg/mL HSPB4. The cells were washed twice with PBS by centrifugation and were fixed with 100% methanol for 5 min. The cells were washed with PBS and blocked with Image-iT™ FX Signal Enhancer (Invitrogen). The cells then were incubated with 1 µg/mL of anti NF-kB p65 antibody (Abcam) in blocking buffer (5% BSA in PBS) overnight at 4° C. The samples were incubated for 1 hour with a 1:2000 dilution of the secondary antibody of anti-rabbit IgG (Alexa Fluor® 488 goat; Invitrogen). The DAPI solution was used to stain the cell nuclei. The slides were visualized with fluorescent microscopy using an upright microscope (Eclipse 80i, Nikon, Melville, N.Y.)

Statistical Analysis

Comparisons of parameters among the groups were made by the Student's t test, non-parametric Mann-Whitney test or Pearson's correlation test using SPSS software (SPSS 12.0). Differences were considered significant at $p<0.05$.

Results

Two Phases of Neutrophil Infiltration after Sterile Injury to the Cornea

The corneas of Lewis rats, were injured by exposing them to 100% ethanol for 30 seconds and scraping of the cornea and limbus to remove both the epithehum and stem cells found in the limbus. As described previously (Oh et. al, Proc. Nat. Acad. Sci., Vol. 107, No. 34, pgs. 16875-16880 (2010)), neutrophil infiltration was monitored by assays for myeloperoxidase (MPO) that is stored within neutrophil granules and released by activation of the cells (Borregard et al., Blood, Vol. 89, pgs. 3503-3521 (1997)). The neutrophil infiltration occurred in the two phases. There was a small initial phase that began within about 15 min, and reached a plateau level at 4 to 8 hours (Phase I in FIG. 31A). After the plateau, a much larger infiltration of neutrophils followed and reached a maximum at 24 to 48 hours (Phase II in FIG. 31A). The neutrophils then gradually disappeared in a recovery phase over 48 hours to 7 days.

Search for Candidate Signals for Phase I and Phase II

Figure 31:
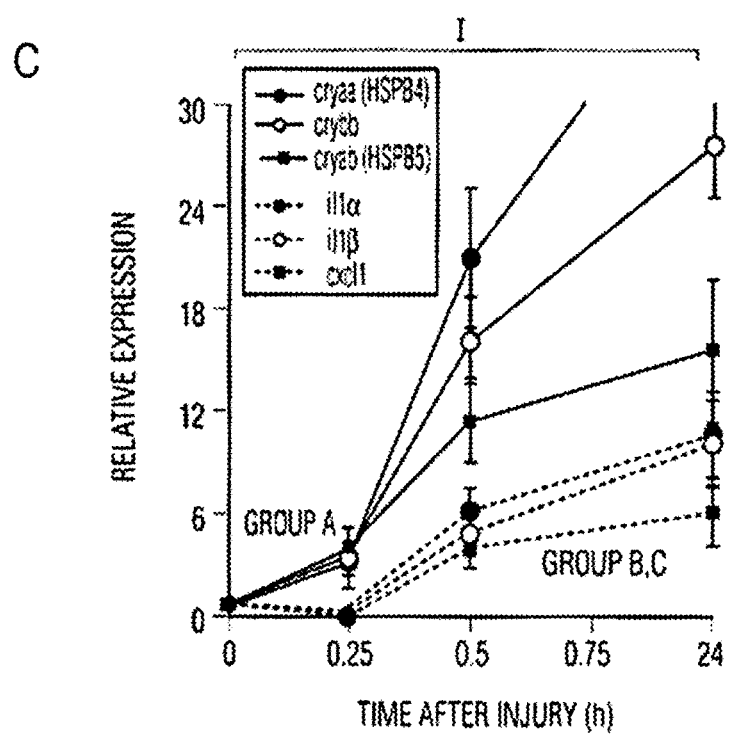
FIG. 31. Early events in the cornea after injury. A. The neutrophil infiltration occurred in the two phases: 1) a small initial phase that began within about 15 min, and reached a plateau level at 4 h (Phase 1) and 2) a much larger infiltration of neutrophils with a peak at 24 to 48 h (Phase II). B. Based on the temporal pattern of expression in microarrays, the up-regulated genes in the injured cornea were divided into three groups. C. Real time RT-PCR analysis of representative genes in each group. The group A genes preceded Group B and C genes in mRNA expression. D. Microarray heat map of genes from the corneas 4 h and 24 h after injury. Gene ontology categories and the number of genes up-regulated (red) or down-regulated (blue)>2-fold are indicated. Based on the expression pattern, genes were categorized into three groups: genes whose expression increased rapidly early after injury and thereafter decreased (Group A), genes that were expressed at steady levels (Group B), and genes increased gradually after injury (Group C).
Figure 31:
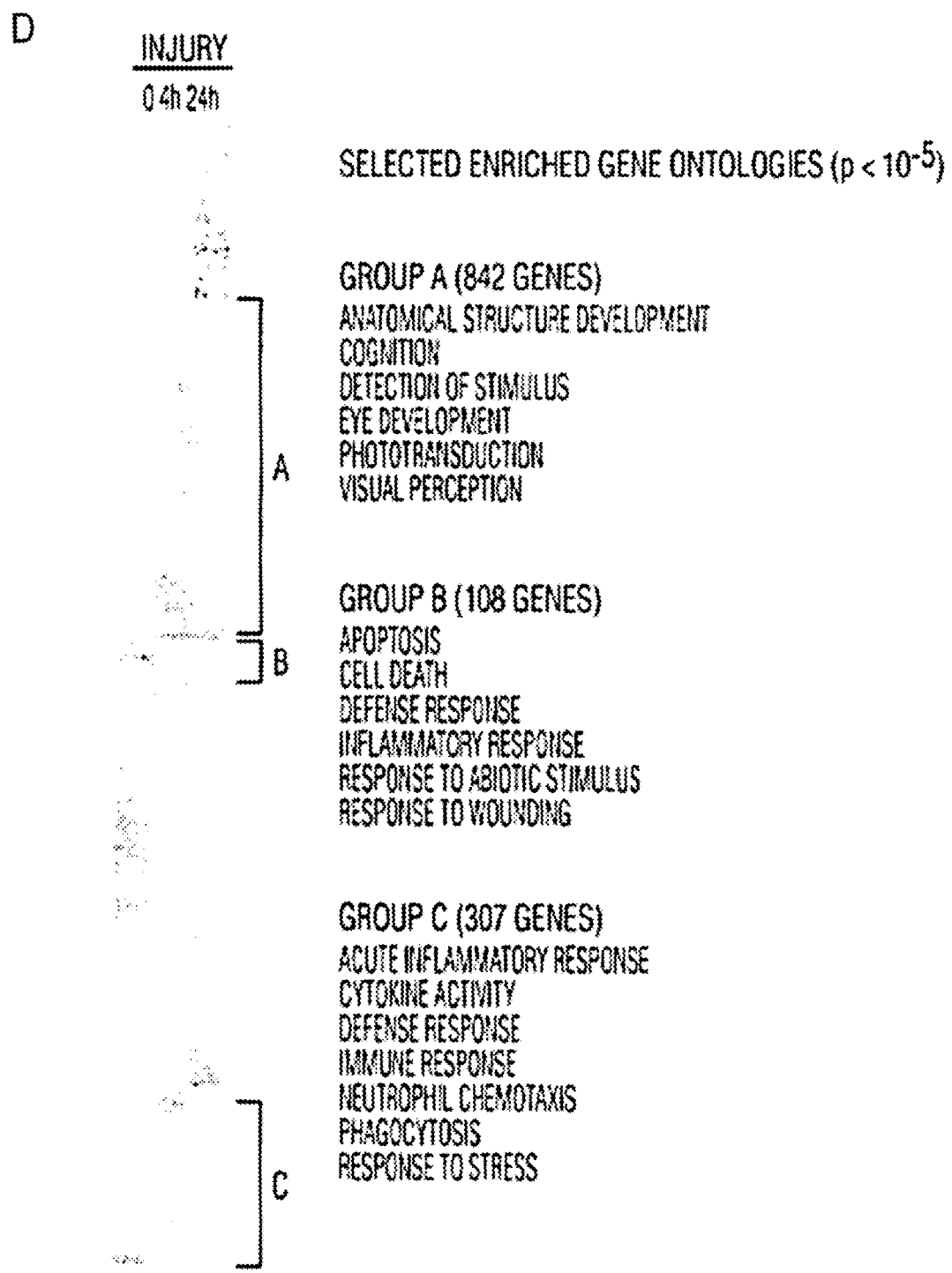

As a strategy to identify candidate signals that initiated the two phases, microarrays were used to survey the response of the cornea to injury. Based on the temporal pattern of gene expression, the genes were classified into three groups (FIG. 31B, FIG. 31D). About 842 Group A genes were up-regulated, about 108 Group B genes were up-regulated, and about 307 Group C genes were up-regulated (FIG. 31D). Focus was directed to the Group A genes, because they were expressed earlier and therefore more likely to include stimuli for Phase I and II (FIGS. 31 B and C). Most of the Group B genes were the molecules related to apoptosis/death and defense response (See Table 11 below, FIG. 31D). Most of the Group C molecules were pro-inflammatory chemokines and cytokines (See Table 11 below, FIG. 31D, FIG. 32M), and therefore were likely to be the genes that peaked late in the inflammatory responses. Most of the Group A genes were genes for nerve/neurotransmission-related and structural proteins of the eye (See Table 11 below.) From the category of Group A genes, the following were selected as attractive candidates for inflammatory signals: the neuropeptide secretoneurin (SN) because it was shown previously to activate chemotaxic migration and transendothelial extravasation of blood cells (Helle, Regul Pept., Vol. 165, No. 1, pgs. 45-51 (2010); Taupenot et al., N. Engl. J. Med., Vol. 348, No. 12, pgs. 1134-1149 (2003)), and two small heat shock proteins (HSPB4 and HSPB5), because some heat shock proteins were previously shown to act as DAMPs (Joly et al., J. Innate Immun., Vol. 2, No. 3, pgs. 238-247 (2010); Van Wijk et al., J. Leukoc. Biol., Vol. 88, No. 3, pgs. 431-434 (2010); Quintana et al., J. Immunol., Vol. 175, No. 5, pgs. 2777-2782 (2005); Asea et al., Nat. Med., Vol. 6, No. 4, pgs. 435-442 (2000)).

TABLE 14

Microarray analysis of gene expression profiles in the cornea at 4 hours and 24 hours after injury. The top 20 transcripts up-regulated by injury were shown in each group (Group A, B, and C).

| Gene Title | Gene symbol | Probe set | Change (x-Fold) Injured (4 h)/con | Change (x-Fold) Injured (24 h)/con |
|---|---|---|---|---|
| Group A | | | | |
| crystallin, alpha A | Cryaa | 1370279_at | 19.468 | 1.620 |
| crystallin, beta B1 | Crybb1 | 1369985_at | 18.541 | 1.062 |
| crystallin, gamma C | Crygc | 1370292_a_at | 17.911 | 1.112 |
| secretogranin II | ScgII | 1368044_at | 15.847 | 1.033 |
| claudin 2 | Cldn2 | 1375933_at | 15.246 | 1.033 |
| crystallin, beta A1 | Cryba1 | 1371408_at | 14.628 | −3.593 |
| crystallin, gamma B | Crygb | 1371413_x_at | 14.311 | 1.025 |
| crystallin, gamma D | Crygd | 136770._at | 13.957 | 1.054 |
| synaptosomal-associated protein 25 | Snap25 | 1387073_at | 13.199 | 1.580 |
| Galectin-related inter-fiber protein | Grifin | 1386936_at | 12.710 | −1.129 |
| solute carrier family 6 (neurotransmitter transporter, GABA), member 1 | Slc6a1 | 1368170_at | 12.359 | −1.704 |
| crystallin, gamma S | Crygs | 1388435_at | 11.969 | −1.096 |
| Calbindin | Calb1 | 1370201_at | 11.542 | −1.184 |
| crystallin, beta A2 | Cryba2 | 1388385_at | 10.349 | −1.497 |
| crystallin, beta B2 | Crybb2 | 1367684_at | 9.918 | −1.738 |
| retinol binding protein 3, interstitial | Rbp3 | 1376777_at | 9.789 | −1.434 |
| collagen, type II, alpha 1 | Col2a1 | 1387767_a_at | 8.615 | −1.224 |
| phosphodiesterase 6A, cGMP-specific, rod, alpha | Pde6a | 1393426_at | 8.500 | −1.011 |
| complexin 3 | Cplx3 | 1384779_at | 8.061 | −1.099 |
| crystallin, alpha B | Cryab | 1370026_at | 7.197 | 1.812 |
| crystallin, beta A4 | Cryba4 | 1367608_at | 7.168 | −1.749 |
| Group B | | | | |
| interleukin 6 | Il6 | 1369191_at | 340.974 | 293.81 |
| colony stimulating factor 3 (granulocyte) | Csf3 | 1369529_at | 70.050 | 62.614 |
| matrix metallopeptidase 13 | Mmp13 | 1388204_at | 30.118 | 28.285 |
| prostaglandin E synthase | Ptges | 1368014_at | 19.449 | 15.069 |
| metallothionein 2A | Mt2A | 1388271_at | 17.356 | 13.067 |
| superoxide dismutase 2, mitochondrial | Sod2 | 1370173_at | 16.915 | 11.803 |
| interleukin I alpha | Il1a | 1371170_a_at | 14.637 | 5.275 |
| prostaglandin-endoperoxide synthase 2 | Ptgs2 | 1368527_at | 10.861 | 8.108 |
| metallothionein 1a | Mt1a | 1371237_a_at | 9.483 | 6.815 |
| lipocalin2 | Lcn2 | 1387011_at | 9.013 | 9.387 |
| immediate early response 3 | Ier3 | 1388587_at | 5.552 | 5.781 |
| prostaglandin E synthase | Ptges | 1368015_at | 5.433 | 5.051 |
| six transmembrane epithelial antigen of the prostate 1 | Steap1 | 1393706_at | 5.221 | 4.467 |
| cAMP responsive element modulator | Crem | 1393550_at | 5.213 | 4.998 |
| transferrin receptor | Tfrc | 1388750_at | 5.182 | 5.061 |
| mitogen-activated protein kinase 8 | Map3k8 | 1369393_at | 4.935 | 5.302 |
| B-cell translocation gene 2, anti-proliferative | Btg2 | 1386994_at | 4.931 | 4.677 |
| runt related transcription factor 1 | Runx 1 | 1368914_at | 4.924 | 3.913 |
| similar to F-box only protein 27 | RGD1563982 | 1375041_at | 4.717 | 3.358 |
| growth arrest, DNA-damage-inducible, alpha | Gadd45a | 1368947_at | 4.026 | 3.756 |
| Group C | | | | |
| secretory leukocyte peptide | Slpi | 1367998_at | 54.415 | 533.847 |
| chemokine (C-X-C motif) ligand 2 | Cxcl2 | 1368760_at | 52.728 | 404.344 |

TABLE 14-continued

Microarray analysis of gene expression profiles in the cornea at 4 hours and 24 hours after injury. The top 20 transcripts up-regulated by injury were shown in each group (Group A, B, and C).

| | | | Change (x-Fold) | |
|---|---|---|---|---|
| Gene Title | Gene symbol | Probe set | Injured (4 h)/ con | Injured (24 h)/ con |
| S100 calcium binding protein A9 | Sl00a9 | 1387125_at | 56.114 | 207.701 |
| interleukin 1 beta | Il1b | 1398256_at | 33.522 | 198.673 |
| chemokine (C-C motif) ligand 7 | Ccl7 | 1379935_at | 40.595 | 159.69 |
| S100 calcium binding protein A8 | Sl00a8 | 1368494_at | 33.206 | 155.69 |
| chemokine (C-X-C motif) ligand 3 | Cxcl3 | 1370633_at | 7.895 | 128.417 |
| chemokine (C-C motif) ligand 3 | Ccl3 | 1369815_at | 6.493 | 95.538 |
| interleukin 1 receptor, type II | Il1r2 | 1387180_at | 24.159 | 60.257 |
| chemokine (C-X-C motif) ligand 3 | Cxcl3 | 1370634_x_at | 4.934 | 59.166 |
| interleukin I alpha | Il1a | 1368592_at | 2.953 | 54.174 |
| Fc fragment of IgG, low affinity IIa. receptor | Fcgr2a | 1367850_at | 8.708 | 41.195 |
| Cd53 molecule | Cd53 | 1368518_at | 6.748 | 31.988 |
| chemokine (C-C motif) receptor I | Ccr1 | 1370083_at | 6.359 | 28.512 |
| chemokine (C-X-C motif) ligand 3 | Cxcl3 | 1388032_a_at | 2.331 | 24.419 |
| colony stimulating factor 3 receptor | Cst3r | 1386009_at | 8.094 | 21.987 |
| Fc fragment of IgG, high affinity Ia, receptor | FcgrIa | 1393038_at | 3.611 | 21.032 |
| laminin, gamma 2 | Lamc2 | 1379340_at | 5.817 | 20.577 |
| immunoglobulin superfamily, member 6 | lgsf6 | 1387687_at | 2.915 | 20.148 |
| complement component 3 | C3 | 1368000_at | 6.292 | 15.602 |

Symbols:
Injured (4 h)/con, cornea at 4 hours after injury vs. cornea right after injury;
Injured (24 h)/con, cornea at 24 hours after injury vs. cornea right after injury;
'–' means down-regulation.
The values are the results from collective samples of n = 4 per each group.

SN as a Candidate for Phase I and HSPB4 for Phase II

Figure 32:
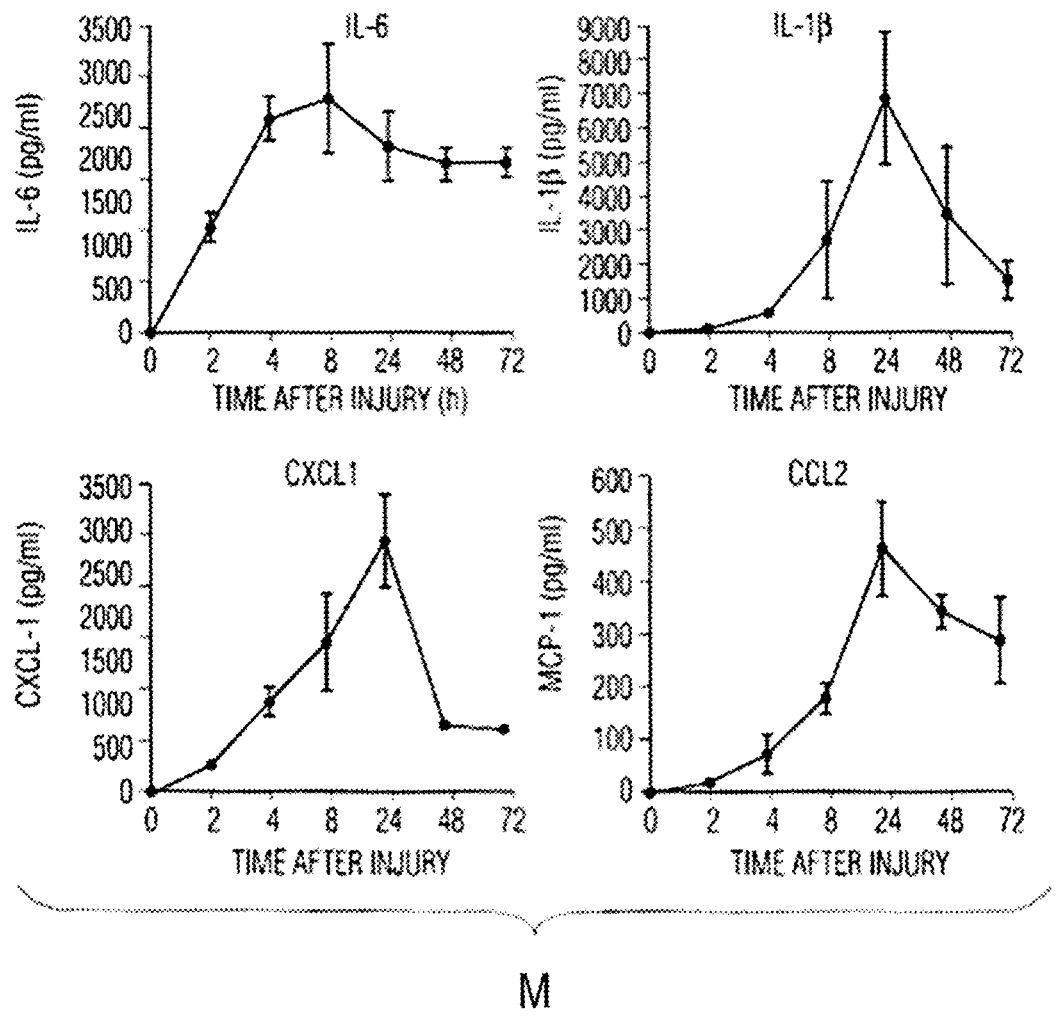
FIG. 32. Expression patterns of secretoneurin (SN) and HSPB4 in the injured cornea. A, E. Western blot of SN and HSPB4 in the cornea. SN was released into the cornea immediately after injury, and HSPB4 reached a peak at 4 h. B, F, G. ELISA of SN and HSPB4 in the serum and cornea. SN was released into the cornea and the serum within 0.25 h of the injury. HSPB4 was released into the extracellular space as measured in the supernatants of the ex vivo culture of corneas after 2 to 4 h. C, H Immunohistochemistry of SN and HSPB4 in the cornea. D, I. Real time RT-PCR of neuropeptides and crystallins. Among neuropeptides and crystallins analyzed, SN and HSPB4 showed the highest expression in the injured cornea. J. In response to necrotic extracts, keratocytes in culture expressed HSPB4. K. As measured by aconitase activity, oxidative stress was generated in the cornea by injury. L. The hydrogen peroxide increased the expression of HSPB4 in keratocytes. M. Temporal expression of IL-6, IL1β, CXCL1, and CCL2 in the cornea. ELISAs demonstrated that the expression of proteins of Group B (IL-6) and Group C (IL-1β, CXCL1, and CCL2) genes paralleled gene expression as assayed for mRNAs with microarrays and real time RT-PCR assays.

Data on the time course of expression were consistent with SN serving as an initiating signal for Phase I. SN was not detected in extracts of uninjured cornea, but appeared both in corneal extracts and the serum of the rats within 0.25 hour of the injury (FIGS. 32A and B). The levels of SN in extracts of injured corneas and the serum decreased at 0.5 hour and then increased apparently as a result of increased expression of the gene (FIGS. 32A-D). In contrast, there were little changes in the expression of genes for substance P and calcitonin gene-related peptide (CGRP), two other neuropeptides known to be expressed in the cornea (FIG. 32D) (Troger et al., Brain Res. Rev., Vol. 53, No. 1, pgs. 39-62 (2007)).

Similar data on the time course of expression were consistent with HSPB4 serving as a stimulus for Phase II. Uninjured cornea contained low levels of HSPB4 protein, but the amount increased beginning after 0.5 hour of the injury and reached a peak at about 4 hours (FIGS. 32E and F). A similar time course was observed in the release of HSPB4 into the medium in experiments in which corneas were injured in vivo and then incubated ex vivo (FIG. 32G). As expected from the microarray data, there was increased expression of mRNAs for HSPB4 and related genes from Group A (FIG. 32I); however, the increases in expression of HSPB4 were delayed compared to the increase in the mRNA for SN (compare FIGS. 32D and I). Immunohistochemistry of injured cornea was consistent with the results. The SN-immunoreactive nerves were increased in the cornea at 2 hours following injury (FIG. 32C). The expression of HSPB4 was increased at about 4 hours following injury (FIG. 32H).

Figure 33:
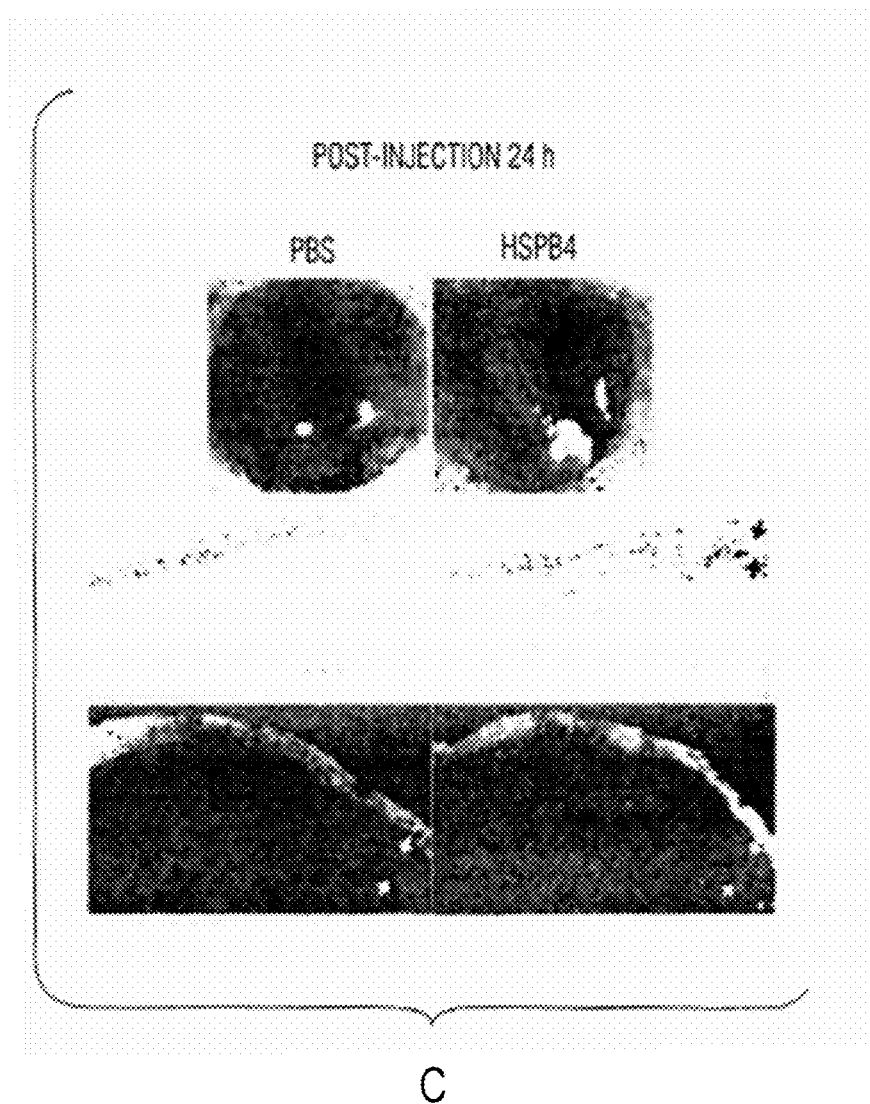
FIG. 33. SN reproduced the Phase I inflammatory response, and HSPB4 reproduced both the Phase I and Phase II. A. The injection of the recombinant SN induced the early infiltration of neutophils of Phase I, but not of Phase II. B, C. HSPB4 injection induced the Phase I and Phase II responses accompanied by corneal opacity and neutrophil infiltration as shown in hematoxylin-eosin staining and immunostaining for neutrophil elastase of the region of the cornea into which HSPB4 was injected. D. The topical application of the calcium channel blocker Diltiazem inhibited significantly the Phase I response in corneal injury to chemical injury. E. The subconjunctival injection of polyclonal (pAb) or monoclonal (mAb) antibodies to HSPB4 decreased significantly the neutrophil infiltration in Phase II, compared to isotype control (IgG)-injected group. F. The amounts of SN and HSPB4 released into the cornea were dependent on the severity of injury as measured by real time PCR of SN and HSPB4 in the injured cornea and ELISA for SN and HSPB4 in the serum or cornea. The concentrations of mRNAs and proteins were higher in the cornea or serum by severe injury (30 sec ethanol and scraping), compared to mild injury (15 sec ethanol and scraping). G. After subconjunctival injections of clodronate-encapsulated liposome ($Cl_2$ MDP-LIP) on day 2 (i.e., 2 days before injury) and day 0 (immediately after injury), sections of the rat cornea were stained with hematoxylin-eosin (H&E), or antibodies to CD11b and CD68 to identify macrophages. The structure of the cornea on H&E was not affected by $Cl_2$ MDP-LIP. CD11b- and CD68-positive cells in the cornea, however, were decreased significantly by $Cl_2$MDP-LIP compared to PBS-encapsulated liposome-injected controls (PBS-LIP).
Figure 33:
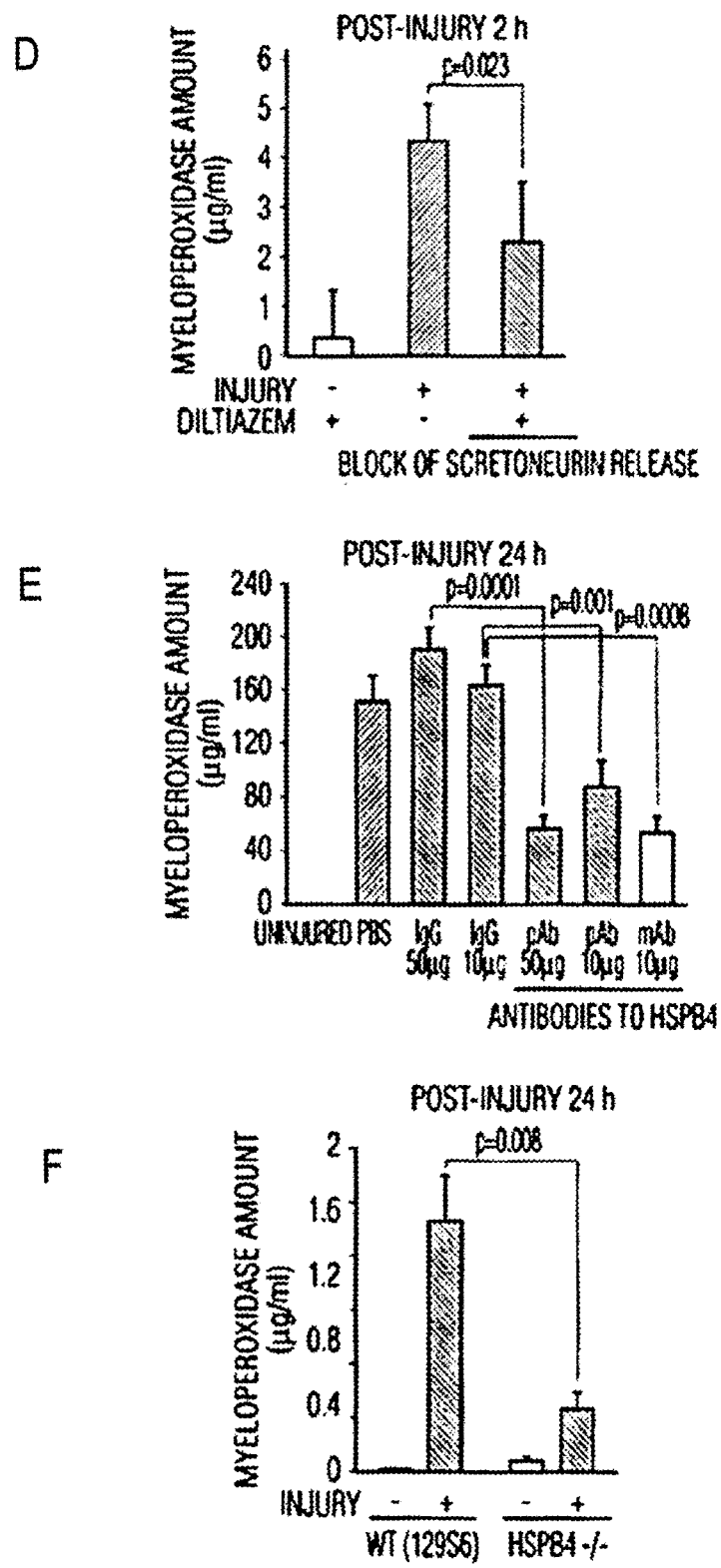
Figure 33:
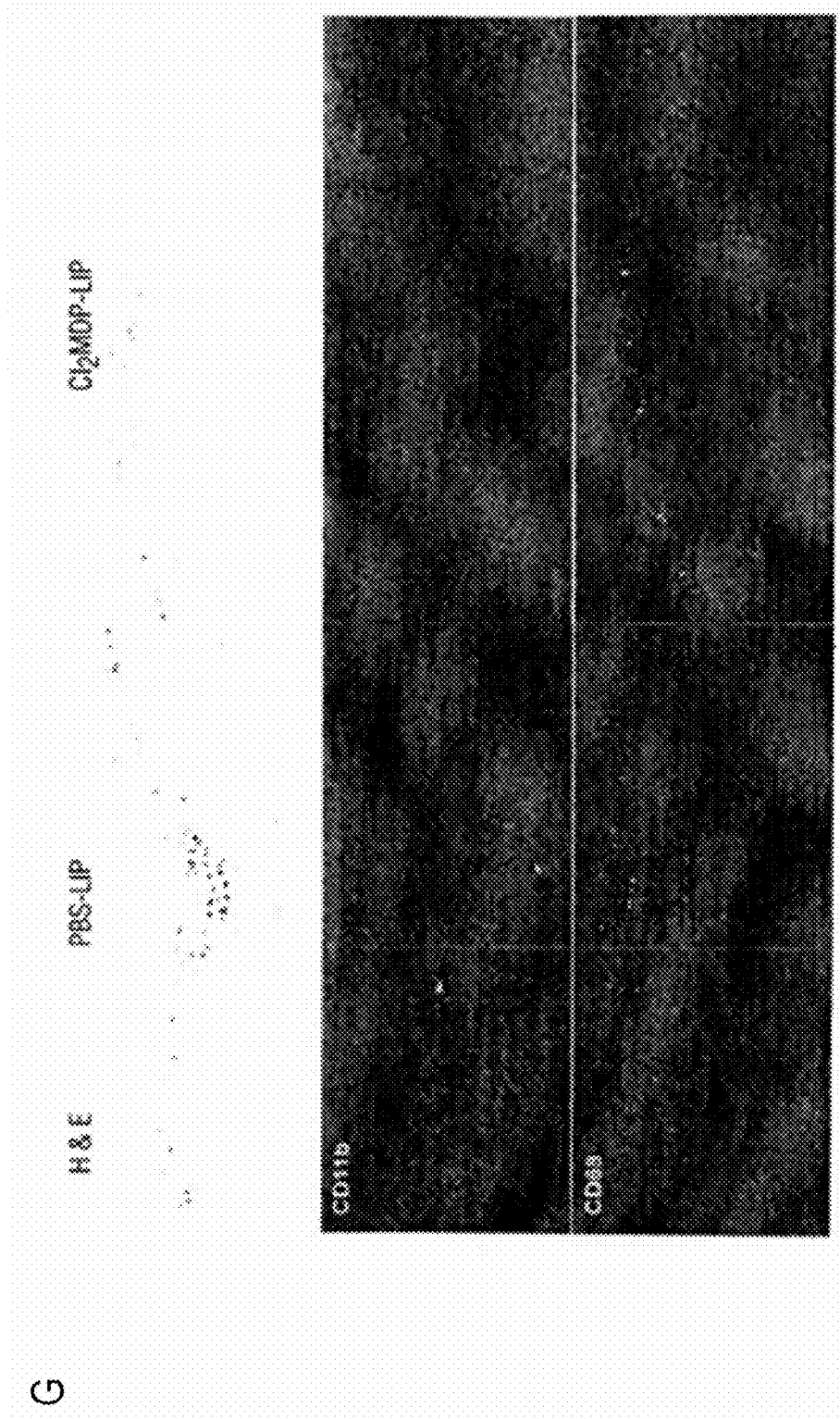

In addition, the expressions of SN and HSPB4 were dependent on the severity of injury. The concentrations of both the proteins and mRNAs were higher in the cornea or serum following severe injury (30 sec ethanol and scraping) compared to mild injury (15 sec ethanol and scraping) (FIG. 33F).

Keratocytes from the Corneal Stroma Synthesized HSBP4 in Response to Injury

To define the cellular origin of HSPB4 in the injured cornea, keratocytes that are fibroblast-like cells from the corneal stroma were incubated with extracts of the cornea that were made necrotic by repeated freezing and thawing. The necrotic extracts induced the expression of HSPB4 in the keratocytes (FIG. 32J). The necrotic extracts did not increase significantly the expression of a second small heat shock protein HSPB5 or a third Group A gene, βB crystallin. Most sterile inflammations produce increases in reactive-oxygen species (ROS) (Kolnitzer et al., Ann. N.Y. Acad. Sci., Vol. 1203, pgs 45-52 (2010); Martinon, Eur. J. Immunol., Vol. 40, No. 3, pgs. 616-619 (2010)). Assays of injured cornea demonstrated a rapid decrease in aconitase activity, a reflection of an increase in ROS (FIG. 32K). As expected, incubation of keratocytes with $H_2O_2$ to increase ROS also produced increased expression of HSPB4 (FIG. 32L).

Recombinant SN Reproduced Phase I and Recombinant HSPB4 Reproduced Phase II

Injection of recombinant SN into the stroma of the cornea stimulated the neutrophil infiltration of Phase C (FIG. 33A). The effect was negated partially by topical application of a calcium blocker (Diltiazem) (FIG. 33D) that inhibits release of neuropeptides (Gonzalez et al, Invest. Ophthalmol. Vis. Sci., Vol. 34, No. 12, pgs. 3329-3335 (1993). The results therefore indicated that SN served as a major stimulus for Phase I, but they did not exclude the possibility that it acted in concert with other signals released by the injured cornea.

Injection of recombinant HSPB4 that was pyrogen-free (see Methods) stimulated the neutrophil infiltration of both Phase I and Phase II (FIGS. 33B and C). Reproduction of Phase I was explained apparently by the protein being injected earlier than it appears in the tissue after injury to the cornea (FIGS. 32E-H). Injection of recombinant HSPB4 into one region of the cornea also reproduced the opacity produced by sterile inflammation (FIG. 33C). The role of HSPB4 was confirmed by experiments in which antibodies to the protein were injected into the corneal stroma immediately after the injury (FIG. 33E). The antibodies to HSPB4 inhibited significantly the Phase II inflammatory response in the cornea after the injury. Also, the neutrophil infiltration of Phase II in the cornea after injury was decreased significantly in the corneas of HSPB4 knockout mice, compared to wild-type controls (FIG. 33F).

HSPB4 Activated Resident Macrophages Through TLR2/NF-kB Signaling.

Figure 34:
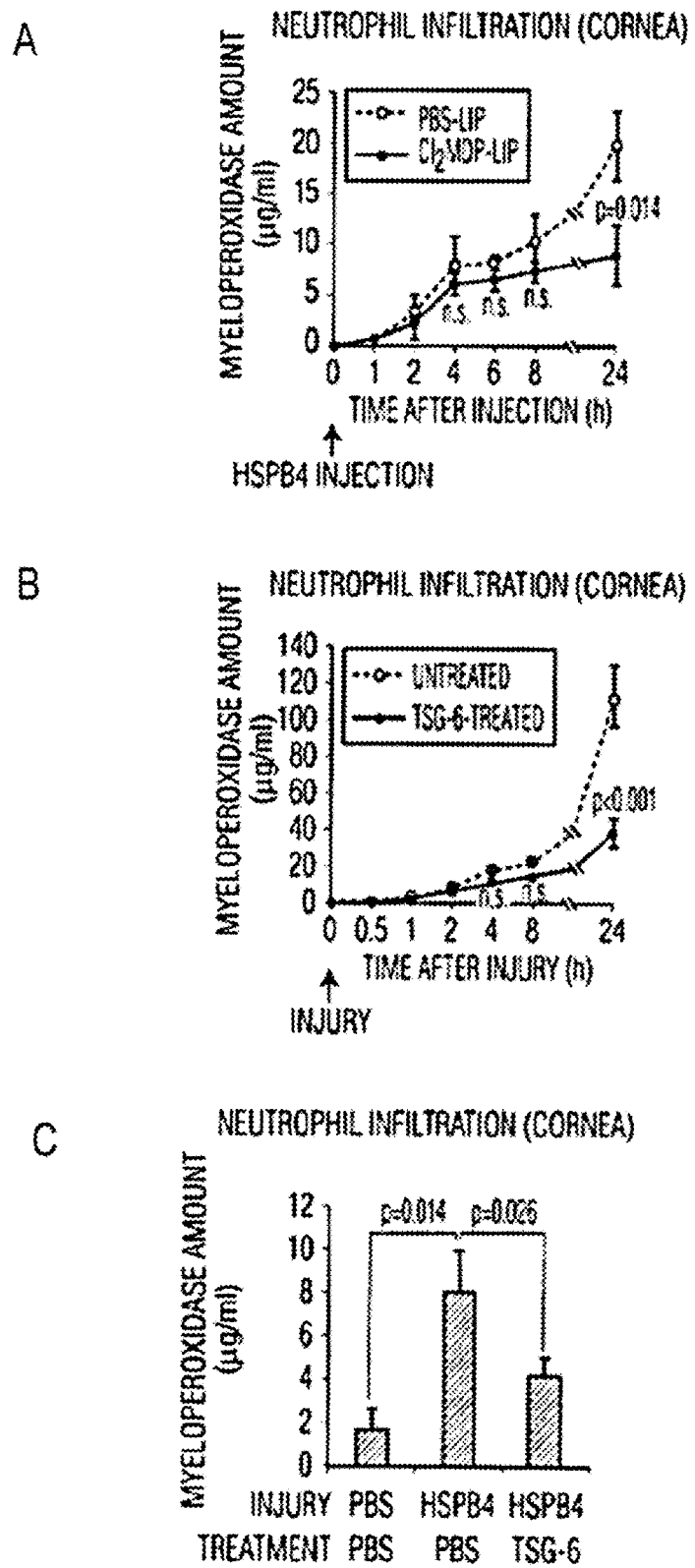
FIG. 34. HSPB4 activated macrophages through TLR2/NK-kB signaling. A. HSPB4 did not induce the Phase II response when corneal macrophages were depleted by subconjunctival injection of liposome-encapsulated clondronate ($Cl_2$MDP-LIP). B. An intracameral injection of TSG-6, an inhibitor of TLR2/NF-kB signaling, suppressed the Phase II inflammatory response of the cornea after injury. C. TSG-6 treatment also decreased significantly the neutrophil infiltration in Phase II in the cornea injected with HSPB4. D. Macrophages were activated to express pro-inflammatory cytokines when incubated with necrotic extracts of the cornea. Blocking HSPB4 with polyclonal (pAb) or monoclonal (mAb) antibodies negated significantly the effects of necrotic corneal extracts on macrophage activation. E. The addition of recombinant HSPB4 activated macrophages in culture in a dose-dependent manner. F. HSPB4 induced the translocation of NK-kB from the cytoplasm into nucleus in macrophages. G. Necrotic extracts of the cornea also stimulate the TLR2/NK-kB pathway in the reporter cell expressing TLR2 (HEK-TLR2), but antibodies to HSPB4 partially inhibited the effects. H, I, J. Recombinant HSPB4 stimulated NF-kB signaling in the cell line expressing TLR2 or TLR4 (HEK-TLR4) in a dose-dependent manner, while it had no effect in the cell without either receptor (HEK-null). K. Murine macrophages (RAW 264.7) were incubated with Group A molecules (HSPB4, HSPB5, or β-crystallin) and evaluated for expression of pro-inflammatory cytokines by real-time RT-PCR. Neither HSPB5 nor β-crystallin activated macrophages, while HSPB4 induced remarkably the expression of pro-inflammatory cytokines in macrophages. In contrast, heat-treated HSPB4 (boiling, 20 min) did not activate macrophages in culture, indicating that HSPB4, and not contaminating pyrogens, induced the macrophage activation. Human embryonic kidney cells expressing TLR-2 (HEK-TLR2) were incubated with HSPB5 or β-crystallin and evaluated for activation of NK-kB signaling. Neither HSPB5 nor 3-crystallin activated TLR2/NK-KB signaling. L. Sterile injury was made to the rat cornea after resident macrophages were depleted by subconjunctival injections of clodronate-encapsulated liposome ($Cl_2$ MDP-LIP) on day 2 (2 days before injury) and day 0 (immediately after injury). The cornea was evaluated for neutrophil infiltration by assays for myeloperoxidase, hematoxylin-eosin (H&E) straining, and immunostaining for neutrophil elastase to identify neutrophils. Neutrophil infiltration measured by MPO was decreased markedly in the cornea 24 hours after injury by injection with clordronate-encapsulated liposome, compared to PBS-encapsulated liposome-injected controls (PBS-LIP). Infiltration of inflammatory cells and neutrophils also was decreased markedly in the macrophage-depleted cornea.
Figure 34:
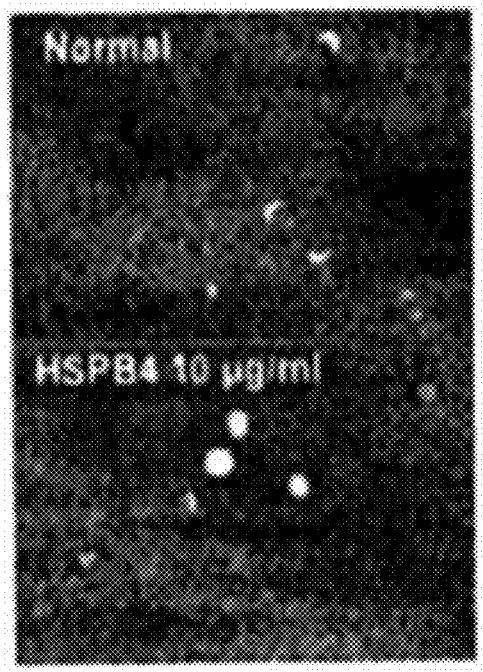
Figure 34:
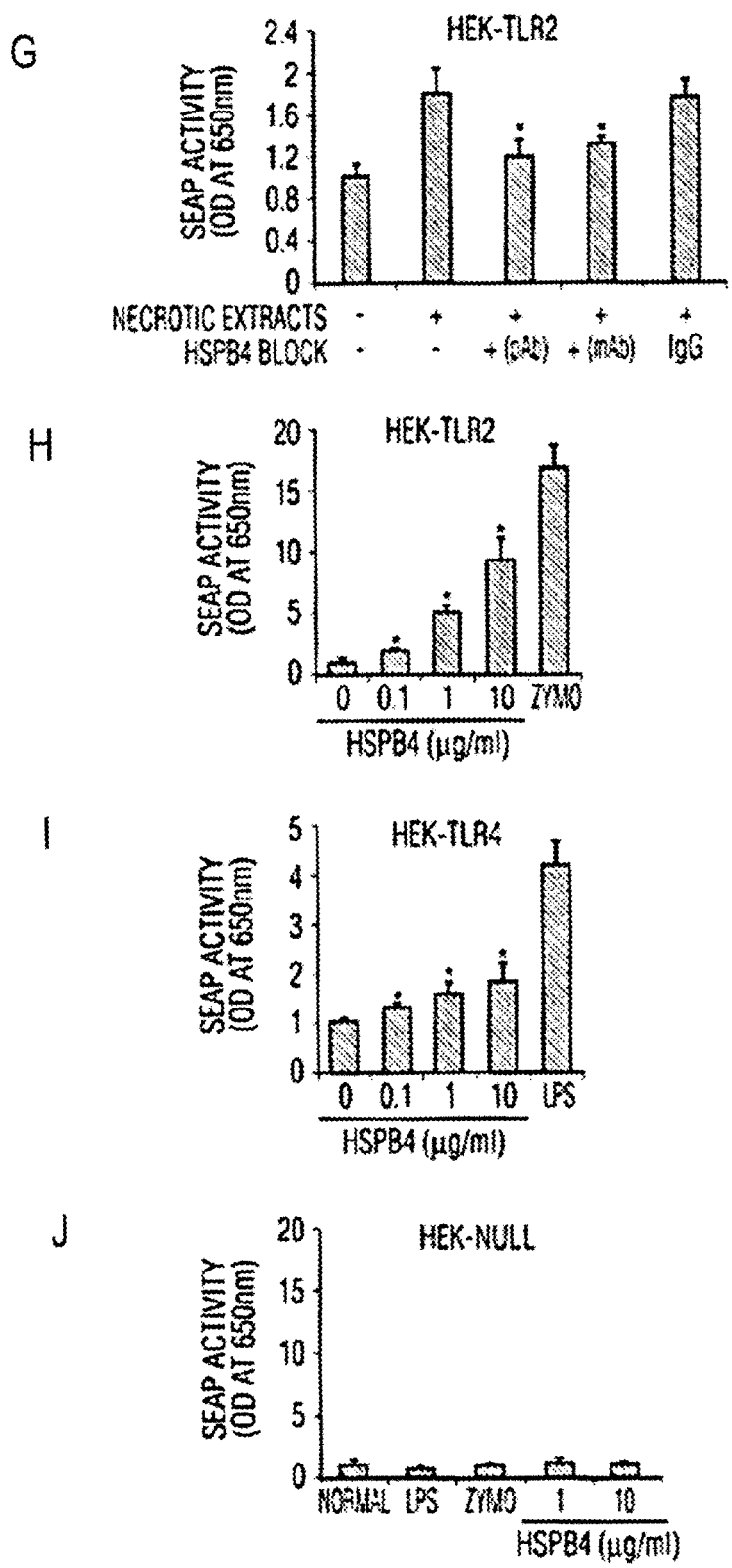
Figure 34:
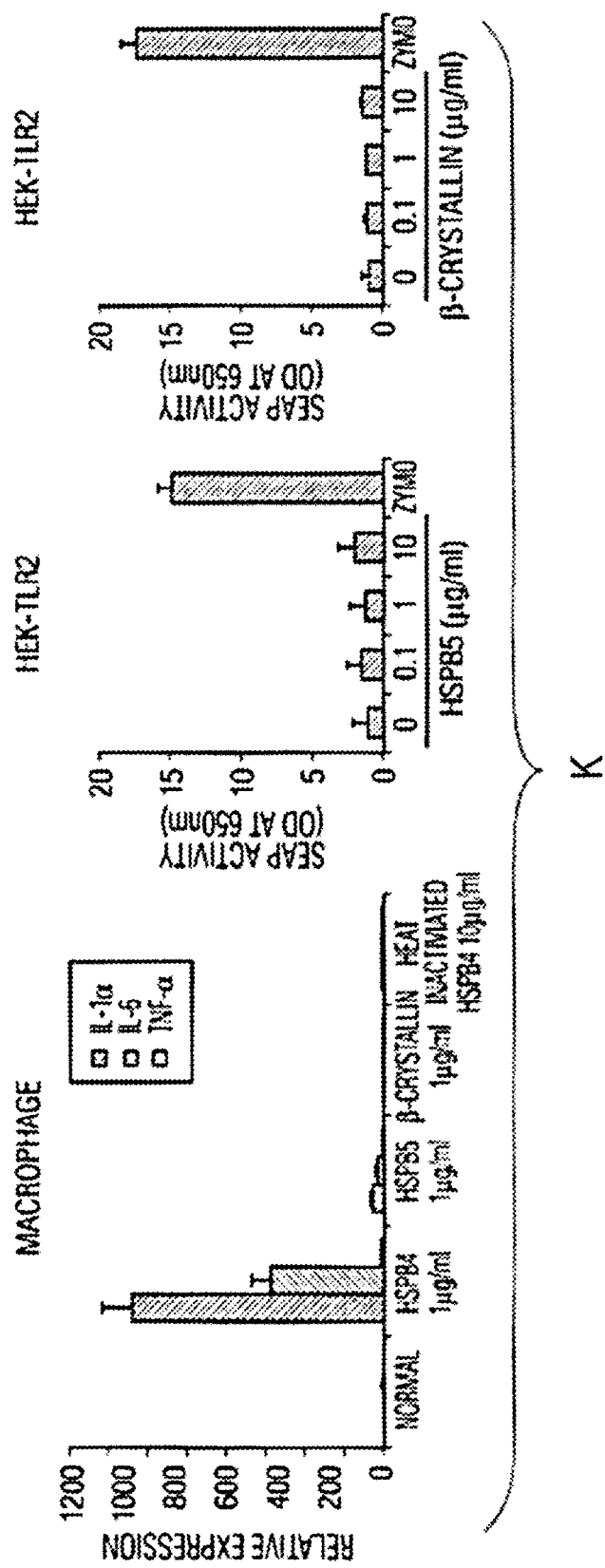
Figure 34:
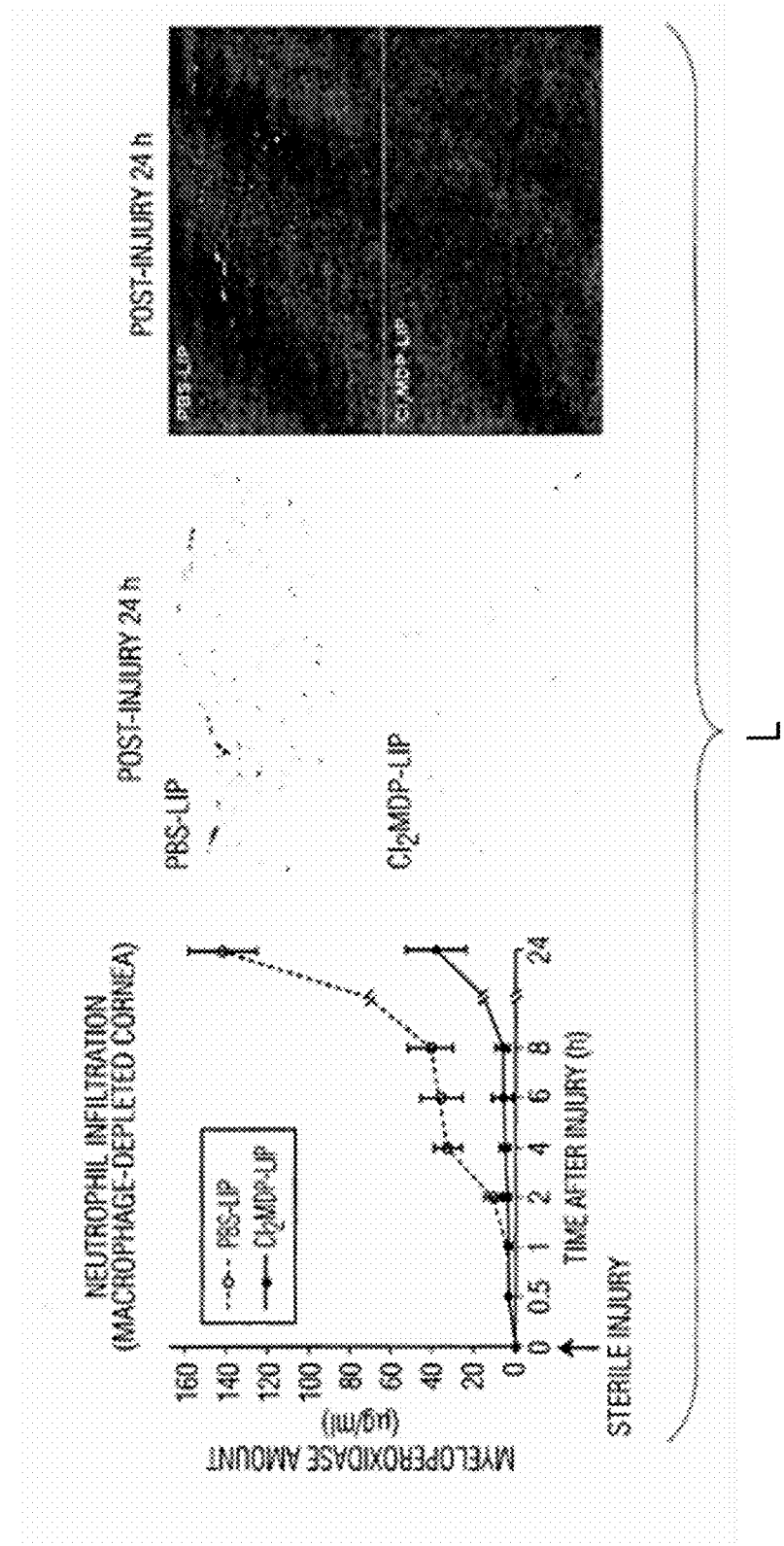

To identify the cells that responded to HSPB4 in the cornea, resident macrophages were depleted from the corneas of Lewis rats by injecting clodronate liposomes subconjunctivally, and then recombinant HSPB4 was injected into the corneal stromas. Macrophage depletion was confirmed with immunostaining for macrophage-specific markers CD68 and CD11b (FIG. 33G). The protein did not reproduce Phase II in rats in which macrophages were depleted (FIG. 34A), suggesting that the effects of HSPB4 were dependent on the presence of resident macrophages. Similarly, the inflammation was decreased markedly in the cornea after chemical/mechanical injury when resident macrophages were depleted prior to an injury (FIG. 34L), indicating a crucial role of resident macrophages in sterile injury-induced inflammation of the cornea. In parallel experiments, it was observed that neutrophil infiltration of Phase II, but not Phase I, was suppressed significantly by an intraocular injection of the anti-inflammatory protein, TSG-6 (FIG. 34B), that inhibits TLR2/NF-kB signaling in macrophages (Choi, Blood, in press; Lesley et al., J. Biol. Chem., Vol. 279, pgs. 25745-25754 (2004)). Also, TSG-6 suppressed significantly the Phase II inflammatory response caused by HSPB4 injection to the corneal stroma (FIG. 34C). The results suggested therefore that HSPB4 signaled Phase II by activating TLR2/NF-kB signaling in resident macrophages.

Figure 35:
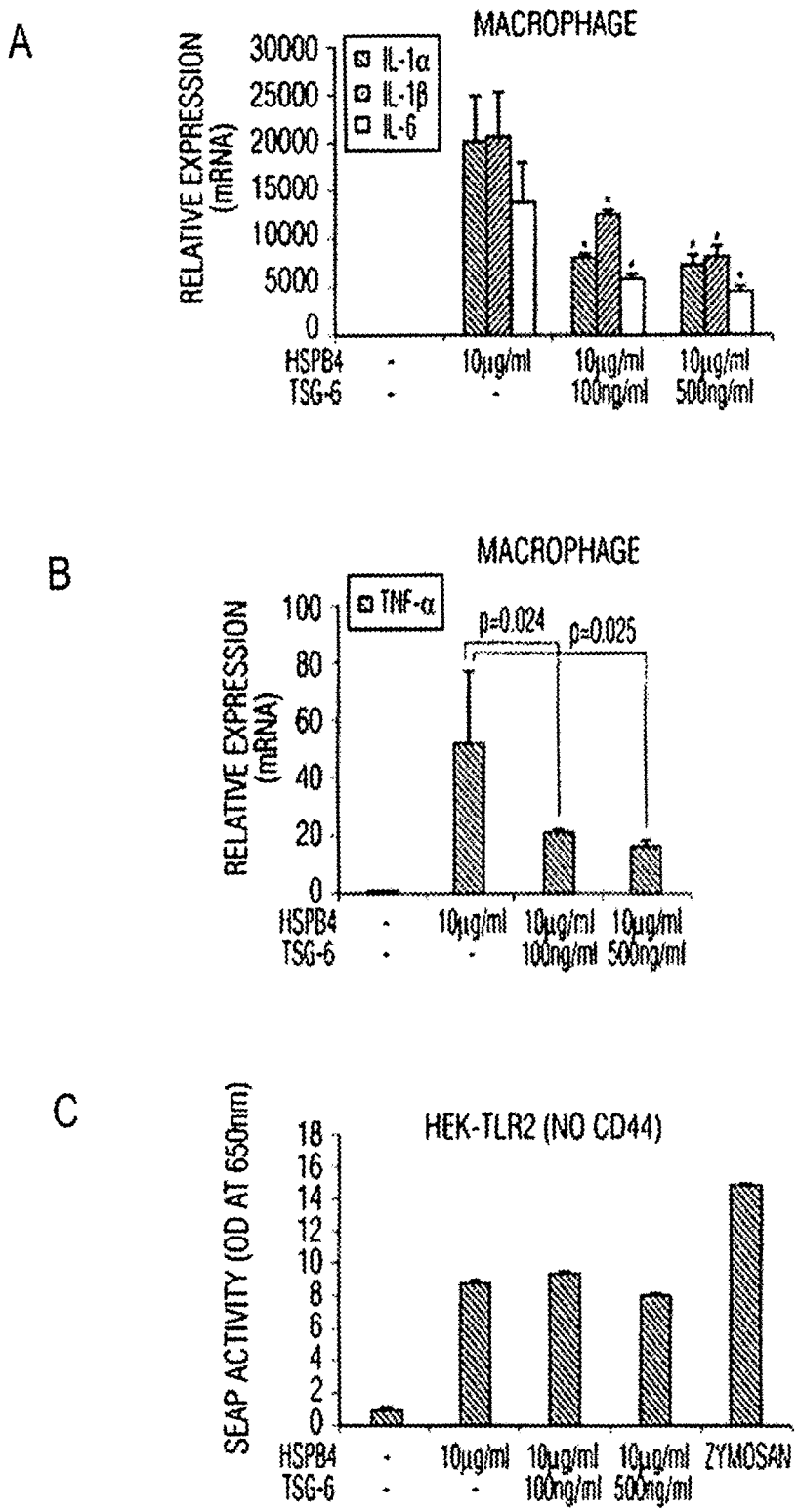
FIG. 35. TSG-6 suppressed HSPB4-induced activation in macrophages in a CD44-dependant manner. A, B. TSG-6 in a dose-dependent manner suppressed the activation of macrophages by HSPB4. C, D. TSG-6 did not inhibit HSPB4-mediated activation of NF-kB signaling in HEK-TLR2 cells which did not express CD44. However, after the cells were transfected to express CD44, TSG-6 dose-dependently inhibited HSPB4-mediated activation of NF-kB signaling. E. TSG-6 inhibited significantly the inflammation in the corneas of wild-type C57BL/6 mice, but it did not suppress inflammation in the corneas of CD44 knockout mice. F. Murine macrophages (RAW 264.7) were incubated with secretoneurin and evaluated for expression of pro-inflammatory cytokines by real time RT-PCR. Secretoneurin did not activate macrophages. Human keratocytes were cultured with either secretoneurin or HSPB4. Neither secretoneurin nor HSPB4 activated keratocytes to produce cytokines.
Figure 35:
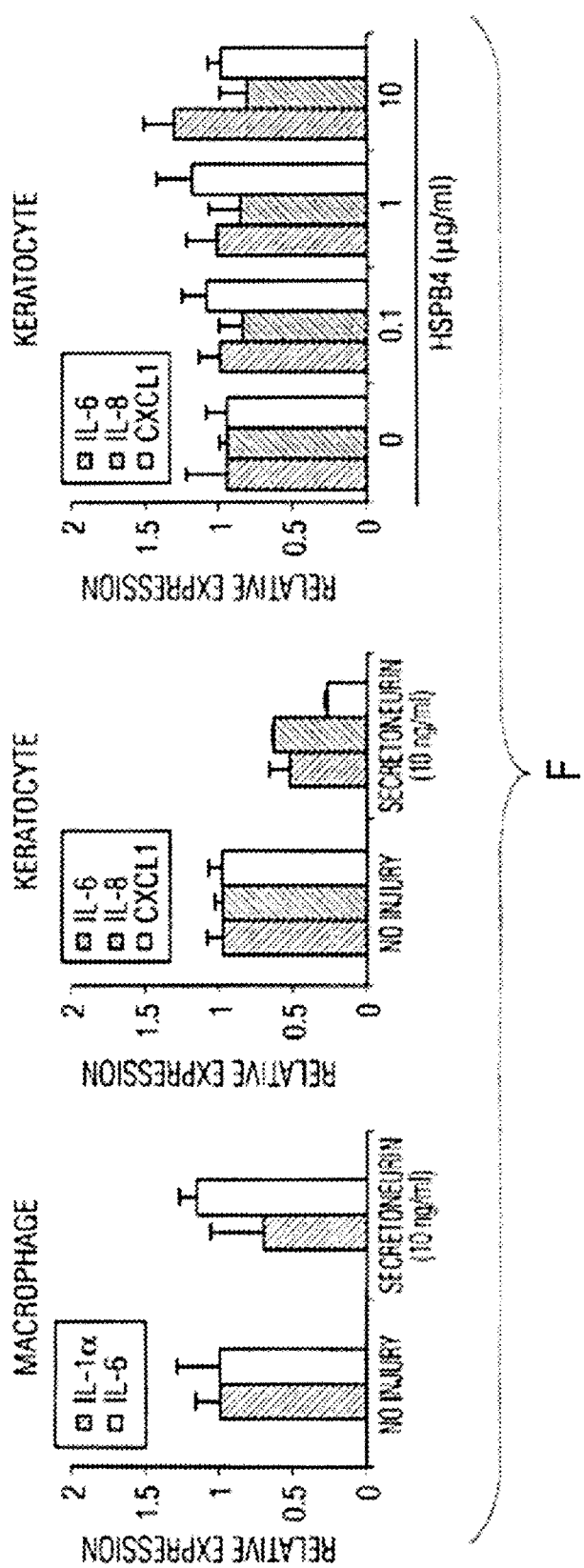
Figure 36:
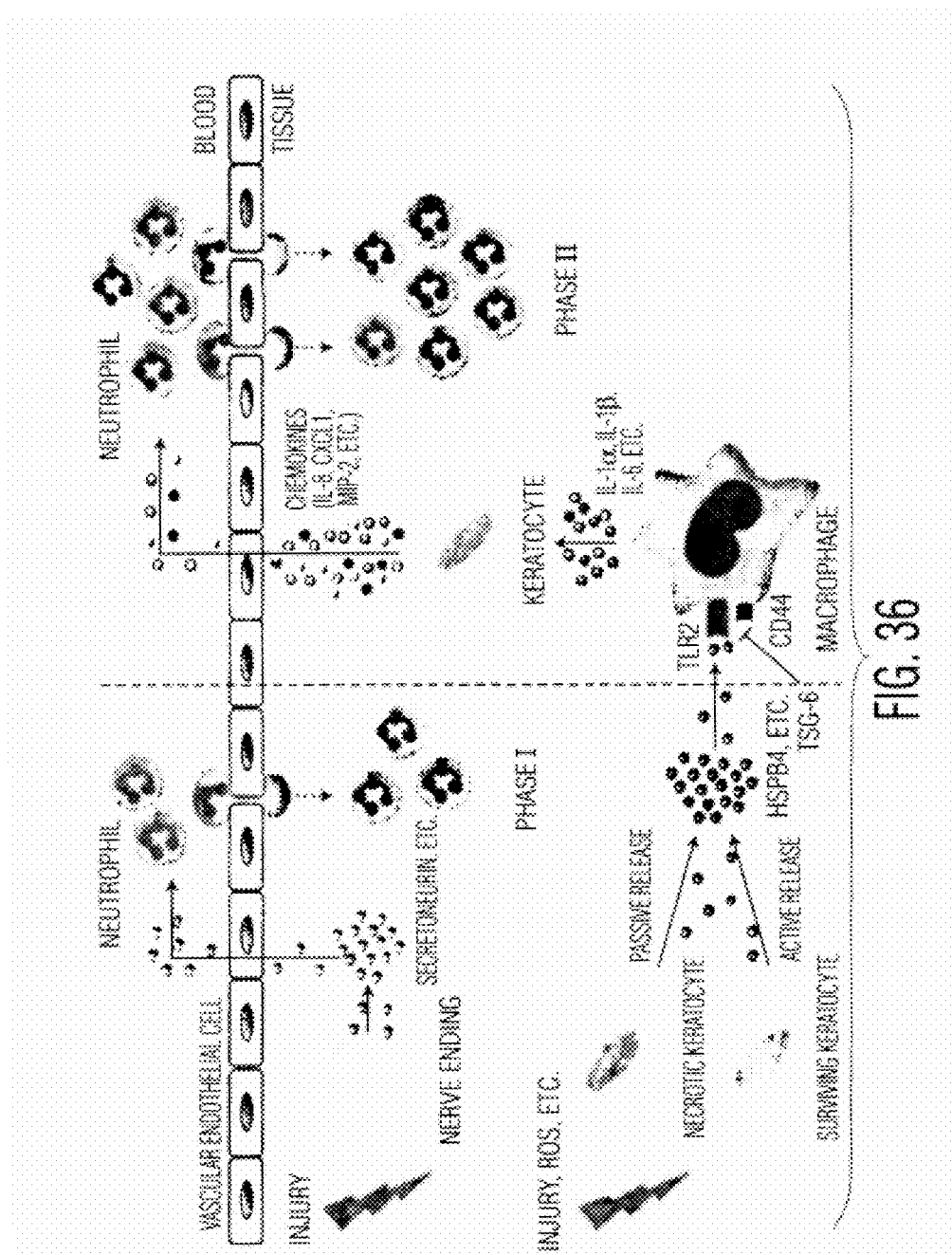
FIG. 36. The schematic diagram of sterile inflammation in the cornea Immediately after injury, SN is released from nerve endings in the cornea and circulating neutrophils are recruited, thereby inducing the Phase I inflammatory response. In response to injury including oxidative stress, necrotic or injured keratocytes secrete HSPB4. The HSPB4 activates resident macrophages in the cornea via the TLR2/NF-kB signaling pathway to produce pro-inflammatory cytokines including IL-1 and IL-6. These injury signals are propagated rapidly and amplified by keratocyte activation to produce chemokines that induce neutrophil infiltration of Phase II. TSG-6 decreased neutrophil infiltration by inhibiting the initial step of macrophage activation via TLR2/CD44/NF-kB signaling.

To test the effects of HSPB4 on macrophages, macrophages were incubated with extracts of necrotic corneas. The extracts increased the expression of the pro-inflammatory cytokines IL-1α, IL-1β, and IL-6 (FIG. 34D); however, heat inactivation of the extracts inhibited their effect, suggesting that the active factor(s) in the extracts was (were) protein(s). Addition of either a polyclonal or monoclonal antibody to HSPB4 suppressed significantly the effect of the necrotic extracts on macrophage activation, indicating that one of the active factors in necrotic corneal extracts was HSPB4 (FIG. 34D). In addition, recombinant HSPB4 increased the expression of the pro-inflammatory cytokines by macrophages in a dose-dependent manner (FIG. 34E). As expected, HSPB4 caused translocation to the nucleus of the NF-kB complex in macrophages (FIG. 34F). To test whether HSPB4 signaled through the TLR2/NF-kB pathway, a reporter cell line transduced was used to assay TLR2/NF-kB signaling (HEK-TLR2). Experiments in a HEK-TLR2 cell line demonstrated that the necrotic extracts of the cornea increased TLR2/NF-kB signaling and that antibodies to HSPB4 inhibited the effect (FIG. 34G). Recombinant HSPB4 stimulated NF-kB signaling in the same cell line in a dose-dependent manner (FIG. 34H). HSPB4 acted primarily through TLR2; it had a smaller effect in the reporter cell line that expressed TLR4 and no effect in the reporter cell without either receptor (FIGS. 34I and J); however, HSPB4 did not stimulate keratocytes in culture to express pro-inflammatory cytokines (FIG. 35F). Also, other Group A molecules such as HSPB5 and βB-crystallin had no effect on pro-inflammatory cytokine production in macrophages or on NF-kB activation in HEK-TLR2 cells (FIG. 34K). In addition, SN did not induce the expression of pro-inflammatory cytokines in either macrophages or keratocytes in vitro (FIG. 35F). Similarly, HSPB4 did not stimulate keratinocytes in culture to express pro-inflammatory cytokines. (FIG. 35F). Together, the results indicated that HSPB4 was a principal DAMP for Phase II and acted through the activation of resident macrophages in the cornea.

TSG-6 Suppressed HSPB4-Induced Activation of Macrophages.

TSG-6 was shown previously to provide a potential therapy for chemical injuries of the cornea but its mechanism of action was not established (Oh, Proc. Nat. Acad. Sci., 2010). Therefore, the hypothesis that TSG-6 inhibited the Phase II response, but not Phase I (FIGS. 34B and C) was tested by decreasing the HSPB4 induced activation of macrophages. Recombinant TSG-6 decreased expression of pro-inflammatory cytokines in macrophages stimulated by HSPB4 (FIGS. 35A and B). Because the protein was shown previously to inhibit TLR2/NFkB signaling in macrophages by interaction with CD44 (Choi, Blood, in press; Lesley J, Gal I, Mahoney D J, et al., TSG-6 modulates the interaction between hyaluronan and cell surface CD44. J Biol Chem., 2004; 279:25745-25754). Whether the effects of TSG-6 were CD44-dependent also were examined. As expected, TSG-6 had no significant effect on NF-kB signaling in the HEK-TLR2 reported cell line unless the cell line were transduced to express CD44 (FIGS. 35C and D); however, TSG-6 had no effect on the parent cell line that did not express CD44. Also, TSG-6 had no effect the Phase II inflammatory response after chemical/mechanical injury to the cornea of CD44 knockout mice (FIG. 35E), indicating that the action of TSG-6 on macrophages was CD44-dependent.

Example 11

Stanniocalcin-1 Rescued Photoreceptor Degeneration in Two Rat Models of Inherited Retinal Degeneration The purpose of this study was to evaluate the neuroprotective potential of STC-1 for the therapy of blinding retinal degenerations (RDs) that include photoreceptor degeneration, such as the retinitis pigmentosa (RP) family of inherited RDs and the epidemic atrophic AMD, which is the leading cause of vision loss among the elderly worldwide (Cook et al., 2008). This study demonstrates that intravitreal administration of STC-1 rescues photoreceptors from degeneration in two rat models of RD with different etiologies.

Materials and Methods
Animals and Reagents

The experimental protocols were approved by the Institutional Animal Care and Use Committees of Texas A&M Health Science Center and the University of California, San Francisco.

Recombinant human STC-1 used in this study was purchased from BioVender Research and Diagnostic Products (Czech Republic). According to the manufacturer's instructions, distilled water was added to a vial of STC-1 that was lyophilized in 20 mM Tris buffer, 20 mM NaCl to yield a final solution of 0.5 mg/mL.

Vials of frozen passage one hMSCs were obtained from the Center for the Preparation and Distribution of Adult Stem Cells (medicine.tamhsc.edu/irm/msc-distribution.html). Following culture at high density for 24 hours to recover viable cells, hMSCs were plated at low density (100 cells/cm$^2$), incubated in complete culture medium (CCM) with 16% FBS for 8 days until approximately 70% confluence was reached, and harvested with 0.25% trypsin/1 mM EDTA at 37° C. for 2 min. The trypsin was inactivated by adding the CCM to the cells, and the cells were washed with PBS by centrifugation at 1,200 rpm for 5 min. The cells were frozen in α-MEM with 30% FBS and 5% DMSO at a concentration of 1 million cells/mL. The same protocol was used to expand the cultures to generate passage two and then passage three cells. Passage three cells were used for all experiments. For injection, the cells were lifted, washed by centrifugation with Hank's Balanced Salt Solution (HBSS; BioWhittaker), and suspended in HBSS at a concentration of 20,000 cells/μL.

Descriptions of the S334ter-3 and RCS rats can be found at the following website: www.ucsfeye.net/mlavailRDratmodels.shtml Intravitreal Injections S334ter-3 and RCS rats were anesthetized by isoflurane inhalation. Following topical betadine (5% ophthalmic prep solution, Alcon, Fort Worth, Tex.) and proparacaine hydrochloride (0.5% ophthalmic solution USP, Bauch & Lomb, Tampa, Fla.), the rats received an intravitreal injection using a Hamilton syringe (Hamilton #80337) with a 32-gauge needle (Hamilton #7803-04). For all experiments in the S334ter-3 rat, 1 μg STC-1 (2 μL; 0.5 μg/μL) was injected into the vitreous cavity either once at P9, or twice with one injection at P9 and another at P12. Animals were sacrificed and tissues were collected at P19. For experiments with RCS rats, 1 μg STC-1 (2 μL; 0.5 μg/μL) was injected for morphometric and ERG analysis. For real time RT-PCR of transcripts and ELISAs for oxidative damage stress, RCS received 2.5 μg STC-1 (5 μL; 0.5 μg/μL). Intravitreal injection was performed either once at P21, or twice at P21 and P28. The rats were sacrificed for tissue collection at P42. For cell therapy experiments, 100,000 hMSCs in 5 μL HBSS were injected into the vitreous cavity at P21 and rats were sacrificed for tissue collection at P42. Initiation of treatment for each model was selected based on the initiation of morphologic degeneration for each model (Martinez-Navarrete et al., 2011; LaVail and Battelle, 1975). Additionally, the volume/dose of STC-1 was based on the age of initiation of treatment. For the 5334 rat which was first injected at P9, a maximum of 2 μL was administered. For the RCS which was first injected at P21, a maximum of 5 μL was administered due to the larger vitreous cavity at this age.

Microarray Assays

A total of 250 ng of RNA from each sample was applied for microarrays using GeneChip 3'IVT Express Kit (Affymetrix) according to manufacturer's directions. Briefly, poly-A RNA controls were added into each sample to provide exogenous positive controls to monitor the eukaryotic target labeling process. T7 oligo(dT) primer was used to generate first strand cDNA followed by second strand cDNA synthesis. To generate biotin modified aRNA, in vitro transcription was performed followed by purification and quantification of labeled aRNA. A total of 15 μg of aRNA was fragmented and hybridized (GeneChip Hybridization Oven 640; Affymetrix) onto rat arrays (RG230 2.0, Affymetrix) followed by array washing and staining (GeneChip Fluidics Station 450; Affymetrix) with GeneChip Hybridization, Wash, and Stain Kit (Affymetrix). Arrays were scanned with GeneChip Scanner (Affymetrix) and images checked for quality. Data were normalized using robust multi-array (RMA) algorithm and gene level analysis was performed with Partek Genomics Suite 6.4 (Partek). To obtain up- and down-regulated genes, STC1-treated samples were compared with PBS-treated samples within each model and expression level changes of at least 1.5-fold were considered significant. Genes upregulated at least 1.5-fold in both models were used for detection of enriched Gene Ontology terms using the Partek Genomics Suite 6.4 software.

Real Time RT-PCR Assays

For RNA extraction, retinas were isolated by surgical excision, immediately placed in RNA isolation reagent (RNA Bee, Tel-Test Inc., Friendswood Tex.), and frozen at −80° C. The samples were rapidly thawed and homogenized on ice, and total RNA was extracted (RNeasy Mini kit; Qiagen). cDNA was generated by reverse transcription (SuperScript III; Invitrogen) using 1 μg total RNA. Real time amplification was performed using TaqMan Universal PCR Master Mix (Applied Biosystems, Carlsbad, Calif.). PCR probe sets and Taqman Gene Expression Assay kits (Applied Biosystems, Carlsbad, Calif.) were used to measure gene expression (Rho: Rn00583728 m1; Rcvrn: Rn00590194 m1; Pdc: Rn00563505 m1; NRLZ: Rn01502072g1; UCP-2: Rn01754856_m1; and 18s: 4352930E). Values were normalized to 18s RNA and expressed as a fold change compared to the fellow eye.

Histological Analysis

Tissue processing and histological analysis was performed as previously described (Lewin et al., 1998). Briefly, following euthanasia by overdose of carbon dioxide, eyes were enucleated and immediately fixed in a mixture of 2.5% glutaraldehyde and 2% paraformaldehyde. Eyes were embedded in epoxy resin, and 1 μm-thick sections were made along the vertical meridian. To quantify photoreceptor loss, a mean ONL thickness was obtained by taking an average of a total of 54 measurements from the superior and inferior hemispheres (27 per hemisphere) using the Bioquant Morphometry System (R & M Biometrics Inc., Nashville, Tenn.). Pyknotic index was determined by counting numbers of pyknotic photoreceptor nuclei as a percent of total photoreceptor nuclei.

Electroretinogram Analysis

Electroretinography was performed as previously described (Lewin et al., 1998). Briefly, following overnight dark-adaption, rats were anesthetized with ketamine (80 mg/kg) and xylazine (16 mg/kg). Pupils were dilated with 1% tropicamide and 2.5% phenylephrine. ERGs were recorded using a wire contacting the corneal surface with 1% methylcellulose. The signal was amplified, digitized, and stored using an LKC UTAS-3000 Diagnostic System (Gaithersburg, Md.).

ELISAs for Markers of Oxidative Damage

For protein extraction, retina was sonicated on ice (Ultrasonic Processor, Cole Parmer Instruments, Vernon Hills Ill.) in a Tris-EDTA solution containing protease inhibitor cocktail (Roche, Indianapolis, Ind.). After centrifugation at 12,000 rpm at 4° C. for 20 min, the supernatant was assayed for protein carbonyl content (OxiSelect™ Protein Carbonyl ELISA Kit, Cell Biolabs, Inc., San Diego Calif.) or nitrotyrosine content (OxiSelect™ Nitrotyrosine ELISA Kit, Cell Biolabs, Inc. San Diago, Calif.).

Real Time RT-PCR Based Standard Curve for hGAPDH

A standard curve was generated by adding serial dilutions of hMSCs to rat tissue as previously described (Lee et al., 2009). Briefly, 100 to 100,000 hMSCs were added to each rat whole globe. Following RNA extraction (RNeasy Mini kit; Qiagen, Valencia, Calif.), cDNA was generated by reverse transcription (SuperScript III; Invitrogen, Carlsbad, Calif.) using 1 µg total RNA. Human-specific GAPDH primers and probe (TaqMan Gene Expression Assays ID, GAPDH HS99999905_05) were used. The standard curve was made based on hGAPDH expression from a known number of hMSCs added to one rat globe and the values were normalized to total eukaryotic 18s rRNA (TaqMan Gene Expression Assays, 4352930E).

Statistics

Paired, 2-tailed Student's t-tests were used to compare treated and control eyes from the same rat in all experiments.

Results

STC-1 in the S334ter-3 Rat: Improved Survival of Photoreceptors

To test the therapeutic effects of STC-1, a model in which there is rapid degeneration of both rod and cone photoreceptors, the S334ter-3 rhodopsin transgenic rat (Liu et al., 1999; Martinez-Navarrete, 2011) was first selected. The early onset of photoreceptor degeneration is seen as an increase in the incidence of pyknotic photoreceptor nuclei in the outer nuclear layer (ONL) beginning at postnatal day 8 (P8), with many more pyknotic nuclei present and obvious disorganization of photoreceptor inner segments at P10, just as photoreceptor outer segment development begins (Liu et al., 1999). Photoreceptor cell loss is then rapid, and only a single row of photoreceptor nuclei remains in the central retina at P20 (Liu et al., 1999), and no rod outer segments ever develop in the S334ter-3 rat (Liu et al., 1999; Martinez-Navarrete et al., 2011). It was elected to test a maximal dose of STC-1 based on the concentration of the undiluted commercially supplied protein (0.5 µg/µl) and volume tolerated for injection into the vitreous. Therefore, 1 µg STC-1 was injected into the vitreous cavity either once at P9, or twice with one injection at P9 and another at P12. In eyes treated with STC-1 (FIGS. 37A, C, and D; Table 15), there was an increased number of surviving photoreceptor nuclei on P19 as assayed by quantitative measure of the ONL thickness (Lewin et al., 1998).

TABLE 15

Intravitreal administration of STC-1 rescued photoreceptors in the S334ter-3 rat. Average measurements of the thickness of outer nuclear layer (ONL) in µm in mean superior (Mean Sup) and mean inferior (Mean Inf) hemispheres from 15 eyes receiving STC-1 (X1) and 10 receiving STC-1 (X2) and their corresponding contralateral controls showed significant rescue following one or two injections of STC-1. Error bars represent means ± standard deviation.

| | No. of animals | ONL thickness (µm) | | |
|---|---|---|---|---|
| | | Mean Sup | Mean Inf | Mean total |
| Uninjected | 15 | 6.9 ± 1.1 | 8.8 ± 1.0 | 7.9 ± 1.0 |
| STC-1 injected (X1) | 15 | 11.2 ± 2.3 | 12.5 ± 2.3 | 11.8 ± 2.2 |
| P-Value | | 0.0000001 | 0.00003 | 0.000001 |
| Uninjected | 10 | 6.7 ± 0.5 | 7.8 ± 1.3 | 7.3 ± 0.7 |
| STC-1 injected (X2) | 10 | 11.4 ± 2.7 | 12.0 ± 2.5 | 11.7 ± 2.4 |
| P-Value | | 0.0005 | 0.0002 | 0.0002 |

Similar results were obtained with one injection (n=15, P=0.000001) or two injections (n=10, P=0.0001) (Table 15). In the histological analysis, no apparent negative effect of STC-1 was found.

STC-1 in S334ter-3 Rat: Improved Retinal Function

Figure 37:
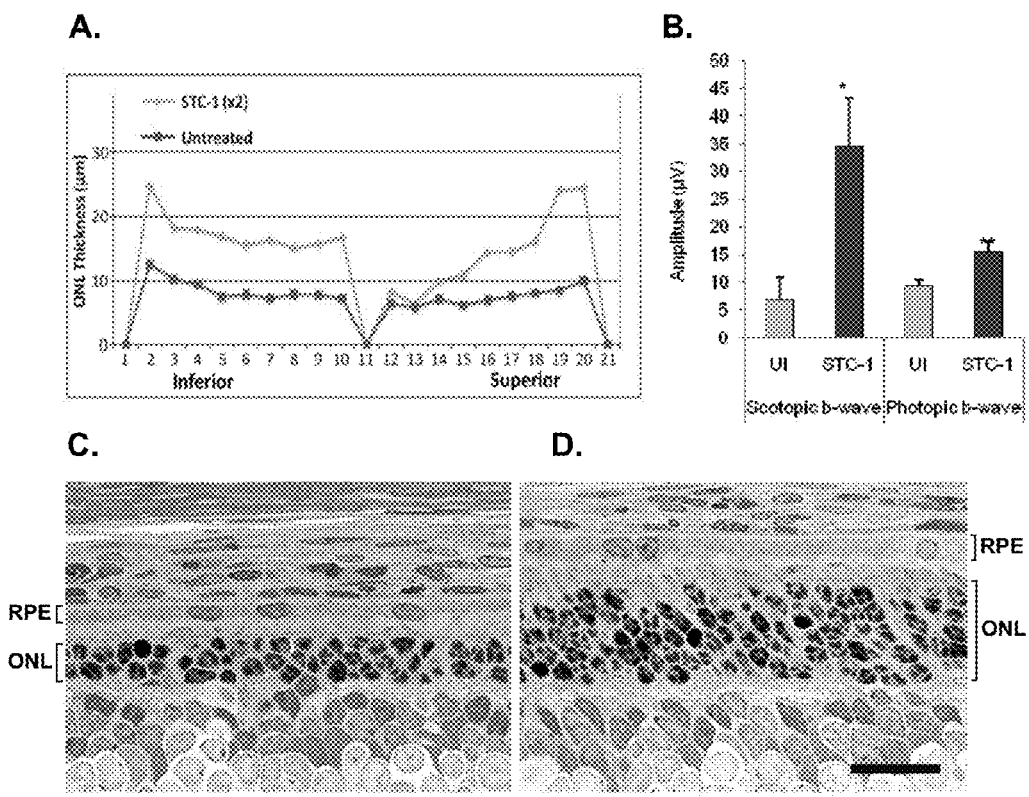
FIG. 37. Intravitreal administration of STC-1 (SEQ ID NO:2, which comprises C-Terminal Flag-tag) rescued photoreceptors in the S334ter-3 rat. (A) Plot of ONL thickness taken from a total of 54 measurements in each retina (27 superior retina and 27 inferior retina) from a representative animal demonstrated that STC-1 injected twice significantly improved outer nuclear layer (ONL) thickness compared to uninjected (UI) controls. (B) Electroretinographic analysis performed at P19 following injection of STC-1 in the S334ter-3 rat at P9 (n=10). Response amplitudes are from a stimulus intensity of 0.4 log cd sec/$m^2$ in dark-adapted rats (scotopic b-wave) and light-adapted rats (photopic b-wave). Significant rescue of both scotopic and photopic b-waves was observed. (C-D) Light micrographs of the posterior retina of an S334ter-3 rat injected twice (at P9 and P12) with STC-1 and eyes taken at P19. The ONL in the treated eye (D) is approximately twice the thickness of that in the control eye (C), i.e., it contains approximately twice the number of photoreceptors. RPE, retinal pigment epithelium. Bar=20 μm. * $P<0.05$; ** $P<0.01$. Error bars represent means±s.e.m.

To test functional improvements in the retina following STC-1 therapy, eyes of the rats were examined with electroretinography (ERG), which provides a measure of rod- and cone-generated responses to varying stimuli of light. The responses from dark-adapted retinas (scotopic) are primarily from rods, and those from light-adapted retinas (photopic) are primarily from cones. ERG responses to light stimuli greater than noise levels require the transduction of light by photoreceptor outer segments. As noted above, rod outer segments never develop in the S334ter-3 rats (Liu et al., 1999; Martinez-Navarrete et al., 2011), and using PNA staining, only a very few, short cone outer segments are found in the central retina of S334ter-2 rats (Martinez-Navarrete et al., 2011). As a consequence, ERG response amplitudes are almost never seen above threshold levels of 20 µV for the scotopic b-wave and 10 µV for the photopic b-wave in this line of rats. However, following a single injection of STC-1 at P9, the amplitudes of both the scotopic and photopic ERG responses at P19 were greater than threshold levels and greater than those in control eyes in the same animals (FIG. 37B). Therefore, STC-1 treatment results in a functional improvement of both rod and cone photoreceptors.

STC-1 in the S334ter-3 Rat: Improved Levels of Photoreceptor mRNAs

For quantitative assays of photoreceptor viability, surveys with microarrays to identify candidate genes whose expression decreased with time in the retinas of the rats were first selected (Table 16 and Table 17).

TABLE 16

Selected Gene Ontology terms enriched in the group of up-regulated genes in S334ter-3 and RCS rat retinas following intravitreal administration of STC-1. Genes up-regulated at least 1.5-fold by STC-1 treatment in both models were used for detection of enriched Gene Ontology terms (Partek Genomics Suite 6.4 software).

| Selected Gene Families (Listed by enrichment p-value) | No. of genes in list |
|---|---|
| P < 0.0001 | |
| phototransduction | 9 |
| detection of light stimulus involved in visual perception | 9 |
| photoreceptor cell development | 6 |
| rhodopsin mediated phototransduction | 3 |
| neuron development | 6 |
| photoreceptor outer segment | 4 |
| nonmotile primary cilium | 4 |
| transcription | 5 |
| photoreceptor cell morphogenesis | 2 |
| P < 0.001 | |
| neurological system process | 8 |
| cell development | 7 |
| intracellular cyclic nucleotide activated cation channel activity | 2 |
| P < 0.01 | |
| photoreceptor cell maintenance | 2 |
| negative regulation of caspase activity | 2 |
| ligand-gated ion channel activity | 3 |
| transmembrane transporter activity | 5 |
| response to stimulus | 17 |
| P < 0.05 | |
| anatomical structure homeostasis | 3 |
| presynaptic membrane | 2 |
| cell morphogenesis involved in differentiation | 2 |
| gated channel activity | 3 |
| positive regulation of transcription from RNA polymerase II promoter | 5 |
| channel activity | 3 |
| passive transmembrane transporter activity | 3 |
| cellular hormone metabolic process | 2 |
| cellular developmental process | 9 |

TABLE 17

Selected genes of interest up-regulated in S334ter-3 and/or RCS rat retinas following intravitreal administration of STC-1. Selected genes up-regulated over 2-fold compared to contralateral controls.

| Gene | Name | Fold change S334ter-3 | Fold change RCS | Function | Reference (PMID) |
|---|---|---|---|---|---|
| Aipl1 | Aryl hydrocarbon receptor interacting protein-like 1 | — | 2.0 | Required for assembly of functional rod phosphodiesterase subunits | 19758987 |
| Cabp4 | Calcium binding protein 4 | 2.2 | 2.8 | Retinal cone and bipolar cell development | 16249514 |
| Cngb1 | Cyclic nucleotide gated channel beta 1 | 2.0 | 2.4 | Subunit of the cyclic nucleotide-gated cation channel in rods | 7682292 |
| Crx | Cone-rod homeobox | — | 2.6 | Coordinates photoreceptor gene expression | 20693478 |
| Drd4 | Dopamine receptor 4 | — | 2.0 | Suppresses adenylate cyclase in the retina | 12763097 |
| Fabp12 | Fatty acid-binding protein 12 | 2.1 | 3.3 | Subunit of rod channel | 18786628 |
| Gnat1 | Guanine nucleotide binding protein, alpha transducing activity polypeptide 1 | 2.2 | 3.9 | Subunit of G protein which stimulates the coupling of rhodopsin and cGMP-phoshodiesterase during visual impulses. | 17584859 |
| Gnb3 | Guanine nucleotide-binding protein beta3 | — | 2.2 | Isoform of the beta subunit of the heterotrimeric G protein second messenger complex. Expressed in photoreceptors | 20538044 |
| Grk5 | G protein-coupled receptor kinase 5 | 2.1 | — | Phosphorylates rhodopsin | 8120045 |
| Guca1a | Guanylate cyclase activating protein 1 | — | 2.0 | Ca2+ dependent negative feedback regulation of membrane bound guanylate cyclases in rods and cones | 19459154 |
| Kcnv2 | Potassium channel, subfamily V, member 2 | 2.2 | — | Voltage-gated potassium channel in rods and cones | 16909397 |
| Lgals3 | Lectin, galactoside-binding, soluble, 3 | 2.2 | — | Expressed in Muller cells | 19816601 |
| Lrp5 | Low-density lipoprotein receptor-related protein 5 | 2.1 | — | Muller cell function | 20652025 |
| Nrl | Neural retina leucine zipper | 2.0 | 3.1 | Regulator of photoreceptor differentiation and function | 1729696 |
| Nxnl1 | Nucleoredoxin- like 1 | — | 2.3 | Defense against oxidative stress Involved in cone survival | 21079812 20949100 |
| Pdc | phosducin | — | 2.2 | Regulates transmission at the photoreceptor-to-ON-bipolar cell synapse | 20203183 |

TABLE 17-continued

Selected genes of interest up-regulated in S334ter-3 and/or RCS rat retinas following intravitreal administration of STC-1. Selected genes up-regulated over 2-fold compared to contralateral controls.

| Gene | Name | Fold change S334ter-3 | RCS | Function | Reference (PMID) |
|---|---|---|---|---|---|
| Pde6b | Phosphodiesterase 6B, cGMP-specific, rod, beta | — | 2.4 | Composes catalytic subunit of key effector enzyme of the phototransduction cascade | 20940301 |
| Prph2 | Peripherin 2 | — | 2.7 | Necessary for cone structure | 1071739 |
| Rcvrn | Recoverin | 2.5 | 3.0 | Termination of the phototransduction cascade in the retina | 1672047 |
| Reep6 | Recoverin | 2.1 | 3.0 | Termination of the phototransduction cascade in the retina | 1672047 |
| Rho | Rhodopsin | — | 3.2 | G-protein-coupled receptor | 20708633 |

Figure 38:
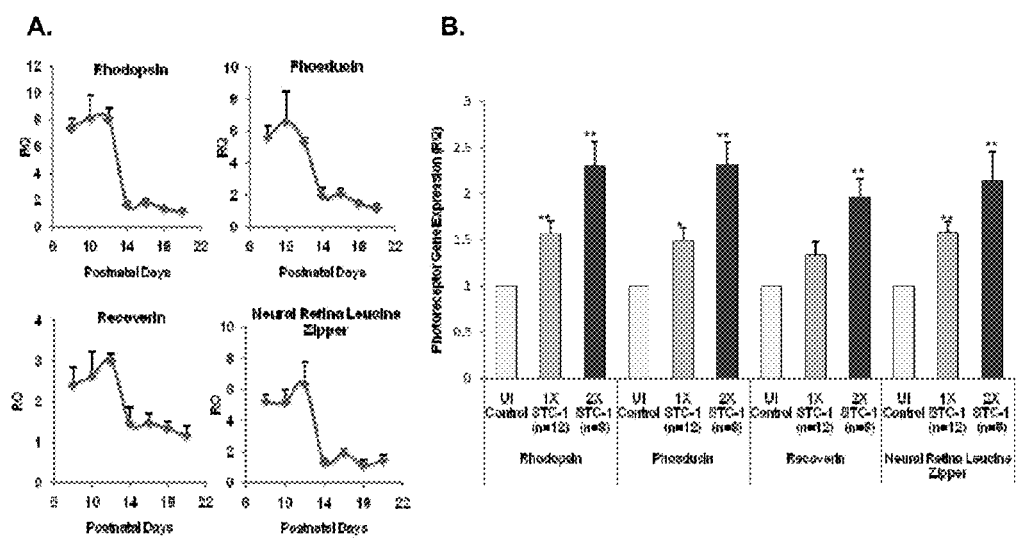
FIG. 38. Intravitreal administration of STC-1 (SEQ ID NO:2) rescued photoreceptor gene expression in the S334ter-3 rat. Real time RT-PCR analysis for the photoreceptor genes. (A) Photoreceptor gene expression declined rapidly from P12-P14. (B) Treatment with STC-1 rescued expression of four photoreceptor genes compared to uninjected (UI) control eyes from the same rats after one injection (1×STC-1) or two injections (2×STC-1). * $P<0.05$; ** $P<0.01$. Error bars represent means±s.e.m.

Real time RT-PCR assays were used for transcripts expressed in photoreceptors. Beginning on about P12, there was a rapid two-day decrease in the levels of mRNAs for four photoreceptor specific genes: rhodopsin, recoverin, phosducin, and neural retina leucine zipper (FIG. 38A). The decrease in the mRNAs occurred with a similar time course as previously observed by morphology of photoreceptor loss in the transgenic rats (Liu et al., 1999). The slight increase in photoreceptor gene expression observed between P8 to P12 is consistent with the observations that photoreceptor development continues to increase postnatally until about P12 (Chiang and Barnstable, 1998). A single intravitreal injection of STC-1 significantly increased the levels of mRNAs for three of the genes: rhodopsin, phosducin, neural retina leucine zipper (FIG. 38B). Two injections significantly increased the levels of all four photoreceptor genes compared to uninjected (UI) controls. Additionally, there appeared to be a dose-dependent trend in rescue of photoreceptor transcripts.

STC-1 in the RCS Rat: Improved Survival of Photoreceptors

Next the effects of STC-1 were examined in a slower model of RD, the Royal College of Surgeons (RCS) rat (LaVail and Battelle, 1975) which is characterized by a dysfunctional RPE that is unable to remove shed outer segments of photoreceptors that accumulate and lead to the death of the photoreceptors. Additionally, other debris including pyknotic photoreceptor nuclei remain due to impaired phagocytic clearing (LaVail and Battelle, 1975). One μg STC-1 was injected into the vitreous cavity either once at P21, or twice with one injection at P21 and another at P28. Quantitative morphometric analysis of the thickness of the ONL at P42 did not show any difference between control eyes and STC-1 injected eyes. However, STC-1 produced a marked improvement in morphology as reflected by longer photoreceptor inner segments and fewer pyknotic nuclei in the STC-1 treated eyes compared to UI controls (FIGS. 39A and B; Table 2).

TABLE 18

Intravitreal administration of STC-1 rescued photoreceptors in the RCS rat. Pyknotic index showed a decreased percent of pyknotic nuclei in STC-1 treated eyes after single injection on P22 and assay on P42, injections on P21 and P28 with assay on P42, or injection on P25 and assay on P51. Pyknotic index was determined as the proportion of the number of pyknotic photoreceptor nuclei to the number of all nuclei in the ONL in ten 440-μm length sections of posterior retina from each animal (5 in the inferior hemisphere and 5 in the superior hemisphere). Error bars represent means ± standard deviation.

| Age(s) Injected-Eyes taken | No. of animals | Uninjected (%) | STC-1 injected (%) | P-Value |
|---|---|---|---|---|
| P22-P42 | 9 | 75.0 ± 3.5 | 47.8 ± 12.3 | <0.0005 |
| P21, P28-P42 | 6 | 67.5 ± 4.2 | 26.7 ± 16.0 | <0.005 |
| P25-P51 | 7 | 60.0 ± 2.9 | 34.6 ± 19.5 | <0.05 |

In the UI control eyes, many of the pyknotic nuclei coalesced with other nuclei to form large masses of chromatin, an observation previously described in the RCS rat (LaVail and Battelle, 1975) and the similar Mer knockout mouse (Duncan et al., 2003). The delay in clearance of pyknotic photoreceptor nuclei in the RCS rat is due to a null mutation in the gene for c-mer proto-oncogene tyrosine kinase (Mertk) that is expressed not only in RPE cells that phagocytose shed outer segments of photoreceptors, but also in macrophages such as those that invade the RCS retina (LaVail, 1979) and that show a generalized defect in removal of some apoptotic cells (Scott et al., 2001). Of note, a single injection of STC-1 produced these morphologic improvements 26 days after treatment providing evidence that the effects are relatively long-lasting. As with the S334ter-3 rats, no negative effects caused by STC-1 in the RCS rats was found.

STC-1 in the RCS Rat: Improved Retinal Function

Figure 39:
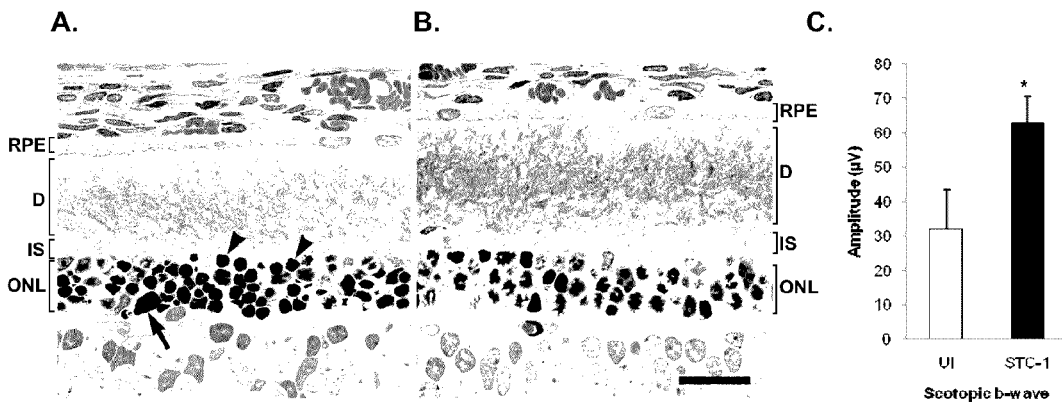
FIG. 39. Intravitreal administration of STC-1 (SEQ ID NO:2) rescued photoreceptors in the RCS rat. (A-B) Light micrographs of the posterior retina of an RCS rat injected twice (at P21 and P28) with STC-1 and eyes taken at P42. The outer nuclear layer (ONL) in the two eyes is similar in thickness. However, in the uninjected control eye (A), a large percentage of photoreceptor nuclei are dead and pyknotic (arrowheads), and some are coalesced into large masses of chromatin (arrows), typical of RCS retinas at this age. In the STC-1 treated eye (B), far fewer pyknotic nuclei are present and the rod outer segment debris zone (D) is thicker than in the control eye. IS, photoreceptor inner segments; RPE, retinal pigment epithelium. Bar=20 μm. (C) Electroretinographic analysis performed at P42 following injections of STC-1 in the RCS rat at P21 and P42. Response amplitudes are from a stimulus intensity of 0.4 log cd sec/$m^2$ in dark-adapted rats (scotopic b-wave). Significant rescue of scotopic b-waves was observed. * $P<0.05$. Error bars represent means±s.e.m.

To test functional improvements following STC-1 therapy, ERG response amplitudes were measured at P42 in RCS rats that received one injection at P21 and a second injection at P28. In the RCS rat, significant improvements in scotopic ERG responses were observed (FIG. 39C). Photopic responses were not improved in the RCS rat; however, this is not surprising as cone degeneration does not begin in the RCS rat until approximately P44 (Pinilla et al., 2004).

STC-1 in the RCS Rat: Improved Levels of Photoreceptor mRNAs

Figure 40:
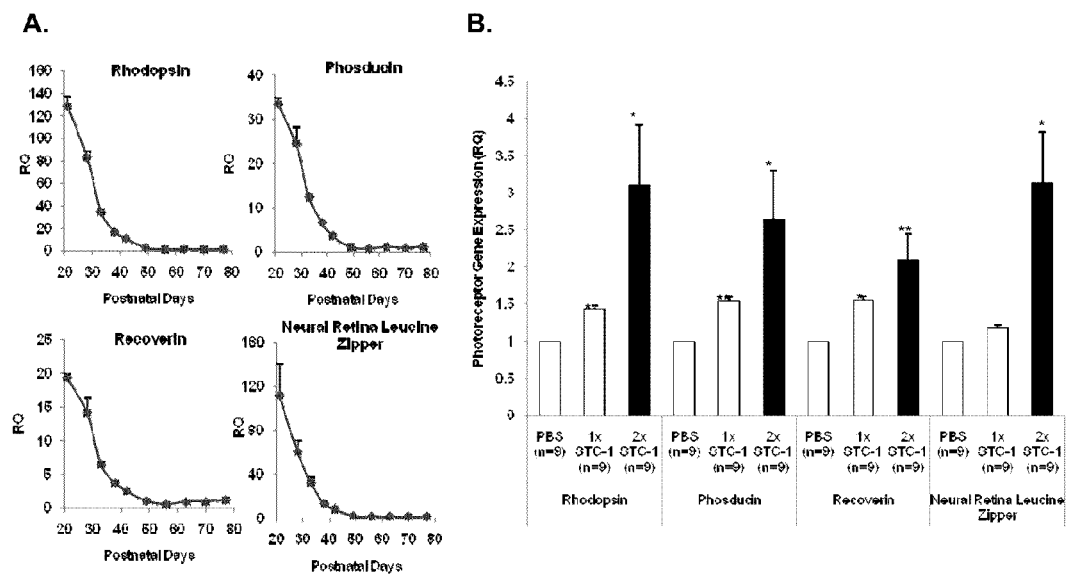
FIG. 40. Intravitreal administration of STC-1 rescued photoreceptor gene expression in the RCS rat. Real time RT-PCR analysis for the photoreceptor genes. (A) Photoreceptor gene expression underwent a gradual decline in the RCS rat between P21 and P45. The decline was more gradual than in the S334ter-3 rat (compare with FIG. 2). (B) Two injections of STC-1 (2×STC-1) rescued expression of the four photoreceptor genes compared to vehicle controls. A single injection of STC-1 (1×STC-1) increased the levels of three of the photoreceptor transcripts. * $P<0.05$; ** $P<0.01$.

As expected, real time RT-PCR assays demonstrated a more gradual decline in photoreceptor gene expression in the RCS rat (FIG. 40A) than in the S334ter-3 rat (FIG. 38A). The rate of loss was similar to the rate of morphological changes previously observed in the retina (LaVail and Battelle, 1975). Intravitreal injection of STC-1 increased the levels of three of the photoreceptor transcripts in the eye at P42 after a single intravitreal injection of 2.5 μg of STC-1 at P21 and of all four photoreceptor transcripts after two injections, one injection at P21 and a second at P28 (FIG. 40B), compared to PBS-injected controls. Additionally, there appeared to be a dose-dependent trend in the rescue of photoreceptor transcripts.

STC-1 in the RCS Rat: Decrease in Products of ROS

Figure 41:
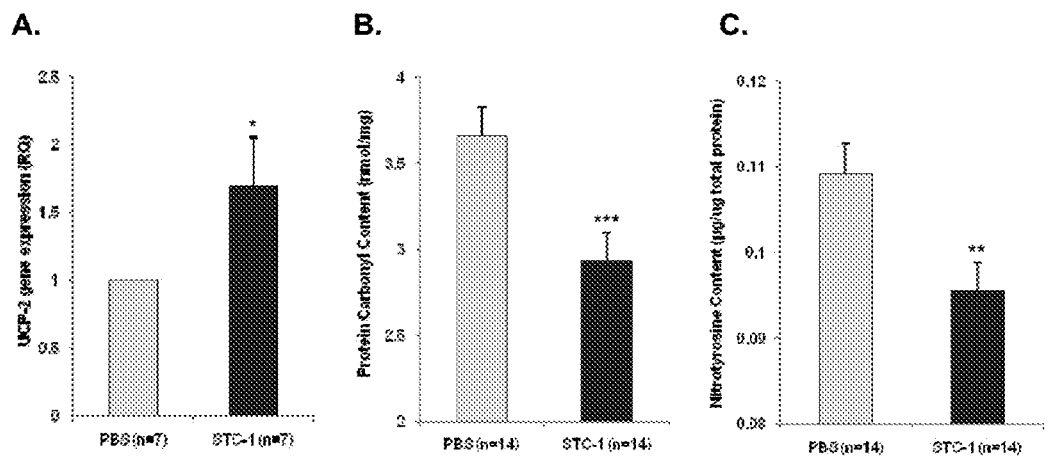
FIG. 41. Intravitreal administration of STC-1 (SEQ ID NO:2) increased UCP-2 gene expression and decreased levels of ROS products in the RCS rat. (A) Real time RT-PCR analysis for the mitochondrial uncoupling protein UCP-2 three days after injection of STC-1 at P21. (B, C) ELISA analysis for two markers of oxidative damage in the retina: protein carbonyl (B) and nitrotyrosine (C) content at P42 after injections of STC-1 at P21 and P28. Error bars represent means±s.e.m. * P<0.05;  P<0.01; * P<0.001.

To test the hypothesis that the improvements of photoreceptor viability were explained by the ability of STC-1 to upregulate UCP-2, expression of UCP-2 was assayed by real time RT-PCR following intravitreal injection of STC-1 in the RCS rat. Significant increases in UCP-2 gene expression were observed in the retina three days following injection of STC-1 at P21 (FIG. 41A). For evidence of a reduction in oxidative stress following STC-1 treatment, the retinas were assayed for protein carbonyl and nitrotyrosine, products of ROS that were used previously to measure oxidative damage in models of RD (Usui et al., 2009; Komeima et al., 2008) and were observed in the eyes of patients with AMD (Murdaugh et al., 2010; Ng et al., 2008). Assays of retinas at P42 demonstrated that injection of STC-1 at P21 and P28 decreased the levels of both protein carbonyl and nitrotyrosine at P42 (FIGS. 41B and C) compared to PBS-injected controls.

STC-1 in Both Models: Common Gene Expression Changes

To make global comparisons between the two models, RNA from S334ter-3 and RCS retinas were analyzed by gene expression microarrays. Visual comparisons of heat maps demonstrated major differences between the two models. However, the data also indicated that administration of STC-1 produced up-regulation of a series of identical genes in both models (Table 16, Table 17). Both models showed significant up-regulation of important recovery associated genes with functions in phototransduction, photoreceptor cell development and morphogenesis, neuron development, negative regulation of caspase activity, and in other related processes (Table 16, Table 17). Additionally, a smaller class of genes was down-regulated following STC-1 injection in both models (Table 19).

TABLE 19

Genes down-regulated in both S334ter-3 and RCS rat retinas following intravitreal administration of STC-1.

| | | Fold change | |
|---|---|---|---|
| Gene | Name | S334ter-3 | RCS |
| Gjb2 | Gap Junction protein, beta 2 | -2.2 | -2.1 |
| Agr2 | Anterior gradient homolog 2 | -2.5 | -2.2 |
| Dcn | Decorin | -6.6 | -3.6 |

Human MSCs as a Vehicle to Deliver STC-1 in the RCS Rat

The hypothesis that intravitreal administration of human MSCs (hMSCs) could be used to deliver STC-1 to the retina was also tested. Previous reports demonstrated that MSCs rescued photoreceptor degeneration in models of RD following subretinal injection (Inoue et al., 2007; Kicic et al., 2003) or intravenous infusions of the cells (Wang et al., 2010). Recent data from our laboratory suggested that in disease models characterized by apoptosis and oxidative stress, MSCs exert their therapeutic effects at least in part by being activated by signals from injured tissues to increase expression of the anti-apoptotic/anti-ROS protein STC-1 (Block et al., 2009).

Figure 43:
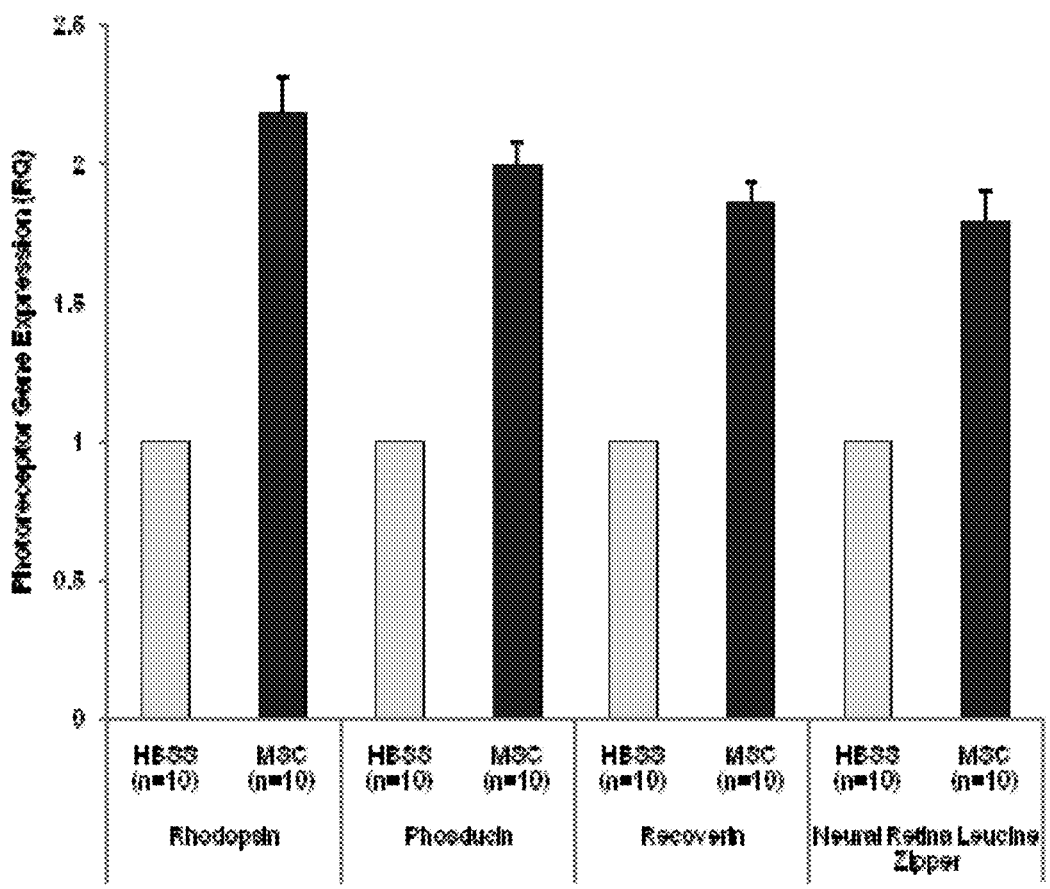
FIG. 43. Rescue of mRNAs for photoreceptors by intravitreal injection of hMSCs in RCS rats. Real time RT-PCR analysis for the photoreceptor genes: rhodopsin, phosducin, neural retina leucine zipper, and recoverin. Injection of hMSCs on P21 rescued expression of the genes at P42. * P<0.05.

Injection of the hMSCs into the eyes of RCS rats at P21 significantly increased levels of transcripts for rhodopsin, phosducin, recoverin, and neural retinal leucine zipper at P42 (FIG. 43). The effects observed were similar to those observed following treatment with STC-1. Therefore, the hypothesis that the effects observed could be explained by the cells remaining viable in the rat vitreous cavity to increase expression of STC-1 was tested.

Figure 42:
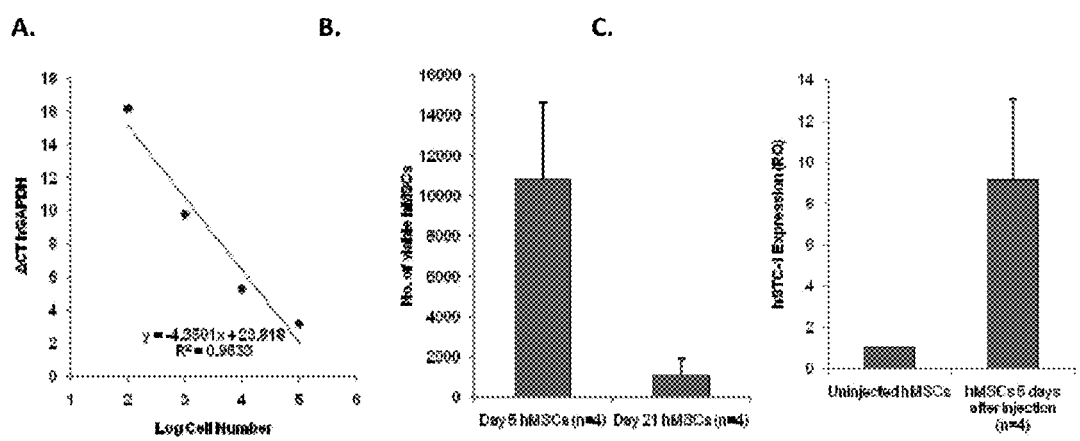
FIG. 42. hMSCs remain viable in the rat vitreous cavity and increase expression of STC-1. (A) Standard curve of real time RT-PCR assays for human GAPDH mRNA as a reflection of viable MSCs. Varying numbers of human MSCs were added to whole globes just before RNA was extracted. (B) Recovery of viable human cells 5 days and 21 days after injection of 100,000 human MSCs into the vitreous cavity of RCS rats. (C) Real time RT-PCR assays of STC-1 expression in hMSCs prior to injections (Uninjected hMSCs) and in hMSCs recovered from globes 5 days after injection. Values were normalized by assays of human GAPDH mRNA for number of hMSCs recovered and calibrated to uninjected hMSCs (RQ).

To follow the fate of the hMSCs following intravitreal injection, a human-specific real time RT-PCR assay for mRNA for human GAPDH (hGAPDH) was used (FIG. 42A) (Lee et al., 2009). After intravitreal injection of 100,000 hMSCs into the eyes of RCS rats, the assay for hGAPDH mRNA indicated that 10% of the injected cells were recovered after 5 days and 1% of the injected cells after 21 days (FIG. 42B). Real time RT-PCR assays also indicated that at day 5, the surviving hMSCs expressed human STC-1. The level of expression of STC-1 per human MSC recovered from the vitreous was about 10-fold higher than in the preparation of hMSCs that was not injected. (FIG. 42C). Therefore the results were another illustration of how hMSCs are activated to express therapeutic genes in response to cross-talk with injured cells and tissues (Lewin et al., 1998). The results may in part provide a molecular explanation for the results observed by others that MSCs reduced degeneration in the retina following subretinal (Inoue et al., 2007; Kicic et al., 2003) or intravenous (Wang et al., 2010) administration. The results also provided evidence that hMSCs could be used to deliver STC-1 in settings where repeated therapeutic injections are not indicated. Based on quantitative gene expression data, a single injection of hMSCs appeared to have a rescue effect superior to a single injection of STC-1, but less than the effects observed with two injections of STC-1. Therefore, it was decided to pursue the more clinically conservative therapy of protein injection since repeated intravitreal protein injections (e.g., anti-VEGF therapy) are now commonly used in the clinical setting for ocular neovascular disease (Tolentino, 2011).

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

REFERENCES

Aggarwal et al., 2005, Blood 105:1815-22
Akiyama et al., 2002, Glia 39(3): 229-36
Armstrong et al., 1998, Angiogenesis. 2(1):93-104.
Avila et al., 2001, Cornea 20:414-20
Block et al., 2009, Stem Cells 27(3):670-81
Callaghan et al., 2001, Rheumatology (Oxford) 46:105-11
Caplan, 1990, Biomaterials 11:44-6
Caplan et al., 2005, Tissue Eng 11:1198-1211
Caplan et al., 2006, J Cell Biochem 98(5):1076-84
Castro-Malaspina et al., 1980, Blood 1980 56(2):289-301
Cauchi et al., 2008, Am J Ophthalmol 146:251-9
Cho et al., 1998, Cornea 17:68-73
Chen et al., 2006, Immunol Cell Biol 84:413-21
Clegg et al., 2006, Ophthalmic Epidemiol 13:263-74
D'Amato et al., 1994, Proc Natl Acad Sci USA 91:4082-5

Daya et al., 2005, Ophthalmology 112:470-7
De Ban et al., 2003. J Cell Biol 160(6) 909-18
Dooner et al., 2004, Blood Cells Mal Dis 32(1):47-51
Eaves et al., 2001, Ann N Y Acad Sci 938:63-70, discussion 70-1
Espana et al., 2003, Br J Ophthalmol 87:1509-14
Fantes et al., 1990, Arch Ophthalmol 108:665-75
Foster C S, Letko E, Ba-Abbad R A Stevens-Johnson Syndrome [Internet] [updated 2007 Dec. 18, cited 2008 Mar. 7] Available from http://emedicine.medscape.com/article/1197450-overview
Fukuda et al., 2006, Circ Res 98(8): 1002-13
Gao et al., 2001, Cells Tissues Organs 169(1):12-20
Gerdoni et al., 2007, Ann Neurol 61(3):219-27
Guilak et al., 2004, Biorheology 41(3-4):389-99
Gupta et al., 2007, J Immunol 179(3):1855-63
Hogg et al., 1994, J Appl Physiol 77(4): 1795-800
Homma et al., 2004, Invest Ophthalmol Vis Sci 45:4320-6
Horwitz et al., 2002, Proc Natl Acad Sci USA 99(13):8932-7
Horwitz et al., 1999, Nat Med 5:309-13
Ilari et al., 2002, Ophthalmology 109:1278-84
Iso et al., 2007, Biochem Biophys Res Commun 354:700-6
Javazon et al., 2001, Stem Cells 19:219-25
Jenkins et al., 1993, Eye 7:629-33
Kim et al., 2006, Brain Res 1123(1):27-33
Koc et al., 2002, Bone Marrow Transplant 30:215-22
Krampera et al., 2007, Bone 40(2):382-90
Kuznetsov et al., 2001, J Cell Biol I53(5):1133-40
Le Blanc et al., 2007, J Intern Med 262(5):509-25
Lee et al., 2006, Proc Natl Acad Sci USA 103:17438-43
Lee et al., 2009, Cell Stem Cell 5:54-63
Limb et al., 2008, Br Med Bull 85:47-61
MacDonald et al., 2002, Bioessays 24(10):885-93
Mareschi et al., 2006, Exp Hematol 34(11) 1563-72
Melsaether C, Rosen C L Burns. Ocular [Internet] [updated 2009 Aug. 12] Available from http://emedicine.medscape.com/article/798696-overview
Mertzants et al., 2005, Invest Ophthalmol Vis Sci 46:46-50
Mets et al., 1981, Mech Ageing Dev 16(1):81-9
Mitjanovic et al., 2007, Am J Ophthalmol 143:409-15
Milner et al., 2003, J Cell Sci 116:1863-73
Milner et al., 2006, Biochem Soc Trans 34:446-50
Mishra, 2008, J Cardiovasc Med (Hagerstown) 9(2):122-8
Moss et al, 2000, Arch Ophthatmol 118:1264-8
Moss et al., 2008, Optom Vis Sci 85:668-74
Munoz et al., 2005, Proc Natl Acad Sci USA 102:18171-6
Nomura et al., 2005, Neuroscience 136(1):16t-9
Oh et al., 2008, Stem Cells 26:1047-55
Oh et al., 2009b, Curr Eye Res 34(2):85-91
Oh et al., 2009a, Cytokine 46(1)100-3
Ohtaki et al., 2008, Proc Natl Acad Sci USA 105:14638-43
Ortiz et al., 2007, Proc Natl Acad Sci USA 104:11002-7
Owen et al., Ciba Found Symp 136:42-60
Penolazzi et al., 2008, Cell Biol Int 32:320-5
Pereira et al., 1998, Proc Natl Acad Sci USA 95(3):! 142-7
Pflugfetder et al., 2008, Am J Manag Care 14:S102-S 106
Piersma et al., 1983, Br J Haematol 54(2):285-90
Prockop, 1985, J Clin Invest 75(3):783-7
Prockop et al., 1995, Annu Rev Biochem 64:403-34
Prockop, 1997, Science 276:71-4
Prockop et al., 2003, Proc Natl Acad Sci USA 100; 119 17-23
Prockop, 2007, Clin Pharmacol Ther 82:241-3
Prockop, 2009, Mol Ther 17:939-46
Rao et al., 1999, Ophthalmology 106:822-8
Reddy et al., 2004, Cornea 23:751-61
Ren et al., 2008, Cell Stem Cell 0.2:141-50
Reinhard et al., 2004, Ophthalmology 111:775-82
Ringden et al., 2006, Transplantation 81:1390-7
Rosada et al., 2003, Calcif Tissue 72(2):135-42
Schaumberg et al., 2003, Am J Ophthalmol 136:318-26
Schinkothe et al, 2008, Stem Cells Dev 17:199-206
Schrepfer et al., 2007, Transplant Proc 39(2) 573-6
Seo et al., 2005, J Dent Res 2005 84(10):907-12
Sharpe et al., 2007, Tissue Eng 13:123-32
Shi et al., 2008, Clin Exp Ophthalmol 36:501-7
Shorn et al., 2007. Sury Ophthalmol 52:483-502
Solomon et al., 2002, Ophthalmology 109:1159-66
Spees et al, 2006, Proc Natl Acad Sci USA 103(5):1283-8
Tang et al., 2007, Cell Transplant 16(2)159-69
Ti et al., 2002, Invest Ophthalmol Vis Sci 43:2584-92
Tseng et al., 1998, Arch Ophthalmol 116:431-41
Tsubota et al., 1999 N Engl J Med 340:1697-703
Ueno et al., 2007, Cornea 26:1220-7
Wakitani et al., 1995, Muscle Nerve 18(12): 1417-26
Wisniewski et al, 2004, Cytokine Growth Factor Rev 15: 129-46
Woodbury et al., 2000, J Neurosci Res 61(4):364-70
Wu et al, 2008, Cell Transplant 16(10):993-l005
Zacharek et al., 2007, J Cereb Blood Flow Metab 27:1684-91

What is claimed is:

1. A method for reducing photoreceptor degeneration in an individual who has glaucoma comprising administering to the eye of the individual a pharmaceutical formulation comprising an effective amount of a stanniocalcin-1 (STC-1) polypeptide.

2. The method of claim 1, wherein the administering is selected from intravitreal, subconjuntival or topical administration.

* * * * *

SEQUENCE LISTING

```
<160> NUMBER OF SEQ ID NOS: 26

<210> SEQ ID NO 1
<211> LENGTH: 230
<212> TYPE: PRT
<213> ORGANISM: Homo sapiens

<400> SEQUENCE: 1

Thr His Glu Ala Glu Gln Asn Asp Ser Val Ser Pro Arg Lys Ser Arg
1               5                   10                  15

Val Ala Ala Gln Asn Ser Ala Glu Val Val Arg Cys Leu Asn Ser Ala
            20                  25                  30

Leu Gln Val Gly Cys Gly Ala Phe Ala Cys Leu Glu Asn Ser Thr Cys
        35                  40                  45

Asp Thr Asp Gly Met Tyr Asp Ile Cys Lys Ser Phe Leu Tyr Ser Ala
    50                  55                  60
```

```
Ala Lys Phe Asp Thr Gln Gly Lys Ala Phe Val Lys Glu Ser Leu Lys
65                  70                  75                  80

Cys Ile Ala Asn Gly Val Thr Ser Lys Val Phe Leu Ala Ile Arg Arg
                85                  90                  95

Cys Ser Thr Phe Gln Arg Met Ile Ala Glu Val Gln Glu Glu Cys Tyr
            100                 105                 110

Ser Lys Leu Asn Val Cys Ser Ile Ala Lys Arg Asn Pro Glu Ala Ile
            115                 120                 125

Thr Glu Val Val Gln Leu Pro Asn His Phe Ser Asn Arg Tyr Tyr Asn
        130                 135                 140

Arg Leu Val Arg Ser Leu Leu Glu Cys Asp Glu Asp Thr Val Ser Thr
145                 150                 155                 160

Ile Arg Asp Ser Leu Met Glu Lys Ile Gly Pro Asn Met Ala Ser Leu
                165                 170                 175

Phe His Ile Leu Gln Thr Asp His Cys Ala Gln Thr His Pro Arg Ala
            180                 185                 190

Asp Phe Asn Arg Arg Thr Asn Glu Pro Gln Lys Leu Lys Val Leu
            195                 200                 205

Leu Arg Asn Leu Arg Gly Glu Glu Asp Ser Pro Ser His Ile Lys Arg
    210                 215                 220

Thr Ser His Glu Ser Ala
225                 230

<210> SEQ ID NO 2
<211> LENGTH: 240
<212> TYPE: PRT
<213> ORGANISM: artificial sequence
<220> FEATURE:
<223> OTHER INFORMATION: Human STC1, Source HEK293, with C-Terminal
      Flag-tag, 10AA

<400> SEQUENCE: 2

Thr His Glu Ala Glu Gln Asn Asp Ser Val Ser Pro Arg Lys Ser Arg
1               5                   10                  15

Val Ala Ala Gln Asn Ser Ala Glu Val Val Arg Cys Leu Asn Ser Ala
                20                  25                  30

Leu Gln Val Gly Cys Gly Ala Phe Ala Cys Leu Glu Asn Ser Thr Cys
            35                  40                  45

Asp Thr Asp Gly Met Tyr Asp Ile Cys Lys Ser Phe Leu Tyr Ser Ala
        50                  55                  60

Ala Lys Phe Asp Thr Gln Gly Lys Ala Phe Val Lys Glu Ser Leu Lys
65                  70                  75                  80

Cys Ile Ala Asn Gly Val Thr Ser Lys Val Phe Leu Ala Ile Arg Arg
                85                  90                  95

Cys Ser Thr Phe Gln Arg Met Ile Ala Glu Val Gln Glu Glu Cys Tyr
            100                 105                 110

Ser Lys Leu Asn Val Cys Ser Ile Ala Lys Arg Asn Pro Glu Ala Ile
            115                 120                 125

Thr Glu Val Val Gln Leu Pro Asn His Phe Ser Asn Arg Tyr Tyr Asn
        130                 135                 140

Arg Leu Val Arg Ser Leu Leu Glu Cys Asp Glu Asp Thr Val Ser Thr
145                 150                 155                 160

Ile Arg Asp Ser Leu Met Glu Lys Ile Gly Pro Asn Met Ala Ser Leu
                165                 170                 175

Phe His Ile Leu Gln Thr Asp His Cys Ala Gln Thr His Pro Arg Ala
```

```
                    180                 185                 190
Asp Phe Asn Arg Arg Thr Asn Glu Pro Gln Lys Leu Lys Val Leu
            195                 200                 205

Leu Arg Asn Leu Arg Gly Glu Glu Asp Ser Pro Ser His Ile Lys Arg
            210                 215                 220

Thr Ser His Glu Ser Ala Ala Ser Asp Tyr Lys Asp Asp Asp Lys
225                 230                 235                 240
```

<210> SEQ ID NO 3
<211> LENGTH: 247
<212> TYPE: PRT
<213> ORGANISM: Homo sapiens

<400> SEQUENCE: 3

```
Met Leu Gln Asn Ser Ala Val Leu Leu Val Leu Val Ile Ser Ala Ser
1               5                   10                  15

Ala Thr His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Val Thr Ser Lys Val Phe Leu Ala Ile Arg
            100                 105                 110

Arg Cys Ser Thr Phe Gln Arg Met Ile Ala Glu Val Gln Glu Glu Cys
        115                 120                 125

Tyr Ser Lys Leu Asn Val Cys Ser Ile Ala Lys Arg Asn Pro Glu Ala
130                 135                 140

Ile Thr Glu Val Val Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190

Leu Phe His Ile Leu Gln Thr Asp His Cys Ala Gln Thr His Pro Arg
        195                 200                 205

Ala Asp Phe Asn Arg Arg Thr Asn Glu Pro Gln Lys Leu Lys Val
    210                 215                 220

Leu Leu Arg Asn Leu Arg Gly Glu Glu Asp Ser Pro Ser His Ile Lys
225                 230                 235                 240

Arg Thr Ser His Glu Ser Ala
                245
```

<210> SEQ ID NO 4
<211> LENGTH: 247
<212> TYPE: PRT
<213> ORGANISM: Homo sapiens

<400> SEQUENCE: 4

```
Met Leu Gln Asn Ser Ala Val Leu Leu Val Leu Val Ile Ser Ala Ser
1               5                   10                  15

Ala Thr His Glu Ala Glu Gln Asn Asp Ser Val Ser Pro Arg Lys Ser
```

```
            20                  25                  30
Arg Val Ala Ala Gln Asn Ser Ala Glu Val Val Arg Cys Leu Asn Ser
        35                  40                  45

Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Val Thr Ser Lys Val Phe Leu Ala Ile Arg
            100                 105                 110

Arg Cys Ser Thr Phe Gln Arg Met Ile Ala Glu Val Gln Glu Glu Cys
            115                 120                 125

Tyr Ser Lys Leu Asn Val Cys Ser Ile Ala Lys Arg Asn Pro Glu Ala
            130                 135                 140

Ile Thr Glu Val Val Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190

Leu Phe His Ile Leu Gln Thr Asp His Cys Ala Gln Thr His Pro Arg
            195                 200                 205

Ala Asp Phe Asn Arg Arg Thr Asn Glu Pro Gln Lys Leu Lys Val
            210                 215                 220

Leu Leu Arg Asn Leu Arg Gly Glu Glu Asp Ser Pro Ser His Ile Lys
225                 230                 235                 240

Arg Thr Ser His Glu Ser Ala
                245

<210> SEQ ID NO 5
<211> LENGTH: 247
<212> TYPE: PRT
<213> ORGANISM: Homo sapiens

<400> SEQUENCE: 5

Met Leu Gln Asn Ser Ala Val Leu Leu Val Leu Val Ile Ser Ala Ser
1               5                   10                  15

Ala Thr His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Val Thr Ser Lys Val Phe Leu Ala Ile Arg
            100                 105                 110

Arg Cys Ser Thr Phe Gln Arg Met Ile Ala Glu Val Gln Glu Glu Cys
            115                 120                 125

Tyr Ser Lys Leu Asn Val Cys Ser Ile Ala Lys Arg Asn Pro Glu Ala
            130                 135                 140
```

```
Ile Thr Glu Val Val Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
            165                 170                 175

Thr Ile Arg Asp Ser Leu Met Glu Lys Ile Gly Pro Asn Met Ala Ser
        180                 185                 190

Leu Phe His Ile Leu Gln Thr Asp His Cys Ala Gln Thr His Pro Arg
            195                 200                 205

Ala Asp Phe Asn Arg Arg Thr Asn Glu Pro Gln Lys Leu Lys Val
        210                 215                 220

Leu Leu Arg Asn Leu Arg Gly Glu Glu Asp Ser Pro Ser His Ile Lys
225                 230                 235                 240

Arg Thr Ser His Glu Ser Ala
                245

<210> SEQ ID NO 6
<211> LENGTH: 247
<212> TYPE: PRT
<213> ORGANISM: artificial sequence
<220> FEATURE:
<223> OTHER INFORMATION: Synthetic STC1 construct

<400> SEQUENCE: 6

Met Leu Gln Asn Ser Ala Val Leu Leu Val Leu Val Ile Ser Ala Ser
1               5                   10                  15

Ala Thr His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Val Thr Ser Lys Val Phe Leu Ala Ile Arg
            100                 105                 110

Arg Cys Ser Thr Phe Gln Arg Met Ile Ala Glu Val Gln Glu Glu Cys
        115                 120                 125

Tyr Ser Lys Leu Asn Val Cys Ser Ile Ala Lys Arg Asn Pro Glu Ala
    130                 135                 140

Ile Thr Glu Val Val Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
            165                 170                 175

Thr Ile Arg Asp Ser Leu Met Glu Lys Ile Gly Pro Asn Met Ala Ser
        180                 185                 190

Leu Phe His Ile Leu Gln Thr Asp His Cys Ala Gln Thr His Pro Arg
            195                 200                 205

Ala Asp Phe Asn Arg Arg Thr Asn Glu Pro Gln Lys Leu Lys Val
        210                 215                 220

Leu Leu Arg Asn Leu Arg Gly Glu Glu Asp Ser Pro Ser His Ile Lys
225                 230                 235                 240

Arg Thr Ser His Glu Ser Ala
                245
```

```
<210> SEQ ID NO 7
<211> LENGTH: 247
<212> TYPE: PRT
<213> ORGANISM: artificial sequence
<220> FEATURE:
<223> OTHER INFORMATION: STC-1 sequence 7 synthetic construct

<400> SEQUENCE: 7

Met Leu Gln Asn Ser Ala Val Leu Leu Val Leu Val Ile Ser Ala Ser
1               5                   10                  15

Ala Thr His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Val Thr Ser Lys Val Phe Leu Ala Ile Arg
            100                 105                 110

Arg Cys Ser Thr Phe Gln Arg Met Ile Ala Glu Val Gln Glu Glu Cys
        115                 120                 125

Tyr Ser Lys Leu Asn Val Cys Ser Ile Ala Lys Arg Asn Pro Glu Ala
    130                 135                 140

Ile Thr Glu Val Val Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190

Leu Phe His Ile Leu Gln Thr Asp His Cys Ala Gln Thr His Pro Arg
        195                 200                 205

Ala Asp Phe Asn Arg Arg Thr Asn Glu Pro Gln Lys Leu Lys Val
    210                 215                 220

Leu Leu Arg Asn Leu Arg Gly Glu Glu Asp Ser Pro Ser His Ile Lys
225                 230                 235                 240

Arg Thr Ser His Glu Ser Ala
                245

<210> SEQ ID NO 8
<211> LENGTH: 247
<212> TYPE: PRT
<213> ORGANISM: Mus musculus

<400> SEQUENCE: 8

Met Leu Gln Asn Ser Ala Val Ile Leu Ala Leu Val Ile Ser Ala Ala
1               5                   10                  15

Ala Ala His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
```

```
            65                  70                  75                  80
Ala Ala Lys Phe Asp Thr Gln Gly Lys Ala Phe Val Lys Glu Ser Leu
                    85                  90                  95

Lys Cys Ile Ala Asn Gly Ile Thr Ser Lys Val Phe Leu Ala Ile Arg
                    100                 105                 110

Arg Cys Ser Thr Phe Gln Arg Met Ile Ala Glu Val Gln Glu Asp Cys
                    115                 120                 125

Tyr Ser Lys Leu Asn Val Cys Ser Ile Ala Lys Arg Asn Pro Glu Ala
                    130                 135                 140

Ile Thr Glu Val Ile Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                    165                 170                 175

Thr Ile Arg Asp Ser Leu Met Glu Lys Ile Gly Pro Asn Met Ala Ser
                    180                 185                 190

Leu Phe His Ile Leu Gln Thr Asp His Cys Ala Gln Thr His Pro Arg
                    195                 200                 205

Ala Asp Phe Asn Arg Arg Thr Asn Glu Pro Gln Lys Leu Lys Val
                    210                 215                 220

Leu Leu Arg Asn Leu Arg Gly Glu Gly Asp Ser Pro Ser His Ile Lys
225                 230                 235                 240

Arg Thr Ser Gln Glu Ser Ala
                    245

<210> SEQ ID NO 9
<211> LENGTH: 247
<212> TYPE: PRT
<213> ORGANISM: Rattus norvegicus

<400> SEQUENCE: 9

Met Leu Gln Asn Ser Ala Val Ile Leu Ala Leu Val Ile Ser Ala Ala
1               5                   10                  15

Ala Ala His Glu Ala Glu Gln Asn Asp Ser Val Ser Pro Arg Lys Ser
                    20                  25                  30

Arg Val Ala Ala Gln Asn Ser Ala Glu Val Val Arg Cys Leu Asn Ser
                    35                  40                  45

Ala Leu Gln Val Gly Cys Gly Ala Phe Ala Cys Leu Glu Asn Ser Thr
                    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                    85                  90                  95

Lys Cys Ile Ala Asn Gly Ile Thr Ser Lys Val Phe Leu Ala Ile Arg
                    100                 105                 110

Arg Cys Ser Thr Phe Gln Arg Met Ile Ala Glu Val Gln Glu Asp Cys
                    115                 120                 125

Tyr Ser Lys Leu Asn Val Cys Ser Ile Ala Lys Arg Asn Pro Glu Ala
                    130                 135                 140

Ile Thr Glu Val Ile Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                    165                 170                 175

Thr Ile Arg Asp Ser Leu Met Glu Lys Ile Gly Pro Asn Met Ala Ser
                    180                 185                 190
```

```
Leu Phe His Ile Leu Gln Thr Asp His Cys Ala Gln Thr His Pro Arg
            195                 200                 205

Ala Asp Phe Asn Arg Arg Thr Asn Glu Pro Gln Lys Leu Lys Val
210                 215                 220

Leu Leu Arg Asn Leu Arg Gly Glu Gly Asp Ser Pro Ser His Ile Lys
225                 230                 235                 240

Arg Thr Ser Gln Glu Asn Ala
                245

<210> SEQ ID NO 10
<211> LENGTH: 247
<212> TYPE: PRT
<213> ORGANISM: Rattus norvegicus

<400> SEQUENCE: 10

Met Leu Gln Asn Ser Ala Val Ile Leu Ala Leu Val Ile Ser Ala Ala
1               5                   10                  15

Ala Ala His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

Ala Leu Gln Val Gly Cys Gly Ala Phe Ala Cys Leu Glu Asn Ser Thr
    50                  55                  60

Cys Asp Thr Asp Gly Met Tyr Asp Ile Cys Lys Ser Phe Leu Tyr Ser
65                  70                  75                  80

Ala Ala Lys Phe Asp Thr Gln Gly Lys Ala Phe Val Lys Glu Ser Leu
                85                  90                  95

Lys Cys Ile Ala Asn Gly Ile Thr Ser Lys Val Phe Leu Ala Ile Arg
            100                 105                 110

Arg Cys Ser Thr Phe Gln Arg Met Ile Ala Glu Val Gln Glu Asp Cys
        115                 120                 125

Tyr Ser Lys Leu Asn Val Cys Ser Ile Ala Lys Arg Asn Pro Glu Ala
    130                 135                 140

Ile Thr Glu Val Ile Gln Leu Pro Asn His Phe Ser Asn Arg Tyr Tyr
145                 150                 155                 160

Asn Arg Leu Val Arg Ser Leu Leu Glu Cys Asp Glu Asp Thr Val Ser
                165                 170                 175

Thr Ile Arg Asp Ser Leu Met Glu Lys Ile Gly Pro Asn Met Ala Ser
            180                 185                 190

Leu Phe His Ile Leu Gln Thr Asp His Cys Ala Gln Thr His Pro Arg
        195                 200                 205

Ala Asp Phe Asn Arg Arg Thr Asn Glu Pro Gln Lys Leu Lys Val
    210                 215                 220

Leu Leu Arg Asn Leu Arg Gly Glu Gly Asp Ser Pro Ser His Ile Lys
225                 230                 235                 240

Arg Thr Ser Gln Glu Asn Ala
                245

<210> SEQ ID NO 11
<211> LENGTH: 246
<212> TYPE: PRT
<213> ORGANISM: Mus musculus

<400> SEQUENCE: 11

Met Leu Gln Asn Ser Ala Val Ile Leu Ala Leu Val Ile Ser Ala Ala
1               5                   10                  15
```

```
Ala Ala His Glu Ala Glu Gln Asn Asp Ser Val Ser Pro Arg Lys Ser
            20                  25                  30

Arg Val Ala Ala Gln Asn Ser Ala Glu Val Val Arg Cys Leu Asn Ser
        35                  40                  45

Ala Cys Arg Leu Ala Ala Gly Phe Ala Cys Leu Glu Asn Ser Thr Cys
    50                  55                  60

Asp Thr Asp Gly Met Tyr Asp Ile Cys Lys Ser Phe Leu Tyr Ser Ala
65                  70                  75                  80

Ala Lys Phe Asp Thr Gln Gly Lys Ala Phe Val Lys Glu Ser Leu Lys
                85                  90                  95

Cys Ile Ala Asn Gly Ile Thr Ser Lys Val Phe Leu Ala Ile Arg Arg
            100                 105                 110

Cys Ser Thr Phe Gln Arg Met Ile Ala Glu Val Gln Glu Asp Cys Tyr
        115                 120                 125

Ser Lys Leu Asn Val Cys Ser Ile Ala Lys Arg Asn Pro Glu Ala Ile
    130                 135                 140

Thr Glu Val Ile Gln Leu Pro Asn His Phe Ser Asn Arg Tyr Tyr Asn
145                 150                 155                 160

Arg Leu Val Arg Ser Leu Leu Glu Cys Asp Glu Asp Thr Val Ser Thr
                165                 170                 175

Ile Arg Asp Ser Leu Met Glu Lys Ile Gly Pro Asn Met Ala Ser Leu
            180                 185                 190

Phe His Ile Leu Gln Thr Asp His Cys Ala Gln Thr His Pro Arg Ala
        195                 200                 205

Asp Phe Asn Arg Arg Arg Thr Asn Glu Pro Gln Lys Leu Lys Val Leu
    210                 215                 220

Leu Arg Asn Leu Arg Gly Glu Gly Asp Ser Pro Ser His Ile Lys Arg
225                 230                 235                 240

Thr Ser Gln Glu Ser Ala
                245

<210> SEQ ID NO 12
<211> LENGTH: 302
<212> TYPE: PRT
<213> ORGANISM: Homo sapiens

<400> SEQUENCE: 12

Met Cys Ala Glu Arg Leu Gly Gln Phe Met Thr Leu Ala Leu Val Leu
1               5                   10                  15

Ala Thr Phe Asp Pro Ala Arg Gly Thr Asp Ala Thr Asn Pro Pro Glu
            20                  25                  30

Gly Pro Gln Asp Arg Ser Ser Gln Gln Lys Gly Arg Leu Ser Leu Gln
        35                  40                  45

Asn Thr Ala Glu Ile Gln His Cys Leu Val Asn Ala Gly Asp Val Gly
    50                  55                  60

Cys Gly Val Phe Glu Cys Phe Glu Asn Asn Ser Cys Glu Ile Arg Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Lys Cys Lys Ala His
            100                 105                 110

Ala Leu Arg His Arg Phe Gly Cys Ile Ser Arg Lys Cys Pro Ala Ile
        115                 120                 125

Arg Glu Met Val Ser Gln Leu Gln Arg Glu Cys Tyr Leu Lys His Asp
    130                 135                 140
```

Leu Cys Ala Ala Ala Gln Glu Asn Thr Arg Val Ile Val Glu Met Ile
145                 150                 155                 160

His Phe Lys Asp Leu Leu Leu His Glu Pro Tyr Val Asp Leu Val Asn
            165                 170                 175

Leu Leu Leu Thr Cys Gly Glu Glu Val Lys Glu Ala Ile Thr His Ser
            180                 185                 190

Val Gln Val Gln Cys Glu Gln Asn Trp Gly Ser Leu Cys Ser Ile Leu
        195                 200                 205

Ser Phe Cys Thr Ser Ala Ile Gln Lys Pro Pro Thr Ala Pro Pro Glu
    210                 215                 220

Arg Gln Pro Gln Val Asp Arg Thr Lys Leu Ser Arg Ala His His Gly
225                 230                 235                 240

Glu Ala Gly His His Leu Pro Glu Pro Ser Ser Arg Glu Thr Gly Arg
                245                 250                 255

Gly Ala Lys Gly Glu Arg Gly Ser Lys Ser His Pro Asn Ala His Ala
            260                 265                 270

Arg Gly Arg Val Gly Gly Leu Gly Ala Gln Gly Pro Ser Gly Ser Ser
        275                 280                 285

Glu Trp Glu Asp Glu Gln Ser Glu Tyr Ser Asp Ile Arg Arg
    290                 295                 300

<210> SEQ ID NO 13
<211> LENGTH: 302
<212> TYPE: PRT
<213> ORGANISM: Homo sapiens

<400> SEQUENCE: 13

Met Cys Ala Glu Arg Leu Gly Gln Phe Met Thr Leu Ala Leu Val Leu
1               5                   10                  15

Ala Thr Phe Asp Pro Ala Arg Gly Thr Asp Ala Thr Asn Pro Pro Glu
            20                  25                  30

Gly Pro Gln Asp Arg Ser Ser Gln Gln Lys Gly Arg Leu Ser Leu Gln
        35                  40                  45

Asn Thr Ala Glu Ile Gln His Cys Leu Val Asn Ala Gly Asp Val Gly
50                  55                  60

Cys Gly Val Phe Glu Cys Phe Glu Asn Asn Ser Cys Glu Ile Arg Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Lys Cys Lys Ala His
            100                 105                 110

Ala Leu Arg His Arg Phe Gly Cys Ile Ser Arg Lys Cys Pro Ala Ile
        115                 120                 125

Arg Glu Met Val Ser Gln Leu Gln Arg Glu Cys Tyr Leu Lys His Asp
130                 135                 140

Leu Cys Ala Ala Ala Gln Glu Asn Thr Arg Val Ile Val Glu Met Ile
145                 150                 155                 160

His Phe Lys Asp Leu Leu Leu His Glu Pro Tyr Val Asp Leu Val Asn
            165                 170                 175

Leu Leu Leu Thr Cys Gly Glu Glu Val Lys Glu Ala Ile Thr His Ser
            180                 185                 190

Val Gln Val Gln Cys Glu Gln Asn Trp Gly Ser Leu Cys Ser Ile Leu
        195                 200                 205

Ser Phe Cys Thr Ser Ala Ile Gln Lys Pro Pro Thr Ala Pro Pro Glu

Arg Gln Pro Gln Val Asp Arg Thr Lys Leu Ser Arg Ala His His Gly
225                 230                 235                 240

Glu Ala Gly His His Leu Pro Glu Pro Ser Ser Arg Glu Thr Gly Arg
            245                 250                 255

Gly Ala Lys Gly Glu Arg Gly Ser Lys Ser His Pro Asn Ala His Ala
            260                 265                 270

Arg Gly Arg Val Gly Gly Leu Gly Ala Gln Gly Pro Ser Gly Ser Ser
            275                 280                 285

Glu Trp Glu Asp Glu Gln Ser Glu Tyr Ser Asp Ile Arg Arg
            290                 295                 300

<210> SEQ ID NO 14
<211> LENGTH: 302
<212> TYPE: PRT
<213> ORGANISM: Homo sapiens

<400> SEQUENCE: 14

Met Cys Ala Glu Arg Leu Gly Gln Phe Met Thr Leu Ala Leu Val Leu
1               5                   10                  15

Ala Thr Phe Asp Pro Ala Arg Gly Thr Asp Ala Thr Asn Pro Pro Glu
            20                  25                  30

Gly Pro Gln Asp Arg Ser Ser Gln Gln Lys Gly Arg Leu Ser Leu Gln
        35                  40                  45

Asn Thr Ala Glu Ile Gln His Cys Leu Val Asn Ala Gly Asp Val Gly
    50                  55                  60

Cys Gly Val Phe Glu Cys Phe Glu Asn Asn Ser Cys Glu Ile Arg Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Lys Cys Lys Ala His
            100                 105                 110

Ala Leu Arg His Arg Phe Gly Cys Ile Ser Arg Lys Cys Pro Ala Ile
            115                 120                 125

Arg Glu Met Val Ser Gln Leu Gln Arg Glu Cys Tyr Leu Lys His Asp
        130                 135                 140

Leu Cys Ala Ala Ala Gln Glu Asn Thr Arg Val Ile Val Glu Met Ile
145                 150                 155                 160

His Phe Lys Asp Leu Leu Leu His Glu Pro Tyr Val Asp Leu Val Asn
                165                 170                 175

Leu Leu Leu Thr Cys Gly Glu Glu Val Lys Glu Ala Ile Thr His Ser
            180                 185                 190

Val Gln Val Gln Cys Glu Gln Asn Trp Gly Ser Leu Cys Ser Ile Leu
        195                 200                 205

Ser Phe Cys Thr Ser Ala Ile Gln Lys Pro Pro Thr Ala Pro Pro Glu
210                 215                 220

Arg Gln Pro Gln Val Asp Arg Thr Lys Leu Ser Arg Ala His His Gly
225                 230                 235                 240

Glu Ala Gly His His Leu Pro Glu Pro Ser Ser Arg Glu Thr Gly Arg
            245                 250                 255

Gly Ala Lys Gly Glu Arg Gly Ser Lys Ser His Pro Asn Ala His Ala
            260                 265                 270

Arg Gly Arg Val Gly Gly Leu Gly Ala Gln Gly Pro Ser Gly Ser Ser
            275                 280                 285

Glu Trp Glu Asp Glu Gln Ser Glu Tyr Ser Asp Ile Arg Arg
    290                 295                 300

<210> SEQ ID NO 15
<211> LENGTH: 302
<212> TYPE: PRT
<213> ORGANISM: Homo sapiens

<400> SEQUENCE: 15

Met Cys Ala Glu Arg Leu Gly Gln Phe Met Thr Leu Ala Leu Val Leu
1               5                   10                  15

Ala Thr Phe Asp Pro Ala Arg Gly Thr Asp Ala Thr Asn Pro Pro Glu
            20                  25                  30

Gly Pro Gln Asp Arg Ser Ser Gln Gln Lys Gly Arg Leu Ser Leu Gln
        35                  40                  45

Asn Thr Ala Glu Ile Gln His Cys Leu Val Asn Ala Gly Asp Val Gly
    50                  55                  60

Cys Gly Val Phe Glu Cys Phe Glu Asn Asn Ser Cys Glu Ile Arg Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Lys Cys Lys Ala His
            100                 105                 110

Ala Leu Arg His Arg Phe Gly Cys Ile Ser Arg Lys Cys Pro Ala Ile
        115                 120                 125

Arg Glu Met Val Ser Gln Leu Gln Arg Glu Cys Tyr Leu Lys His Asp
    130                 135                 140

Leu Cys Ala Ala Ala Gln Glu Asn Thr Arg Val Ile Val Glu Met Ile
145                 150                 155                 160

His Phe Lys Asp Leu Leu His Glu Pro Tyr Val Asp Leu Val Asn
                165                 170                 175

Leu Leu Leu Thr Cys Gly Glu Glu Val Lys Glu Ala Ile Thr His Ser
            180                 185                 190

Val Gln Val Gln Cys Glu Gln Asn Trp Gly Ser Leu Cys Ser Ile Leu
        195                 200                 205

Ser Phe Cys Thr Ser Ala Ile Gln Lys Pro Pro Thr Ala Pro Pro Glu
    210                 215                 220

Arg Gln Pro Gln Val Asp Arg Thr Lys Leu Ser Arg Ala His His Gly
225                 230                 235                 240

Glu Ala Gly His His Leu Pro Glu Pro Ser Ser Arg Glu Thr Gly Arg
                245                 250                 255

Gly Ala Lys Gly Glu Arg Gly Ser Lys Ser His Pro Asn Ala His Ala
            260                 265                 270

Arg Gly Arg Val Gly Gly Leu Gly Ala Gln Gly Pro Ser Gly Ser Ser
        275                 280                 285

Glu Trp Glu Asp Glu Gln Ser Glu Tyr Ser Asp Ile Arg Arg
    290                 295                 300

<210> SEQ ID NO 16
<211> LENGTH: 302
<212> TYPE: PRT
<213> ORGANISM: Homo sapiens

<400> SEQUENCE: 16

Met Cys Ala Glu Arg Leu Gly Gln Phe Met Thr Leu Ala Leu Val Leu
1               5                   10                  15

-continued

```
Ala Thr Phe Asp Pro Ala Arg Gly Thr Asp Ala Thr Asn Pro Pro Glu
            20                  25                  30

Gly Pro Gln Asp Arg Ser Ser Gln Gln Lys Gly Arg Leu Ser Leu Gln
            35                  40                  45

Asn Thr Ala Glu Ile Gln His Cys Leu Val Asn Ala Gly Asp Val Gly
    50                  55                  60

Cys Gly Val Phe Glu Cys Phe Glu Asn Asn Ser Cys Glu Ile Arg Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Lys Cys Lys Ala His
            100                 105                 110

Ala Leu Arg His Arg Phe Gly Cys Ile Ser Arg Lys Cys Pro Ala Ile
            115                 120                 125

Arg Glu Met Val Ser Gln Leu Gln Arg Glu Cys Tyr Leu Lys His Asp
            130                 135                 140

Leu Cys Ala Ala Ala Gln Glu Asn Thr Arg Val Ile Val Glu Met Ile
145                 150                 155                 160

His Phe Lys Asp Leu Leu Leu His Glu Pro Tyr Val Asp Leu Val Asn
                165                 170                 175

Leu Leu Leu Thr Cys Gly Glu Glu Val Lys Glu Ala Ile Thr His Ser
            180                 185                 190

Val Gln Val Gln Cys Glu Gln Asn Trp Gly Ser Leu Cys Ser Ile Leu
            195                 200                 205

Ser Phe Cys Thr Ser Ala Ile Gln Lys Pro Pro Thr Ala Pro Pro Glu
    210                 215                 220

Arg Gln Pro Gln Val Asp Arg Thr Lys Leu Ser Arg Ala His His Gly
225                 230                 235                 240

Glu Ala Gly His His Leu Pro Glu Pro Ser Ser Arg Glu Thr Gly Arg
                245                 250                 255

Gly Ala Lys Gly Glu Arg Gly Ser Lys Ser His Pro Asn Ala His Ala
            260                 265                 270

Arg Gly Arg Val Gly Gly Leu Gly Ala Gln Gly Pro Ser Gly Ser Ser
            275                 280                 285

Glu Trp Glu Asp Glu Gln Ser Glu Tyr Ser Asp Ile Arg Arg
            290                 295                 300

<210> SEQ ID NO 17
<211> LENGTH: 296
<212> TYPE: PRT
<213> ORGANISM: Mus musculus

<400> SEQUENCE: 17

Met Cys Ala Glu Arg Leu Gly Gln Phe Val Thr Leu Ala Leu Val Phe
1               5                   10                  15

Ala Thr Leu Asp Pro Ala Gln Gly Thr Asp Ser Thr Asn Pro Pro Glu
            20                  25                  30

Gly Pro Gln Asp Arg Ser Ser Gln Gln Lys Gly Arg Leu Ser Leu Gln
            35                  40                  45

Asn Thr Ala Glu Ile Gln His Cys Leu Val Asn Ala Gly Asp Val Gly
    50                  55                  60

Cys Gly Val Phe Glu Cys Phe Glu Asn Asn Ser Cys Glu Ile Gln Gly
65                  70                  75                  80

Leu His Gly Ile Cys Met Thr Phe Leu His Asn Ala Gly Lys Phe Asp
                85                  90                  95
```

Ala Gln Gly Lys Ser Phe Ile Lys Asp Ala Leu Arg Cys Lys Ala His
            100                 105                 110

Ala Leu Arg His Lys Phe Gly Cys Ile Ser Arg Lys Cys Pro Ala Ile
        115                 120                 125

Arg Glu Met Val Phe Gln Leu Gln Arg Glu Cys Tyr Leu Lys His Asp
    130                 135                 140

Leu Cys Ser Ala Ala Gln Glu Asn Val Gly Val Ile Val Glu Met Ile
145                 150                 155                 160

His Phe Lys Asp Leu Leu Leu His Glu Pro Tyr Val Asp Leu Val Asn
                165                 170                 175

Leu Leu Leu Thr Cys Gly Glu Asp Val Lys Glu Ala Val Thr Arg Ser
            180                 185                 190

Val Gln Ala Gln Cys Glu Gln Ser Trp Gly Gly Leu Cys Ser Ile Leu
        195                 200                 205

Ser Phe Cys Thr Ser Asn Ile Gln Arg Pro Thr Ala Ala Pro Glu
    210                 215                 220

His Gln Pro Leu Ala Asp Arg Ala Gln Leu Ser Arg Pro His His Arg
225                 230                 235                 240

Asp Thr Asp His His Leu Thr Ala Asn Arg Gly Ala Lys Gly Glu Arg
                245                 250                 255

Gly Ser Lys Ser His Pro Asn Ala His Ala Arg Gly Arg Thr Gly Gly
            260                 265                 270

Gln Ser Ala Gln Gly Pro Ser Gly Ser Ser Glu Trp Glu Asp Glu Gln
        275                 280                 285

Ser Glu Tyr Ser Asp Ile Arg Arg
    290                 295

<210> SEQ ID NO 18
<211> LENGTH: 296
<212> TYPE: PRT
<213> ORGANISM: Mus musculus

<400> SEQUENCE: 18

Met Cys Ala Glu Arg Leu Gly Gln Phe Val Thr Leu Ala Leu Val Phe
1               5                   10                  15

Ala Thr Leu Asp Pro Ala Gln Gly Thr Asp Ser Thr Asn Pro Pro Glu
            20                  25                  30

Gly Pro Gln Asp Arg Ser Ser Gln Gln Lys Gly Arg Leu Ser Leu Gln
        35                  40                  45

Asn Thr Ala Glu Ile Gln His Cys Leu Val Asn Ala Gly Asp Val Gly
50                  55                  60

Cys Gly Val Phe Glu Cys Phe Glu Asn Asn Ser Cys Glu Ile Gln Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Arg Cys Lys Ala His
            100                 105                 110

Ala Leu Arg His Lys Phe Gly Cys Ile Ser Arg Lys Cys Pro Ala Ile
        115                 120                 125

Arg Glu Met Val Phe Gln Leu Gln Arg Glu Cys Tyr Leu Lys His Asp
    130                 135                 140

Leu Cys Ser Ala Ala Gln Glu Asn Val Gly Val Ile Val Glu Met Ile
145                 150                 155                 160

His Phe Lys Asp Leu Leu Leu His Glu Pro Tyr Val Asp Leu Val Asn

```
                    165                 170                 175
Leu Leu Leu Thr Cys Gly Glu Asp Val Lys Glu Ala Val Thr Arg Ser
            180                 185                 190

Val Gln Ala Gln Cys Glu Gln Ser Trp Gly Gly Leu Cys Ser Ile Leu
        195                 200                 205

Ser Phe Cys Thr Ser Asn Ile Gln Arg Pro Pro Thr Ala Ala Pro Glu
    210                 215                 220

His Gln Pro Leu Ala Asp Arg Ala Gln Leu Ser Arg Pro His His Arg
225                 230                 235                 240

Asp Thr Asp His His Leu Thr Ala Asn Arg Gly Ala Lys Gly Glu Arg
                245                 250                 255

Gly Ser Lys Ser His Pro Asn Ala His Ala Arg Gly Arg Thr Gly Gly
            260                 265                 270

Gln Ser Ala Gln Gly Pro Ser Gly Ser Ser Glu Trp Glu Asp Glu Gln
        275                 280                 285

Ser Glu Tyr Ser Asp Ile Arg Arg
    290                 295

<210> SEQ ID NO 19
<211> LENGTH: 296
<212> TYPE: PRT
<213> ORGANISM: Rattus norvegicus

<400> SEQUENCE: 19

Met Cys Ala Glu Arg Leu Gly Gln Phe Val Thr Leu Ala Leu Val Phe
1               5                   10                  15

Ala Thr Leu Asp Pro Ala Arg Gly Thr Asp Ser Thr Asn Pro Pro Glu
            20                  25                  30

Gly Pro Gln Asp Arg Gly Ser Gln Gln Lys Gly Arg Leu Ser Leu Gln
        35                  40                  45

Asn Thr Ala Glu Ile Gln His Cys Leu Val Asn Ala Gly Asp Val Gly
    50                  55                  60

Cys Gly Val Phe Glu Cys Phe Glu Asn Asn Ser Cys Glu Ile Gln Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Arg Cys Lys Ala His
            100                 105                 110

Ala Leu Arg His Lys Phe Gly Cys Ile Ser Arg Lys Cys Pro Ala Ile
        115                 120                 125

Arg Glu Met Val Tyr Gln Leu Gln Arg Glu Cys Tyr Leu Lys His Asp
    130                 135                 140

Leu Cys Ser Ala Ala Gln Glu Asn Val Val Ile Val Glu Met Ile
145                 150                 155                 160

His Phe Lys Asp Leu Leu His Glu Pro Tyr Val Asp Leu Val Asn
                165                 170                 175

Leu Leu Leu Thr Cys Gly Glu Asp Val Arg Glu Ala Val Thr Arg Ser
            180                 185                 190

Val Gln Ala Gln Cys Glu Gln Ser Trp Gly Gly Leu Cys Ser Ile Leu
        195                 200                 205

Ser Phe Cys Thr Ser Asn Ile Gln Arg Pro Pro Thr Ala Ala Pro Glu
    210                 215                 220

His Gln Pro Leu Ala Asp Arg Ala Gln Leu Ser Arg Pro Tyr His Arg
225                 230                 235                 240
```

```
Asp Thr Asp His His Leu Thr Ala Asn Arg Gly Ala Lys Gly Glu Arg
            245                 250                 255

Gly Ser Lys Ser His Leu His Ala His Ala Arg Gly Gly Ala Gly Gly
        260                 265                 270

Gln Ser Ala Gln Gly Pro Ser Gly Ser Ser Glu Trp Glu Asp Glu Gln
        275                 280                 285

Ser Glu Tyr Ser Asp Ile Arg Arg
        290                 295

<210> SEQ ID NO 20
<211> LENGTH: 296
<212> TYPE: PRT
<213> ORGANISM: Rattus norvegicus

<400> SEQUENCE: 20

Met Cys Ala Glu Arg Leu Gly Gln Phe Val Thr Leu Ala Leu Val Phe
1               5                   10                  15

Ala Thr Leu Asp Pro Ala Arg Gly Thr Asp Ser Thr Asn Pro Pro Glu
            20                  25                  30

Gly Pro Gln Asp Arg Gly Ser Gln Gln Lys Gly Arg Leu Ser Leu Gln
        35                  40                  45

Asn Thr Ala Glu Ile Gln His Cys Leu Val Asn Ala Gly Asp Val Gly
    50                  55                  60

Cys Gly Val Phe Glu Cys Phe Glu Asn Ser Cys Glu Ile Gln Gly
65                  70                  75                  80

Leu His Gly Ile Cys Met Thr Phe Leu His Asn Ala Gly Lys Phe Asp
                85                  90                  95

Ala Gln Gly Lys Ser Phe Ile Lys Asp Ala Leu Arg Cys Lys Ala His
            100                 105                 110

Ala Leu Arg His Lys Phe Gly Cys Ile Ser Arg Lys Cys Pro Ala Ile
        115                 120                 125

Arg Glu Met Val Tyr Gln Leu Gln Arg Glu Cys Tyr Leu Lys His Asp
    130                 135                 140

Leu Cys Ser Ala Ala Gln Glu Asn Val Val Ile Val Glu Met Ile
145                 150                 155                 160

His Phe Lys Asp Leu Leu Leu His Glu Pro Tyr Val Asp Leu Val Asn
                165                 170                 175

Leu Leu Leu Thr Cys Gly Glu Asp Val Arg Glu Ala Val Thr Arg Ser
            180                 185                 190

Val Gln Ala Gln Cys Glu Gln Ser Trp Gly Gly Leu Cys Ser Ile Leu
        195                 200                 205

Ser Phe Cys Thr Ser Asn Ile Gln Arg Pro Pro Thr Ala Ala Pro Glu
    210                 215                 220

His Gln Pro Leu Ala Asp Arg Ala Gln Leu Ser Arg Pro Tyr His Arg
225                 230                 235                 240

Asp Thr Asp His His Leu Thr Ala Asn Arg Gly Ala Lys Gly Glu Arg
                245                 250                 255

Gly Ser Lys Ser His Leu His Ala His Ala Arg Gly Gly Ala Gly Gly
            260                 265                 270

Gln Ser Ala Gln Gly Pro Ser Gly Ser Ser Glu Trp Glu Asp Glu Gln
        275                 280                 285

Ser Glu Tyr Ser Asp Ile Arg Arg
        290                 295

<210> SEQ ID NO 21
```

<211> LENGTH: 277
<212> TYPE: PRT
<213> ORGANISM: Homo sapiens

<400> SEQUENCE: 21

```
Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Gln
    130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Asp Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
        275
```

<210> SEQ ID NO 22
<211> LENGTH: 277
<212> TYPE: PRT
<213> ORGANISM: Homo sapiens

<400> SEQUENCE: 22

```
Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60
```

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
            115                 120                 125

Asn Pro His Ala Lys Glu Cys Gly Gly Val Phe Thr Asp Pro Lys Arg
            130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
            195                 200                 205

Tyr Cys Gly Asp Glu Leu Pro Asp Asp Ile Ile Ser Thr Gly Asn Val
210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
                260                 265                 270

Arg Phe Ser His Leu
            275

<210> SEQ ID NO 23
<211> LENGTH: 277
<212> TYPE: PRT
<213> ORGANISM: Homo sapiens

<400> SEQUENCE: 23

Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
                20                  25                  30

Arg Ala Ala Gly Val Tyr His Arg Glu Ala Arg Ser Gly Lys Tyr Lys
            35                  40                  45

Leu Thr Tyr Ala Glu Ala Lys Ala Val Cys Glu Phe Glu Gly Gly His
        50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
            115                 120                 125

Asn Pro His Ala Lys Glu Cys Gly Gly Val Phe Thr Asp Pro Lys Gln
            130                 135                 140

Ile Phe Lys Ser Pro Gly Phe Pro Asn Glu Tyr Glu Asp Asn Gln Ile

```
145                 150                 155                 160
Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
                180                 185                 190

Val Glu Ile Tyr Asp Ser Tyr Asp Val His Gly Phe Val Gly Arg
                195                 200                 205

Tyr Cys Gly Asp Glu Leu Pro Asp Asp Ile Ile Ser Thr Gly Asn Val
                210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
                260                 265                 270

Arg Phe Ser His Leu
                275

<210> SEQ ID NO 24
<211> LENGTH: 277
<212> TYPE: PRT
<213> ORGANISM: Homo sapiens

<400> SEQUENCE: 24

Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
                20                  25                  30

Arg Ala Ala Gly Val Tyr His Arg Glu Ala Arg Ser Gly Lys Tyr Lys
                35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
                100                 105                 110

Tyr Gly Ile Arg Leu Asn Arg Ser Glu Arg Trp Asp Ala Tyr Cys Tyr
                115                 120                 125

Asn Pro His Ala Lys Glu Cys Gly Gly Val Phe Thr Asp Pro Lys Gln
                130                 135                 140

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
                180                 185                 190

Val Glu Ile Tyr Asp Ser Tyr Asp Asp Val His Gly Phe Val Gly Arg
                195                 200                 205

Tyr Cys Gly Asp Glu Leu Pro Asp Asp Ile Ile Ser Thr Gly Asn Val
                210                 215                 220

Met Thr Leu Lys Phe Leu Ser Asp Ala Ser Val Thr Ala Gly Gly Phe
225                 230                 235                 240
```

```
Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
            275

<210> SEQ ID NO 25
<211> LENGTH: 275
<212> TYPE: PRT
<213> ORGANISM: Mus musculus

<400> SEQUENCE: 25

Met Val Val Leu Leu Cys Leu Cys Val Leu Leu Trp Glu Glu Ala His
1               5                   10                  15

Gly Trp Gly Phe Lys Asn Gly Ile Phe His Asn Ser Ile Trp Leu Glu
            20                  25                  30

Gln Ala Ala Gly Val Tyr His Arg Glu Ala Arg Ala Gly Arg Tyr Lys
        35                  40                  45

Leu Thr Tyr Ala Glu Ala Lys Ala Val Cys Glu Phe Glu Gly Gly Arg
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr
        115                 120                 125

Asn Pro His Ala Lys Glu Cys Gly Gly Val Phe Thr Asp Pro Lys Arg
    130                 135                 140

Ile Phe Lys Ser Pro Gly Phe Pro Asn Glu Tyr Asp Asp Asn Gln Val
145                 150                 155                 160

Cys Tyr Trp His Ile Arg Leu Lys Tyr Gly Gln Arg Ile His Leu Ser
                165                 170                 175

Phe Leu Asp Phe Asp Leu Glu His Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Glu Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Thr Val Asp Pro Ala Ser Lys Ser Ser Gln Ala
                245                 250                 255

Lys Asn Thr Ser Thr Thr Gly Asn Lys Lys Phe Leu Pro Gly Arg Phe
            260                 265                 270

Ser His Leu
    275

<210> SEQ ID NO 26
<211> LENGTH: 128
<212> TYPE: PRT
<213> ORGANISM: Homo sapiens

<400> SEQUENCE: 26
```

-continued

```
Met Gly Ile Gln Gly Gly Ser Val Leu Phe Gly Leu Leu Leu Val Leu
1               5                   10                  15

Ala Val Phe Cys His Ser Gly His Ser Leu Gln Cys Tyr Asn Cys Pro
            20                  25                  30

Asn Pro Thr Ala Asp Cys Lys Thr Ala Val Asn Cys Ser Ser Asp Phe
            35                  40                  45

Asp Ala Cys Leu Ile Thr Lys Ala Gly Leu Gln Val Tyr Asn Lys Cys
        50                  55                  60

Trp Lys Phe Glu His Cys Asn Phe Asn Asp Val Thr Thr Arg Leu Arg
65                  70                  75                  80

Glu Asn Glu Leu Thr Tyr Tyr Cys Cys Lys Lys Asp Leu Cys Asn Phe
                85                  90                  95

Asn Glu Gln Leu Glu Asn Gly Gly Thr Ser Leu Ser Glu Lys Thr Val
            100                 105                 110

Leu Leu Leu Val Thr Pro Phe Leu Ala Ala Ala Trp Ser Leu His Pro
        115                 120                 125
```